US012680122B2

(12) United States Patent
Zheng et al.

(10) Patent No.: US 12,680,122 B2
(45) Date of Patent: Jul. 14, 2026

(54) PROTEINS CONTAINING MULTIPLE, DIFFERENT UNNATURAL AMINO ACIDS AND METHODS OF MAKING AND USING SUCH PROTEINS

(71) Applicant: TRUSTEES OF BOSTON COLLEGE, Chestnut Hill, MA (US)

(72) Inventors: Yunan Zheng, Vernon Hills, IL (US); James Sebastian Italia, Charlestown, MA (US); Abhishek Chatterjee, Lexington, MA (US)

(73) Assignee: TRUSTEES OF BOSTON COLLEGE, Chestnut Hall, MA (US)

( * ) Notice: Subject to any disclaimer, the term of this patent is extended or adjusted under 35 U.S.C. 154(b) by 1133 days.

(21) Appl. No.: 17/767,361

(22) PCT Filed: Oct. 8, 2020

(86) PCT No.: PCT/US2020/054859
§ 371 (c)(1),
(2) Date: Apr. 7, 2022

(87) PCT Pub. No.: WO2021/072129
PCT Pub. Date: Apr. 15, 2021

(65) Prior Publication Data
US 2022/0403438 A1 Dec. 22, 2022

Related U.S. Application Data

(60) Provisional application No. 62/912,171, filed on Oct. 8, 2019.

(51) Int. Cl.
| | |
|---|---|
| *C12P 21/02* | (2006.01) |
| *C07K 14/47* | (2006.01) |
| *C12N 9/00* | (2006.01) |
| *C12N 15/11* | (2006.01) |
| *C12N 15/67* | (2006.01) |

(52) U.S. Cl.
CPC .............. *C12P 21/02* (2013.01); *C07K 14/47* (2013.01); *C12N 9/93* (2013.01); *C12N 15/111* (2013.01); *C12N 15/67* (2013.01); *C12Y 601/01001* (2013.01); *C12Y 601/01002* (2013.01); *C12Y 601/01004* (2013.01); *C12Y 601/01026* (2013.01)

(58) Field of Classification Search
CPC ......... C12P 21/02; C12P 21/00; C07K 14/47; C12N 9/93; C12N 15/111; C12N 15/67; C12Y 601/01001; C12Y 601/01002; C12Y 601/01004; C12Y 601/01026
See application file for complete search history.

(56) References Cited

U.S. PATENT DOCUMENTS

| | | | |
|---|---|---|---|
| 5,387,484 | A | 2/1995 | Doany et al. |
| 5,559,099 | A | 9/1996 | Wickham et al. |
| 5,688,676 | A | 11/1997 | Zhou et al. |
| 5,691,176 | A | 11/1997 | Lebkowski et al. |
| 5,741,683 | A | 4/1998 | Zhou et al. |
| 5,801,030 | A | 9/1998 | McVey et al. |
| 5,834,256 | A | 11/1998 | Finer et al. |
| 5,837,511 | A | 11/1998 | Falck-Pedersen et al. |
| 5,846,782 | A | 12/1998 | Wickham et al. |
| 5,849,561 | A | 12/1998 | Falck-Pedersen |
| 5,851,806 | A | 12/1998 | Kovesdi et al. |
| 5,871,982 | A | 2/1999 | Wilson et al. |
| 5,965,541 | A | 10/1999 | Wickham et al. |
| 5,981,225 | A | 11/1999 | Kochanek et al. |
| 5,994,106 | A | 11/1999 | Kovesdi et al. |
| 5,994,128 | A | 11/1999 | Fallaux et al. |
| 5,994,136 | A | 11/1999 | Naldini et al. |
| 5,998,205 | A | 12/1999 | Hallenbeck et al. |
| 6,013,516 | A | 1/2000 | Verma et al. |
| 6,020,191 | A | 2/2000 | Scaria et al. |
| 6,033,908 | A | 3/2000 | Bout et al. |
| 6,040,174 | A | 3/2000 | Imler et al. |
| 6,083,716 | A | 7/2000 | Wilson et al. |
| 6,113,913 | A | 9/2000 | Brough et al. |
| 6,127,175 | A | 10/2000 | Vigne et al. |
| 6,156,303 | A | 12/2000 | Russell et al. |
| 6,207,455 | B1 | 3/2001 | Chang |
| 6,225,289 | B1 | 5/2001 | Kovesdi et al. |
| 6,270,996 | B1 | 8/2001 | Wilson et al. |
| 6,287,814 | B1 | 9/2001 | Hope et al. |
| 6,303,362 | B1 | 10/2001 | Kay et al. |
| 6,352,694 | B1 | 3/2002 | June et al. |
| 6,482,616 | B1 | 11/2002 | Kovesdi et al. |

(Continued)

FOREIGN PATENT DOCUMENTS

| | | |
|---|---|---|
| CN | 101048506 A | 10/2007 |
| CN | 101273140 A | 9/2008 |

(Continued)

OTHER PUBLICATIONS

Whisstock et al. Quaterly Reviews of Biophysics, 2003, "Prediction of protein function from protein sequence and structure", 36(3):307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*
Pojitkov et al. (Unnatural amino acids in enzymes and proteins. Journal of Molecular Catalysis B: Enzymatic 10 (2000), 47-55) (Year: 2000).*

(Continued)

*Primary Examiner* — Iqbal H Chowdhury
(74) *Attorney, Agent, or Firm* — HoustonHogle LLP

(57) ABSTRACT

The invention relates generally to methods of producing a protein comprising a first unnatural amino acid (UAA) and a second, different UAA, and proteins comprising a first UAA and a second, different UAA.

9 Claims, 25 Drawing Sheets

Specification includes a Sequence Listing.

(56) References Cited

U.S. PATENT DOCUMENTS

| | | | |
|---|---|---|---|
| 6,514,943 B2 | 2/2003 | Kovesdi et al. | |
| 6,531,123 B1 | 3/2003 | Chang | |
| 6,544,771 B1 | 4/2003 | Riviere et al. | |
| 6,677,156 B2 | 1/2004 | Brough et al. | |
| 6,682,907 B1 | 1/2004 | Charneau et al. | |
| 6,682,929 B2 | 1/2004 | Brough et al. | |
| 6,797,512 B1 | 9/2004 | McGuinness et al. | |
| 6,863,884 B2 | 3/2005 | Schauber et al. | |
| 6,943,019 B2 | 9/2005 | Wilson et al. | |
| 6,953,690 B1 | 10/2005 | Gao et al. | |
| 6,958,226 B1 | 10/2005 | Gray et al. | |
| 7,067,310 B2 | 6/2006 | Chartier et al. | |
| 7,195,896 B2 | 3/2007 | Kovesdi et al. | |
| 7,198,950 B2 | 4/2007 | Trono et al. | |
| 7,198,951 B2 | 4/2007 | Gao et al. | |
| 7,238,526 B2 | 7/2007 | Wilson et al. | |
| 7,250,299 B1 | 7/2007 | Naldini et al. | |
| 7,629,153 B2 | 12/2009 | Trono et al. | |
| 7,745,179 B2 | 6/2010 | McArthur et al. | |
| 7,785,827 B2 | 8/2010 | Martinis et al. | |
| 7,906,111 B2 | 3/2011 | Wilson et al. | |
| 8,163,543 B2 | 4/2012 | Urabe et al. | |
| 8,298,818 B2 | 10/2012 | Boye et al. | |
| 8,329,462 B2 | 12/2012 | Trono et al. | |
| 9,073,980 B2 | 7/2015 | Reid et al. | |
| 9,150,882 B2 | 10/2015 | Kay et al. | |
| 9,493,788 B2 | 11/2016 | Gao et al. | |
| 2002/0081721 A1 | 6/2002 | Allen et al. | |
| 2003/0082575 A1 | 5/2003 | Schultz et al. | |
| 2003/0108885 A1 | 6/2003 | Schultz et al. | |
| 2003/0228593 A1 | 12/2003 | Suga et al. | |
| 2004/0198637 A1 | 10/2004 | Schultz et al. | |
| 2005/0009049 A1 | 1/2005 | Chin et al. | |
| 2008/0233650 A1 | 9/2008 | Gall et al. | |
| 2009/0087413 A1 | 4/2009 | Shepard | |
| 2013/0244245 A1* | 9/2013 | Schultz | C12P 21/00 435/68.1 |
| 2017/0349891 A1 | 12/2017 | Chatterjee et al. | |

FOREIGN PATENT DOCUMENTS

| | | | |
|---|---|---|---|
| CN | 101303238 A | 11/2008 | |
| WO | WO 1994/028152 | 12/1994 | |
| WO | WO 1995/002697 | 1/1995 | |
| WO | WO 1995/016772 | 6/1995 | |
| WO | WO 1995/034671 | 12/1995 | |
| WO | WO 1996/017947 | 6/1996 | |
| WO | WO 1996/022378 | 7/1996 | |
| WO | WO 1997/000326 | 1/1997 | |
| WO | WO 1997/012986 | 4/1997 | |
| WO | WO 1997/021826 | 6/1997 | |
| WO | WO 1998/053087 | 11/1998 | |
| WO | WO 2000/024916 | 5/2000 | |
| WO | WO 2000/03444 | 6/2000 | |
| WO | WO 2000/047757 | 8/2000 | |
| WO | WO 2002/085923 | 10/2002 | |
| WO | WO 2003/020879 | 3/2003 | |
| WO | WO 2003/022311 | 3/2003 | |
| WO | WO 2005/007870 | 1/2005 | |
| WO | WO 2008030614 | 3/2008 | |
| WO | WO 2013/052799 | 4/2013 | |
| WO | WO 2013/052832 | 4/2013 | |
| WO | WO 2017/075335 | 5/2017 | |
| WO | WO 2017/075338 | 5/2017 | |
| WO | WO 2017/091786 | 6/2017 | |
| WO | WO 2017/201258 | 11/2017 | |
| WO | WO 2017189967 | 11/2017 | |
| WO | WO 2018039438 | 3/2018 | |
| WO | WO 2021026506 A2 | 2/2021 | |
| WO | WO 2022115625 | 6/2022 | |

OTHER PUBLICATIONS

Zheng et al. Expanding the Scope of Single- and Double-Noncanonical Amino Acid Mutagenesis in Mammalian Cells Using Orthogonal Poly-specific Leucyl-tRNA Synthetases. Biochemistry 2018, 57, 441-441). (Year: 2017).*

Josephson, K. et al., "Ribosomal Synthesis of Unnatural Peptides", Journal of the American Chemical Society, vol. 127(33), Mar. 11, 2005. 11727-11735.

Azoulay, M. et al., "Glutamine analogues as potential antimalarials", European Journal of Medicinal Chemistry, vol. 26(2), 1991. 201-205.

Chothia, C. et al., "Canonical structures for the hypervariable regions of immunoglobulins," Journal of Molecular Biology, vol. 196(4), 1987. 901-917.

Chung, J.H., et al., "A 5' element of the chicken beta-globin domain serves as an insulator in human erythroid cells and protects against position effect in *Drosophila*," Cell, vol. 74(3), 1993. 505-514.

Examiner Requisition received for Canadian Patent Application No. 3,154,115, mailed on Feb. 15, 2024, 4 pages.

Notice for Reasons for Rejection received for Japanese Patent Application No. 2022-521387, mailed on Sep. 3, 2024, 11 pages.

"*E.coli* Trp-tRNA," GenBank: M24301.1 (1994). 1 page.

Hartman, M.C., et al., "An Expanded Set of Amino Acid Analogs for the Ribosomal Translation of Unnatural Peptides," PloS One, 2(10): e972 (2007).

Schmied, W.H., et al., "Efficient Multisite Unnantural Amino Acid Incorporation in Mammalian Cells via Optimized Pyrrolysyl tRNA Synthetas/tRNA Expression and Engineered eRF1," J. Am. Chem. Soc. 136: 15577-15583 (2014).

International Search Report of the International Searching Authority, mailed on Apr. 2, 2021, from International Application No. PCT/US20/54859, filed on Oct. 8, 2020. 6 pages.

Written Opinion mailed on Apr. 2, 2021, from International Application No. PCT/US20/54859, filed on Oct. 8, 2020. 11 pages.

Altschul, S.F., et al., "Gapped BLAST and PSI-BLAST: a new generation of protein database search programs," Nucleic Acids Res., 25(17): 3389-3402 (1997).

Anderson, J.C., et al. "Exploring the limits of codon and anticodon size," 9(2): 237-244 (2002).

Bell, A.C., et al., "The protein CTCF is required for the enhancer blocking activity of vertebrate insulators," Cell, 98(3): 387-396 (1999).

Burgess-Beusse, B., et al., "The insulation of genes from external enhancers and silencing chromatin," Proc. Natl Acad Sci USA, 99(Suppl 4):16433-16437 (2002).

Chen, H.H., et al., "Persistence in muscle of an adenoviral vector that lacks all viral genes," Proc. Natl Acad Sci USA, 94(5): 1645-1650 (1997).

Chung, J.H. et al., "Characterization of the chicken beta-globin insulator," Proc. Natl. Acad. Sci USA, 94(2):575-580 (1997).

Cullen, B.R., et al., "Human immunodeficiency virus as a prototypic complex retrovirus," J. Virol., 65(3): 1053-1056 (1991).

Feng, L., et al., "Expanding tRNA recognition of a tRNA synthetase by a single amino acid change," Proc. Natl. Acad. Sci USA, 100(10): 5676-5681 (2003).

Forster, A.C., et al., "Programming peptidomimetic syntheses by translating genetic codes designed de novo," 100(11): 6353-6357 (2003).

Hecht, S.M, et al., "Chemical aminoacylation' of tRNA's," J. Biol Chem., 253(13): 4517-4520 (1978).

Henikoff, S. et al., "Amino acid substitution matrices from protein blocks," Proc Natl Acad Sci USA, 89(22):10915-10919 (1992).

Huang, Z.M., et al., "Role of the hepatitis B virus posttranscriptional regulatory element in export of intronless transcripts," Mol Cell Biol., 15(7): 3864-3869 (1995).

Karlin, S., et al., "Methods for assessing the statistical significance of molecular sequence features by using general scoring schemes," Proc Natl Acad Sci USA, 87(6): 2264-2268 (1990).

Kiga, D., et al., "An engineered *Escherichia coli* tyrosyl-tRNA synthetase for site-specific incorporation of an unnatural amino acid into proteins in eukaryotic translation and its application in a wheat germ cell-free system," Proc Natl Acad Sci USA, 99(15): 9715-9723 (2002).

(56) References Cited

OTHER PUBLICATIONS

Kiick, K.L., et al., "Incorporation of azides into recombinant proteins for chemoselective modification by the Staudinger ligation," Proc Natl Acad Sci USA, 99(1):19-24 (2002).

Liu, X., et al., "HnRNP L binds a cis-acting RNA sequence element that enables intron-dependent gene expression," Genes Dev., 9(14):1766-1780 (1995).

Magliery, T.J., et al., "Expanding the genetic code: selection of efficient suppressors of four-base codons and identification of "shifty" four-base codons with a library approach in Escherichia coli," J. Mol Biol., 307(3): 755-769 (2001).

Mueller, C., et al., "Production and discovery of novel recombinant adeno-associated viral vectors," Curr Protoc Microbiol, 14D.1.1-14D.1.21 (2012).

Murakami, H., et al., "Using a solid-phase ribozyme aminoacylation system to reprogram the genetic code," Chem Biol., 10(11): 1077-1084 (2003).

Roy, S., et al., "Isolation and characterization of adenoviruses persistently shed from the gastrointestinal tract of non-human primates," PLoS Pathog., 5(7): e1000503 (2009).

Srivastava, A., "Adeno-associated virus-mediated gene transfer," J. Cell Biochem., 105(1): 17-24 (2008).

Turcatti, G., et al., "Probing the structure and function of the tachykinin neurokinin-2 receptor through biosynthetic incorporation of fluorescent amino acids at specific sites," J. Biol Chem., 271(33): 19991-19998 (1996).

Zheng, Y., et al., "Expanding the Scope of Single- and Double Noncanonical Amino Acid Mutagenesis in Mammalian Cells Using Orthogonal Polyspecific Leucyl-tRNA Synthetases," Biochemistry, 57(4): 441-445 (2018).

Zufferey, R., et al., "Woodchuck hepatitis virus posttranscriptional regulatory element enhances expression of transgenes delivered by retroviral vectors," J. Virol., 73(4): 2886-2892 (1999).

Eisenberg, S.P., "The effect of an Escherichia coli regulatory mutation on transfer RNA structure", Journal of Micro Biology. vol. 135 (1) , pp. 111-126 (1979).

"Multispecies: tryptophan—tRNA ligase [Proteobacteria]", NCBI Reference Sequence: WP_000165552.1, National Library of Medicine, 2 pages.

Bain, J.D. et al., "Biosynthetic site-specific incorporation of a non-natural amino acid into a polypeptide", Journal of the American Chemical Society, vol. 111(20), 1989. 8013-8014.

Bain, J.D. et al., "Ribosome-mediated incorporation of a non-standard amino acid into a peptide through expansion of the genetic code", Nature, vol. 356(6369), Apr. 9, 1992. 537-539.

Barton, D.H.R. et al., "Synthesis of novel a-amino-acids and derivatives using radical chemistry: synthesis of L-and D-α-amino-adipic acids, L-α", Tetrahedron, vol. 43(19), 1987. 4297-4308.

Brough, D.E. et al., "Activation of Transgene Expression by Early Region 4 Is Responsible for a High Level of Persistent Transgene Expression from Adenovirus Vectors In Vivo," Journal of Virology, 71(12), Dec. 1997. 9206-9213.

Christie, B.D. et al., "Synthesis of Optically Pure Pipecolates from L-Asparagine. Application to the Total Synthesis of (+)-Apovincamine through Amino Acid Decarbonylation and Iminium Ion Cyclization", Journal of Organic Chemistry, vol. 50(8), 1985. 1239-1246.

Cornish, V.W. et al., "Probing Protein Structure and Function with an Expanded Genetic Code", Angewandte Chemie International Edition in English, vol. 34(6), 1995. 621-633.

Craig, J.C. et al., "Absolute Configuration of the Enantiomers of 7-Chloro-4-[[4-(diethylamino)-1-methylbutyl]amino]quinoline (Chloroquine)", Journal of Organic Checmistry, vol. 53(6), 1988. 1167-1170.

Francklyn, C. et al., "Aminoacyl-tRNA synthetases: Versatile players in the changing theater of translation", RNA, vol. 8(11), 2002. 1363-1372.

Friedman, O.M. et al., "Synthesis of Derivatives of Glutamine as Model Substrates for Anti-tumor Agents", Journal of the American Chemical Society, vol. 81(14), Jul. 20, 1959. 3750-3752.

Gao, G. et al., "Clades of Adeno-Associated Viruses Are Widely Disseminated in Human Tissues", Journal of Virology, vol. 78(12), Jun. 2004. 6381-6388.

Graham, F.L. et al., "Characteristics of a Human Cell Line Transformed by DNA from Human Adenovirus Type 5", Journal of General Virology, vol. 36(1), 1977. 59-72.

Hamano-Takaku, F. et al., "A Mutant Escherichia coli Tyrosyl-tRNA Synthetase Utilizes the Unnatural Amino Acid Azatyrosine More Efficiently than Tyrosine", Journal of Biological Chemistry, vol. 275(51), 2000. 40324-40328.

Hecht, S.M., "Probing the Synthetic Capabilities of a Center of Biochemical Catalysis", Accounts of Chemical Research, vol. 25(12), 1992. 545-552.

Heckler, T.G. et al., "Ribosomal Binding and Dipeptide Formation by Misacylated tRNA(Phe)'s", Biochemistry, vol. 27(19), 1988. 7254-7262.

Hohsaka, T. et al., "Incorporation of Two Different Nonnatural Amino Acids Independently into a Single Protein through Extension of the Genetic Code", Journal of the American Chemical Society, vol. 121(51), 1999. 12194-12195.

Illangakekare, M. et al., "Aminoacyl-RNA Synthesis Catalyzed by an RNA", Science, vol. 267(5198), Feb. 3, 1995. 643-647.

King, F.E. et al., "New Synthesis of Glutamine and of y-Dipeptides of Gluctamic Acid from Phthalylated Intermediates", Journal of the Chemical Society (Resumed), 1949. 3315-3319.

Kochanek, S., "High-Capacity Adenoviral Vectors for Gene Transfer and Somatic Gene Therapy", Human Gene Therapy, vol. 10(15), Oct. 10, 1999. 2451-2459.

Koskinen, A.M.P. et al., "Synthesis of 4-Substituted Prolines as Conformationally Constrained Amino Acid Analogues", Journal of Organic Chemistry, vol. 54(8), 1989. 1859-1866.

Lohse, P.A. et al., "Ribozyme-Catalysed amino-acid transfer reactions", Nature, vol. 381(6581), May 30, 1996. 442-444.

Moore, B. et al., "Quadruplet Codons: Implications for Code Expansion and the Specification of Translation Step Size", Journal of Molecular Biology, vol. 298(2), 2000. 195-209.

Noren, C.J. et al., "A General Method for Site-Specific Incorporation of Unnatural Amino Acids into Proteins", Science, vol. 244(4901), Apr. 14, 1989. 182-188.

Nowak, M.W. et al., "Nicotinic Receptor Binding Site Probed with Unnatural Amino Acid Incorporation in Intact Cells", Science, vol. 268(5209), Apr. 21, 1995. 439-442.

Robertson, S.A. et al., "A General and Efficient Route for Chemical Aminoacylation of Transfer RNAs", Journal of the American Chemical Society, vol. 113(7), 1991. 2722-2729.

Roy, G. et al., "Development of a high yielding expression platform for the introduction of non-natural amino acids in protein sequences", MAbs, vol. 12(1), Jan. 2020. 19 pages.

Saks, M.E. et al., "An Engineered Tetrahymena tRNAGln for in Vivo Incorporation of Unnatural Amino Acids into Proteins by Nonsense Suppression", Journal of Biological Chemistry, vol. 271(38), 1996. 23169-23175.

Subasinghe, N. et al., "Quisqualic Acid Analogues: Synthesis of Beta-Heterocyclic 2-Aminopropanoic Acid Derivatives and Their Activity at a Novel Quisqualate-Sensitized Site", Journal of Medicinal Chemistry, vol. 35(24), 1992. 4602-4607.

Zhan, H.C. et al., "Insulator: from chromatin domain boundary to gene regulation", Human Genetics, vol. 109(5), 2001. 471-478.

Gallivan et al., "Site-specific incorporation of biotinylated amino acids to identify surface-exposed residues in integral membrane proteins", Chemistry & Biology, 4:739-749 (1997).

Morsy et al., "An adenoviral vector deleted for all viral coding sequences results in enhanced safety and extended expression of a leptin transgene", Proc. Natl. Acad. Sci. USA 95: 7866-7871 (1998).

Extended European Search Report, mailed on Sep. 22, 2023, from European Application No. 20873915.1, filed on Oct. 8, 2020. 10 pages.

Xiao, H. et al., "Genetic Incorporation of Multiple Unnatural Amino Acids into Proteins in Mammalian Cells", Angewandte Chemie International Edition, vol. 52(52), Nov. 8, 2013. 14080-14083.

Hoesl, M.G. et al., "In Vivo Incorporation of Multiple Noncanonical Amino Acids into Proteins", Angewandte Chemie International Edition, vol. 50(13), Feb. 25, 2011. 2896-2902.

(56) References Cited

OTHER PUBLICATIONS

Chatterjee, A. et al., "Evolution of multiple, mutually orthogonal prolyl-tRNA synthetase/tRNA pairs for unnatural amino acid mutagenesis in *Escherichia coli*", Proceedings of the National Academy of Sciences, vol. 109(37), Sep. 11, 2012. 14841-14846.
International Preliminary Report on Patentability issued on Apr. 12, 2022, from International Application No. PCT/US20/54859, filed on Oct. 8, 2020. 12 pages.
Notice to Submit Response received for Korean Patent Application No. 10-2022-7015097, mailed on Nov. 20, 2025, 10 pages.

* cited by examiner

Formula A
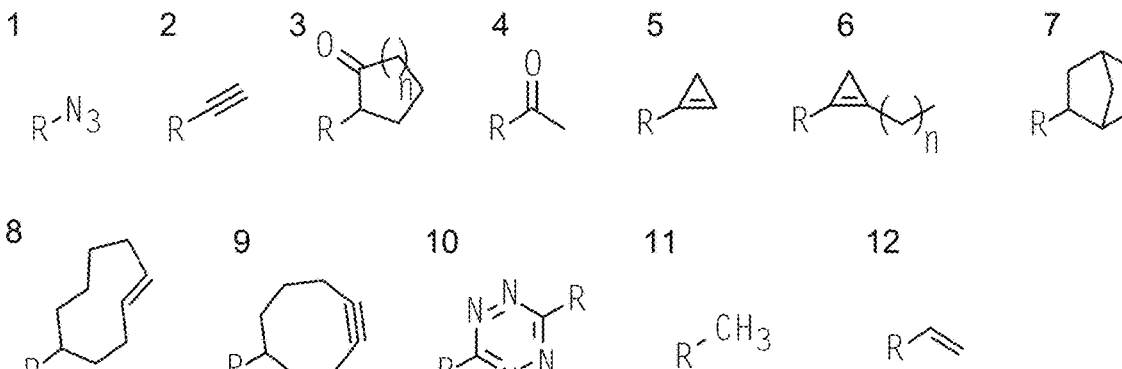
X = O, S, CH₂, NH
n = any integer 0-20
Y = Functional group 1-12 (outlined above)
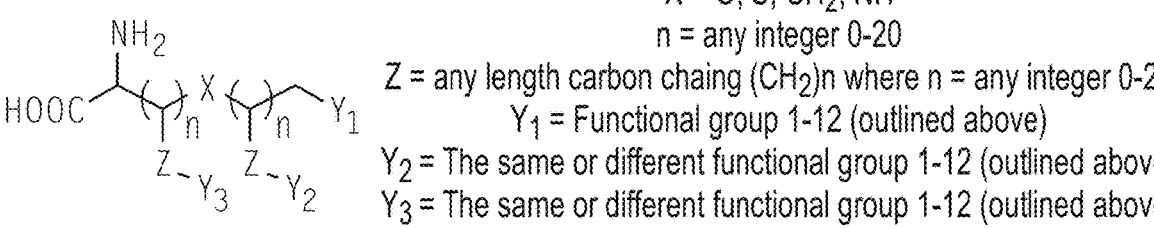
Formula B
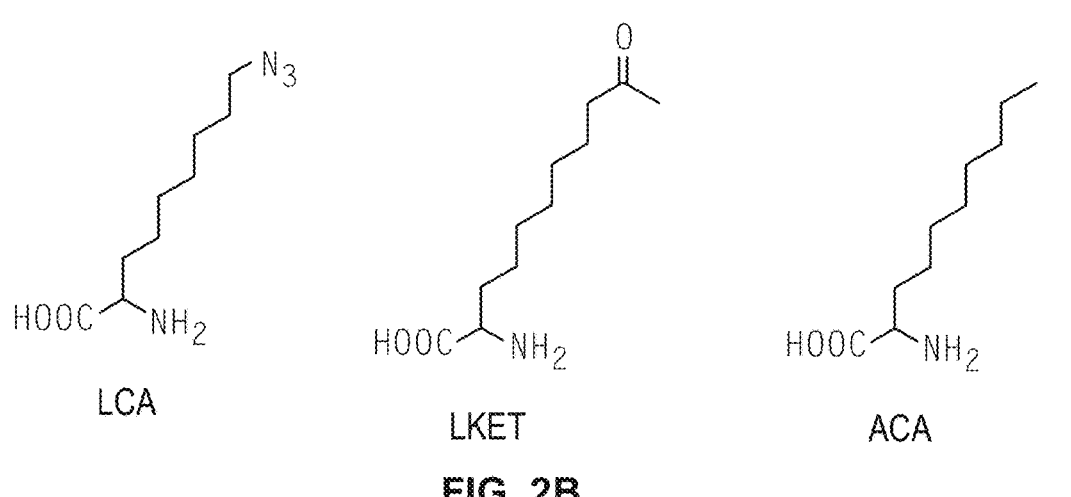
X = O, S, CH₂, NH
n = any integer 0-20
Z = any length carbon chaing (CH₂)n where n = any integer 0-20
Y₁ = Functional group 1-12 (outlined above)
Y₂ = The same or different functional group 1-12 (outlined above)
Y₃ = The same or different functional group 1-12 (outlined above)
FIG. 2A
LCA          LKET          ACA
FIG. 2B

OmeY              AzF              PrY              ACF

FIG. 5

Cap          BocK     AzK          hPrK          CpK

FIG. 6

Lane 1: EGFP**+ BocK+ 5HTP
Lane 2: EGFP**+ OMeY+ 5HTP
Lane 2: EGFP+ Cys-5-N3+ 5HTP EGFP+5HTP+OMeY Expected mass=30559
Observed mass=30559

30559

EGFP**+5HTP+Cys-5-N3

Expected mass=30596
Observed mass=30596

30596

EGFP**+5HTP+Cyclopropene-K

Expected mass=30620
Observed mass=30620

EGFP**+AzW+Cyclopropene-K

Expected mass=30645
Observed mass=30645

**EGFP\*\*+5HTP+AzK**

Expected mass=30622
Observed mass=30622

**EGFP\*\*+5HTP+AzK+Diazo-FL**

Expected mass=30980
Observed mass=30980

**EGFP\*\*+5HTP+AzK+DBCO-TAMRA**

Expected mass=31558
Observed mass=31558

**EGFP\*\*+5HTP+AzK+DBCO-TAMRA+Diazo-FL**

Expected mass=31916
Observed mass=31916

HC-T202 Context

...VVTVPSSSLGTQTYICNVNHKPSN... (SEQ ID NO: 116)

LC-K113 Context

...TFGQGTKVEIKRTVAAPSVFIF... (SEQ ID NO: 117)

PROTEINS CONTAINING MULTIPLE, DIFFERENT UNNATURAL AMINO ACIDS AND METHODS OF MAKING AND USING SUCH PROTEINS

CROSS-REFERENCE TO RELATED APPLICATIONS

This application is a § 371 National Phase Application of International Application No. PCT/US2020/054859, filed Oct. 8, 2020, which claims the benefit of and priority to U.S. Provisional Patent Application No. 62/912,171, filed Oct. 8, 2019, both of which are incorporated herein by reference in their entirety for all purposes.

FIELD OF THE INVENTION

The present disclosure relates, in general, to the field where orthogonal tRNA/aminoacyl-tRNA synthetase pairs are used for the incorporation of multiple, different UAAs into a protein of interest as it is being synthesized.

BACKGROUND

In nature, proteins are produced in cells via processes known as transcription and translation. During transcription, a gene comprising a series of codons that collectively encode a protein of interest is transcribed into messenger RNA (mRNA). During translation, a ribosome, attaches to and moves along the mRNA and incorporates specific amino acids into a polypeptide chain being synthesized (translated) from the mRNA at positions corresponding to the codons to produce the protein. During translation specific, naturally occurring amino acids coupled to transfer RNAs (tRNAs) enter the ribosome. The tRNAs, which contain an anti-codon sequence, hybridize to their respective codon sequences in mRNA and transfer the amino acid they are carrying into the nascent protein chain at the appropriate position as the protein is synthesized.

Over the last few decades, significant efforts have been made to produce homogenous preparations of site-specifically modified proteins, e.g., mammalian proteins, on commercial scale quantities for use in a variety of applications, including, for example, therapeutics and diagnostics. Furthermore, efforts have been made to produce these modified mammalian proteins in eukaryotic cells (e.g., mammalian cells) because the proteins may be more readily produced in a properly folded and fully active form and/or post-translationally modified in a manner similar to the native protein naturally produced in a mammalian cell.

One approach for producing proteins that contain site-specific modifications involves the site-specific incorporation of one or more unnatural amino acids (UAAs) into a protein of interest. The ability to site-specifically incorporate UAAs into proteins in vivo has become a powerful tool to augment protein function or introduce new chemical functionalities not found in nature. The core elements required for this technology include: an engineered tRNA, an engineered aminoacyl-tRNA synthetase (aaRS) that charges the tRNA with a UAA, and a unique codon, e.g., a stop codon, directing the incorporation of the UAA into the protein as it is being synthesized.

Central to this approach is the use of an engineered tRNA/aaRS pair in which the aaRS charges the tRNA with the UAA of interest without cross-reacting with the tRNAs and amino acids normally present in the expression host cell. This has been accomplished by using an engineered tRNA/ aaRS pair derived from an organism in different domain of life as the expression host cell so as to maximize the orthogonality between the engineered tRNA/aaRS pair (e.g., an engineered bacterial tRNA/aaRS pair) and the tRNA/aaRS pairs naturally found in the expression host cell (e.g., mammalian cell). The engineered tRNA, which is charged with the UAA via the aaRS, binds or hybridizes to the unique codon, such as a premature stop codon (UAG, UGA, UAA) present in the mRNA encoding the protein to be expressed. See, for example, FIG. 1, which shows the synthesis of a protein using an endogenous tRNA and an endogenous aaRS from the expression host cell and an engineered orthogonal tRNA and an orthogonal aaRS introduced into the host cell so as to facilitate the incorporation of a UAA into the protein as it is synthesized via the ribosome. To date, a variety of orthogonal tRNA/aaRS pairs have been produced for certain of the naturally occurring amino acids (see, e.g., U.S. Patent Publication US2017/0349891, and Zheng et al. (2018) BIOCHEM. 57:441-445). The approach facilitates the expression of proteins containing site specific modifications such as bioconjugation handles and photoactivatable crosslinkers, which can be used as therapeutics (e.g., antibody drug conjugates (ADCs), bi-specific antibodies (e.g., bispecific monoclonal antibodies), nanobodies, chemokines, vaccines, coagulation factors, hormones, and enzymes).

Despite the efforts made to date, there has been limited success in utilizing this technology to incorporate multiple, different UAAs into a single polypeptide. To incorporate multiple, different UAAs into one polypeptide, each UAA must be encoded by a distinct nonsense codon, and each UAA must be charged by different orthogonal aaRS/tRNA pairs, where each pair must also be orthogonal to each other (mutually orthogonal). A significant degree of cross-reactivity has been found between aaRS/tRNA pairs, which together with an inability to decode the full complement of nonsense codons has limited the overall efficiency of site-specific incorporation of two distinct UAAs in mammalian cells.

Accordingly, there remains a need for mammalian-based expression platforms that allow for the incorporation of multiple, distinct unnatural amino acids into proteins with high efficiency.

SUMMARY OF THE INVENTION

The invention is based, in part, on the discovery of combinations of nonsense codons, tRNAs, aminoacyl-tRNA synthetases, and UAAs that allow for efficient site-specific incorporation of multiple, different UAAs into a protein expressed in mammalian cells.

In one aspect, the invention provides a method of producing a protein comprising a first unnatural amino acid (UAA) and a second, different UAA (e.g., wherein the first and second UAA are each incorporated into the protein at specific, different positions in the protein polypeptide chain). The method comprises culturing a mammalian cell with: (i) a nucleic acid comprising a nucleotide sequence encoding a first tRNA comprising an anticodon that hybridizes to a first codon selected from UAG, UGA, and UAA, and is capable of being charged with the first UAA; (ii) a nucleic acid comprising a nucleotide sequence encoding a first aminoacyl-tRNA synthetase capable of charging the first tRNA with the first UAA; (iii) a nucleic acid comprising a nucleotide sequence encoding a second tRNA comprising an anticodon that hybridizes to a second codon selected from UAG, UGA, and UAA, and is capable of being charged with the second UAA, wherein the first and second tRNA do not contain the same anticodon; (iv) a nucleic acid comprising a nucleotide sequence encoding a second aminoacyl-tRNA synthetase capable of charging the second tRNA with the second UAA; and (v) a nucleic acid comprising a nucleotide sequence encoding the protein comprising the first codon and the second codon; under conditions that permit the first tRNA, when expressed in the cell and charged with the first UAA, to hybridize to the first codon and direct the incorporation of the first UAA into the protein, and the second tRNA, when expressed in the cell and charged with the second UAA, to hybridize to the second codon and direct the incorporation of the second UAA into the protein.

In certain embodiments, the expression yield of the protein comprising both the first and second UAA expressed by the cell is at least 10%, 20%, 30%, 40%, 50%, 60%, 70%, 80%, or 90% of the expression yield of a reference protein. For example, in certain embodiments, the amount of the protein comprising the first and second UAA expressed by the cell is at least 10%, 20%, 30%, 40%, 50%, 60%, 70%, 80%, or 90% of the amount of a reference protein expressed by the same cell or a similar cell. In certain embodiments, the reference protein is a protein that does not comprise the first and second UAA but is otherwise identical to the protein comprising the first and second UAA. For example, the reference protein may comprise a wild-type amino acid sequence, or comprise a wild-type amino acid residue at the positions corresponding to the first and second UAA.

In certain embodiments, the first or second tRNA is an analog or derivative of a prokaryotic tryptophanyl-tRNA, e.g., an *E. coli* tryptophanyl-tRNA. For example, the first or second tRNA may comprise a nucleotide sequence selected from any one of SEQ ID NOs: 49-54 or 108-113. In certain embodiments, the first or second aminoacyl-tRNA synthetase is an analog or derivative of a prokaryotic tryptophanyl-tRNA synthetase, e.g., an *E. coli* tryptophanyl-tRNA synthetase. For example, the first aminoacyl-tRNA synthetase may comprise an amino acid sequence selected from any one of SEQ ID NOs: 44-48. In certain embodiments, the first or second codon is UGA. In certain embodiments, the first or second UAA is a tryptophan analog, e.g., a non-naturally occurring tryptophan analog. In certain embodiments, the first or second UAA is 5-HTP or 5-AzW.

In certain embodiments, the first or second tRNA is an analog or derivative of a prokaryotic leucyl-tRNA, e.g., an *E. coli* leucyl-tRNA. For example, the first or second tRNA may comprise a nucleotide sequence selected from any one of SEQ ID NOs: 16-43. In certain embodiments, the first or second aminoacyl-tRNA synthetase is an analog or derivative of a prokaryotic leucyl-tRNA synthetase, e.g., an *E. coli* leucyl-tRNA synthetase. For example, the first aminoacyl-tRNA synthetase may comprise an amino acid sequence selected from any one of SEQ ID NOs: 1-15. In certain embodiments, the first or second codon is UAG. In certain embodiments, the first or second UAA is a leucine analog, e.g., a non-naturally occurring leucine analog. In certain embodiments, the first or second UAA is LCA or Cys-5-N3.

In certain embodiments, the first or second tRNA is an analog or derivative of a prokaryotic tyrosyl-tRNA, e.g., an *E. coli* tyrosyl-tRNA. For example, the first or second tRNA may comprise a nucleotide sequence selected from any one of SEQ ID NOs: 68-69 or 104-105. In certain embodiments, the first or second aminoacyl-tRNA synthetase is an analog or derivative of a prokaryotic tyrosyl-tRNA synthetase, e.g., an *E. coli* tyrosyl-tRNA synthetase. For example, the first aminoacyl-tRNA synthetase may comprise the amino acid sequence of SEQ ID NO: 70. In certain embodiments, the first or second codon is UAG. In certain embodiments, the first or second UAA is a tyrosine analog, e.g., a non-naturally occurring tyrosine analog. In certain embodiments, the first or second UAA is OmeY, AzF, or OpropY.

In certain embodiments, the first or second tRNA is an analog or derivative of an archael pyrrolysyl-tRNA, e.g., an *M. barkeri* pyrrolysyl-tRNA. For example, the first or second tRNA may comprise a nucleotide sequence selected from any one of SEQ ID NOs: 72-100 or 106-107. In certain embodiments, the first or second aminoacyl-tRNA synthetase is an analog or derivative of an archael pyrrolysyl-tRNA synthetase, e.g., an *M. barkeri* pyrrolysyl-tRNA synthetase. For example, the first aminoacyl-tRNA synthetase may comprise the amino acid sequence of SEQ ID NO: 101. In certain embodiments, the first or second codon is UAG. In certain embodiments, the first or second UAA is a pyrrolysine analog, e.g., a non-naturally occurring pyrrolysine analog. In certain embodiments, the first or second UAA is BocK, CpK, or AzK.

In certain embodiments, the protein is an antibody (or a fragment thereof, e.g., an antigen-binding fragment thereof), bispecific antibody, nanobody, affibody, viral protein, chemokine, cytokine, antigen, blood coagulation factor, hormone, growth factor, enzyme, cell signaling protein, or any other polypeptide or protein. In certain embodiments, the protein is an antibody (or a fragment thereof, e.g., an antigen-binding fragment thereof) and the first UAA and/or the second UAA are located in a constant region of the antibody.

In certain embodiments, the cell is a human cell, e.g., a human embryonic kidney (HEK) or a Chinese hamster ovary (CHO) cell.

In certain embodiments, the method further comprises contacting the cell with the first and/or second UAA. In certain embodiments, the method further comprises purifying the protein. In certain embodiments, the method further comprises chemically modifying the first and/or second UAA. For example, the chemical modification may comprise conjugation to a detectable label or molecule, e.g., a drug, e.g., a small molecule drug.

In another aspect, the invention provides a method of producing a protein comprising a tryptophan analog (e.g., a non-naturally occurring tryptophan analog) and a leucine analog (e.g., a non-naturally occurring leucine analog). The method comprises culturing a mammalian cell with: (i) a nucleic acid comprising a nucleotide sequence encoding a derivative of an *E. coli* tryptophanyl-tRNA comprising an anticodon that hybridizes to a UGA codon, and is capable of being charged with the tryptophan analog; (ii) a nucleic acid comprising a nucleotide sequence encoding a derivative of an *E. coli* tryptophanyl-tRNA synthetase capable of charging the derivative of the *E. coli* tryptophanyl-tRNA with the tryptophan analog; (iii) a nucleic acid comprising a nucleotide sequence encoding a derivative of an *E. coli* leucyl-tRNA comprising an anticodon that hybridizes to UAG codon, and is capable of being charged with the leucine analog; (iv) a nucleic acid comprising a nucleotide sequence encoding a derivative of an *E. coli* leucyl-tRNA synthetase capable of charging the derivative of the *E. coli* leucyl-tRNA with the leucine analog; and (v) a nucleic acid comprising a nucleotide sequence encoding the protein comprising the UGA codon and the UAG codon; under conditions that permit the derivative of the *E. coli* tryptophanyl-tRNA, when expressed in the cell and charged with the tryptophan analog, to hybridize to the UGA codon and direct the incorporation of the tryptophan into the protein, and the derivative of the *E. coli* leucyl-tRNA, when expressed in the cell and charged with the leucine analog, to hybridize to the UAG codon and direct the incorporation of the leucine analog into the protein.

In another aspect, the invention provides a method of producing a protein comprising a tryptophan analog (e.g., a non-naturally occurring tryptophan analog) and a tyrosine analog (e.g., a non-naturally occurring tyrosine analog). The method comprises culturing a mammalian cell with: (i) a nucleic acid comprising a nucleotide sequence encoding a derivative of an E. coli tryptophanyl-tRNA comprising an anticodon that hybridizes to a UGA codon, and is capable of being charged with the tryptophan analog; (ii) a nucleic acid comprising a nucleotide sequence encoding a derivative of an E. coli tryptophanyl-tRNA synthetase capable of charging the derivative of the E. coli tryptophanyl-tRNA with the tryptophan analog; (iii) a nucleic acid comprising a nucleotide sequence encoding a derivative of an E. coli tyrosyl-tRNA comprising an anticodon that hybridizes to UAG codon, and is capable of being charged with the tyrosine analog; (iv) a nucleic acid comprising a nucleotide sequence encoding a derivative of an E. coli tyrosyl-tRNA synthetase capable of charging the derivative of the E. coli tyrosyl-tRNA with the tyrosine analog; and (v) a nucleic acid comprising a nucleotide sequence encoding the protein comprising the UGA codon and the UAG codon; under conditions that permit the derivative of the E. coli tryptophanyl-tRNA, when expressed in the cell and charged with the tryptophan analog, to hybridize to the UGA codon and direct the incorporation of the tryptophan into the protein, and the derivative of the E. coli tyrosyl-tRNA, when expressed in the cell and charged with the tyrosine analog, to hybridize to the UAG codon and direct the incorporation of the tyrosine analog into the protein.

In another aspect, the invention provides a method of producing a protein comprising a tryptophan analog (e.g., a non-naturally occurring tryptophan analog) and a pyrrolysine analog (e.g., a non-naturally occurring pyrrolysine analog). The method comprises culturing a mammalian cell with: (i) a nucleic acid comprising a nucleotide sequence encoding a derivative of an E. coli tryptophanyl-tRNA comprising an anticodon that hybridizes to a UGA codon, and is capable of being charged with the tryptophan analog; (ii) a nucleic acid comprising a nucleotide sequence encoding a derivative of an E. coli tryptophanyl-tRNA synthetase capable of charging the derivative of the E. coli tryptophanyl-tRNA with the tryptophan analog; (iii) a nucleic acid comprising a nucleotide sequence encoding a derivative of an M. barkeri pyrrolysyl-tRNA comprising an anticodon that hybridizes to UAG codon, and is capable of being charged with the pyrrolysine analog; (iv) a nucleic acid comprising a nucleotide sequence encoding a derivative of an M. barkeri pyrrolysyl-tRNA synthetase capable of charging the derivative of the M. barkeri pyrrolysyl-tRNA with the pyrrolysine analog; and (v) a nucleic acid comprising a nucleotide sequence encoding the protein comprising the UGA codon and the UAG codon; under conditions that permit the derivative of the E. coli tryptophanyl-tRNA, when expressed in the cell and charged with the tryptophan analog, to hybridize to the UGA codon and direct the incorporation of the tryptophan into the protein, and the derivative of the E. coli pyrrolysyl-tRNA, when expressed in the cell and charged with the pyrrolysine analog, to hybridize to the UAG codon and direct the incorporation of the pyrrolysine analog into the protein.

In another aspect, the invention provides a protein comprising a first unnatural amino acid (UAA) and a second UAA produced by any of the foregoing methods.

In another aspect, the invention provides a protein expressed in a mammalian cell comprising a first unnatural amino acid (UAA) that is a tryptophan analog (e.g., a non-naturally occurring tryptophan analog) and a second UAA that is a leucine analog (e.g., a non-naturally occurring leucine analog). In certain embodiments, the tryptophan analog is selected from 5-HTP and 5-AzW and/or the leucine analog is selected from LCA and Cys-5-N3.

In another aspect, the invention provides a protein expressed in a mammalian cell comprising a first unnatural amino acid (UAA) that is a tryptophan analog (e.g., a non-naturally occurring tryptophan analog) and a second UAA that is a tyrosine analog (e.g., a non-naturally occurring tyrosine analog). In certain embodiments, the tryptophan analog is selected from 5-HTP and 5-AzW and/or the tyrosine analog is selected from OmeY, AzF, and OpropY UAA.

In another aspect, the invention provides a protein expressed in a mammalian cell comprising a first unnatural amino acid (UAA) that is a tryptophan analog (e.g., a non-naturally occurring tryptophan analog) and a second UAA that is a pyrrolysine analog (e.g., a non-naturally occurring pyrrolysine analog). In certain embodiments, the tryptophan analog is selected from 5-HTP and 5-AzW and/or the pyrrolysine analog is selected from BocK, CpK, AzK, and CpK.

In certain embodiments of any of the foregoing proteins, a detectable label or molecule (e.g., a drug, e.g., a small molecule drug) is covalently coupled to the protein via the first UAA and/or the second UAA. In certain embodiments, the protein is an antibody (or a fragment thereof, e.g., an antigen-binding fragment thereof), bispecific antibody, nanobody, affibody, viral protein, chemokine, cytokine, antigen, blood coagulation factor, hormone, growth factor, enzyme, cell signaling protein, or any other polypeptide or protein.

These and other aspects and features of the invention are described in the following detailed description and claims.

DESCRIPTION OF THE DRAWINGS

The invention can be more completely understood with reference to the following drawings.

FIGS. 2A-2C depicts a subset of UAAs that are exemplary substrates for a leucyl tRNA-synthetase.

FIG. 3 depicts a subset of UAAs that are exemplary substrates for a tryptophanyl tRNA-synthetase.

FIG. 4A depicts UAAs C5Az, LCA, and AzW. FIG. 4B depicts a synthetic route for C5Az. FIG. 4C depicts a synthetic route for AzW. FIGS. 4D-F depict synthetic routes for LCA.

FIG. 5 depicts a subset of UAAs that are exemplary substrates for a tyrosyl tRNA-synthetase.

FIG. 6 depicts a subset of UAAs that are exemplary substrates for a pyrrolysyl tRNA-synthetase.

FIG. 9A depicts a comparison of TAG-stop codon suppression in mammalian cells of LeuRS, EcTyrRS, PyIRS, and EcTrpRS pairs using a fluorescent reporter. FIG. 9B depicts a comparison of TGA-stop codon suppression in mammalian cells of LeuRS, EcTyrRS, PyIRS, and EcTrpRS pairs using a fluorescent reporter.

FIG. 10A is a bar graph demonstrating site-specific incorporation efficiency of exemplary UAA pairs using EGFP fluorescence as a reporter for incorporation. FIG. 10B is an SDS-PAGE gel demonstrating production of exemplary proteins with two UAAs, using GFP protein production as a readout of site-specific incorporation.

FIG. 11A is a histogram demonstrating mass spectrometry results of EGFP containing the exemplary UAAs HTP and BocK. FIG. 11B is a histogram demonstrating mass spectrometry results of EGFP containing the exemplary UAAs 5HTP and OMeY. FIG. 11C is a histogram demonstrating mass spectrometry results of EGFP containing the exemplary UAAs 5HTP and Cys-5-N3. FIG. 11D is a histogram demonstrating mass spectrometry results of EGFP containing the exemplary UAAs 5HTP and BocK. FIG. 11E is a histogram demonstrating mass spectrometry results of EGFP containing the exemplary UAAs 5HTP and Cyclopropene-K. FIG. 11F is a histogram demonstrating mass spectrometry results of EGFP containing the exemplary UAAs AzW and Cyclopropene-K. FIG. 11G is a histogram demonstrating mass spectrometry results of EGFP containing the exemplary UAAs 5HTP and AzK. FIG. 11H is a histogram demonstrating mass spectrometry results of fluorescent Diazo-labeled EGFP containing the exemplary UAAs 5HTP and AzK. FIG. 11I is a histogram demonstrating mass spectrometry results of DBCO-TAMRA-labeled EGFP containing the exemplary UAAs 5HTP and AzK. FIG. 11J is a histogram demonstrating mass spectrometry results of fluorescent Diazo and DBCO-TAMRA-labeled EGFP containing the exemplary UAAs 5HTP and AzK.

FIG. 13A is a bar graph demonstrating total protein yield in mg/L for IgG with UAA incorporation at T202 (heavy chain) and K113 (light chain). FIG. 13B is an SDS-PAGE gel of IgG with UAA incorporation at T202 and K113.

FIG. 14A is a histogram demonstrating mass spectrometry results of the PNGase-reduced IgG heavy chain (HC) containing the exemplary UAA HTP. FIG. 14B is a histogram demonstrating mass spectrometry results of PNGase-reduced IgG-light chain (LC) containing the exemplary UAA LCA.

DETAILED DESCRIPTION

Figure 1:
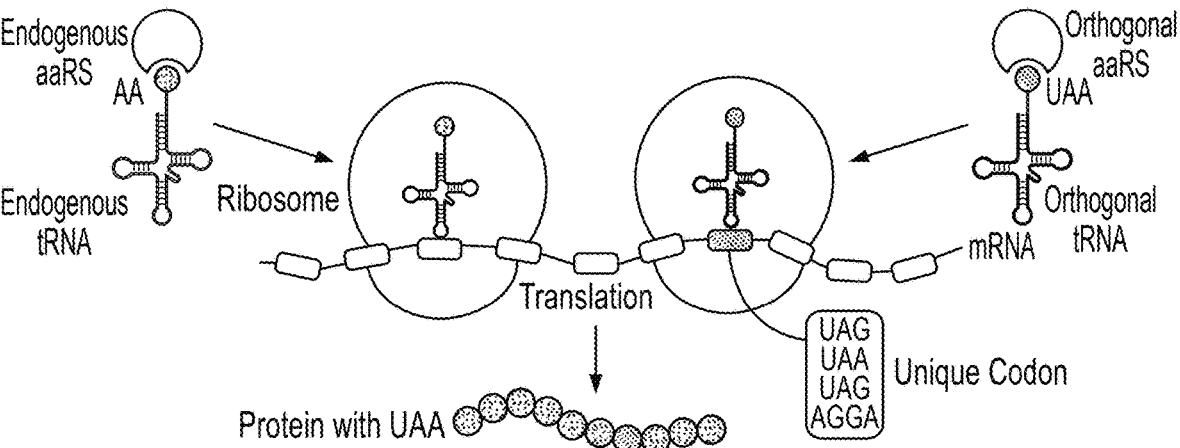
FIG. 1 depicts a schematic overview of genetic code expansion using unnatural amino acids (UAAs).

The invention is based, in part, on the discovery of combinations of nonsense codons, tRNAs, aminoacyl-tRNA synthetases, and UAAs that allow for efficient site-specific incorporation of multiple, different UAAs into a protein produced in mammalian cells. Selection of the components that allow for successful, efficient incorporation of multiple UAAs in a protein is challenging given that there are over two million possible combinations of distinct aaRS, tRNA, UAA, codon, and pair combinations that could be used for such multisite incorporation. As a result, it is challenging to find specific combinations of these elements that are suitable for use for site-specific incorporation of two distinct bioconjugation handles.

In one aspect, the invention provides a method of producing a protein comprising a first unnatural amino acid (UAA) and a second, different UAA (e.g., wherein the first and second UAA are each incorporated into the protein at specific, different positions in the protein polypeptide chain). The method comprises culturing a mammalian cell with: (i) a nucleic acid comprising a nucleotide sequence encoding a first tRNA comprising an anticodon that hybridizes to a first codon selected from UAG, UGA, and UAA, and is capable of being charged with the first UAA; (ii) a nucleic acid comprising a nucleotide sequence encoding a first aminoacyl-tRNA synthetase capable of charging the first tRNA with the first UAA; (iii) a nucleic acid comprising a nucleotide sequence encoding a second tRNA comprising an anticodon that hybridizes to a second codon selected from UAG, UGA, and UAA, and is capable of being charged with the second UAA, wherein the first and second tRNA do not contain the same anticodon; (iv) a nucleic acid comprising a nucleotide sequence encoding a second aminoacyl-tRNA synthetase capable of charging the second tRNA with the second UAA; and (v) a nucleic acid comprising a nucleotide sequence encoding the protein comprising the first codon and the second codon; under conditions that permit the first tRNA, when expressed in the cell and charged with the first UAA, to hybridize to the first codon and direct the incorporation of the first UAA into the protein, and the second tRNA, when expressed in the cell and charged with the second UAA, to hybridize to the second codon and direct the incorporation of the second UAA into the protein.

In certain embodiments, the expression yield of the protein comprising the first and second UAA expressed by the cell is at least 10%, 20%, 30%, 40%, 50%, 60%, 70%, 80%, or 90% of the expression yield of a reference protein. For example, in certain embodiments, the amount of protein comprising the first and second UAA expressed by the cell is at least 10%, 20%, 30%, 40%, 50%, 60%, 70%, 80%, or 90% of the amount of a reference protein expressed by the same cell or a similar cell. In certain embodiments, the reference protein is a protein that does not comprise the first and second UAA but is otherwise identical to the protein comprising the first and second UAA. For example, the reference protein may comprise a wild-type amino acid sequence, or comprise a wild-type amino acid residue at the positions corresponding to the first and second UAA. Protein expression may be measured by any method known in the art, including for example, Western blot or ELISA. Expression may be measured by measuring protein concentration (e.g., by ultraviolet (UV) absorption at 280 nm or Bradford assay) in a solution of defined volume and purity following purification of the protein. Expression of a fluorescent protein (e.g., a reporter protein) may be measured by fluorescence microscopy as described in Examples 2-4 herein. In certain embodiments, a disclosed method will result in an expression yield of an EGFP reporter protein containing a first and second UAA (e.g., an EGFP reporter protein encoded by a nucleotide sequence containing two stop codons, e.g., EGFP-39TAG-151TGA containing stop codons TAG and TGA, as described in Example 4) that is at least 10%, 20%, 30%, 40%, 50%, 60%, 70%, 80%, or 90% of the expression yield of a corresponding EGFP reporter protein that does not contain the first and second UAA (e.g., a wild-type EGFP protein).

In another aspect, the invention provides a method of producing a protein comprising a tryptophan analog and a leucine analog. The method comprises culturing a mammalian cell with: (i) a nucleic acid comprising a nucleotide sequence encoding a derivative of an *E. coli* tryptophanyl-tRNA comprising an anticodon that hybridizes to a UGA codon, and is capable of being charged with the tryptophan analog; (ii) a nucleic acid comprising a nucleotide sequence encoding a derivative of an *E. coli* tryptophanyl-tRNA synthetase capable of charging the derivative of the *E. coli* tryptophanyl-tRNA with the tryptophan analog; (iii) a nucleic acid comprising a nucleotide sequence encoding a derivative of an *E. coli* leucyl-tRNA comprising an anticodon that hybridizes to UAG codon, and is capable of being charged with the leucine analog; (iv) a nucleic acid comprising a nucleotide sequence encoding a derivative of an *E. coli* leucyl-tRNA synthetase capable of charging the derivative of the *E. coli* leucyl-tRNA with the leucine analog; and (v) a nucleic acid comprising a nucleotide sequence encoding the protein comprising the UGA codon and the UAG codon; under conditions that permit the derivative of the *E. coli* tryptophanyl-tRNA, when expressed in the cell and charged with the tryptophan analog, to hybridize to the UGA codon and direct the incorporation of the tryptophan into the protein, and the derivative of the *E. coli* leucyl-tRNA, when expressed in the cell and charged with the leucine analog, to hybridize to the UAG codon and direct the incorporation of the leucine analog into the protein.

In another aspect, the invention provides a method of producing a protein comprising a tryptophan analog and a tyrosine analog. The method comprises culturing a mammalian cell with: (i) a nucleic acid comprising a nucleotide sequence encoding a derivative of an *E. coli* tryptophanyl-tRNA comprising an anticodon that hybridizes to a UGA codon, and is capable of being charged with the tryptophan analog; (ii) a nucleic acid comprising a nucleotide sequence encoding a derivative of an *E. coli* tryptophanyl-tRNA synthetase capable of charging the derivative of the *E. coli* tryptophanyl-tRNA with the tryptophan analog; (iii) a nucleic acid comprising a nucleotide sequence encoding a derivative of an *E. coli* tyrosyl-tRNA comprising an anticodon that hybridizes to UAG codon, and is capable of being charged with the tyrosine analog; (iv) a nucleic acid comprising a nucleotide sequence encoding a derivative of an *E. coli* tyrosyl-tRNA synthetase capable of charging the derivative of the *E. coli* tyrosyl-tRNA with the tyrosine analog; and (v) a nucleic acid comprising a nucleotide sequence encoding the protein comprising the UGA codon and the UAG codon; under conditions that permit the derivative of the *E. coli* tryptophanyl-tRNA, when expressed in the cell and charged with the tryptophan analog, to hybridize to the UGA codon and direct the incorporation of the tryptophan into the protein, and the derivative of the *E. coli* tyrosyl-tRNA, when expressed in the cell and charged with the tyrosine analog, to hybridize to the UAG codon and direct the incorporation of the tyrosine analog into the protein.

In another aspect, the invention provides a method of producing a protein comprising a tryptophan analog and a pyrrolysine analog. The method comprises culturing a mammalian cell with: (i) a nucleic acid comprising a nucleotide sequence encoding a derivative of an *E. coli* tryptophanyltRNA comprising an anticodon that hybridizes to a UGA codon, and is capable of being charged with the tryptophan analog; (ii) a nucleic acid comprising a nucleotide sequence encoding a derivative of an *E. coli* tryptophanyl-tRNA synthetase capable of charging the derivative of the *E. coli* tryptophanyl-tRNA with the tryptophan analog; (iii) a nucleic acid comprising a nucleotide sequence encoding a derivative of an *M. barkeri* pyrrolysyl-tRNA comprising an anticodon that hybridizes to UAG codon, and is capable of being charged with the pyrrolysine analog; (iv) a nucleic acid comprising a nucleotide sequence encoding a derivative of an *M. barkeri* pyrrolysyl-tRNA synthetase capable of charging the derivative of the *M. barkeri* pyrrolysyl-tRNA with the pyrrolysine analog; and (v) a nucleic acid comprising a nucleotide sequence encoding the protein comprising the UGA codon and the UAG codon; under conditions that permit the derivative of the *E. coli* tryptophanyl-tRNA, when expressed in the cell and charged with the tryptophan analog, to hybridize to the UGA codon and direct the incorporation of the tryptophan into the protein, and the derivative of the *E. coli* pyrrolysyl-tRNA, when expressed in the cell and charged with the pyrrolysine analog, to hybridize to the UAG codon and direct the incorporation of the pyrrolysine analog into the protein.

In another aspect, the invention provides a protein comprising a first unnatural amino acid (UAA) and a second UAA made by any of the foregoing methods.

In another aspect, the invention provides a protein expressed in a mammalian cell comprising a first unnatural amino acid (UAA) that is a tryptophan analog and a second UAA that is a leucine analog. In certain embodiments, the tryptophan analog is selected from 5-HTP and 5-AzW and/or the leucine analog is selected from LCA and Cys-5-N3.

In another aspect, the invention provides a protein expressed in a mammalian cell comprising a first unnatural amino acid (UAA) that is a tryptophan analog and a second UAA that is a tyrosine analog. In certain embodiments, the tryptophan analog is selected from 5-HTP and 5-AzW and/or the tyrosine analog is selected from OmeY, AzF, and OpropY UAA.

In another aspect, the invention provides a protein expressed in a mammalian cell comprising a first unnatural amino acid (UAA) that is a tryptophan analog and a second UAA that is a pyrrolysine analog. In certain embodiments, the tryptophan analog is selected from 5-HTP and 5-AzW and/or the pyrrolysine analog is selected from BocK, CpK, AzK, and CpK.

In another aspect, the invention provides a composition comprising any of the foregoing proteins. In certain embodiments, the purity of the comprising the first and second UAA in composition is at least 50% (i.e., the protein comprising the first and second UAA is at least 50% of the total protein in the composition). In certain embodiments, the purity of the protein in composition is at least 60%, at least 70%, at least 80%, at least 90%, at least 95%, at least 96%, at least 97%, at least 98%, or at least 99%. In certain embodiments, less than 50%, less than 40%, less than 30%, less than 20%, less than 10%, less than 5%, less than 4%, less than 3%, less than 2% or less than 1% of the total protein in the composition is any protein that is otherwise identical to the protein comprising the first and second UAA but does not comprise the first or second UAA.

As used herein, the term "orthogonal" refers to a molecule (e.g., an orthogonal tRNA or an orthogonal aminoacyl-tRNA synthetase) that is used with reduced efficiency by an expression system of interest (e.g., an endogenous cellular translation system). For example, an orthogonal tRNA in a translation system of interest is aminoacylated by any endogenous aminoacyl-tRNA synthetase of the translation system of interest with reduced or even zero efficiency, when compared to aminoacylation of an endogenous tRNA by an endogenous aminoacyl-tRNA synthetase. In another example, an orthogonal aminoacyl-tRNA synthetase aminoacylates any endogenous tRNA in the translation system of interest with reduced or even zero efficiency, as compared to aminoacylation of an endogenous tRNA by an endogenous aminoacyl-tRNA synthetase.

Various features and aspects of the invention are discussed in more detail below.

I. Aminoacyl-tRNA Synthetases

The invention relates to engineered aminoacyl-tRNA synthetases (or aaRSs) capable of charging a tRNA with an unnatural amino acid for incorporation into a protein. As used herein, the term "aminoacyl-tRNA synthetase" refers to any enzyme, or a functional fragment thereof, that charges, or is capable of charging, a tRNA with an amino acid (e.g., an unnatural amino acid) for incorporation into a protein. As used herein, the term "functional fragment" of an aminoacyl-tRNA synthetase refers to fragment of a full-length aminoacyl-tRNA synthetase that retains, for example, at least 10%, at least 20%, at least 30%, at least 40%, at least 50%, at least 60%, at least 70%, at least 80%, at least 90%, at least 95%, or 100% of the enzymatic activity of the corresponding full-length tRNA synthetase (e.g., a naturally occurring tRNA synthetase). Aminoacyl-tRNA synthetase enzymatic activity may be assayed by any method known in the art. For example, in vitro aminoacylation assays are described in Hoben et al. (1985) METHODS ENZYMOL. 113:55-59 and in U.S. Patent Application Publication No. 2003/0228593 and cell-based aminoacylation assays are described in U.S. Patent Application Publication Nos. 2003/0082575 and 2005/0009049. In certain embodiments, the functional fragment comprises at least 100, 150, 200, 250, 300, 350, 400, 450, 500, 550, 600, 650, 700, 750, or 800 consecutive amino acids present in a full-length tRNA synthetase (e.g., a naturally occurring aminoacyl-tRNA synthetase).

The term aminoacyl-tRNA synthetase includes variants (i.e., muteins) having one or more mutations (e.g., amino acid substitutions, deletions, or insertions) relative to a wild-type aminoacyl-tRNA synthetase sequence. In certain embodiments, an aminoacyl-tRNA synthetase mutein may comprise, consist, or consist essentially of, a single mutation (e.g., a mutation contemplated herein), or a combination of 2, 3, 4, 5, 6, 7, 8, 9, 10, 11, 12, 13, 14, 15 or more than 15 mutations (e.g., mutations contemplated herein). It is contemplated that an aminoacyl-tRNA synthetase mutein may comprise, consist, or consist essentially 1-15, 1-10, 1-7, 1-6, 1-5, 1-4, 1-3, 1-2, 2-15, 2-10, 2-7, 2-6, 2-5, 2-4, 2-3, 3-15, 3-10, 3-7, 3-6, 3-5, or 4-10, 4-7, 4-6, 4-5, 5-10, 5-7, 5-6, 6-10, 6-7, 7-10, 7-8, or 8-10 mutations (e.g., mutations contemplated herein).

An aminoacyl-tRNA synthetase mutein may comprise a conservative substitution relative to a wild-type sequence or a sequence disclosed herein. As used herein, the term "conservative substitution" refers to a substitution with a structurally similar amino acid. For example, conservative substitutions may include those within the following groups: Ser and Cys; Leu, Ile, and Val; Glu and Asp; Lys and Arg; Phe, Tyr, and Trp; and Gln, Asn, Glu, Asp, and His. Conservative substitutions may also be defined by the BLAST (Basic Local Alignment Search Tool) algorithm, the BLOSUM substitution matrix (e.g., BLOSUM 62 matrix), or the PAM substitution:p matrix (e.g., the PAM 250 matrix).

In certain embodiments, the substrate specificity of the aminoacyl-tRNA synthetase mutein is altered relative to a corresponding (or template) wild-type aminoacyl-tRNA synthetase such that only a desired unnatural amino acid, but not any of the common 20 amino acids, is charged to the substrate tRNA.

An aminoacyl-tRNA synthetase may be derived from a bacterial source, e.g., Escherichia coli, Thermus thermophilus, or Bacillus stearothermphilus. An aminoacyl-tRNA synthetase may also be derived from an archaeal source, e.g, from the Methanosarcinacaea or Desulfitobacterium families, any of the M. barkeri (Mb), M. alvus (Ma), M. mazei (Mm) or D. hafnisense (Dh) families, Methanobacterium thermoautotrophicum, Haloferax volcanii, Halobacterium species NRC-1, or Archaeoglobus fulgidus. In other embodiments, eukaryotic sources can also be used, for example, plants, algae, protists, fungi, yeasts, or animals (e.g., mammals, insects, arthropods, etc.). As used herein, the terms "derivative" or "derived from" refer to a component that is isolated from or made using information from a specified molecule or organism. As used herein, the term "analog" refers to a component (e.g., a tRNA, tRNA synthetase, or unnatural amino acid) that is derived from or analogous with (in terms of structure and/or function) a reference component (e.g., a wild-type tRNA, a wild-type tRNA synthetase, or a natural amino acid). In certain embodiments, derivatives or analogs have at least 40%, 50%, 60%, 70%, 80%, 90%, 100% or more of a given activity as a reference or originator component (e.g., wild type component).

It is contemplated that the aminoacyl-tRNA synthetase may aminoacylate a substrate tRNA in vitro or in vivo, and can be provided to a translation system (e.g., an in vitro translation system or a cell) as a polypeptide or protein, or as a polynucleotide that encodes the aminoacyl-tRNA synthetase.

In certain embodiments, the aminoacyl-tRNA synthetase is derived from an E. coli leucyl-tRNA synthetase and, for example, the aminoacyl-tRNA synthetase preferentially aminoacylates an E. coli leucyl tRNA (or a variant thereof) with a leucine analog over the naturally-occurring leucine amino acid.

For example, the aminoacyl-tRNA synthetase may comprise SEQ ID NO: 1, or an amino acid sequence that has at least 85%, 90%, 95%, 96%, 97%, 98%, or 99% sequence identity to SEQ ID NO: 1. In certain embodiments, the aminoacyl-tRNA synthetase comprises SEQ ID NO: 1, or a functional fragment or variant thereof, and with one, two, three, four, five or more of the following mutations: (i) a substitution of a glutamine residue at a position corresponding to position 2 of SEQ ID NO: 1, e.g., a substitution by glutamic acid (Q2E); (ii) a substitution of a glutamic acid residue at a position corresponding to position 20 of SEQ ID NO: 1, e.g., a substitution by lysine (E20K), methionine (E20M), or valine (E20V); (iii) a substitution of a methionine residue at a position corresponding to position 40 of SEQ ID NO: 1, e.g., a substitution by isoleucine (M40I) or valine (M40V); (iv) a substitution of a leucine residue at a position corresponding to position 41 of SEQ ID NO: 1, e.g., a substitution by serine (L41S), valine (L41V), or alanine (L41A); (v) a substitution of a threonine residue at a position corresponding to position 252 of SEQ ID NO: 1, e.g., a substitution by alanine (T252A) or arginine (T252R); (vi) a substitution of a tyrosine residue at a position corresponding to position 499 of SEQ ID NO: 1, e.g., a substitution by isoleucine (Y499I), serine (Y499S), alanine (Y499A), or histidine (Y499H); (vii) a substitution of a tyrosine residue at a position corresponding to position 527 of SEQ ID NO:

1, e.g., a substitution by alanine (Y527A), leucine (Y527L), isoleucine (Y527I), valine (Y527V), or glycine (Y527G); or (viii) a substitution of a histidine residue at a position corresponding to position 537 of SEQ ID NO: 1, e.g., a substitution by glycine (H537G), or any combination of the foregoing.

In certain embodiments, the aminoacyl-tRNA synthetase comprises (i) at least one substitution (e.g., a substitution with a hydrophobic amino acid) at a position corresponding to His537 of SEQ ID NO: 1, (ii) at least one amino acid substitution selected from E20V, E20M, L41V, L41A, Y499H, Y499A, Y527I, Y527V, Y527G, and any combination thereof, (iii) at least one amino acid substitution selected from E20K and L41S and any combination thereof and at least one amino acid substitution selected from M40I, T252A, Y499I, and Y527A, and any combination thereof, or (iv) a combination of two or more of (i), (ii) and (iii), for example, (i) and (ii), (i) and (iii), (ii) and (iii) and (i), (ii) and (iii).

In certain embodiments, the aminoacyl-tRNA synthetase comprises a substitution of a glutamic acid residue at a position corresponding to position 20 of SEQ ID NO: 1, e.g., a substitution with an amino acid other than a Glu or Lys, e.g., a substitution with a hydrophobic amino acid (e.g., Leu, Val, or Met). In certain embodiments, the aminoacyl-tRNA synthetase comprises a substitution of a leucine residue at a position corresponding to position 41 of SEQ ID NO: 1, e.g., a substitution with an amino acid other than a Leu or Ser, e.g., a substitution with a hydrophobic amino acid other than Leu (e.g., Gly, Ala, Val, or Met). In certain embodiments, the aminoacyl-tRNA synthetase comprises a substitution of a tyrosine residue at a position corresponding to position 499 of SEQ ID NO: 1, e.g., a substitution with a small hydrophobic amino acid (e.g., Gly, Ala, or Val) or a substitution with a positively charged amino acid (e.g., Lys, Arg, or His). In certain embodiments, the aminoacyl-tRNA synthetase comprises a substitution of a tyrosine residue at a position corresponding to position 527 of SEQ ID NO: 1, e.g., a substitution with a hydrophobic amino acid other than Ala or Leu (e.g., Gly, Ile, Met, or Val). In certain embodiments, the tRNA synthetase mutein comprises L41V.

In certain embodiments, the aminoacyl-tRNA synthetase comprises a combination of mutations selected from: (i) Q2E, E20K, M40I, L41S, T252A, Y499I, Y527A, and H537G; (ii) Q2E, E20K, M40V, L41S, T252R, Y499S, Y527L, and H537G; (iii) Q2E, M40I, T252A, Y499I, Y527A, and H537G; (iv) Q2E, E20M, M40I, L41S, T252A, Y499I, Y527A, and H537G; (v) Q2E, E20V, M40I, L41S, T252A, Y499I, Y527A, and H537G; (vi) Q2E, E20K, M40I, L41V, T252A, Y499I, Y527A, and H537G; (vii) Q2E, E20K, M40I, L41A, T252A, Y499I, Y527A, and H537G; (viii) Q2E, E20K, M40I, L41S, T252A, Y499A, Y527A, and H537G; (ix) Q2E, E20K, M40I, L41S, T252A, Y499H, Y527A, and H537G; (x) Q2E, E20K, M40I, L41S, T252A, Y499I, Y527I, and H537G; (xi) Q2E, E20K, M40I, L41S, T252A, Y499I, Y527V, and H537G; (xii) Q2E, E20K, M40I, L41S, T252A, Y499I, Y527G, and H537G; (xiii) E20K, M40I, L41S, T252A, Y499I, Y527A, and H537G; (xiv) E20M, M40I, L41S, T252A, Y499I, Y527A, and H537G; (xv) E20V, M40I, L41S, T252A, Y499I, Y527A, and H537G; (xvi) E20K, M40I, L41V, T252A, Y499I, Y527A, and H537G; (vii) E20K, M40I, L41A, T252A, Y499L, Y527A, and H537G; (xviii) E20K, M40I, L41S, T252A, Y499A, Y527A, and H537G; (xix) E20K, M40I, L41S, T252A, Y499H, Y527A, and H537G; (xx) E20K, M40I, L41S, T252A, Y499I, Y527I, and H537G; (xxi) E20K, M40I, L41S, T252A, Y499I, Y527V, and H537G; and (xxii) E20K, M40I, L41S, T252A, Y499L, Y527G, and H537G.

In certain embodiments, the aminoacyl-tRNA synthetase comprises the amino acid sequence of any one of SEQ ID NOs: 2-13, or an amino acid sequence that has at least 85%, 90%, 95%, 96%, 97%, 98%, or 99% sequence identity to any one of SEQ ID NOs: 2-13.

In certain embodiments, the tRNA synthetase mutein comprises the amino acid sequence of SEQ ID NO: 14, wherein $X_2$ is Q or E, $X_{20}$ is E, K, V or M, $X_{40}$ is M, I, or V, $X_{41}$ is L, S, V, or A, $X_{252}$ is T, A, or R, $X_{499}$ is Y, A, I, H, or S, $X_{527}$ is Y, A, I, L, or V, and $X_{537}$ is H or G, and the tRNA synthetase mutein comprises at least one mutation (for example, 2, 3, 4, 5, 6, 7, 8, 9, or more mutations) relative to SEQ ID NO: 1. In certain embodiments, the tRNA synthetase mutein comprises the amino acid sequence of SEQ ID NO: 15, wherein $X_{20}$ is K, V or M, $X_{41}$ is S, V, or A, $X_{499}$ is A, I, or H, and $X_{527}$ is A, I, or V, and the tRNA synthetase mutein comprises at least one mutation relative to SEQ ID NO: 1.

In certain embodiments, the aminoacyl-tRNA synthetase is derived from an *E. coli* tryptophanyl-tRNA synthetase and, for example, the aminoacyl-tRNA synthetase preferentially aminoacylates an *E. coli* tryptophanyl tRNA (or a variant thereof) with a tryptophan analog over the naturally-occurring tryptophan amino acid.

For example, the aminoacyl-tRNA synthetase may comprise SEQ ID NO: 44, or an amino acid sequence that has at least 85%, 90%, 95%, 96%, 97%, 98%, or 99% sequence identity to SEQ ID NO: 44. In certain embodiments, the aminoacyl-tRNA synthetase comprises SEQ ID NO: 44, or a functional fragment or variant thereof, but with one or more of the following mutations: (i) a substitution of a serine residue at a position corresponding to position 8 of SEQ ID NO: 44, e.g., a substitution by alanine (S8A); (ii) a substitution of a valine residue at a position corresponding to position 144 of SEQ ID NO: 44, e.g., a substitution by serine (V144S), glycine (V144G) or alanine (V144A); (iii) a substitution of a valine residue at a position corresponding to position 146 of SEQ ID NO: 44, e.g., a substitution by alanine (V146A), isoleucine (V146I), or cysteine (V146C). In certain embodiments, the aminoacyl-tRNA synthetase comprises a combination of mutations selected from: (i) S8A, V144S, and V146A, (ii) S8A, V144G, and V146I, (iii) S8A, V144A, and V146A, and (iv) S8A, V144G, and V146C.

In certain embodiments, the aminoacyl-tRNA synthetase comprises the amino acid sequence of any one of SEQ ID NOs: 45-48, or an amino acid sequence that has at least 85%, 90%, 95%, 96%, 97%, 98%, or 99% sequence identity to any one of SEQ ID NOs: 45-48.

In certain embodiments, the aminoacyl-tRNA synthetase is derived from an *E. coli* tyrosyl-tRNA synthetase and, for example, the aminoacyl-tRNA synthetase preferentially aminoacylates an *E. coli* tyrosyl tRNA (or a variant thereof) with a tyrosine analog over the naturally-occurring tryptophan amino acid. For example, the aminoacyl-tRNA synthetase may comprise SEQ ID NO: 70, or an amino acid sequence that has at least 85%, 90%, 95%, 96%, 97%, 98%, or 99% sequence identity to SEQ ID NO: 70, or a functional fragment or variant thereof.

In certain embodiments, the aminoacyl-tRNA synthetase is derived from an *M. barkeri* pyrrolysyl-tRNA synthetase and, for example, the aminoacyl-tRNA synthetase preferentially aminoacylates an *M. barkeri* pyrrolysyl tRNA (or a variant thereof) with a pyrrolysine analog over the naturally-occurring pyrrolysine amino acid. For example, the aminoacyl-tRNA synthetase may comprise SEQ ID NO: 101, or an amino acid sequence that has at least 85%, 90%, 95%, 96%, 97%, 98%, or 99% sequence identity to SEQ ID NO: 101, or a functional fragment or variant thereof.

Sequence identity may be determined in various ways that are within the skill of a person skilled in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36:290-300; Altschul et al., (1997) Nucleic Acids Res. 25:3389-3402, incorporated by reference herein) are tailored for sequence similarity searching. For a discussion of basic issues in searching sequence databases see Altschul et al., (1994) Nature Genetics 6:119-129, which is fully incorporated by reference herein. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference herein). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent blastp parameter settings may be Q=9; R=2; wink=1; and gapw=32. Searches may also be conducted using the NCBI (National Center for Biotechnology Information) BLAST Advanced Option parameter (e.g.: -G, Cost to open gap [Integer]: default=5 for nucleotides/11 for proteins; -E, Cost to extend gap [Integer]: default=2 for nucleotides/1 for proteins; -q, Penalty for nucleotide mismatch [Integer]: default=-3; -r, reward for nucleotide match [Integer]: default=1; -e, expect value [Real]: default=10; —W, wordsize [Integer]: default=11 for nucleotides/28 for megablast/3 for proteins; -y, Dropoff (X) for blast extensions in bits: default=20 for blastn/7 for others; –X, X dropoff value for gapped alignment (in bits): default=15 for all programs, not applicable to blastn; and –Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty). The equivalent settings in Bestfit protein comparisons are GAP=8 and LEN=2.

Methods for producing proteins, e.g., aminoacyl-tRNA synthetases, are known in the art. For example, DNA molecules encoding a protein of interest can be synthesized chemically or by recombinant DNA methodologies. The resulting DNA molecules encoding the protein interest can be ligated to other appropriate nucleotide sequences, including, for example, expression control sequences, to produce conventional gene expression constructs (i.e., expression vectors) encoding the desired protein. Production of defined gene constructs is within routine skill in the art.

Nucleic acids encoding desired proteins (e.g, aminoacyl-tRNA synthetases) can be incorporated (ligated) into expression vectors, which can be introduced into host cells through conventional transfection or transformation techniques. Exemplary host cells are E. coli cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the desired protein.

Specific expression and purification conditions will vary depending upon the expression system employed. For example, if a gene is to be expressed in E. coli, it is first cloned into an expression vector by positioning the engineered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies then are solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhancers and introns. The gene construct can be introduced into eukaryotic host cells using conventional techniques.

A protein of interest (e.g, an aminoacyl-tRNA synthetase) can be produced by growing (culturing) a host cell transfected with an expression vector encoding such a protein under conditions that permit expression of the protein. Following expression, the protein can be harvested and purified or isolated using techniques known in the art, e.g., affinity tags such as glutathione-S-transferase (GST) or histidine tags.

Additional methods for producing aminoacyl-tRNA synthetases, and for altering the substrate specificity of the synthetase can be found in U.S. Patent Application Publication Nos. 2003/0108885 and 2005/0009049, Hamano-Takaku et al. (2000) Journal of Biol. Chem. 275(51):40324-40328, Kiga et al. (2002) Proc. Natl. Acad. Sci. USA 99(15): 9715-9723, and Francklyn et al. (2002) RNA, 8:1363-1372.

The invention also encompasses nucleic acids encoding aminoacyl-tRNA synthetases disclosed herein. For example, nucleotide sequences encoding leucyl-tRNA synthetase muteins disclosed herein are depicted in SEQ ID NOs: 55-67. Accordingly, the invention provides a nucleic acid comprising the nucleotide sequence of any one of SEQ ID NOs: 55-67, or a nucleotide sequence that has at least 85%, 90%, 95%, 96%, 97%, 98%, or 99% sequence identity to any one of SEQ ID NOs: 55-67. The invention also provides a nucleic acid comprising a nucleotide sequence encoding the amino acid sequence encoded by any one of SEQ ID NOs: 55-67, or a nucleotide sequence that has at least 85%, 90%, 95%, 96%, 97%, 98%, or 99% sequence identity to a nucleotide sequence encoding the amino acid sequence encoded by any one of SEQ ID NOs: 55-67.

A nucleotide sequence encoding a tryptophanyl-tRNA synthetase disclosed herein is depicted in SEQ ID NO: 103. Accordingly, the invention provides a nucleic acid comprising the nucleotide sequence of SEQ ID NO: 103, or a nucleotide sequence that has at least 85%, 90%, 95%, 96%, 97%, 98%, or 99% sequence identity to SEQ ID NO: 103.

The invention also provides a nucleic acid comprising a nucleotide sequence encoding the amino acid sequence encoded by SEQ ID NO: 103, or a nucleotide sequence that has at least 85%, 90%, 95%, 96%, 97%, 98%, or 99% sequence identity to a nucleotide sequence encoding the amino acid sequence encoded by SEQ ID NO: 103.

A nucleotide sequence encoding a tyrosyl-tRNA synthetase disclosed herein is depicted in SEQ ID NO: 71. Accordingly, the invention provides a nucleic acid comprising the nucleotide sequence of SEQ ID NO: 71, or a nucleotide sequence that has at least 85%, 90%, 95%, 96%, 97%, 98%, or 99% sequence identity to SEQ ID NO: 71. The invention also provides a nucleic acid comprising a nucleotide sequence encoding the amino acid sequence encoded by SEQ ID NO: 71, or a nucleotide sequence that has at least 85%, 90%, 95%, 96%, 97%, 98%, or 99% sequence identity to a nucleotide sequence encoding the amino acid sequence encoded by SEQ ID NO: 71.

A nucleotide sequence encoding a pyrrolysyl-tRNA synthetase disclosed herein is depicted in SEQ ID NO: 102. Accordingly, the invention provides a nucleic acid comprising the nucleotide sequence of SEQ ID NO: 102, or a nucleotide sequence that has at least 85%, 90%, 95%, 96%, 97%, 98%, or 99% sequence identity to SEQ ID NO: 102. The invention also provides a nucleic acid comprising a nucleotide sequence encoding the amino acid sequence encoded by SEQ ID NO: 102, or a nucleotide sequence that has at least 85%, 90%, 95%, 96%, 97%, 98%, or 99% sequence identity to a nucleotide sequence encoding the amino acid sequence encoded by SEQ ID NO: 102.

II. tRNAs

The invention relates to transfer RNAs (tRNAs) that mediate the incorporation of unnatural amino acids into proteins.

During protein synthesis, a tRNA molecule delivers an amino acid to a ribosome for incorporation into a growing protein (polypeptide) chain. tRNAs typically are about 70 to 100 nucleotides in length. Active tRNAs contain a 3' CCA sequence that may be transcribed into the tRNA during its synthesis or may be added later during post-transcriptional processing. During aminoacylation, the amino acid that is attached to a given tRNA molecule is covalently attached to the 2' or 3' hydroxyl group of the 3'-terminal ribose to form an aminoacyl-tRNA (aa-tRNA). It is understood that an amino acid can spontaneously migrate from the 2'-hydroxyl group to the 3'-hydroxyl group and vice versa, but it is incorporated into a growing protein chain at the ribosome from the 3-OH position. A loop at the other end of the folded aa-tRNA molecule contains a sequence of three bases known as the anticodon. When this anticodon sequence hybridizes or base-pairs with a complementary three-base codon sequence in a ribosome-bound mRNA, the aa-tRNA binds to the ribosome and its amino acid is incorporated into the polypeptide chain being synthesized by the ribosome. Because all tRNAs that base-pair with a specific codon are aminoacylated with a single specific amino acid, the translation of the genetic code is effected by tRNAs. Each of the 61 non-termination codons in an mRNA directs the binding of its cognate aa-tRNA and the addition of a single specific amino acid to the growing polypeptide chain being synthesized by the ribosome. The term "cognate" refers to components that function together, e.g., a tRNA and an aminoacyl-tRNA synthetase.

Suppressor tRNAs are modified tRNAs that alter the reading of a mRNA in a given translation system. For example, a suppressor tRNA may read through a codon such as a stop codon, a four base codon, or a rare codon. The use of the word in suppressor is based on the fact, that under certain circumstance, the modified tRNA "suppresses" the typical phenotypic effect of the codon in the mRNA. Suppressor tRNAs typically contain a mutation (modification) in either the anticodon, changing codon specificity, or at some position that alters the aminoacylation identity of the tRNA. The term "suppression activity" refers to the ability of a tRNA, e.g., a suppressor tRNA, to read through a codon (e.g., a premature stop codon) that would not be read through by the endogenous translation machinery in a system of interest.

In certain embodiments, a tRNA (e.g., a suppressor tRNA) contains a modified anticodon region, such that the modified anticodon hybridizes with a different codon than the corresponding naturally occurring anticodon.

In certain embodiments, a tRNA comprises an anticodon that hybridizes to a codon selected from UAG (i.e., an "amber" termination codon), UGA (i.e., an "opal" termination codon), and UAA (i.e., an "ochre" termination codon).

In certain embodiments, a tRNA comprises an anticodon that hybridizes to a non-standard codon, e.g., a 4- or 5-nucleotide codon. Examples of four base codons include AGGA, CUAG, UAGA, and CCCU. Examples of five base codons include AGGAC, CCCCU, CCCUC, CUAGA, CUACU, and UAGGC. tRNAs comprising an anticodon that hybridizes to a non-standard codon, e.g., a 4- or 5-nucleotide codon, and methods of using such tRNAs to incorporate unnatural amino acids into proteins are described, for example, in Moore et al. (2000) J. MOL. BIOL. 298:195; Hohsaka et al. (1999) J. AM. CHEM. SOC. 121: 12194; Anderson et al. (2002) CHEMISTRY AND BIOLOGY 9:237-244; Magliery (2001) J. MOL. BIOL. 307: 755-769; and PCT Publication No. WO2005/007870.

As used herein, the term "tRNA" includes variants having one or more mutations (e.g., nucleotide substitutions, deletions, or insertions) relative to a reference (e.g., a wild-type) tRNA sequence. In certain embodiments, a tRNA may comprise, consist, or consist essentially of, a single mutation (e.g., a mutation contemplated herein), or a combination of 2, 3, 4, 5, 6, 7, 8, 9, 10, 11, 12, 13, 14, 15 or more than 15 mutations (e.g., mutations contemplated herein). It is contemplated that a tRNA may comprise, consist, or consist essentially 1-15, 1-10, 1-7, 1-6, 1-5, 1-4, 1-3, 1-2, 2-15, 2-10, 2-7, 2-6, 2-5, 2-4, 2-3, 3-15, 3-10, 3-7, 3-6, 3-5, or 3-4 mutations (e.g., mutations contemplated herein).

In certain embodiments, a variant suppressor tRNA has increased activity to incorporate an unnatural amino acid (e.g., an unnatural amino acid contemplated herein) into a mammalian protein relative to a counterpart wild-type suppressor tRNA (in this context, a wild-type suppressor tRNA refers to a suppressor tRNA that corresponds to a wild-type tRNA molecule but for any modifications to the anti-codon region to impart suppression activity). The activity of the variant suppressor tRNA may be increased relative to the wild type suppressor tRNA, for example, by about 2.5 to about 200 fold, about 2.5 to about 150 fold, about 2.5 to about 100 fold about 2.5 to about 80 fold, about 2.5 to about 60 fold, about 2.5 to about 40 fold, about 2.5 to about 20 fold, about 2.5 to about 10 fold, about 2.5 to about 5 fold, about 5 to about 200 fold, about 5 to about 150 fold, about 5 to about 100 fold, about 5 to about 80 fold, about 5 to about 60 fold, about 5 to about 40 fold, about 5 to about 20 fold, about 5 to about 10 fold, about 10 to about 200 fold, about 10 to about 150 fold, about 10 to about 100 fold, about 10 to about 80 fold, about 10 to about 60 fold, about 10 to about 40 fold, about 10 to about 20 fold, about 20 to about 200 fold, about 20 to about 150 fold, about 20 to about 100 fold, about 20 to about 80 fold, about 20 to about 60 fold, about 20 to about 40 fold, about 40 to about 200 fold, about 40 to about 150 fold, about 40 to about 100 fold, about 40 to about 80 fold, about 40 to about 60 fold, about 60 to about 200 fold, about 60 to about 150 fold, about 60 to about 100 fold, about 60 to about 80 fold, about 80 to about 200 fold, about 80 to about 150 fold, about 80 to about 100 fold, about 100 to about 200 fold, about 100 to about 150 fold, or about 150 to about 200 fold.

It is contemplated that the tRNA may function in vitro or in vivo and can be provided to a translation system (e.g., an in vitro translation system or a cell) as a mature tRNA (e.g., an aminoacylated tRNA), or as a polynucleotide that encodes the tRNA.

A tRNA may be derived from a bacterial source, e.g., *Escherichia coli, Thermus thermophilus*, or *Bacillus stearothermphilus*. A tRNA may also be derived from an archaeal source, e.g, from the Methanosarcinacaea or Desulfitobacterium families, any of the *M. barkeri* (Mb), *M. alvus* (Ma), *M. mazei* (Mm) or *D. hafnisense* (Dh) families, *Methanobacterium thermoautotrophicum, Haloferax volcanii, Halobacterium* species NRC-1, or *Archaeoglobus fulgidus*. In other embodiments, eukaryotic sources can also be used, for example, plants, algae, protists, fungi, yeasts, or animals (e.g., mammals, insects, arthropods, etc.).

In certain embodiments, the tRNA is derived from an *E. coli* leucyl tRNA and, for example, is preferentially charged with a leucine analog over the naturally-occurring leucine amino acid by an aminoacyl-tRNA synthetase derived from an *E. coli* leucyl-tRNA synthetase, e.g., an aminoacyl-tRNA synthetase contemplated herein.

For example, the tRNA may comprise, consist essentially of, or consist of the nucleotide sequence of any one of SEQ ID NOs: 16-43, or a nucleotide sequence that has at least 85%, 90%, 95%, 96%, 97%, 98%, or 99% sequence identity to any one of SEQ ID NOs: 16-43.

In certain embodiments, the tRNA is derived from an *E. coli* tryptophanyl tRNA and, for example, is preferentially charged with a tryptophan analog over the naturally-occurring tryptophan amino acid by an aminoacyl-tRNA synthetase derived from an *E. coli* tryptophanyl-tRNA synthetase, e.g., an aminoacyl-tRNA synthetase contemplated herein.

For example, the tRNA may comprise, consist essentially of, or consist of the nucleotide sequence of any one of SEQ ID NOs: 49-54 or 108-113, or a nucleotide sequence that has at least 85%, 90%, 95%, 96%, 97%, 98%, or 99% sequence identity to any one of SEQ ID NOs: 49-54 or 108-113.

In certain embodiments, the tRNA is derived from an *E. coli* tyrosyl tRNA and, for example, is preferentially charged with a tyrosine analog over the naturally-occurring tyrosine amino acid by an aminoacyl-tRNA synthetase derived from an *E. coli* tyrosyl-tRNA synthetase, e.g., an aminoacyl-tRNA synthetase contemplated herein.

For example, the tRNA may comprise, consist essentially of, or consist of the nucleotide sequence of any one of SEQ ID NOs: 68-69 or 104-105, or a nucleotide sequence that has at least 85%, 90%, 95%, 96%, 97%, 98%, or 99% sequence identity to any one of SEQ ID NOs: 68-69 or 104-105.

In certain embodiments, the tRNA is derived from a *M. barkeri* pyrrolysyl tRNA and, for example, is preferentially charged with a pyrrolysine analog over the naturally-occurring pyrrolysine amino acid by an aminoacyl-tRNA synthetase derived from a *M. barkeri* pyrrolysyl-tRNA synthetase, e.g., an aminoacyl-tRNA synthetase contemplated herein.

For example, the tRNA may comprise, consist essentially of, or consist of the nucleotide sequence of any one of SEQ ID NOs: 72-100 or 106-107, or a nucleotide sequence that has at least 85%, 90%, 95%, 96%, 97%, 98%, or 99% sequence identity to any one of SEQ ID NOs: 72-100 or 106-107.

It is understood that, throughout the description, in each instance where a tRNA comprises, consists essentially of, or consists of a nucleotide sequence including one or more thymines (T), a tRNA is also contemplated that comprises, consists essentially of, or consists of the same nucleotide sequence including a uracil (U) in place of one or more of the thymines (T), or a uracil (U) in place of all the thymines (T). Similarly, in each instance where a tRNA comprises, consists essentially of, or consists of a nucleotide sequence including one or more uracils (U), a tRNA is also contemplated that comprises, consists essentially of, or consists of a nucleotide sequence including a thymine (T) in place of the one or more of the uracils (U), or a thymine (T) in place of all the uracils (U). In addition, additional modifications to the bases can be present.

Methods for producing recombinant tRNA are described in U.S. Patent Application Publication Nos. 2003/0108885 and 2005/0009049, Forster et al. (2003) PROC. NATL. ACAD. SCI. USA 100(11):6353-6357, and Feng et al. (2003), PROC. NATL. ACAD. SCI. USA 100(10): 5676-5681.

A tRNA may be aminoacylated (i.e., charged) with a desired unnatural amino acid (UAA) by any method, including enzymatic or chemical methods.

Enzymatic molecules capable of charging a tRNA include aminoacyl-tRNA synthetases, e.g., aminoacyl-tRNA synthetases disclosed herein. Additional enzymatic molecules capable of charging tRNA include ribozymes, for example, as described in Illangakekare et al. (1995) SCIENCE 267:643-647, Lohse et al. (1996) NATURE 381:442-444, Murakami et al. (2003) CHEMISTRY AND BIOLOGY 10:1077-1084, U.S. Patent Application Publication No. 2003/0228593, Chemical aminoacylation methods include those described in Hecht (1992) ACC. CHEM. RES. 25:545, Heckler et al. (1988) BIOCHEM. 1988, 27:7254, Hecht et al. (1978) J. BIOL. CHEM. 253:4517, Cornish et al. (1995) ANGEW. CHEM. INT. ED. ENGL. 34:621, Robertson et al. (1991) J. AM. CHEM. SOC. 113:2722, Noren et al. (1989) SCIENCE 244:182, Bain et al. (1989) J. AM. CHEM. SOC. 111:8013, Bain et al. (1992) NATURE 356:537, Gallivan et al. (1997) CHEM. BIOL. 4:740, Turcatti et al. (1996) J. BIOL. CHEM. 271:19991, Nowak et al. (1995) SCIENCE 268:439, Saks et al. (1996) J. BIOL. CHEM. 271:23169, and Hohsaka et al. (1999) J. AM. CHEM. SOC. 121:34.

III. Unnatural Amino Acids (UAAs)

The invention relates to unnatural amino acids (UAAs) and their incorporation into proteins.

As used herein, an unnatural amino acid refers to any amino acid, modified amino acid, or amino acid analogue other than the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. See, e.g., Biochemistry by L. Stryer, 3rd ed. 1988, Freeman and Company, New York, for structures of the twenty natural amino acids. The term unnatural amino acid also includes amino acids that occur by modification (e.g. post-translational modifications) of a natural amino acid but are not themselves naturally incorporated into a growing polypeptide chain by the translation complex.

Because unnatural amino acids typically differ from natural amino acids only in the structure of the side chain, unnatural amino acids may, for example, form amide bonds with other amino acids in the same manner in which they are formed in naturally occurring proteins. However, the unnatural amino acids have side chain groups that distinguish them from the natural amino acids. For example, the side chain may comprise an alkyl-, aryl-, acyl-, keto-, azido-, hydroxyl-, hydrazine, cyano-, halo-, hydrazide, alkenyl, alkyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other non-naturally occurring amino acids include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In addition to unnatural amino acids that contain novel side chains, unnatural amino acids also optionally comprise modified backbone structures.

Many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, α-hydroxy derivatives, γ-substituted derivatives, cyclic derivatives, and amide substituted glutamine derivatives. Exemplary phenylalanine analogs include, but are not limited to, para-substituted phenylalanines, ortho-substituted phenylalanines, and meta-substituted phenylalanines, wherein the substituent comprises a hydroxy group, a methoxy group, a methyl group, an allyl group, an aldehyde, an azido, an iodo, a bromo, a keto group (including but not limited to, an acetyl group), or the like. Specific examples of unnatural amino acids include, but are not limited to, a p-acetyl-L-phenylalanine, a p-propargyl-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like.

Examples of structures of a variety of unnatural amino acids are provided in U.S. Patent Application Publication Nos. 2003/0082575 and 2003/0108885, PCT Publication No. WO 2002/085923, and Kiick et al. (2002) PROC. NATL. ACAD. SCI. USA 99:19-24.

In certain embodiments, an unnatural amino acid (UAA) comprises a bioconjugation handle. In certain embodiments, a method disclosed herein can be used to site-specifically incorporate two different UAAs, each with a different bioconjugation handle, into a single protein. In certain embodiments, the two bioconjugation handles can be chosen such that they each can be chemoselectively conjugated to two different labels using mutually orthogonal conjugation chemistries. Such pairs of bioconjugation handles include, for example: azide and alkyne, azide and ketone/aldehyde, azide and cyclopropene, ketone/aldehyde and cyclopropene, 5-hydroxyindole and azide, 5-hydroxyindole and cyclopropene, and 5-hydroxyindole and ketone/aldehyde, An unnatural amino acid in a polypeptide may be used to attach another molecule to the polypeptide, including but not limited to, a label, a dye, a polymer, a water-soluble polymer, a stabilizing agent (e.g., a derivative of polyethylene glycol, a photoactivatable crosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid (e.g., a small interfering RNA (siRNA), a small nuclear RNA (snRNA), or a non-coding RNA), a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe or biochemical probe (e.g., a PET probe, a fluorescent probe or an EPR probe), a phosphorescent group, a chemiluminescent group, an electron dense group, a magnetic group, an intercalating group, a chromophore, an energy transfer agent, a biologically active agent, a detectable label (e.g., for analysis of uptake in viable cells versus non-viable cells), a small molecule, a quantum dot, a nanotransmitter, an immunomodulatory molecule, a targeting agent, a lipid based structure (e.g., a lipid-based nanoparticle), a microsphere, or any combination of the above.

Any suitable unnatural amino acid can be used with the methods described herein for incorporation into a protein of interest.

Figure 2C:
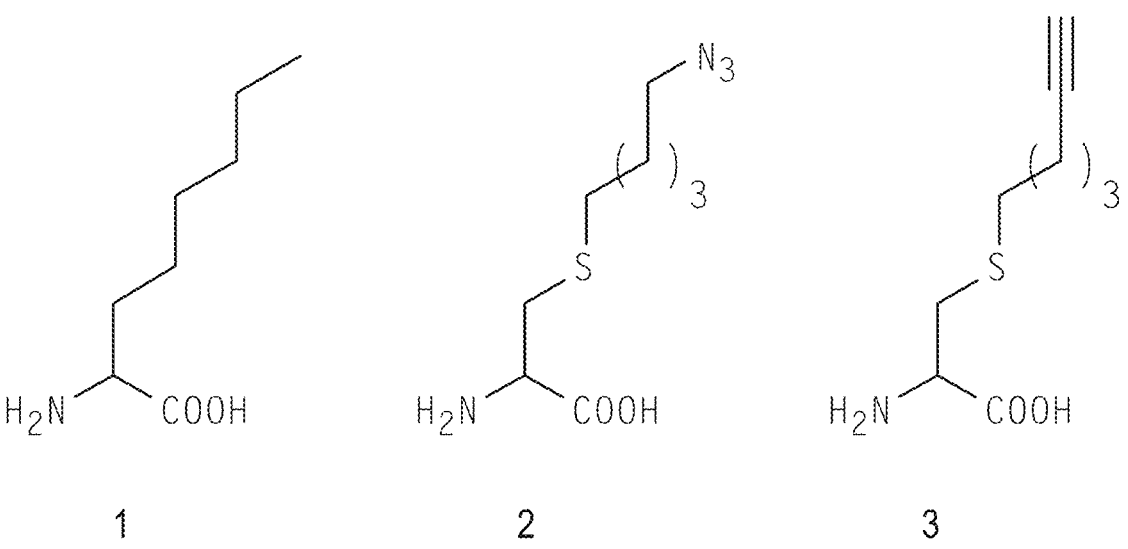

The unnatural amino acid may be a leucine analog (also referred to herein as a derivative). In certain embodiments, the leucine analog is a non-naturally occurring leucine analog. The invention provides a leucine analog depicted in FIG. 2A, or a composition comprising the leucine analog. For example, Formula A in FIG. 2A depicts an amino acid analog containing a side chain including a carbon containing chain n units (0-20 units) long. An O, S, $CH_2$, or NH is present in at position X, and another carbon containing chain of n units (0-20 units) long can follow. A functional group Y is attached to the terminal carbon of second carbon containing chain (for example, functional groups 1-12 as depicted in FIG. 2A, where R represents a linkage to the terminal carbon atom the second carbon containing side chain). In one example, these functional groups can be used for bioconjugation of any amenable ligand to any protein of interest that is amenable to site-specific UAA incorporation. Formula B in FIG. 2A depicts a similar amino acid analog containing an side chains denoted as either $Z—Y_2$ or $Z—Y_3$ attached to the second carbon containing chain or the first carbon containing chain, respectively. Z represents a carbon chain comprising $(CH_2)n$ units, where n is any integer from 0-20. $Y_2$ or $Y_3$, independently, can be the same or different groups as those of $Y_1$. The invention also provides a leucine analog depicted in FIG. 2B (LCA, LKET, or ACA), or a composition comprising the leucine analog depicted in FIG. 2B. Additional exemplary leucine analogs include those selected from linear alkyl halides and linear aliphatic chains comprising a functional group, for example, an alkyne, azide, cyclopropene, alkene, ketone, aldehyde, diazirine, or tetrazine functional group, as well as structures 1-6 shown in FIG. 2C. However, it is contemplated that the amino and carboxylate groups both attached to the first carbon of any amino acid shown in FIGS. 2A-2C would constitute portions of peptide bonds when the leucine analog is incorporated into a protein or polypeptide chain.

Figures 4A, 4B:
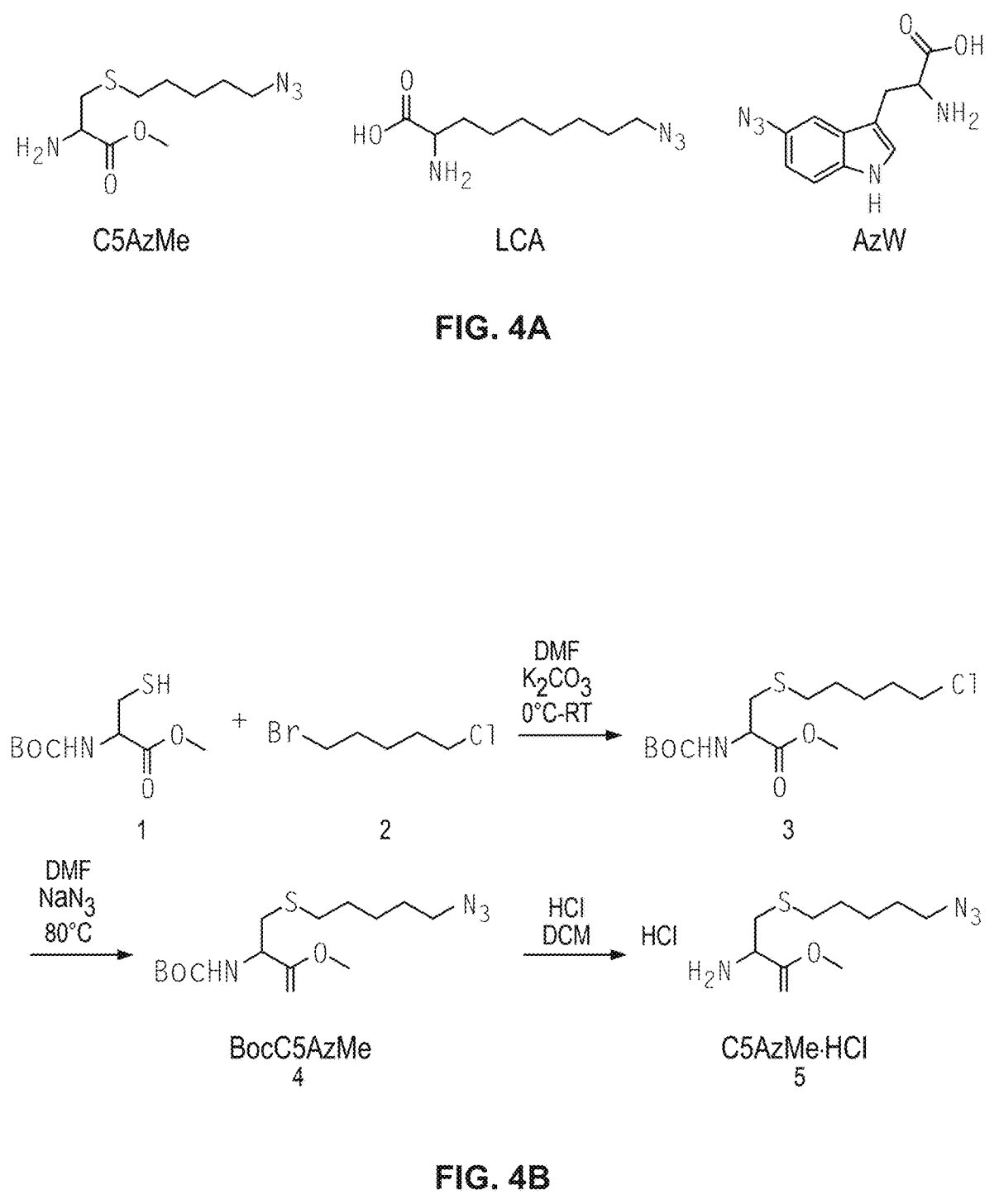

In addition, the leucine analogs set forth in FIG. 4A, referred to as C5AzMe and LCA can be used in the practice of the invention.

C5AzMe (Compound 5 as shown in FIG. 4B) can be prepared in a manner similar to the synthesis outlined in FIG. 4B. Compound 5 can be furnished by, for example, the deprotection of Compound 4. Deprotection of Compound 4 comprises the removal of a protecting group (e.g. Boc). Conditions for deprotection may include, but are not limited to, HCl in DCM. Compound 4 can be generated, for example, via nucleophilic substitution of Compound 3 when exposed to a suitable nucleophile (e.g. $N_3^-$). Exemplary conditions for nucleophilic substitution include, but are not limited to, $NaN_3$ in DMF at 80° C. Compound 3 can be prepared, for example, via nucleophilic addition of Compound 1 to Compound 2. Exemplary conditions for nucleophilic addition include, but are not limited to, $K2CO_3$ at 0° C. to RT. Furthermore, if desired, the ester of Compound 3 can be removed by exposure to mild aqueous basic conditions to produce the carboxylic acid form of the UAA.

Figure 4C:
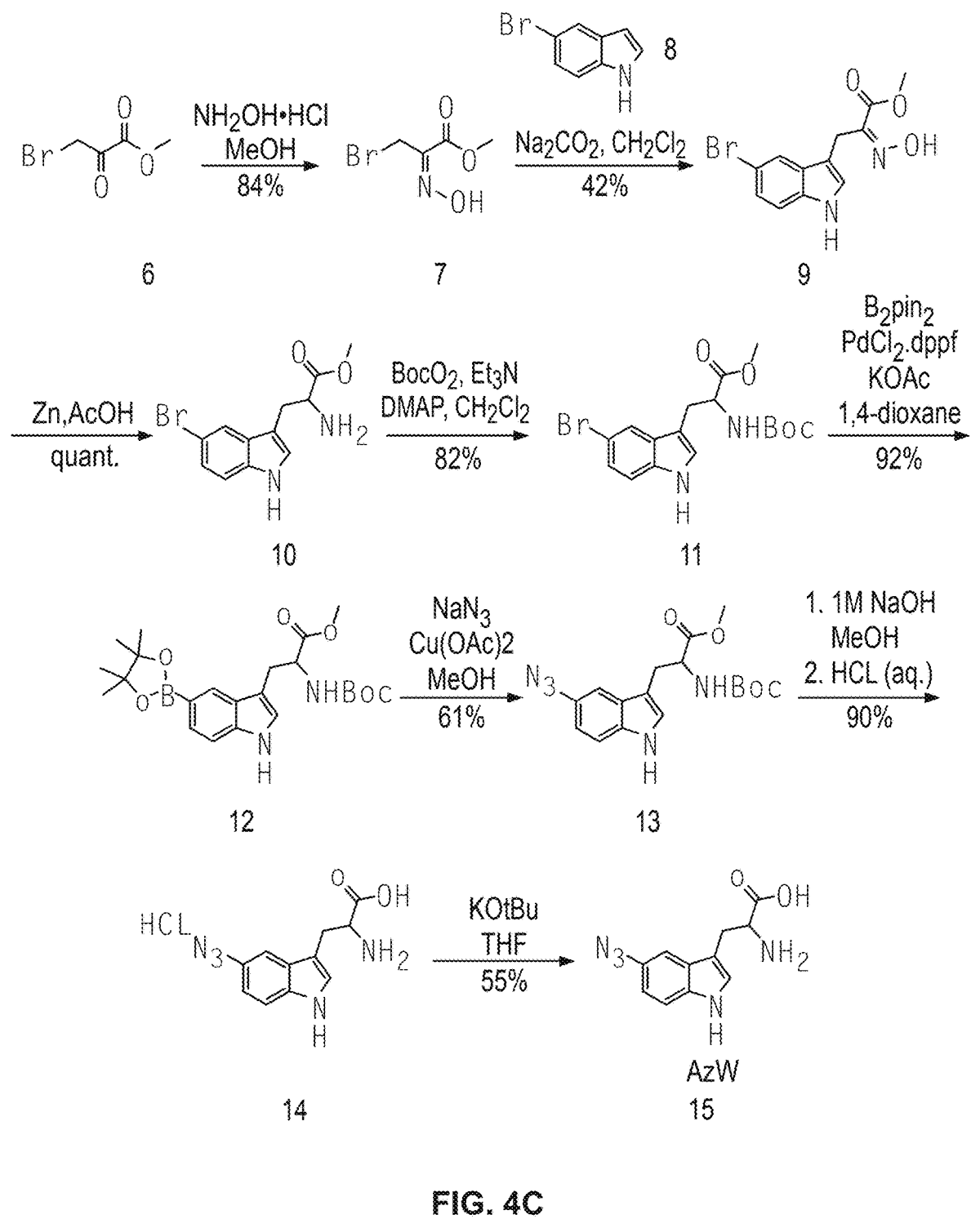
Figures 4D, 4E:
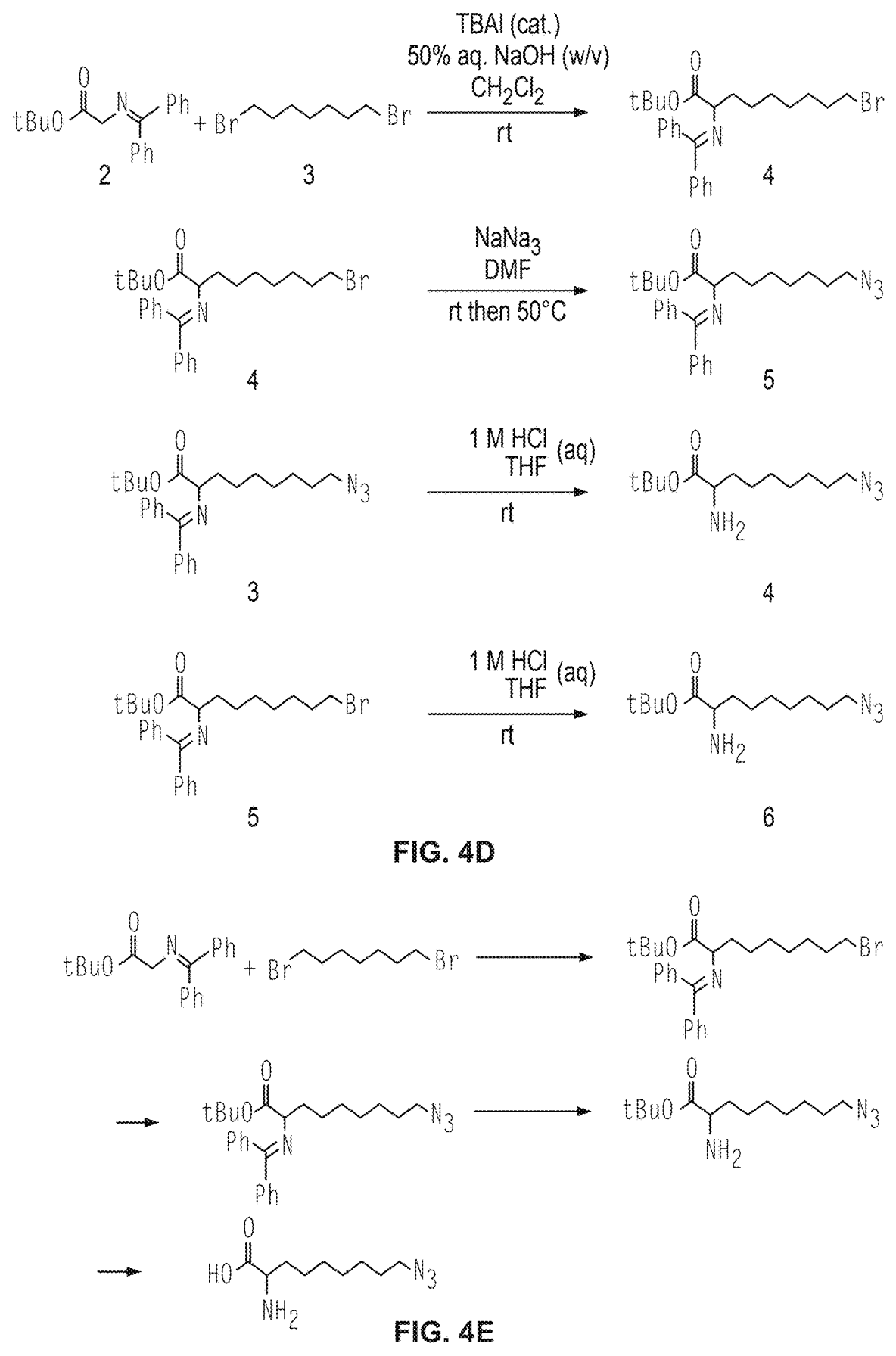
Figure 4F:
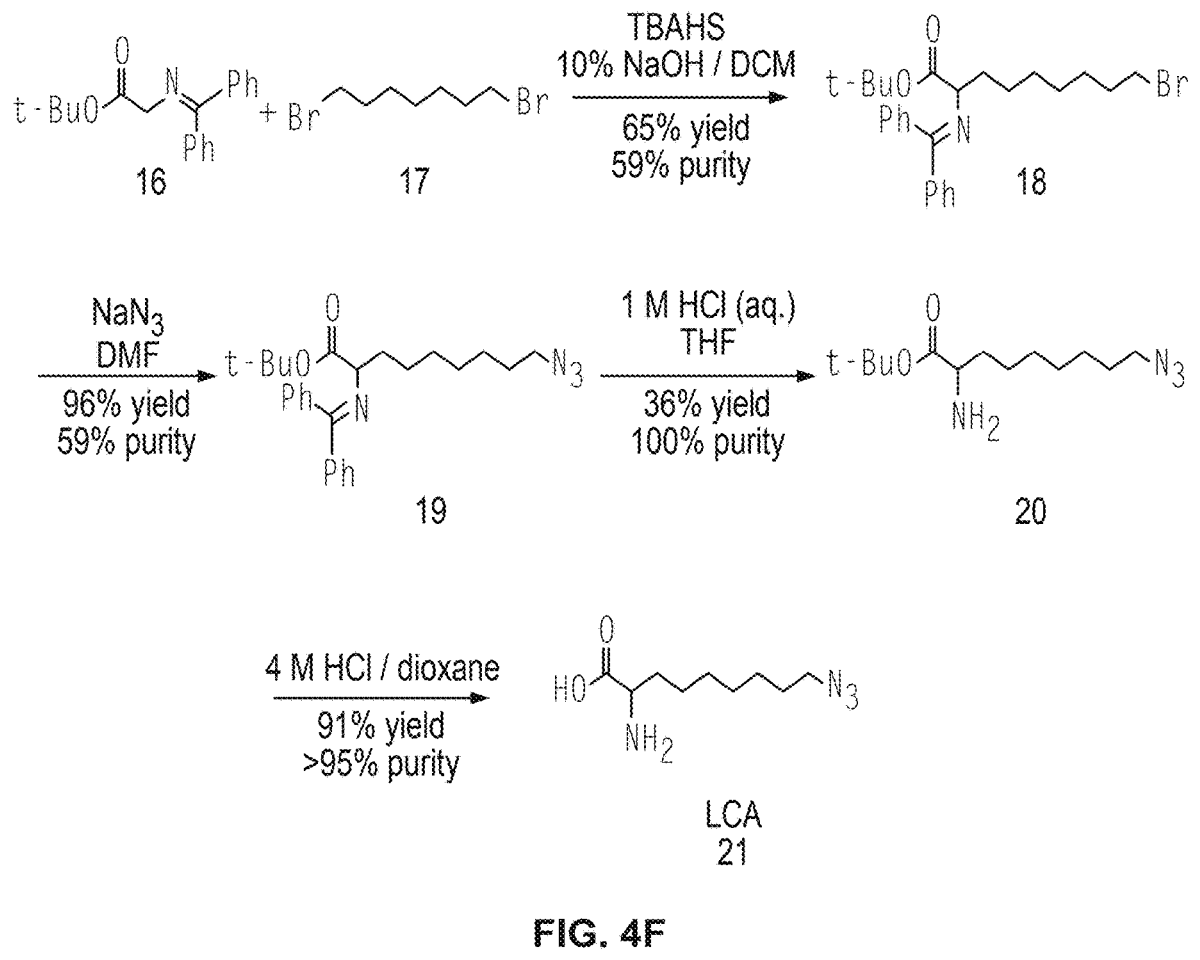

LCA (Compound 21 as shown in FIG. 4F) can be prepared in a manner similar to the synthesis outlined in FIG. 4F. Compound 21 can be prepared, for example, from Compound 20 through exposure of Compound 20 to a suitable acid, for example, but not limited to, 4M HCl in dioxane. Compound 20 can be generated through hydrolyzation of imine 19. Hydrolyzation of imine 19 can be accomplished, for example, using 1M HCl (aq.) in THF. Compound 19 can be generated, for example, via nucleophilic substitution of Compound 18 when exposed to a suitable nucleophile (e.g. $N_3^-$). Exemplary conditions for nucleophilic substitution include, but are not limited to, $NaN_3$ in DMF. Compound 18 can be prepared via nucleophilic addition of the enolate of Compound 16 to Compound 17. Suitable conditions for accomplishing synthesis of compound from Compounds 16 and 17 include, but are not limited to, tetrabutylammonium hydrogensulfate (TBAHS) and 10% NaOH in DCM. Additional methods for synthesis of LCA are shown in FIGS. 4D and 4E.

Figure 3:
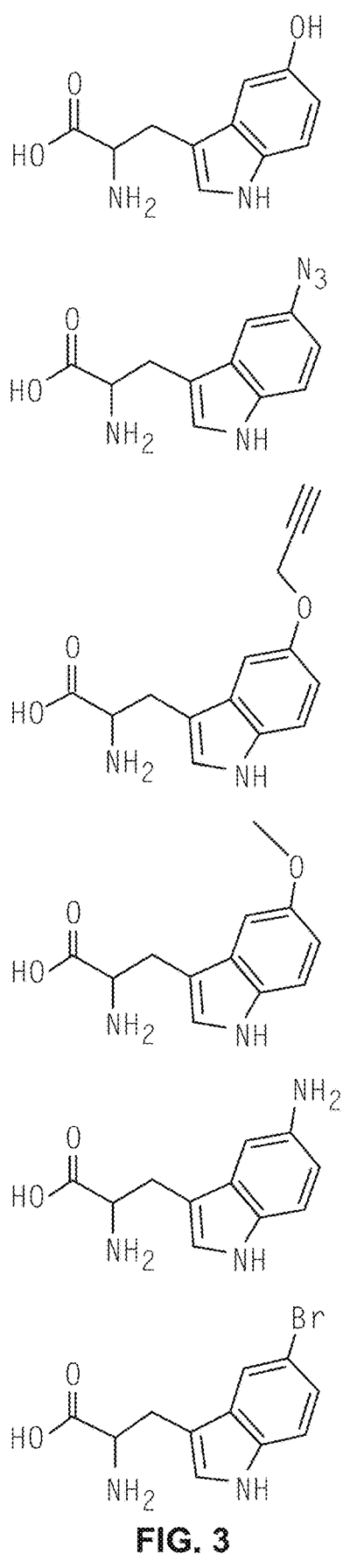

In certain embodiments, the unnatural amino acid is a tryptophan analog (also referred to herein as a derivative). In certain embodiments, the tryptophan analog is a non-naturally occurring tryptophan analog. Exemplary tryptophan analogs include 5-azidotryptophan, 5-propargyloxytryptophan, 5-aminotryptophan, 5-methoxytryptophan, 5-O-allyltryptophan or 5-bromotryptophan. Additional exemplary tryptophan analogs are depicted in FIG. 3. However, it is contemplated that the amino and carboxylate groups both attached to the first carbon of the tryptophan analogs in FIG. 3 would constitute portions of peptide bonds when the tryptophan analog is incorporated into a protein or polypeptide chain.

In addition, the tryptophan analog set forth in FIG. 4A, referred to as AzW, can be used in the practice of the invention.

AzW (Compound 15 as shown in FIG. 4C) can be prepared in a manner similar to the synthesis outlined in FIG. 4C. Compound 15 can be prepared, for example, under basic conditions from its hydrochloride salt 14. Exemplary basic conditions include, but are not limited to, KOtBu in THF. Hydrochloride salt 14 can be prepared, for example, via saponification followed by deprotection of Compound 13. Conditions for saponification and deprotection of a protecting group (e.g., Boc) are known to a person of ordinary skill in the art. For example, saponification can be accomplished using 1M NaOH in MeOH. In certain embodiments, conditions for deprotection include, but are not limited to, HCl (aq.). Compound 13 can be synthesized, for example, through a metal-mediated coupling of Compound 12 with a suitable azide source. Compound 13 can be made, for example, from Compound 12 using $NaN_3$, $Cu(OAc)_2$ in MeOH. Compound 12 can, for example, be prepared from Compound 11 through metal-catalyzed boronation of Compound 11. Exemplary conditions for metal-catalyzed boronation include, but are not limited to $B_2pin_2$, $PdCl_2·dppf$, and KOAc in 1,4-dioxane. Compound 11 can be prepared, for example, via protection of Compound 10 using a suitable protecting group (e.g., Boc). Protection of Compound 10 can be accomplished using $Boc_2O$, $Et_3N$, and DMAP in $CH_2Cl_2$. Compound 10 can be synthesized, for example, from Compound 9 under conditions suitable for reducing an oxime, for example, using Zn in AcOH. Compound 9 can synthesized, for example, via nucleophilic addition of indole 8 to Compound 7. Narcoleptic addition of Compound 8 to Compound 7 can occur in the presence of $Na_2CO_3$ in $CH_2Cl_2$. Compound 7 can be prepared, for example, by exposing Compound 6 to hydroxylamine hydrochloride in methanol.

Figure 5:
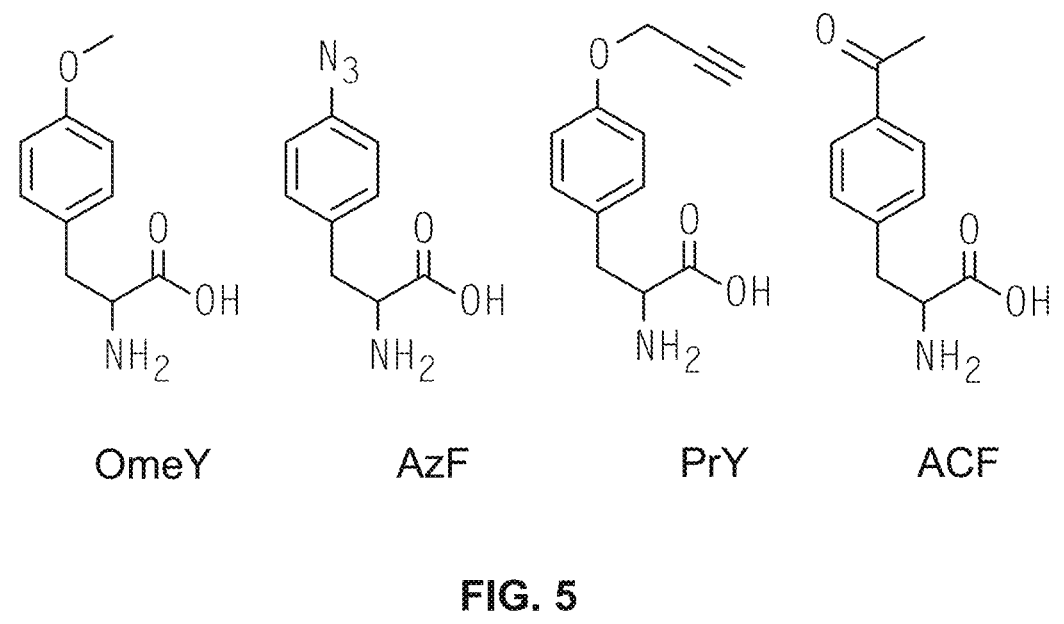

In certain embodiments, the unnatural amino acid is a tyrosine analog (also referred to herein as a derivative). In certain embodiments, the tyrosine analog is a non-naturally occurring tyrosine analog. Exemplary tyrosine analogs include o-methyltyrosine (OmeY), p-azidophenylalanine (AzF), o-propargyltyrosine (OpropY or PrY), and p-acetylphenylalanine (AcF). Exemplary tryptophan analogs are depicted in FIG. 5.

Figure 6:
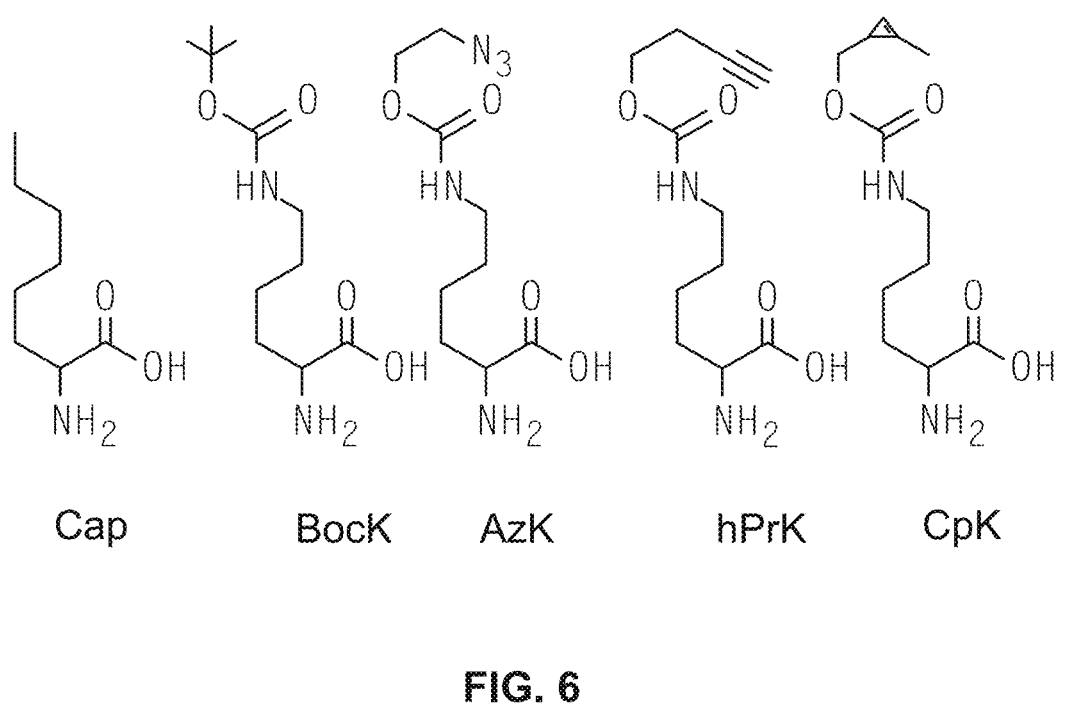

In certain embodiments, the unnatural amino acid is a pyrrolysine analog (also referred to herein as a derivative). In certain embodiments, the pyrrolysine analog is a non-naturally occurring pyrrolysine analog. Exemplary pyrrolysine analogs include aminocaprylic acid (Cap), H-Lys(Boc)-OH (Boc-Lysine, BocK), azidolysine (AzK), H-propargyl-lysine (hPrK), and cyclopropenelysine (CpK). Exemplary pyrrolysine analogs are depicted in FIG. 6.

Many unnatural amino acids are commercially available, e.g., from Sigma-Aldrich (St. Louis, Mo., USA), Novabiochem (Darmstadt, Germany), or Peptech (Burlington, Mass., USA). Those that are not commercially available can be synthesized using standard methods known to those of ordinary skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional exemplary publications describing the synthesis of unnatural amino acids appear in PCT Publication No. WO2002/085923, U.S. Patent Application Publication No. 2004/0198637, Matsoukas et al. (1995) J. MED. CHEM. 38:4660-4669, King et al. (1949) J. CHEM. SOC. 3315-3319, Friedman et al. (1959) J. AM. CHEM. SOC. 81:3750-3752, Craig et al. (1988) J. ORG. CHEM. 53:1167-1170, Azoulay et al. (1991) EUR. J. MED. CHEM. 26:201-5, Koskinen et al. (1989) J. ORG. CHEM. 54:1859-1866, Christie et al. (1985) J. ORG. CHEM. 50:1239-1246, Barton et al. (1987) TETRAHEDRON 43:4297-4308, and Subasinghe et al. (1992) J. MED. CHEM. 35:4602-7.

IV. Vectors tRNAs, aminoacyl-tRNA synthetases, or any other molecules of interest may be expressed in a cell of interest by incorporating a gene encoding the molecule into an appropriate expression vector. As used herein, "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system.

tRNAs, aminoacyl-tRNA synthetases, or any other molecules of interest may be introduced to a cell of interest by incorporating a gene encoding the molecule into an appropriate transfer vector. The term "transfer vector" refers to a vector comprising a recombinant polynucleotide which can be used to deliver the polynucleotide to the interior of a cell. It is understood that a vector may be both an expression vector and a transfer vector.

Vectors (e.g., expression vectors or transfer vectors) include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide of interest.

Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (including but not limited to, shuttle vectors) and selection markers for both prokaryotic and eukaryotic systems.

In certain embodiments, the vector comprises a regulatory sequence or promoter operably linked to the nucleotide sequence encoding the suppressor tRNA and/or the tRNA synthetase. The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

Exemplary promoters which may be employed include, but are not limited to, the retroviral LTR, the SV40 promoter, the human cytomegalovirus (CMV) promoter, the U6 promoter, the EF1α promoter, the CAG promoter, the H1 promoter, the UbiC promoter, the PGK promoter, the 7SK promoter, a pol II promoter, a pol III promoter, or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein. In certain embodiments, a vector comprises a nucleotide sequence encoding an aminoacyl-tRNA synthetase operably linked to a CMV or an EF1α promoter and/or a nucleotide sequence encoding a suppressor tRNA operably linked to a U6 or an H1 promoter.

In certain embodiments, the vector is a viral vector. The term "virus" is used herein to refer to an obligate intracellular parasite having no protein-synthesizing or energy-generating mechanism. Exemplary viral vectors include retroviral vectors (e.g., lentiviral vectors), adenoviral vectors, adeno-associated viral vectors, herpesviruses vectors, epstein-barr virus (EBV) vectors, polyomavirus vectors (e.g., simian vacuolating virus 40 (SV40) vectors), poxvirus vectors, and pseudotype virus vectors.

The virus may be a RNA virus (having a genome that is composed of RNA) or a DNA virus (having a genome composed of DNA). In certain embodiments, the viral vector is a DNA virus vector. Exemplary DNA viruses include parvoviruses (e.g., adeno-associated viruses). adenoviruses, asfarviruses, herpesviruses (e.g., herpes simplex virus 1 and 2 (HSV-1 and HSV-2), epstein-barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). In certain embodiments, the viral vector is a RNA virus vector. Exemplary RNA viruses include bunyaviruses (e.g., hantavirus), coronaviruses, flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses.

Adeno-Associated Virus (AAV) Vectors

In certain embodiments, a vector is an adeno-associated virus (AAV) vector. AAV is a small, nonenveloped icosahedral virus of the genus Dependoparvovirus and family Parvovirus. AAV has a single-stranded linear DNA genome of approximately 4.7 kb. AAV is capable of infecting both dividing and quiescent cells of several tissue types, with different AAV serotypes exhibiting different tissue tropism.

AAV includes numerous serologically distinguishable types including serotypes AAV-1 to AAV-12, as well as more than 100 serotypes from nonhuman primates (See, e.g., Srivastava (2008) J. CELL BIOCHEM., 105(1): 17-24, and Gao et al. (2004) J. VIROL., 78(12), 6381-6388). The serotype of the AAV vector used in the present invention can be selected by a skilled person in the art based on the efficiency of delivery, tissue tropism, and immunogenicity. For example, AAV-1, AAV-2, AAV-4, AAV-5, AAV-8, and AAV-9 can be used for delivery to the central nervous system; AAV-1, AAV-8, and AAV-9 can be used for delivery to the heart; AAV-2 can be used for delivery to the kidney; AAV-7, AAV-8, and AAV-9 can be used for delivery to the liver; AAV-4, AAV-5, AAV-6, AAV-9 can be used for delivery to the lung, AAV-8 can be used for delivery to the pancreas, AAV-2, AAV-5, and AAV-8 can be used for delivery to the photoreceptor cells; AAV-1, AAV-2, AAV-4, AAV-5, and AAV-8 can be used for delivery to the retinal pigment epithelium; AAV-1, AAV-6, AAV-7, AAV-8, and AAV-9 can be used for delivery to the skeletal muscle. In certain embodiments, the AAV capsid protein comprises a sequence as disclosed in U.S. Pat. No. 7,198,951, such as, but not limited to, AAV-9 (SEQ ID NOs: 1-3 of U.S. Pat. No. 7,198,951), AAV-2 (SEQ ID NO: 4 of U.S. Pat. No. 7,198, 951), AAV-1 (SEQ ID NO: 5 of U.S. Pat. No. 7,198,951), AAV-3 (SEQ ID NO: 6 of U.S. Pat. No. 7,198,951), and AAV-8 (SEQ ID NO: 7 of U.S. Pat. No. 7,198,951). AAV serotypes identified from rhesus monkeys, e.g., rh.8, rh.10, rh.39, rh.43, and rh.74, are also contemplated in the instant invention. Besides the natural AAV serotypes, modified AAV capsids have been developed for improving efficiency of delivery, tissue tropism, and immunogenicity. Exemplary natural and modified AAV capsids are disclosed in U.S. Pat. Nos. 7,906,111, 9,493,788, and 7,198,951, and PCT Publication No. WO2017189964A2.

The wild-type AAV genome contains two 145 nucleotide inverted terminal repeats (ITRs), which contain signal sequences directing AAV replication, genome encapsidation and integration. In addition to the ITRs, three AAV promoters, p5, p19, and p40, drive expression of two open reading frames encoding rep and cap genes. Two rep promoters, coupled with differential splicing of the single AAV intron, result in the production of four rep proteins (Rep 78, Rep 68, Rep 52, and Rep 40) from the rep gene. Rep proteins are responsible for genomic replication. The Cap gene is expressed from the p40 promoter, and encodes three capsid proteins (VP1, VP2, and VP3) which are splice variants of the cap gene. These proteins form the capsid of the AAV particle.

Because the cis-acting signals for replication, encapsidation, and integration are contained within the ITRs, some or all of the 4.3 kb internal genome may be replaced with foreign DNA, for example, an expression cassette for an exogenous gene of interest. Accordingly, in certain embodiments, the AAV vector comprises a genome comprising an expression cassette for an exogenous gene flanked by a 5' ITR and a 3' ITR. The ITRs may be derived from the same serotype as the capsid or a derivative thereof. Alternatively, the ITRs may be of a different serotype from the capsid, thereby generating a pseudotyped AAV. In certain embodiments, the ITRs are derived from AAV-2. In certain embodiments, the ITRs are derived from AAV-5. At least one of the ITRs may be modified to mutate or delete the terminal resolution site, thereby allowing production of a self-complementary AAV vector.

The rep and cap proteins can be provided in trans, for example, on a plasmid, to produce an AAV vector. A host cell line permissive of AAV replication must express the rep and cap genes, the ITR-flanked expression cassette, and helper functions provided by a helper virus, for example adenoviral genes E1a, E1b55K, E2a, E4orf6, and VA (Weitzman et al., Adeno-associated virus biology. Adeno-Associated Virus: Methods and Protocols, pp. 1-23, 2011). Methods for generating and purifying AAV vectors have been described in detail (See e.g., Mueller et al., (2012) CURRENT PROTCOLS IN MICROBIOLOGY, 14D.1.1-14D.1.21, Production and Discovery of Novel Recombinant Adeno-Associated Viral Vectors). Numerous cell types are suitable for producing AAV vectors, including HEK293 cells, COS cells, HeLa cells, BHK cells, Vero cells, as well as insect cells (See e.g. U.S. Pat. Nos. 6,156,303, 5,387,484, 5,741,683, 5,691,176, 5,688,676, and 8,163,543, U.S. Patent Publication No. 20020081721, and PCT Publication Nos. WO00/47757, WO00/24916, and WO96/17947). AAV vectors are typically produced in these cell types by one plasmid containing the ITR-flanked expression cassette, and one or more additional plasmids providing the additional AAV and helper virus genes.

AAV of any serotype may be used in the present invention. Similarly, it is contemplated that any adenoviral type may be used, and a person of skill in the art will be able to identify AAV and adenoviral types suitable for the production of their desired recombinant AAV vector (rAAV). AAV particles may be purified, for example by affinity chromatography, iodixonal gradient, or CsCl gradient.

AAV vectors may have single-stranded genomes that are 4.7 kb in size, or are larger or smaller than 4.7 kb, including oversized genomes that are as large as 5.2 kb, or as small as 3.0 kb. Thus, where the exogenous gene of interest to be expressed from the AAV vector is small, the AAV genome may comprise a stuffer sequence. Further, vector genomes may be substantially self-complementary thereby allowing for rapid expression in the cell. In certain embodiments, the genome of a self-complementary AAV vector comprises from 5' to 3': a 5' ITR; a first nucleic acid sequence comprising a promoter and/or enhancer operably linked to a coding sequence of a gene of interest; a modified ITR that does not have a functional terminal resolution site; a second nucleic acid sequence complementary or substantially complementary to the first nucleic acid sequence; and a 3' ITR. AAV vectors containing genomes of all types are suitable for use in the method of the present invention.

Non-limiting examples of AAV vectors include pAAV-MCS (Agilent Technologies), pAAVK-EF1α-MCS (System Bio Catalog # AAV502A-1), pAAVK-EF1α-MCS1-CMV-MCS2 (System Bio Catalog # AAV503A-1), pAAV-Zs-Green1 (Clontech Catalog #6231), pAAV-MCS2 (Addgene Plasmid #46954), AAV-Stuffer (Addgene Plasmid #106248), pAAVscCBPIGpluc (Addgene Plasmid #35645), AAVS1_Puro_PGK1_3xFLAG Twin_Strep (Addgene Plasmid #68375), pAAV-RAM-d2TTA::TRE-MCS-WPRE-pA (Addgene Plasmid #63931), pAAV-UbC (Addgene Plasmid #62806), pAAVS1-P-MCS (Addgene Plasmid #80488), pAAV-Gateway (Addgene Plasmid #32671), pAAV-Puro_siKD (Addgene Plasmid #86695), pAAVS1-Nst-MCS (Addgene Plasmid #80487), pAAVS1-Nst-CAG-DEST (Addgene Plasmid #80489), pAAVS1-P-CAG-DEST (Addgene Plasmid #80490), pAAVf-EnhCB-lacZnls (Addgene Plasmid #35642), and pAAVS1-shRNA (Addgene Plasmid #82697). These vectors can be modified to be suitable for therapeutic use. For example, an exogenous gene of interest can be inserted in a multiple cloning site, and a selection marker (e.g., puro or a gene encoding a fluorescent protein) can be deleted or replaced with another (same or different) exogenous gene of interest. Further examples of AAV vectors are disclosed in U.S. Pat. Nos. 5,871,982, 6,270,996, 7,238,526, 6,943,019, 6,953,690, 9,150,882, and 8,298,818, U.S. Patent Publication No. 2009/0087413, and PCT Publication Nos. WO2017075335A1, WO2017075338A2, and WO2017201258A1.

Lentivirus Vectors

In certain embodiments, the viral vector can be a retroviral vector. Examples of retroviral vectors include moloney murine leukemia virus vectors, spleen necrosis virus vectors, and vectors derived from retroviruses such as rous sarcoma virus, harvey sarcoma virus, avian leukosis virus, human immunodeficiency virus, myeloproliferative sarcoma virus, and mammary tumor virus. Retroviral vectors are useful as agents to mediate retroviral-mediated gene transfer into eukaryotic cells.

In certain embodiments, the retroviral vector is a lentiviral vector. Exemplary lentiviral vectors include vectors derived from human immunodeficiency virus-1 (HIV-1), human immunodeficiency virus-2 (HIV-2), simian immunodeficiency virus (SIV), feline immunodeficiency virus (FIV), bovine immunodeficiency virus (BIV), Jembrana Disease Virus (JDV), equine infectious anemia virus (EIAV), and caprine arthritis encephalitis virus (CAEV).

Retroviral vectors typically are constructed such that the majority of sequences coding for the structural genes of the virus are deleted and replaced by the gene(s) of interest. Often, the structural genes (i.e., gag, pol, and env), are removed from the retroviral backbone using genetic engineering techniques known in the art. Accordingly, a minimum retroviral vector comprises from 5' to 3': a 5' long terminal repeat (LTR), a packaging signal, an optional exogenous promoter and/or enhancer, an exogenous gene of interest, and a 3' LTR. If no exogenous promoter is provided, gene expression is driven by the 5' LTR, which is a weak promoter and requires the presence of Tat to activate expression. The structural genes can be provided in separate vectors for manufacture of the lentivirus, rendering the produced virions replication-defective. Specifically, with respect to lentivirus, the packaging system may comprise a single packaging vector encoding the Gag, Pol, Rev, and Tat genes, and a third, separate vector encoding the envelope protein Env (usually VSV-G due to its wide infectivity). To improve the safety of the packaging system, the packaging vector can be split, expressing Rev from one vector, Gag and Pol from another vector. Tat can also be eliminated from the packaging system by using a retroviral vector comprising a chimeric 5' LTR, wherein the U3 region of the 5' LTR is replaced with a heterologous regulatory element.

The genes can be incorporated into the proviral backbone in several general ways. The most straightforward constructions are ones in which the structural genes of the retrovirus are replaced by a single gene that is transcribed under the control of the viral regulatory sequences within the LTR. Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Accordingly, the new gene(s) are flanked by 5' and 3' LTRs, which serve to promote transcription and polyadenylation of the virion RNAs, respectively. The term "long terminal repeat" or "LTR" refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals, and sequences needed for replication and integration of the viral genome. The U3 region contains the enhancer and promoter elements. The U5 region is the sequence between the primer binding site and the R region and contains the polyadenylation sequence. The R (repeat) region is flanked by the U3 and U5 regions. In certain embodiments, the R region comprises a trans-activation response (TAR) genetic element, which interacts with the trans-activator (tat) genetic element to enhance viral replication. This element is not required in embodiments wherein the U3 region of the 5' LTR is replaced by a heterologous promoter.

In certain embodiments, the retroviral vector comprises a modified 5' LTR and/or 3' LTR. Modifications of the 3' LTR are often made to improve the safety of lentiviral or retroviral systems by rendering viruses replication-defective. In specific embodiments, the retroviral vector is a self-inactivating (SIN) vector. As used herein, a SIN retroviral vector refers to a replication-defective retroviral vector in which the 3' LTR U3 region has been modified (e.g., by deletion or substitution) to prevent viral transcription beyond the first round of viral replication. This is because the 3' LTR U3 region is used as a template for the 5' LTR U3 region during viral replication and, thus, the viral transcript cannot be made without the U3 enhancer-promoter. In a further embodiment, the 3' LTR is modified such that the U5 region is replaced, for example, with an ideal polyadenylation sequence. It should be noted that modifications to the LTRs such as modifications to the 3' LTR, the 5' LTR, or both 3' and 5' LTRs, are also included in the invention.

In certain embodiments, the U3 region of the 5' LTR is replaced with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus, because there is no complete U3 sequence in the virus production system.

Adjacent the 5' LTR are sequences necessary for reverse transcription of the genome (the tRNA primer binding site) and for efficient packaging of viral RNA into particles (the Psi site). As used herein, the term "packaging signal" or "packaging sequence" refers to sequences located within the retroviral genome which are required for encapsidation of retroviral RNA strands during viral particle formation (see e.g., Clever et al., 1995 J. Virology, 69(4):2101-09). The packaging signal may be a minimal packaging signal (also referred to as the psi [Ψ] sequence) needed for encapsidation of the viral genome.

In certain embodiments, the retroviral vector (e.g., lentiviral vector) further comprises a FLAP. As used herein, the term "FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou et al. (2000) Cell, 101:173. During reverse transcription, central initiation of the plus-strand DNA at the cPPT and central termination at the CTS lead to the formation of a three-stranded DNA structure: a central DNA flap. While not wishing to be bound by any theory, the DNA flap may act as a cis-active determinant of lentiviral genome nuclear import and/or may increase the titer of the virus. In particular embodiments, the retroviral vector backbones comprise one or more FLAP elements upstream or downstream of the heterologous genes of interest in the vectors. For example, in particular embodiments, a transfer plasmid includes a FLAP element. In one embodiment, a vector of the invention comprises a FLAP element isolated from HIV-1.

In certain embodiments, the retroviral vector (e.g., lentiviral vector) further comprises an export element. In one embodiment, retroviral vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) RRE (see e.g., Cullen et al., (1991) J. VIROL. 65: 1053; and Cullen et al., (1991) CELL 58: 423) and the hepatitis B virus post-transcriptional regulatory element (HPRE). Generally, the RNA export element is placed within the 3' UTR of a gene, and can be inserted as one or multiple copies.

In certain embodiments, the retroviral vector (e.g., lentiviral vector) further comprises a posttranscriptional regulatory element. A variety of posttranscriptional regulatory elements can increase expression of a heterologous nucleic acid, e.g., woodchuck hepatitis virus posttranscriptional regulatory element (WPRE; see Zufferey et al., (1999) J. VIROL., 73:2886); the posttranscriptional regulatory element present in hepatitis B virus (HPRE) (Huang et al., MOL. CELL. BIOL., 5:3864); and the like (Liu et al., (1995), GENES DEV., 9:1766). The posttranscriptional regulatory element is generally positioned at the 3' end the heterologous nucleic acid sequence. This configuration results in synthesis of an mRNA transcript whose 5' portion comprises the heterologous nucleic acid coding sequences and whose 3' portion comprises the posttranscriptional regulatory element sequence. In certain embodiments, vectors of the invention lack or do not comprise a posttranscriptional regulatory element such as a WPRE or HPRE, because in some instances these elements increase the risk of cellular transformation and/or do not substantially or significantly increase the amount of mRNA transcript or increase mRNA stability. Therefore, in certain embodiments, vectors of the invention lack or do not comprise a WPRE or HPRE as an added safety measure.

Elements directing the efficient termination and polyadenylation of the heterologous nucleic acid transcripts increase heterologous gene expression. Transcription termination signals are generally found downstream of the polyadenylation signal. Accordingly, in certain embodiments, the retroviral vector (e.g., lentiviral vector) further comprises a polyadenylation signal. The term "polyadenylation signal" or "polyadenylation sequence" as used herein denotes a DNA sequence which directs both the termination and polyadenylation of the nascent RNA transcript by RNA polymerase H. Efficient polyadenylation of the recombinant transcript is desirable as transcripts lacking a polyadenylation signal are unstable and are rapidly degraded. Illustrative examples of polyadenylation signals that can be used in a vector of the invention, includes an ideal polyadenylation sequence (e.g., AATAAA, ATTAAA AGTAAA), a bovine growth hormone polyadenylation sequence (BGHpA), a rabbit β-globin polyadenylation sequence (rogpA), or another suitable heterologous or endogenous polyadenylation sequence known in the art.

In certain embodiments, a retroviral vector further comprises an insulator element. Insulator elements may contribute to protecting retrovirus-expressed sequences, e.g., therapeutic genes, from integration site effects, which may be mediated by cis-acting elements present in genomic DNA and lead to deregulated expression of transferred sequences (i.e., position effect; see, e.g., Burgess-Beusse et al., (2002) PROC. NATL. ACAD. SCI., USA, 99:16433; and Zhan et al., 2001, HUM. GENET., 109:471). In certain embodiments, the retroviral vector comprises an insulator element in one or both LTRs or elsewhere in the region of the vector that integrates into the cellular genome. Suitable insulators for use in the invention include, but are not limited to, the chicken β-globin insulator (see Chung et al., (1993). CELL 74:505; Chung et al., (1997) PROC. NATL. ACAD. SCI., USA 94:575; and Bell et al., 1999. CELL 98:387). Examples of insulator elements include, but are not limited to, an insulator from a β-globin locus, such as chicken HS4.

Non-limiting examples of lentiviral vectors include pLVX-EF1alpha-AcGFP1-C1 (Clontech Catalog #631984), pLVX-EF1alpha-IRES-mCherry (Clontech Catalog #631987), pLVX-Puro (Clontech Catalog #632159), pLVX-IRES-Puro (Clontech Catalog #632186), pLenti6N5-DEST™ (Thermo Fisher), pLenti6.2N5-DEST™ (Thermo Fisher), pLKO.1 (Plasmid #10878 at Addgene), pLKO.3G (Plasmid #14748 at Addgene), pSico (Plasmid #11578 at Addgene), pLJM1-EGFP (Plasmid #19319 at Addgene), FUGW (Plasmid #14883 at Addgene), pLVTHM (Plasmid #12247 at Addgene), pLVUT-tTR-KRAB (Plasmid #11651 at Addgene), pLL3.7 (Plasmid #11795 at Addgene), pLB (Plasmid #11619 at Addgene), pWPXL (Plasmid #12257 at Addgene), pWPI (Plasmid #12254 at Addgene), EF.CMV.RFP (Plasmid #17619 at Addgene), pLenti CMV Puro DEST (Plasmid #17452 at Addgene), pLenti-puro (Plasmid #39481 at Addgene), pULTRA (Plasmid #24129 at Addgene), pLX301 (Plasmid #25895 at Addgene), pHIV-EGFP (Plasmid #21373 at Addgene), pLV-mCherry (Plasmid #36084 at Addgene), pLionII (Plasmid #1730 at Addgene), pInducer10-mir-RUP-PheS (Plasmid #44011 at Addgene). These vectors can be modified to be suitable for therapeutic use. For example, a selection marker (e.g., puro, EGFP, or mCherry) can be deleted or replaced with a second exogenous gene of interest. Further examples of lentiviral vectors are disclosed in U.S. Pat. Nos. 7,629,153, 7,198,950, 8,329,462, 6,863,884, 6,682,907, 7,745,179, 7,250,299, 5,994,136, 6,287,814, 6,013,516, 6,797,512, 6,544,771, 5,834,256, 6,958,226, 6,207,455, 6,531,123, and 6,352,694, and PCT Publication No. WO2017/091786.

Adenoviral Vectors

In certain embodiments, the viral vector can be an adenoviral vector. Adenoviruses are medium-sized (90-100 nm), non-enveloped (naked), icosahedral viruses composed of a nucleocapsid and a double-stranded linear DNA genome. The term "adenovirus" refers to any virus in the genus Adenoviridiae including, but not limited to, human, bovine, ovine, equine, canine, porcine, murine, and simian adenovirus subgenera. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

A human adenovirus can be used as the source of the adenoviral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serogroup or serotype. Adenoviral serotypes 1 through 51 are available from the American Type Culture Collection (ATCC, Manassas, Virginia). Non-group C adenoviral vectors, methods of producing non-group C adenoviral vectors, and methods of using non-group C adenoviral vectors are disclosed in, for example, U.S. Pat. Nos. 5,801,030, 5,837, 511, and 5,849,561, and PCT Publication Nos. WO1997/ 012986 and WO1998/053087.

Non-human adenovirus (e.g., ape, simian, avian, canine, ovine, or bovine adenoviruses) can be used to generate the adenoviral vector (i.e., as a source of the adenoviral genome for the adenoviral vector). For example, the adenoviral vector can be based on a simian adenovirus, including both new world and old world monkeys (see, e.g., Virus Taxonomy: VHIth Report of the International Committee on Taxonomy of Viruses (2005)). A phylogeny analysis of adenoviruses that infect primates is disclosed in, e.g., Roy et al. (2009) PLoS Pathog. 5(7):e1000503. A gorilla adenovirus can be used as the source of the adenoviral genome for the adenoviral vector. Gorilla adenoviruses and adenoviral vectors are described in, e.g., PCT Publication Nos.WO2013/ 052799, WO2013/052811, and WO2013/052832. The adenoviral vector can also comprise a combination of subtypes and thereby be a "chimeric" adenoviral vector.

The adenoviral vector can be replication-competent, conditionally replication-competent, or replication-deficient. A replication-competent adenoviral vector can replicate in typical host cells, i.e., cells typically capable of being infected by an adenovirus. A conditionally-replicating adenoviral vector is an adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., a promoter. Conditionally-replicating adenoviral vectors are further described in U.S. Pat. No. 5,998,205. A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

Preferably, the adenoviral vector is replication-deficient, such that the replication-deficient adenoviral vector requires complementation of at least one replication-essential gene function of one or more regions of the adenoviral genome for propagation (e.g., to form adenoviral vector particles). The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad)). See, e.g., Morsy et al. (1998) Proc. Natl. Acad. Sci. USA 95: 965-976, Chen et al. (1997) Proc. Natl. Acad. Sci. USA 94: 1645-1650, and Kochanek et al. (1999) Hum. Gene Ther. 10(15):2451-9. Examples of replication-deficient adenoviral vectors are disclosed in U.S. Pat. Nos. 5,837,511, 5,851,806, 5,994,106, 6,127,175, 6,482,616, and 7,195,896, and PCT Publication Nos. WO1994/028152, WO1995/ 002697, WO1995/016772, WO1995/034671, WO1996/ 022378, WO1997/012986, WO1997/021826, and WO2003/ 022311.

The replication-deficient adenoviral vector of the invention can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al. (1977) J. Gen. Virol. 36: 59-72), PER.C6 cells (described in, e.g., PCT Publication No. WO1997/ 000326, and U.S. Pat. Nos. 5,994,128 and 6,033,908), and 293-ORF6 cells (described in, e.g., PCT Publication No. WO1995/034671 and Brough et al. (1997) J. Virol. 71: 9206-9213). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Publication No. 2008/0233650). Additional suitable complementing cells are described in, for example, U.S. Pat. Nos. 6,677,156 and 6,682,929, and PCT Publication No. WO2003/020879. Formulations for adenoviral vector-containing compositions are further described in, for example, U.S. Pat. Nos. 6,225,289, and 6,514,943, and PCT Publication No. WO2000/034444.

Additional exemplary adenoviral vectors, and/or methods for making or propagating adenoviral vectors are described in U.S. Pat. Nos. 5,559,099, 5,837,511, 5,846,782, 5,851, 806, 5,994,106, 5,994,128, 5,965,541, 5,981,225, 6,040,174, 6,020,191, 6,083,716, 6,113,913, 6,303,362, 7,067,310, and 9,073,980.

Commercially available adenoviral vector systems include the ViraPower™ Adenoviral Expression System available from Thermo Fisher Scientific, the AdEasy™ adenoviral vector system available from Agilent Technologies, and the Adeno-X™ Expression System 3 available from Takara Bio USA, Inc.

V. Host Cells and Cell Lines

Also encompassed by the invention are host cells or cell lines (e.g., prokaryotic or eukaryotic host cells or cell lines) that include a tRNA, aminoacyl-tRNA synthetase, unnatural amino acid, nucleic acid, and/or vector disclosed herein. The nucleic acid encoding the engineered tRNA and aminoacyl-tRNA synthetase can be expressed in an expression host cell either as an autonomously replicating vector within the expression host cell (e.g., a plasmid, or viral particle) or via a stable integrated element or series of stable integrated elements in the genome of the expression host cell, e.g., a mammalian host cell.

Host cells are genetically engineered (including but not limited to, transformed, transduced or transfected), for example, using nucleic acids or vectors disclosed herein. For example, in certain embodiments, one or more vectors include coding regions for an orthogonal tRNA, an orthogonal aminoacyl-tRNA synthetase, and, optionally, a protein to be modified by the inclusion of one or more UAAs, which are operably linked to gene expression control elements that are functional in the desired host cell or cell line. For example, the genes encoding tRNA synthetase and tRNA and an optional selectable marker (e.g., an antibiotic resistance gene, e.g., a puromycin resistance cassette) can be integrated in a transfer vector (e.g., a plasmid, which can be linearized prior to transfection), where for example, the genes encoding the tRNA synthetase can be under the control of a polymerase II promoter (e.g., CMV, EF1α, UbiC, or PGK, e.g., CMV or EF1α) and the genes encoding the tRNA can be under the control of a polymerase III promoter (e.g., U6, 7SK, or H1, e.g., U6). The vectors are transfected into cells and/or microorganisms by standard methods including electroporation or infection by viral vectors, and clones can selected via expression of the selectable marker (for example, by antibiotic resistance).

Exemplary prokaryotic host cells or cell lines include cells derived from a bacteria, e.g., *Escherichia coli, Thermus thermophilus, Bacillus stearothermophilus, Pseudomonas fluorescens, Pseudomonas aeruginosa*, and *Pseudomonas putida*. Exemplary eukaryotic host cells or cell lines include cells derived from a plant (e.g., a complex plant such as a monocot or dicot), an algae, a protist, a fungus, a yeast (including *Saccharomyces cerevisiae*), or an animal (including a mammal, an insect, an arthropod, etc.). Additional exemplary host cells or cell lines include HEK293, HEK293T, Expi293, CHO, CHOK1, Sf9, Sf21, HeLa, U20S, A549, HT1080, CAD, P19, NIH 3T3, L929, N2a, MCF-7, Y79, SO-RB50, HepG2, DUKX-X11, J558L, BHK, COS, Vero, NSO, or ESCs. It is understood that a host cell or cell line can include individual colonies, isolated populations (monoclonal), or a heterogeneous mixture of cells.

A contemplated cell or cell line includes, for example, one or multiple copies of an orthogonal tRNA/aminoacyl-tRNA synthetase pair, optionally stably maintained in the cell's genome or another piece of DNA maintained by the cell. For example, the cell or cell line may contain one or more copies of (i) a tryptophanyl tRNA/aminoacyl-tRNA synthetase pair (wild type or engineered) stably maintained by the cell, and/or (ii) a leucyl tRNA/aminoacyl-tRNA synthetase pair (wild-type or engineered) stably maintained by the cell.

For example, in certain embodiments, the cell line is a stable cell line and the cell line comprises a genome having stably integrated therein (i) a nucleic acid sequence encoding an aminoacyl-tRNA synthetase (e.g., a prokaryotic tryptophanyl-tRNA synthetase mutein capable of charging a tRNA with an unnatural amino acid or a prokaryotic leucyl-tRNA synthetase mutein capable of charging a tRNA with an unnatural amino acid, e.g., a tRNA synthetase mutein disclosed herein); and/or (ii) a nucleic acid sequence encoding a suppressor tRNA (e.g., prokaryotic suppressor tryptophanyl-tRNA capable of being charged with an unnatural amino acid or prokaryotic suppressor leucyl-tRNA capable of being charged with an unnatural amino acid, e.g., a suppressor tRNA disclosed herein).

Methods to introduce a nucleic acid encoding a tRNA and/or an aminoacyl-tRNA synthetase into the genome of a cell of interest, or to stably maintain the nucleic acid in DNA replicated by the cell that is outside of the genome, are well known in the art.

The nucleic acid encoding the tRNA and/or an aminoacyl-tRNA synthetase can be provided to the cell in an expression vector, transfer vector, or DNA cassette, e.g., an expression vector, transfer vector, or DNA cassette disclosed herein. The expression vector transfer vector, or DNA cassette encoding the tRNA and/or aminoacyl-tRNA synthetase can contain one or more copies of the tRNA and/or aminoacyl-tRNA synthetase optionally under the control of an inducible or constitutively active promoter. The expression vector, transfer vector, or DNA cassette may, for example, contain other standard components (enhancers, terminators, etc.). It is contemplated that the nucleic acid encoding the tRNA and the nucleic acid encoding the aminoacyl-tRNA synthetase may be on the same or different vector, may be present in the same or different ratios, and may be introduced into the cell, or stably integrated in the cellular genome, at the same time or sequentially.

One or multiple copies of a DNA cassette encoding the tRNA and/or aminoacyl-tRNA synthetase can be integrated into a host cell genome or stably maintained in the cell using a transposon system (e.g., PiggyBac), a viral vector (e.g., a lentiviral vector or other retroviral vector), CRISPR/Cas9 based recombination, electroporation and natural recombination, a BxB1 recombinase system, or using a replicating/maintained piece of DNA (such as one derived from Epstein-Barr virus).

In order to select for cell lines which stably maintain the nucleic acid encoding the tRNA and/or aminoacyl-tRNA synthetase and/or are efficient at incorporating UAAs into a protein of interest, a selectable marker can be used. Exemplary selectable markers include zeocin, puromycin, neomycin, dihydrofolate reductase (DHFR), glutamine synthetase (GS), mCherry-EGFP fusion, or other fluorescent proteins. In certain embodiments, a gene encoding a selectable marker protein (or a gene encoding a protein required for a detectable function, e.g., viability, in the presence of the selectable marker) may include a premature stop codon, such that the protein will only be expressed if the cell line is capable of incorporating a UAA at the site of the premature stop codon.

In certain embodiments, to develop a host cell or cell line including two or more tRNA/aminoacyl-tRNA synthetase pairs, one can use multiple identical or distinct UAA directing codons in order to identify host cells or cell lines which have incorporated multiple copies of the two or more tRNA/aminoacyl-tRNA synthetase pairs through iterative rounds of genomic integration and selection. Host cells or cell lines which contain enhanced UAA incorporation efficiency, low background, and decreased toxicity can first be isolated via a selectable marker containing one or more stop codons. Subsequently, the host cells or cell lines can be subjected to a selection scheme to identify host cells or cell lines which contain the desired copies of tRNA/aminoacyl-tRNA synthetase pairs and express a gene of interest (either genomically integrated or not) containing one or more stop codons. Protein expression may be assayed using any method known in the art, including for example, Western blot using an antibody that binds the protein of interest or a C-terminal tag.

The host cells or cell lines be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) Culture of Animal Cells, a Manual of Basic Technique, third edition, Wiley-Liss, New York; Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg N.Y.) and Atlas and Parks (eds.) The Handbook of Microbiological Media (1993) CRC Press, Boca Raton, Fla.

The production of an exemplary cell line capable of producing antibodies incorporating a UAA is described in Roy et al. (2020) MABS 12(1), e1684749).

VI. Proteins Including Unnatural Amino Acids (UAAs) and Methods of Making the Same Also encompassed by the invention are proteins including unnatural amino acids (UAAs) and methods of making the same.

The incorporation of an unnatural amino acid can be done for a variety of purposes, including tailoring changes in protein structure and/or function, changing size, acidity, nucleophilicity, hydrogen bonding, hydrophobicity, accessibility of protease target sites, targeting to a moiety (e.g., for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: toxicity, biodistribution, structural properties, spectroscopic properties, chemical and/or photochemical properties, catalytic ability, half-life (including but not limited to, serum half-life), ability to react with other molecules, including but not limited to, covalently or noncovalently, and the like. The compositions including proteins that include at least one unnatural amino acid are useful for, including but not limited to, novel therapeutics, diagnostics, enzymes, and binding proteins (e.g., therapeutic antibodies).

A protein may have at least one, for example, at least two, at least three, at least four, at least five, at least six, at least seven, at least eight, at least nine, or at least ten or more UAAs. The UAAs can be the same or different. For example, there can be 1, 2, 3, 4, 5, 6, 7, 8, 9, or 10 or more different sites in the protein that comprise 1, 2, 3, 4, 5, 6, 7, 8, 9, or 10 or more different UAAs. A protein may have at least one, but fewer than all, of a particular amino acid present in the protein substituted with the UAA. For a given protein with more than one UAA, the UAA can be identical or different (for example, the protein can include two or more different types of UAAs, or can include two of the same UAA). For a given protein with more than two UAAs, the UAAs can be the same, different or a combination of a multiple unnatural amino acid of the same kind with at least one different UAA.

In certain embodiments, the protein is an antibody (or a fragment thereof, e.g., an antigen-binding fragment thereof), bispecific antibody, nanobody, affibody, viral protein, chemokine, cytokine, antigen, blood coagulation factor, hormone, growth factor, enzyme, cell signaling protein, or any other polypeptide or protein.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. Examples of antigen-binding fragments include Fab, Fab', (Fab')$_2$, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

Typically, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$) and one constant region ($C_L$). The heavy chain consists of one variable region ($V_H$) and at least three constant regions (CH$_1$, CH$_2$ and CH$_3$). The variable regions determine the binding specificity of the antibody.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been defined (Kabat, E. A., et al. (1991) SEQUENCES OF PROTEINS OF IMMUNOLOGICAL INTEREST, FIFTH EDITION, U.S. Department of Health and Human Services, NIH Publication No. 91-3242; and Chothia, C. et al. (1987) J. MOL. BIOL. 196:901-917). Each VH and VL is typically composed of three CDRs and four FRs, arranged from amino-terminus to carboxyl-terminus in the following order: FR1, CDR1, FR2, CDR2, FR3, CDR3, and FR4.

An antibody molecule may have (i) a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4, and/or (ii) a light chain constant region chosen from, e.g., the (e.g., human) light chain constant regions of kappa or lambda.

In certain embodiments, an UAA, e.g., a first and/or second UAA, is located in a heavy chain or light chain constant region of an antibody. For example, in certain embodiments, a protein comprising a first and/or second UAA is an antibody, or a fragment thereof, comprising a heavy chain constant region of human IgG1 isotype (for example, having the amino acid sequence of SEQ ID NO: 114, or an amino acid sequence having at least 85%, 90%, 95%, 96%, 97%, 98%, or 99% sequence identity to SEQ ID NO: 114) and the first and/or second UAA is located within the heavy chain constant region of human IgG1 isotype (for example, at a position corresponding to the threonine at position 78 of SEQ ID NO: 114). In certain embodiments, a protein comprising a first and/or second UAA is an antibody, or a fragment thereof, comprising a human kappa constant region (for example, having the amino acid sequence of SEQ ID NO: 115, or an amino acid sequence having at least 85%, 90%, 95%, 96%, 97%, 98%, or 99% sequence identity to SEQ ID NO: 115) and the first and/or second UAA is located within the human kappa constant region.

In certain embodiments, an UAA, e.g., a first and/or second UAA, is located in a framework region, e.g., FR4, of a variable heavy (VH) and/or a variable light (VL) region of an antibody.

In certain embodiments, a protein comprising a first and/or second UAA is an antibody, or a fragment thereof, comprising the amino acid sequence of SEQ ID NO: 116, or an amino acid sequence having at least 85%, 90%, 95%, 96%, 97%, 98%, or 99% sequence identity to SEQ ID NO: 116, and the first and/or second UAA is located within SEQ ID NO: 116 (for example, at a position corresponding to the threonine at position 11 of SEQ ID NO: 116). In certain embodiments, a protein comprising a first and/or second UAA is an antibody, or a fragment thereof, comprising the amino acid sequence of SEQ ID NO: 117, or an amino acid sequence having at least 85%, 90%, 95%, 96%, 97%, 98%, or 99% sequence identity to SEQ ID NO: 117, and the first and/or second UAA is located within SEQ ID NO: 117 (for example, at a position corresponding to the lysine at position 11 of SEQ ID NO: 117).

Additional examples of therapeutic, diagnostic, and other proteins that can be modified to comprise one or more unnatural amino acids are described in U.S. Patent Application Publication Nos. 2003/0082575 and 2005/0009049.

tRNAS, aminoacyl-tRNA synthetases, and/or unnatural amino acids disclosed herein may be used to incorporate an unnatural amino acid into a protein of interest using any appropriate translation system.

The term "translation system" refers to a system including components necessary to incorporate an amino acid into a growing polypeptide chain (protein). Components of a translation system can include, e.g., ribosomes, tRNA's, synthetases, mRNA and the like. Translation systems may be cellular or cell-free, and may be prokaryotic or eukaryotic. For example, translation systems may include, or be derived from, a non-eukaryotic cell, e.g., a bacterium (such as *E. coli*), a eukaryotic cell, e.g., a yeast cell, a mammalian cell, a plant cell, an algae cell, a fungus cell, or an insect cell.

Translation systems include host cells or cell lines, e.g., host cells or cell lines contemplated herein. To express a polypeptide of interest with an unnatural amino acid in a host cell, one may clone a polynucleotide encoding the polypeptide into an expression vector that contains, for example, a promoter to direct transcription, a transcription/translation terminator, and if for a nucleic acid encoding a protein, a ribosome binding site for translational initiation.

Translation systems also include whole cell preparations such as permeabilized cells or cell cultures wherein a desired nucleic acid sequence can be transcribed to mRNA and the mRNA translated. Cell-free translation systems are commercially available and many different types and systems are well-known. Examples of cell-free systems include, but are not limited to, prokaryotic lysates such as *Escherichia coli* lysates, and eukaryotic lysates such as wheat germ extracts, insect cell lysates, rabbit reticulocyte lysates, rabbit oocyte lysates and human cell lysates. Reconstituted translation systems may also be used. Reconstituted translation systems may include mixtures of purified translation factors as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA is translated.

The invention provides methods of expressing a protein containing an unnatural amino acid and methods of producing a protein with one, or more, unnatural amino acids at specified positions in the protein. The methods comprise incubating a translation system (e.g., culturing or growing a host cell or cell line, e.g., a host cell or cell line disclosed herein) under conditions that permit incorporation of the unnatural amino acid into the protein being expressed in the cell. The translation system may be contacted with (e.g. the cell culture medium may be contacted with) one, or more, unnatural amino acids (e.g., leucyl or tryptophanyl analogs) under conditions suitable for incorporation of the one, or more, unnatural amino acids into the protein.

In certain embodiments, the protein is expressed from a nucleic acid sequence comprising a premature stop codon. The translation system (e.g., host cell or cell line) may, for example, contain a leucyl-tRNA synthetase mutein (e.g., a leucyl-tRNA synthetase mutein disclosed herein) capable of charging a suppressor leucyl tRNA (e.g., a suppressor leucyl tRNA disclosed herein) with an unnatural amino acid (e.g., a leucyl analog) which is incorporated into the protein at a position corresponding to the premature stop codon. In certain embodiments, the leucyl suppressor tRNA comprises an anticodon sequence that hybridizes to the premature stop codon and permits the unnatural amino to be incorporated into the protein at the position corresponding to the premature stop codon.

In certain embodiments, the protein is expressed from a nucleic acid sequence comprising a premature stop codon. The translation system (e.g., host cell or cell line) may, for example, contain a tryptophanyl-tRNA synthetase mutein (e.g., a tryptophanyl-tRNA synthetase mutein disclosed herein) capable of charging a suppressor tryptophanyl tRNA (e.g., a suppressor tryptophanyl tRNA disclosed herein) with an unnatural amino acid (e.g., a tryptophan analog) which is incorporated into the protein at a position corresponding to the premature stop codon. In certain embodiments, the tryptophanyl suppressor tRNA comprises an anticodon sequence that hybridizes to the premature stop codon and permits the unnatural amino to be incorporated into the protein at the position corresponding to the premature stop codon.

In certain embodiments, a protein (e.g., a protein containing a UAA, e.g., a first and/or second UAA) is expressed or produced in a eukaryotic cell (e.g., a mammalian cell). Features may distinguish proteins produced in prokaryotic cells (e.g., bacteria) from those produced in eukaryotic cells (e.g., mammalian cells). For example, proteins produced in mammalian cells may undergo post-translational modifications, e.g., modifications that are dependent upon enzymes located in organelles, e.g., the endoplasmic reticulum or Golgi apparatus. For example, disulfide bond formation in the endoplasmic reticulum may influence protein conformation and/or stabilization. Additional examples of such post-translational modifications include, without limitation, sulfation, amidation, palmitation, and glycosylation (e.g., N-linked glycosylation and O-linked glycosylation). Accordingly, in certain embodiments, a protein (e.g., a protein containing a UAA, e.g., a first and/or second UAA) comprises one or more post-translational modifications selected from sulfation, amidation, palmitation, and glycosylation (e.g., N-linked glycosylation and O-linked glycosylation).

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a 10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

SEQUENCE LISTING

| SEQ ID NO | Description | Sequence |
|---|---|---|
| 1 | *E. coli* LeuRS | MQEQYRPEEIESKVQLHWDEKRTFEVTEDESKEKYYCLSMLPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDTFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWYYARYTCPQYKEGMLDSEA ANYWLPVDIYIGGIEHAIMHLLYFRFFHKLMRDAGMVNSDEPAKQLL CQGMVLADAFYVGENGERNWVSPVDAIVERDEKGRIVKAKDAAGHE LVYTGMSKMSKSKNNGIDPQVMVERYGADTVRLFMMFASPADMTLEW QESGVEGANRFLKRVWKLVYEHTAKGDVAALNVDALTENQKALRRDV HKTIAKVTDDIGRRQTFNTAIAAIMELMNKLAKAPTDGEQDRALMQE ALLAVVRMLNPFTPHICFTLWQELKGEGDIDNAPWPVADEKAMVEDS TLVVVQVNGKVRAKITVPVDATEEQVRERAGQEHLVAKYLDGVTVRK VIYVPGKLLNLVVGGPV |
| 2 | LeuRS.v1 | MEEQYRPEEIESKVQLHWDKKRTFEVTEDESKEKYYCLSISPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDAFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWIYARYTCPQYKEGMLDSEA ANYWLPVDIAIGGIEHAIMGLLYFRFFHKLMRDAGMVNSDEPAKQLL CQGMVLADAFYVGENGERNWVSPVDAIVERDEKGRIVKAKDAAGHE LVYTGMSKMSKSKNNGIDPQVMVERYGADTVRLFMMFASPADMTLEW QESGVEGANRFLKRVWKLVYEHTAKGDVAALNVDALTENQKALRRDV HKTIAKVTDDIGRRQTFNTAIAAIMELMNKLAKAPTDGEQDRALMQE ALLAVVRMLNPFTPHICFTLWQELKGEGDIDNAPWPVADEKAMVEDS TLVVVQVNGKVRAKITVPVDATEEQVRERAGQEHLVAKYLDGVTVRK VIYVPGKLLNLVVGGPV |
| 3 | LeuRS.v2 | MEEQYRPEEIESKVQLHWDKKRTFEVTEDESKEKYYCLSVSPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDRFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS |

-continued

| | | |
|---|---|---|
| SEQUENCE LISTING | | |

| SEQ ID NO | Description | Sequence |
|---|---|---|
| | | RQRYWGAPIPMVTLEDGTVMPTPDDQLPVILPEDVVMDGITSPIKAD<br>PEWAKTTVNGMPALRETDTFDTFMESSWSYARYTCPQYKEGMLDSEA<br>ANYWLPVDILIGGIEHAIMGLLYFRFFHKLMRDAGMVNSDEPAKQLL<br>CQGMVLADAFYYVGENGERNWVSPVDAIVERDEKGRIVKAKDAAGHE<br>LVYTGMSKMSKSKNNGIDPQVMVERYGADTVRLFMMFASPADMTLEW<br>QESGVEGANRFLKRVWKLVYEHTAKGDVAALNVDALTENQKALRRDV<br>HKTIAKVTDDIGRRQTFNTAIAAIMELMNKLAKAPTDGEQDRALMQE<br>ALLAVVRMLNPFTPHICFTLWQELKGEGDIDNAPWPVADEKAMVEDS<br>TLVVVQVNGKVRAKITVPVDATEEQVRERAGQEHLVAKYLDGVTVRK<br>VIYVPGKLLNLVVGGPV |
| 4 | LeuRS.v3 | MEEQYRPEEIESKVQLHWDEKRTFEVTEDESKEKYYCLSILPYPSGR<br>LHMGHVRNYTIGDVIARYQRMLGKNVLQPIGWDAFGLPAEGAAVKNN<br>TAPAPWTYDNIAYMKNQLKMLGFGYDWSRELATCTPEYYRWEQKFFT<br>ELYKKGLVYKKTSAVNWCPNDQTVLANEQVIDGCCWRCDTKVERKEI<br>PQWFIKITAYADELLNDLDKLDHWPDTVKTMQRNWIGRSEGVEITFN<br>VNDYDNTLTVYTTRPDAFMGCTYLAVAAGHPLAQKAAENNPELAAFI<br>DECRNTKVAEAEMATMEKKGVDTGFKAVHPLTGEEIPVWAANFVLME<br>YGTGAVMAVPGHDQRDYEFASKYGLNIKPVILAADGSEPDLSQQALT<br>EKGVLFNSGEFNGLDHEAAFNAIADKLTAMGVGERKVNYRLRDWGVS<br>RQRYWGAPIPMVTLEDGTVMPTPDDQLPVILPEDVVMDGITSPIKAD<br>PEWAKTTVNGMPALRETDTFDTFMESSWIYARYTCPQYKEGMLDSEA<br>ANYWLPVDIAIGGIEHAIMGLLYFRFFHKLMRDAGMVNSDEPAKQLL<br>CQGMVLADAFYYVGENGERNWVSPVDAIVERDEKGRIVKAKDAAGHE<br>LVYTGMSKMSKSKNNGIDPQVMVERYGADTVRLFMMFASPADMTLEW<br>QESGVEGANRFLKRVWKLVYEHTAKGDVAALNVDALTENQKALRRDV<br>HKTIAKVTDDIGRRQTFNTAIAAIMELMNKLAKAPTDGEQDRALMQE<br>ALLAVVRMLNPFTPHICFTLWQELKGEGDIDNAPWPVADEKAMVEDS<br>TLVVVQVNGKVRAKITVPVDATEEQVRERAGQEHLVAKYLDGVTVRK<br>VIYVPGKLLNLVVGGPV |
| 5 | V9 | MEEQYRPEEIESKVQLHWDMKRTFEVTEDESKEKYYCLSISPYPSGR<br>LHMGHVRNYTIGDVIARYQRMLGKNVLQPIGWDAFGLPAEGAAVKNN<br>TAPAPWTYDNIAYMKNQLKMLGFGYDWSRELATCTPEYYRWEQKFFT<br>ELYKKGLVYKKTSAVNWCPNDQTVLANEQVIDGCCWRCDTKVERKEI<br>PQWFIKITAYADELLNDLDKLDHWPDTVKTMQRNWIGRSEGVEITFN<br>VNDYDNTLTVYTTRPDAFMGCTYLAVAAGHPLAQKAAENNPELAAFI<br>DECRNTKVAEAEMATMEKKGVDTGFKAVHPLTGEEIPVWAANFVLME<br>YGTGAVMAVPGHDQRDYEFASKYGLNIKPVILAADGSEPDLSQQALT<br>EKGVLFNSGEFNGLDHEAAFNAIADKLTAMGVGERKVNYRLRDWGVS<br>RQRYWGAPIPMVTLEDGTVMPTPDDQLPVILPEDVVMDGITSPIKAD<br>PEWAKTTVNGMPALRETDTFDTFMESSWIYARYTCPQYKEGMLDSEA<br>ANYWLPVDIAIGGIEHAIMGLLYFRFFHKLMRDAGMVNSDEPAKQLL<br>CQGMVLADAFYYVGENGERNWVSPVDAIVERDEKGRIVKAKDAAGHE<br>LVYTGMSKMSKSKNNGIDPQVMVERYGADTVRLFMMFASPADMTLEW<br>QESGVEGANRFLKRVWKLVYEHTAKGDVAALNVDALTENQKALRRDV<br>HKTIAKVTDDIGRRQTFNTAIAAIMELMNKLAKAPTDGEQDRALMQE<br>ALLAVVRMLNPFTPHICFTLWQELKGEGDIDNAPWPVADEKAMVEDS<br>TLVVVQVNGKVRAKITVPVDATEEQVRERAGQEHLVAKYLDGVTVRK<br>VIYVPGKLLNLVVGGPV |
| 6 | V10 | MEEQYRPEEIESKVQLHWDVKRTFEVTEDESKEKYYCLSISPYPSGR<br>LHMGHVRNYTIGDVIARYQRMLGKNVLQPIGWDAFGLPAEGAAVKNN<br>TAPAPWTYDNIAYMKNQLKMLGFGYDWSRELATCTPEYYRWEQKFFT<br>ELYKKGLVYKKTSAVNWCPNDQTVLANEQVIDGCCWRCDTKVERKEI<br>PQWFIKITAYADELLNDLDKLDHWPDTVKTMQRNWIGRSEGVEITFN<br>VNDYDNTLTVYTTRPDAFMGCTYLAVAAGHPLAQKAAENNPELAAFI<br>DECRNTKVAEAEMATMEKKGVDTGFKAVHPLTGEEIPVWAANFVLME<br>YGTGAVMAVPGHDQRDYEFASKYGLNIKPVILAADGSEPDLSQQALT<br>EKGVLFNSGEFNGLDHEAAFNAIADKLTAMGVGERKVNYRLRDWGVS<br>RQRYWGAPIPMVTLEDGTVMPTPDDQLPVILPEDVVMDGITSPIKAD<br>PEWAKTTVNGMPALRETDTFDTFMESSWIYARYTCPQYKEGMLDSEA<br>ANYWLPVDIAIGGIEHAIMGLLYFRFFHKLMRDAGMVNSDEPAKQLL<br>CQGMVLADAFYYVGENGERNWVSPVDAIVERDEKGRIVKAKDAAGHE<br>LVYTGMSKMSKSKNNGIDPQVMVERYGADTVRLFMMFASPADMTLEW<br>QESGVEGANRFLKRVWKLVYEHTAKGDVAALNVDALTENQKALRRDV<br>HKTIAKVTDDIGRRQTFNTAIAAIMELMNKLAKAPTDGEQDRALMQE<br>ALLAVVRMLNPFTPHICFTLWQELKGEGDIDNAPWPVADEKAMVEDS<br>TLVVVQVNGKVRAKITVPVDATEEQVRERAGQEHLVAKYLDGVTVRK<br>VIYVPGKLLNLVVGGPV |

-continued

| SEQUENCE LISTING | | |
|---|---|---|
| SEQ ID NO | Description | Sequence |
| 7 | V26 | MEEQYRPEEIESKVQLHWDKKRTFEVTEDESKEKYYCLSIVPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDAFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWIYARYTCPQYKEGMLDSEA ANYWLPVDIAIGGIEHAIMGLLYFRFFHKLMRDAGMVNSDEPAKQLL CQGMVLADAFYYVGENGERNWVSPVDAIVERDEKGRIVKAKDAAGHE LVYTGMSKMSKSKNNGIDPQVMVERYGADTVRLFMMFASPADMTLEW QESGVEGANRFLKRVWKLVYEHTAKGDVAALNVDALTENQKALRRDV HKTIAKVTDDIGRRQTFNTAIAAIMELMNKLAKAPTDGEQDRALMQE ALLAVVRMLNPFTPHICFTLWQELKGEGDIDNAPWPVADEKAMVEDS TLVVVQVNGKVRAKITVPVDATEEQVRERAGQEHLVAKYLDGVTVRK VIYVPGKLLNLVVGGPV |
| 8 | V29 | MEEQYRPEEIESKVQLHWDKKRTFEVTEDESKEKYYCLSIAPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDAFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWIYARYTCPQYKEGMLDSEA ANYWLPVDIAIGGIEHAIMGLLYFRFFHKLMRDAGMVNSDEPAKQLL CQGMVLADAFYYVGENGERNWVSPVDAIVERDEKGRIVKAKDAAGHE LVYTGMSKMSKSKNNGIDPQVMVERYGADTVRLFMMFASPADMTLEW QESGVEGANRFLKRVWKLVYEHTAKGDVAALNVDALTENQKALRRDV HKTIAKVTDDIGRRQTFNTAIAAIMELMNKLAKAPTDGEQDRALMQE ALLAVVRMLNPFTPHICFTLWQELKGEGDIDNAPWPVADEKAMVEDS TLVVVQVNGKVRAKITVPVDATEEQVRERAGQEHLVAKYLDGVTVRK VIYVPGKLLNLVVGGPV |
| 9 | V48 | MEEQYRPEEIESKVQLHWDkKRTFEVTEDESKEKYYCLSISPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDAFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWAYARYTCPQYKEGMLDSEA ANYWLPVDIAIGGIEHAIMGLLYFRFFHKLMRDAGMVNSDEPAKQLL CQGMVLADAFYYVGENGERNWVSPVDAIVERDEKGRIVKAKDAAGHE LVYTGMSKMSKSKNNGIDPQVMVERYGADTVRLFMMFASPADMTLEW QESGVEGANRFKRVWKLVYEHTAKGDVAALNVDALTENQKALRRDVH KTIAKVTDDIGRRQTFNTAIAAIMELMNKLAKAPTDGEQDRALMQEA LLAVVRMLNPFTPHICFTLWQELKGEGDIDNAPWPVADEKAMVEDST LVVVQVNGKVRAKITVPVDATEEQVRERAGQEHLVAKYLDGVTVRKV IYVPGKLLNLVVGGPV |
| 10 | V50 | MEEQYRPEEIESKVQLHWDkKRTFEVTEDESKEKYYCLSISPYPSGR LHMGHVRNYTIGDVIARYQRMLGKNVLQPIGWDAFGLPAEGAAVKNN TAPAPWTYDNIAYMKNQLKMLGFGYDWSRELATCTPEYYRWEQKFFT ELYKKGLVYKKTSAVNWCPNDQTVLANEQVIDGCCWRCDTKVERKEI PQWFIKITAYADELLNDLDKLDHWPDTVKTMQRNWIGRSEGVEITFN VNDYDNTLTVYTTRPDAFMGCTYLAVAAGHPLAQKAAENNPELAAFI DECRNTKVAEAEMATMEKKGVDTGFKAVHPLTGEEIPVWAANFVLME YGTGAVMAVPGHDQRDYEFASKYGLNIKPVILAADGSEPDLSQQALT EKGVLFNSGEFNGLDHEAAFNAIADKLTAMGVGERKVNYRLRDWGVS RQRYWGAPIPMVTLEDGTVMPTPDDQLPVILPEDVVMDGITSPIKAD PEWAKTTVNGMPALRETDTFDTFMESSWHYARYTCPQYKEGMLDSEA ANYWLPVDIAIGGIEHAIMGLLYFRFFHKLMRDAGMVNSDEPAKQLL |

| SEQUENCE LISTING | | |
|---|---|---|
| SEQ ID NO | Description | Sequence |

CQGMVLADAFYYVGENGERNWVSPVDAIVERDEKGRIVKAKDAAGHE
LVYTGMSKMSKSKNNGIDPQVMVERYGADTVRLEMMFASPADMTLEW
QESGVEGANRFLKRVWKLVYEHTAKGDVAALNVDALTENQKALRRDV
HKTIAKVTDDIGRRQTFNTAIAAIMELMNKLAKAPTDGEQDRALMQE
ALLAVVRMLNPFTPHICFTLWQELKGEGDIDNAPWPVADEKAMVEDS
TLVVVQVNGKVRAKITVPVDATEEQVRERAGQEHLVAKYLDGVTVRK
VIYVPGKLLNLVVGGPV

11    V54    MEEQYRPEEIESKVQLHWDkKRTFEVTEDESKEKYYCLSISPYPSGR
LHMGHVRNYTIGDVIARYQRMLGKNVLQPIGWDAFGLPAEGAAVKNN
TAPAPWTYDNIAYMKNQLKMLGFGYDWSRELATCTPEYYRWEQKFFT
ELYKKGLVYKKTSAVNWCPNDQTVLANEQVIDGCCWRCDTKVERKEI
PQWFIKITAYADELLNDLDKLDHWPDTVKTMQRNWIGRSEGVEITFN
VNDYDNTLTVYTTRPDAFMGCTYLAVAAGHPLAQKAAENNPELAAFI
DECRNTKVAEAEMATMEKKGVDTGFKAVHPLTGEEIPVWAANFVLME
YGTGAVMAVPGHDQRDYEFASKYGLNIKPVILAADGSEPDLSQQALT
EKGVLFNSGEFNGLDHEAAFNAIADKLTAMGVGERKVNYRLRDWGVS
RQRYWGAPIPMVTLEDGTVMPTPDDQLPVILPEDVVMDGITSPIKAD
PEWAKTTVNGMPALRETDTFDTFMESSWIYARYTCPQYKEGMLDSEA
ANYWLPVDIIIGGIEHAIMGLLYFRFFHKLMRDAGMVNSDEPAKQLL
CQGMVLADAFYYVGENGERNWVSPVDAIVERDEKGRIVKAKDAAGHE
LVYTGMSKMSKSKNNGIDPQVMVERYGADTVRLFMMFASPADMTLEW
QESGVEGANRFLKRVWKLVYEHTAKGDVAALNVDALTENQKALRRDV
HKTIAKVTDDIGRRQTFNTAIAAIMELMNKLAKAPTDGEQDRALMQE
ALLAVVRMLNPFTPHICFTLWQELKGEGDIDNAPWPVADEKAMVEDS
TLVVVQVNGKVRAKITVPVDATEEQVRERAGQEHLVAKYLDGVTVRK
VIYVPGKLLNLVVGGPV

12    V55    MEEQYRPEEIESKVQLHWDKKRTFEVTEDESKEKYYCLSISPYPSGR
LHMGHVRNYTIGDVIARYQRMLGKNVLQPIGWDAFGLPAEGAAVKNN
TAPAPWTYDNIAYMKNQLKMLGFGYDWSRELATCTPEYYRWEQKFFT
ELYKKGLVYKKTSAVNWCPNDQTVLANEQVIDGCCWRCDTKVERKEI
PQWFIKITAYADELLNDLDKLDHWPDTVKTMQRNWIGRSEGVEITFN
VNDYDNTLTVYTTRPDAFMGCTYLAVAAGHPLAQKAAENNPELAAFI
DECRNTKVAEAEMATMEKKGVDTGFKAVHPLTGEEIPVWAANFVLME
YGTGAVMAVPGHDQRDYEFASKYGLNIKPVILAADGSEPDLSQQALT
EKGVLFNSGEFNGLDHEAAFNAIADKLTAMGVGERKVNYRLRDWGVS
RQRYWGAPIPMVTLEDGTVMPTPDDQLPVILPEDVVMDGITSPIKAD
PEWAKTTVNGMPALRETDTFDTFMESSWIYARYTCPQYKEGMLDSEA
ANYWLPVDIVIGGIEHAIMGLLYFRFFHKLMRDAGMVNSDEPAKQLL
CQGMVLADAFYYVGENGERNWVSPVDAIVERDEKGRIVKAKDAAGHE
LVYTGMSKMSKSKNNGIDPQVMVERYGADTVRLFMMFASPADMTLEW
QESGVEGANRFLKRVWKLVYEHTAKGDVAALNVDALTENQKALRRDV
HKTIAKVTDDIGRRQTFNTAIAAIMELMNKLAKAPTDGEQDRALMQE
ALLAVVRMLNPFTPHICFTLWQELKGEGDIDNAPWPVADEKAMVEDS
TLVVVQVNGKVRAKITVPVDATEEQVRERAGQEHLVAKYLDGVTVRK
VIYVPGKLLNLVVGGPV

13    V56    MEEQYRPEEIESKVQLHWDKKRTFEVTEDESKEKYYCLSISPYPSGR
LHMGHVRNYTIGDVIARYQRMLGKNVLQPIGWDAFGLPAEGAAVKNN
TAPAPWTYDNIAYMKNQLKMLGFGYDWSRELATCTPEYYRWEQKFFT
ELYKKGLVYKKTSAVNWCPNDQTVLANEQVIDGCCWRCDTKVERKEI
PQWFIKITAYADELLNDLDKLDHWPDTVKTMQRNWIGRSEGVEITFN
VNDYDNTLTVYTTRPDAFMGCTYLAVAAGHPLAQKAAENNPELAAFI
DECRNTKVAEAEMATMEKKGVDTGFKAVHPLTGEEIPVWAANFVLME
YGTGAVMAVPGHDQRDYEFASKYGLNIKPVILAADGSEPDLSQQALT
EKGVLFNSGEFNGLDHEAAFNAIADKLTAMGVGERKVNYRLRDWGVS
RQRYWGAPIPMVTLEDGTVMPTPDDQLPVILPEDVVMDGITSPIKAD
PEWAKTTVNGMPALRETDTFDTFMESSWIYARYTCPQYKEGMLDSEA
ANYWLPVDIGIGGIEHAIMGLLYFRFFHKLMRDAGMVNSDEPAKQLL
CQGMVLADAFYYVGENGERNWVSPVDAIVERDEKGRIVKAKDAAGHE
LVYTGMSKMSKSKNNGIDPQVMVERYGADTVRLFMMFASPADMTLEW
QESGVEGANRFLKRVWKLVYEHTAKGDVAALNVDALTENQKALRRDV
HKTIAKVTDDIGRRQTFNTAIAAIMELMNKLAKAPTDGEQDRALMQE
ALLAVVRMLNPFTPHICFTLWQELKGEGDIDNAPWPVADEKAMVEDS
TLVVVQVNGKVRAKITVPVDATEEQVRERAGQEHLVAKYLDGVTVRK
VIYVPGKLLNLVVGGPV

14    $MX_2EQYRPEEIESKVQLHWDX_{20}KRTFEVTEDESKEKYYCLSX_{40}X_{41}P$
YPSGRLHMGHVRNYTIGDVIARYQRMLGKNVLQPIGWDAFGLPAEGA
AVKNNTAPAPWTYDNIAYMKNQLKMLGFGYDWSRELATCTPEYYRWE
QKFFTELYKKGLVYKKTSAVNWCPNDQTVLANEQVIDGCCWRCDTKV
ERKEIPQWFIKITAYADELLNDLDKLDHWPDTVKTMQRNWIGRSEGV

-continued

| SEQUENCE LISTING | | |
|---|---|---|

| SEQ ID NO | Description | Sequence |
|---|---|---|
| | | EITFNVNDYDNTLTVYTTRPDX$_{252}$FMGCTYLAVAAGHPLAQKAAENN PELAAFIDECRNTKVAEAEMATMEKKGVDTGFKAVHPLTGEEIPVWA ANFVLMEYGTGAVMAVPGHDQRDYEFASKYGLNIKPVILAADGSEPD LSQQALTEKGVLFNSGEFNGLDHEAAFNAIADKLTAMGVGERKVNYR LRDWGVSRQRYWGAPIPMVTLEDGTVMPTPDDQLPVILPEDVVMDGI TSPIKADPEWAKTTVNGMPALRETDTFDTFMESSWX$_{499}$YARYTCPQY KEGMLDSEAANYWLPVDIX$_{527}$IGGIEHAIMX$_{537}$LLYFRFFHKLMRDA GMVNSDEPAKQLLCQGMVLADAFYYVGENGERNWVSPVDAIVERDEK GRIVKAKDAAGHELVYTGMSKMSKSKNNGIDPQVMVERYGADTVRLF MMFASPADMTLEWQESGVEGANRFLKRVWKLVYEHTAKGDVAALNVD ALTENQKALRRDVHKTIAKVTDDIGRRQTFNTAIAAIMELMNKLAKA PTDGEQDRALMQEALLAVVRMLNPFTPHICFTLWQELKGEGDIDNAP WPVADEKAMVEDSTLVVVQVNGKVRAKITVPVDATEEQVRERAGQEH LVAKYLDGVTVRKVIYVPGKLLNLVVGGPV wherein X$_2$ is Q or E, X$_{20}$ is E, K, V or M, X$_{40}$ is M, I, or V, X$_{41}$ is L, S, V, or A, X$_{252}$ is T, A, or R, X$_{499}$ is Y, A, I, H, or S, X$_{527}$ is Y, A, I, L, or V, and X$_{537}$ is H or G |
| 15 | | MEEQYRPEEIESKVQLHWDX$_{20}$KRTFEVTEDESKEKYYCLSIX$_{41}$PYP SGRLHMGHVRNYTIGDVIARYQRMLGKNVLQPIGWDAFGLPAEGAAV KNNTAPAPWTYDNIAYMKNQLKMLGFGYDWSRELATCTPEYYRWEQK FFTELYKKGLVYKKTSAVNWCPNDQTVLANEQVIDGCCWRCDTKVER KEIPQWFIKITAYADELLNDLDKLDHWPDTVKTMQRNWIGRSEGVEI TFNVNDYDNTLTVYTTRPDAFMGCTYLAVAAGHPLAQKAAENNPELA AFIDECRNTKVAEAEMATMEKKGVDTGFKAVHPLTGEEIPVWAANFV LMEYGTGAVMAVPGHDQRDYEFASKYGLNIKPVILAADGSEPDLSQQ ALTEKGVLFNSGEFNGLDHEAAFNAIADKLTAMGVGERKVNYRLRDW GVSRQRYWGAPIPMVTLEDGTVMPTPDDQLPVILPEDVVMDGITSPI KADPEWAKTTVNGMPALRETDTFDTFMESSWX$_{499}$YARYTCPQYKEGM LDSEAANYWLPVDIX$_{527}$IGGIEHAIMGLLYFRFFHKLMRDAGMVNSD EPAKQLLCQGMVLADAFYYVGENGERNWVSPVDAIVERDEKGRIVKA KDAAGHELVYTGMSKMSKSKNNGIDPQVMVERYGADTVRLFMMFASP ADMTLEWQESGVEGANRFLKRVWKLVYEHTAKGDVAALNVDALTENQ KALRRDVHKTIAKVTDDIGRRQTFNTAIAAIMELMNKLAKAPTDGEQ DRALMQEALLAVVRMLNPFTPHICFTLWQELKGEGDIDNAPWPVADE KAMVEDSTLVVVQVNGKVRAKITVPVDATEEQVRERAGQEHLVAKYL DGVTVRKVIYVPGKLLNLVVGGPV wherein X$_{20}$ is K, V or M, X$_{41}$ is S, V, or A, X$_{499}$ is A, I, or H, and X$_{527}$ is A, I, or V |
| 16 | Leu-tRNA. wtCUA | GCCCGGATGGTGGAATCGGTAGACACAAGGGATTctaAATCCCTCGG CGTTCGCGCTGTGCGGGTTCAAGTCCCGCTCCGGGtA |
| 17 | Leu-tRNA. wtUCA | GCCCGGATGGTGGAATCGGTAGACACAAGGGATTtcaAATCCCTCGG CGTTCGCGCTGTGCGGGTTCAAGTCCCGCTCCGGGtA |
| 18 | Leu-tRNA. wtUUA | GCCCGGATGGTGGAATCGGTAGACACAAGGGATTttaAATCCCTCGG CGTTCGCGCTGTGCGGGTTCAAGTCCCGCTCCGGGtA |
| 19 | Leu-tRNA. h1CUA | GCCCGGATGGTGGAATCGGTAGACACAAGGGACTctaAATCCCTCGG CGTTCGCGCTGTGCGGGTTCAAGTCCCGCTCCGGGcA |
| 20 | Leu-tRNA. h1UCA | GCCCGGATGGTGGAATCGGTAGACACAAGGGACTtcaAATCCCTCGG CGTTCGCGCTGTGCGGGTTCAAGTCCCGCTCCGGGcA |
| 21 | Leu-tRNA. h1UUA | GCCCGGATGGTGGAATCGGTAGACACAAGGGACTttaAATCCCTCGG CGTTCGCGCTGTGCGGGTTCAAGTCCCGCTCCGGGcA |
| 22 | Leu-tRNA. wtCUA_cca | GCCCGGATGGTGGAATCGGTAGACACAAGGGATTctaAATCCCTCGG CGTTCGCGCTGTGCGGGTTCAAGTCCCGCTCCGGGtACCA |
| 23 | Leu-tRNA. wtUCA_cca | GCCCGGATGGTGGAATCGGTAGACACAAGGGATTtcaAATCCCTCGG CGTTCGCGCTGTGCGGGTTCAAGTCCCGCTCCGGGtACCA |

-continued

| SEQ ID NO | Description | Sequence |
|---|---|---|
| 24 | Leu-tRNA.wtUUA_cca | GCCCGGATGGTGGAATCGGTAGACACAAGGGGATTttaAATCCCTCGG<br>CGTTCGCGCTGTGCGGGTTCAAGTCCCGCTCCGGGtACCA |
| 25 | Leu-tRNA.h1CUA_cca | GCCCGGATGGTGGAATCGGTAGACACAAGGGGACTctaAATCCCTCGG<br>CGTTCGCGCTGTGCGGGTTCAAGTCCCGCTCCGGGcACCA |
| 26 | Leu-tRNA.h1UCA_cca | GCCCGGATGGTGGAATCGGTAGACACAAGGGGACTtcaAATCCCTCGG<br>CGTTCGCGCTGTGCGGGTTCAAGTCCCGCTCCGGGcACCA |
| 27 | Leu-tRNA.h1UUA_cca | GCCCGGATGGTGGAATCGGTAGACACAAGGGGACTttaAATCCCTCGG<br>CGTTCGCGCTGTGCGGGTTCAAGTCCCGCTCCGGGcACCA |
| 28 | Leu-tRNA.003.30 | GCCCGGATGGTGGAATCGGTAGACACAAGGGGACTnnnAATCCCTCGG<br>CGTTCGCGCTGTGCGGGTTCAAGTCCCGCTCCGGGCACCA<br>wherein nnn is CTA, TCA, or TTA |
| 29 | Leu-tRNA.003.31 | GGGCGTGTGGTGGAATCGGTAGACACAAGGGGATTnnnAATCCCTCGG<br>CGTTCGCGCTGTGCGGGTTCAAGTCCCGCCGCGCCCACCA<br>wherein nnn is CTA, TCA, or TTA |
| 30 | Leu-tRNA.003.32 | GGGCGCGTGGTGGAATCGGTAGACACAAGGGGATTnnnAATCCCTCGG<br>CGTTCGCGCTGTGCGGGTTCAAGTCCCGCCGCGCCCACCA<br>wherein nnn is CTA, TCA, or TTA |
| 31 | Leu-tRNA.003.33 | GGGCATGTGGTGGAATCGGTAGACACAAGGGGATTnnnAATCCCTCGG<br>CGTTCGCGCTGTGCGGGTTCAAGTCCCGCCATGCCCACCA<br>wherein nnn is CTA, TCA, or TTA |
| 32 | Leu-tRNA.003.34 | GGGCACGTGGTGGAATCGGTAGACACAAGGGGATTnnnAATCCCTCGG<br>CGTTCGCGCTGTGCGGGTTCAAGTCCCGCCGTGCCCACCA<br>wherein nnn is CTA, TCA, or TTA |
| 33 | Leu-tRNA.003.35 | GGGGGTGTGGTGGAATCGGTAGACACAAGGGGATTnnnAATCCCTCGG<br>CGTTCGCGCTGTGCGGGTTCAAGTCCCGCCGCCCCCACCA<br>wherein nnn is CTA, TCA, or TTA |
| 34 | Leu-tRNA.003.36 | GGGGGCGTGGTGGAATCGGTAGACACAAGGGGATTnnnAATCCCTCGG<br>CGTTCGCGCTGTGCGGGTTCAAGTCCCGCCGTCCCCACCA<br>wherein nnn is CTA, TCA, or TTA |
| 35 | Leu-tRNA.003.37 | GGGGATGTGGTGGAATCGGTAGACACAAGGGGATTnnnAATCCCTCGG<br>CGTTCGCGCTGTGCGGGTTCAAGTCCCGCCGTCCCCACCA<br>wherein nnn is CTA, TCA, or TTA |
| 36 | Leu-tRNA.003.38 | GGGGACGTGGTGGAATCGGTAGACACAAGGGGATTnnnAATCCCTCGG<br>CGTTCGCGCTGTGCGGGTTCAAGTCCCGCCGTCCCCACCA<br>wherein nnn is CTA, TCA, or TTA |
| 37 | Leu-tRNA.003.39 | GCCCGTATGGTGGAATCGGTAGACACAAGGGGATTnnnAATCCCTCGG<br>CGTTCGCGCTGTGCGGGTTCAAGTCCCGCTGCGGGCACCA<br>wherein nnn is CTA, TCA, or TTA |
| 38 | Leu-tRNA.003.40 | GGGATAGTGGTGGAATCGGTAGACACAAGGGGATTnnnAATCCCTCGG<br>CGTTCGCGCTGTGCGGGTTCAAGTCCCGCCTATCCCACCA<br>wherein nnn is CTA, TCA, or TTA |
| 39 | Leu-tRNA.003.41 | GGGCATGTGGTGGAATCGGTAGACACAAGGGGATTnnnAATCCCTCGG<br>CGTTCGCGCTGTGCGGGTTCAAGTCCCGCCGTGCCCACCA<br>wherein nnn is CTA, TCA, or TTA |
| 40 | Leu-tRNA.003.42 | GGGCAGATGGTGGAATCGGTAGACACAAGGGGATTnnnAATCCCTCGG<br>CGTTCGCGCTGTGCGGGTTCAAGTCCCGCTCTGCCCACCA<br>wherein nnn is CTA, TCA, or TTA |
| 41 | Leu-tRNA.003.43 | GGGCGTATGGTGGAATCGGTAGACACAAGGGGATTnnnAATCCCTCGG<br>CGTTCGCGCTGTGCGGGTTCAAGTCCCGCTGCGCCCACCA<br>wherein nnn is CTA, TCA, or TTA |

SEQUENCE LISTING

| SEQ ID NO | Description | Sequence |
| --- | --- | --- |
| 42 | Leu-tRNA.003.44 | GGGCAAGTGGTGGAATCGGTAGACACAAGGGATTnnnAATCCCTCGG CGTTCGCGCTGTGCGGGTTCAAGTCCCGCCTTGCCCACCA wherein nnn is CTA, TCA, or TTA |
| 43 | Leu-tRNA.003.45 | GCACACATGGTGGAATCGGTAGACACAAGGGATTnnnAATCCCTCGG CGTTCGCGCTGTGCGGGTTCAAGTCCCGCTGTGTGCACCA wherein nnn is CTA, TCA, or TTA |
| 44 | *E. coli* TrpRS.wt | MTKPIVFSGAQPSGELTIGNYMGALRQWVNMQDDYHCIYCIVDQHAI TVRQDAQKLRKATLDTLALYLACGIDPEKSTIFVQSHVPEHAQLGWA LNCVPVGEDQKQHLELSRDIAQRFNALYGEIFKVPEPFIPKSGARVMS LLEPTKKMSKSDDNRNNVIGLLEDPKSVVKKIKRAVTDSDEPPVVRY DVQNKAGVSNLLDILSAVTGQSIPELEKQFEGKMYGHLKGEVADAVS GMLTELQERYHRFRNDEAFLQQVMKDGAEKASAHASRTLKAVYEAIG FVAKP |
| 45 | TrpRS.h14 | MTKPIVFAGAQPSGELTIGNYMGALRQWVNMQDDYHCIYCIVDQHAI TVRQDAQKLRKATLDTLALYLACGIDPEKSTIFVQSHVPEHAQLGWA LNCYTYFGELSRMTQFKDKSARYAENINAGLFDYPVLMAADILLYQT NLGPCGEDQKQHLELSRDIAQRFNALYGEIFKVPEPFIPKSGARVMS LLEPTKKMSKSDDNRNNVIGLLEDPKSVVKKIKRAVTDSDEPPVVRY DVQNKAGVSNLLDILSAVTGQSIPELEKQFEGKMYGHLKGEVADAVS GMLTELQERYHRFRNDEAFLQQVMKDGAEKASAHASRTLKAVYEAIG FVAKP |
| 46 | TrpRS.h13 | MTKPIVFAGAQPSGELTIGNYMGALRQWVNMQDDYHCIYCIVDQHAI TVRQDAQKLRKATLDTLALYLACGIDPEKSTIFVQSHVPEHAQLGWA LNCYTYFGELSRMTQFKDKSARYAENINAGLFDYPVLMAADILLYQT NLAPAGEDQKQHLELSRDIAQRFNALYGEIFKVPEPFIPKSGARVMS LLEPTKKMSKSDDNRNNVIGLLEDPKSVVKKIKRAVTDSDEPPVVRY DVQNKAGVSNLLDILSAVTGQSIPELEKQFEGKMYGHLKGEVADAVS GMLTELQERYHRFRNDEAFLQQVMKDGAEKASAHASRTLKAVYEAIG FVAKP |
| 47 | TrpRS.h9 | MTKPIVFAGAQPSGELTIGNYMGALRQWVNMQDDYHCIYCIVDQHAI TVRQDAQKLRKATLDTLALYLACGIDPEKSTIFVQSHVPEHAQLGWA LNCYTYFGELSRMTQFKDKSARYAENINAGLFDYPVLMAADILLYQT NLSPAGEDQKQHLELSRDIAQRFNALYGEIFKVPEPFIPKSGARVMS LLEPTKKMSKSDDNRNNVIGLLEDPKSVVKKIKRAVTDSDEPPVVRY DVQNKAGVSNLLDILSAVTGQSIPELEKQFEGKMYGHLKGEVADAVS GMLTELQERYHRFRNDEAFLQQVMKDGAEKASAHASRTLKAVYEAIG FVAKP |
| 48 | TrpRS.h10 | MTKPIVFAGAQPSGELTIGNYMGALRQWVNMQDDYHCIYCIVDQHAI TVRQDAQKLRKATLDTLALYLACGIDPEKSTIFVQSHVPEHAQLGWA LNCYTYFGELSRMTQFKDKSARYAENINAGLFDYPVLMAADILLYQT NLGPAGEDQKQHLELSRDIAQRFNALYGEIFKVPEPFIPKSGARVMS LLEPTKKMSKSDDNRNNVIGLLEDPKSVVKKIKRAVTDSDEPPVVRY DVQNKAGVSNLLDILSAVTGQSIPELEKQFEGKMYGHLKGEVADAVS GMLTELQERYHRFRNDEAFLQQVMKDGAEKASAHASRTLKAVYEAIG FVAKP |
| 49 | *E. coli* Trp-tRNA | AGGGGCGTAGTTCAATTGGTAGAGCACCGGTCTccaAAACCGGGTGT TGGGAGTTCGAGTCTCTCCGCCCCTGCCA |
| 50 | Trp-tRNACUA | AGGGGCGTAGTTCAATTGGTAGAGCACCGGTCTctaAAACCGGGTGT TGGGAGTTCGAGTCTCTCCGCCCCTGCCA |
| 51 | Trp-tRNAUCA | AGGGGCGTAGTTCAATTGGTAGAGCACCGGTCTtcaAAACCGGGTGT TGGGAGTTCGAGTCTCTCCGCCCCTGCCA |
| 52 | Trp-tRNAUUA | AGGGGCGTAGTTCAATTGGTAGAGCACCGGTCTttaAAACCGGGTGT TGGGAGTTCGAGTCTCTCCGCCCCTGCCA |
| 53 | Trp-tRNA.001.4 | TGGGGTATCGCCAAGCGGTAAGGCACCGGATTCnnnTTCCGGCATTC CGAGGTTCGAATCCTCGTACCCCAGCCA wherein nnn is CTA, TCA, or TTA |
| 54 | Trp-tRNA.001.5 | AGGGGCATAGCTCAAGCGGTAAAGCACCGGACTnnnAAACCGGCAGT CCGAAGTTCGAATCCCCCCACCCCAGCCA wherein nnn is CTA, TCA, or TTA |

| SEQ ID NO | Description | Sequence |
|---|---|---|
| | SEQUENCE LISTING | |
| 55 | *E. coli* LeuRS | ATGCAGGAACAGTATCGCCCGGAAGAAATTGAAAGCAAAGTGCAGCT<br>GCATTGGGATGAAAAACGCACCTTTGAAGTGACCGAAGATGAAAGCA<br>AAGAAAAATATTATTGCCTGAGCATGCTGCCGTATCCGAGCGGCCGC<br>CTGCATATGGGCCATGTGCGCAACTATACCATTGGCGATGTGATTGC<br>GCGCTATCAGCGCATGCTGGGCAAAAACGTGCTGCAGCCGATTGGCT<br>GGGATGCGTTTGGCCTGCCGGCGGAAGGCGCGGCGGTGAAAAACAAC<br>ACCGCGCCGGCGCCGTGGACCTATGATAACATTGCGTATATGAAAAA<br>CCAGCTGAAAATGCTGGGCTTTGGCTATGATTGGAGCCGCGAACTGG<br>CGACCTGCACCCCGGAATATTATCGCTGGGAACAGAAATTTTTTACC<br>GAACTGTATAAAAAAGGCCTGGTGTATAAAAAAACCAGCGCGGTGAA<br>CTGGTGCCCGAACGATCAGACCGTGCTGGCGAACGAACAGGTGATTG<br>ATGGCTGCTGCTGGCGCTGCGATACCAAAGTGGAACGCAAAGAAATT<br>CCGCAGTGGTTTATTAAAATTACCGCGTATGCGGATGAACTGCTGAA<br>CGATCTGGATAAACTGGATCATTGGCCGGATACCGTGAAAACCATGC<br>AGCGCAACTGGATTGGCCGCAGCGAAGGCGTGGAAATTACCTTTAAC<br>GTGAACGATTATGATAACACCCTGACCGTGTATACCACCCGCCCGGA<br>TACCTTTATGGGCTGCACCTATCTGGCGGTGGCGGCGGGCCATCCGC<br>TGGCGCAGAAAGCGGCGGAAAACAACCCGGAACTGGCGGCGTTTATT<br>GATGAATGCCGCAACACCAAAGTGGCGGAAGCGGAAATGGCGACCAT<br>GGAAAAAAAAGGCGTGGATACCGGCTTTAAAGCGGTGCATCCGCTGA<br>CCGGCGAAGAAATTCCGGTGTGGGCGGCGAACTTTGTGCTGATGGAA<br>TATGGCACCGGCGCGGTGATGGCGGTGCCGGGCCATGATCAGCGCGA<br>TTATGAATTTGCGAGCAAATATGGCCTGAACATTAAACCGGTGATTC<br>TGGCGGCGGATGGCAGCGAACCGGATCTGAGCCAGCAGGCGCTGACC<br>GAAAAAGGCGTGCTGTTTAACAGCGGCGAATTTAACGGCCTGGATCA<br>TGAAGCGGCGTTTAACGCGATTGCGGATAAACTGACCGCGATGGGCG<br>TGGGCGAACGCAAAGTGAACTATCGCCTGCGCGATTGGGGCGTGAGC<br>CGCCAGCGCTATTGGGGCGCGCCGATTCCGATGGTGACCCTGGAAGA<br>TGGCACCGTGATGCCGACCCCGGATGATCAGCTGCCGGTGATTCTGC<br>CGGAAGATGTGGTGATGGATGGCATTACCAGCCCGATTAAAGCGGAT<br>CCGGAATGGGCGAAAACCACCGTGAACGGCATGCCGGCGCTGCGCGA<br>AACCGATACCTTTGATACCTTTATGGAAAGCAGCTGGTATTATGCGC<br>GCTATACCTGCCCGCAGTATAAAGAAGGCATGCTGGATAGCGAAGCG<br>GCGAACTATTGGCTGCCGGTGGATATTTATATTGGCGGCATTGAACA<br>TGCGATTATGCATCTGCTGTATTTTCGCTTTTTTCATAAACTGATGC<br>GCGATGCGGGCATGGTGAACAGCGATGAACCGGCGAAACAGCTGCTG<br>TGCCAGGGCATGGTGCTGGCGGATGCGTTTTATTATGTGGGCGAAAA<br>CGGCGAACGCAACTGGGTGAGCCCGGTGGATGCGATTGTGGAACGCG<br>ATGAAAAAGGCCGCATTGTGAAAGCGAAAGATGCGGCGGGCCATGAA<br>CTGGTGTATACCGGCATGAGCAAAATGAGCAAAAGCAAAAACAACGG<br>CATTGATCCGCAGGTGATGGTGGAACGCTATGGCGCGGATACCGTGC<br>GCCTGTTTATGATGTTTGCGAGCCCGGCCGGATATGACCCTGGAATGG<br>CAGGAAAGCGGCGTGGAAGGCGCGAACCGCTTTCTGAAACGCGTGTG<br>GAAACTGGTGTATGAACATACCGCGAAAGGCGATGTGGCGGCGCTGA<br>ACGTGGATGCGCTGACCGAAAACCAGAAAGCGCTGCGCCGCGATGTG<br>CATAAAACCATTGCGAAAGTGACCGATGATATTGGCCGCCGCCAGAC<br>CTTTAACACCGCGATTGCGGCGATTATGGAACTGATGAACAAACTGG<br>CGAAAGCGCCGACCGATGGCGAACAGGATCGCGCGCTGATGCAGGAA<br>GCGCTGCTGGCGGTGGTGCGCATGCTGAACCCGTTTACCCCGCATAT<br>TTGCTTTACCCTGTGGCAGGAACTGAAAGGCGAAGGCGATATTGATA<br>ACGCGCCGTGGCCGGTGGCGGATGAAAAAGCGATGGTGGAAGATAGC<br>ACCCTGGTGGTGGTGCAGGTGAACGGCAAAGTGCGCGCGAAAATTAC<br>CGTGCCGGTGGATGCGACCGAAGAACAGGTGCGCGAACGCGCGGGCC<br>AGGAACATCTGGTGGCGAAATATCTGGATGGCGTGACCGTGCGCAAA<br>GTGATTTATGTGCCGGGCAAACTGCTGAACCTGGTGGTGGGCGGCCC<br>GGTG |
| 56 | LeuRS.v1 | ATGGAAGAACAGTATCGCCCGGAAGAAATTGAAAGCAAAGTGCAGCT<br>GCATTGGGATAAAAAACGCACCTTTGAAGTGACCGAAGATGAAAGCA<br>AAGAAAAATATTATTGCCTGAGCATTAGCCCGTATCCGAGCGGCCGC<br>CTGCATATGGGCCATGTGCGCAACTATACCATTGGCGATGTGATTGC<br>GCGCTATCAGCGCATGCTGGGCAAAAACGTGCTGCAGCCGATTGGCT<br>GGGATGCGTTTGGCCTGCCGGCGGAAGGCGCGGCGGTGAAAAACAAC<br>ACCGCGCCGGCGCCGTGGACCTATGATAACATTGCGTATATGAAAAA<br>CCAGCTGAAAATGCTGGGCTTTGGCTATGATTGGAGCCGCGAACTGG<br>CGACCTGCACCCCGGAATATTATCGCTGGGAACAGAAATTTTTTACC<br>GAACTGTATAAAAAAGGCCTGGTGTATAAAAAAACCAGCGCGGTGAA<br>CTGGTGCCCGAACGATCAGACCGTGCTGGCGAACGAACAGGTGATTG<br>ATGGCTGCTGCTGGCGCTGCGATACCAAAGTGGAACGCAAAGAAATT<br>CCGCAGTGGTTTATTAAAATTACCGCGTATGCGGATGAACTGCTGAA<br>CGATCTGGATAAACTGGATCATTGGCCGGATACCGTGAAAACCATGC<br>AGCGCAACTGGATTGGCCGCAGCGAAGGCGTGGAAATTACCTTTAAC |

| SEQUENCE LISTING | | |
|---|---|---|
| SEQ ID NO | Description | Sequence |
| | | GTGAACGATTATGATAACACCCTGACCGTGTATACCACCCGCCCGGA TGCGTTTATGGGCTGCACCTATCTGGCGGTGGCGGCGGGCCATCCGC TGGCGCAGAAAGCGGCGGAAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGGCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGATTTATGCGC GCTATACCTGCCCGCAGTATAAAGAAGGCATGCTGGATAGCGAAGCG GCGAACTATTGGCTGCCGGTGGATATTGCGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGTGCAGGTGAACGGCAAAGTGCGCGCGAAAATTAC CGTGCCGGTGGATGCGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 57 | LeuRS.v2 | ATGGAAGAACAGTATCGCCCGGAAGAAATTGAAAGCAAAGTGCAGCT GCATTGGGATAAAAAACGCACCTTTGAAGTGACCGAAGATGAAAGCA AGAAAAATATTATTGCCTGAGCGTGAGCCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT CCGCAGTGGTTTATTAAAATTACCGCGTATGCGGATGAACTGCTGAA CGATCTGGATAAACTGGATCATTGGCCGGATACCGTGAAAACCATGC AGCGCAACTGGATTGGCCGCAGCGAAGGCGTGGAAATTACCTTTAAC GTGAACGATTATGATAACACCCTGACCGTGTATACCACCCGCCCGGA TCGCTTTATGGGCTGCACCTATCTGGCGGTGGCGGCGGGCCATCCGC TGGCGCAGAAAGCGGCGGAAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGGCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA |

| SEQUENCE LISTING | | |
| --- | --- | --- |
| SEQ ID NO | Description | Sequence |
| | | AACCGATACCTTTGATACCTTTATGGAAAGCAGCTGGAGCTATGCGC GCTATACCTGCCCGCAGTATAAAGAAGGCATGCTGGATAGCGAAGCG GCGAACTATTGGCTGCCGGTGGATATTCTGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGTGCAGGTGAACGGCAAAGTGCGCGCGAAAATTAC CGTGCCGGTGGATGCGGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 58 | LeuRS.v3 | ATGGAAGAACAGTATCGCCCGGAAGAAATTGAAAGCAAAGTGCAGCT GCATTGGGATGAAAAACGCACCTTTGAAGTGACCGAAGATGAAAGCA AAGAAAAATATTATTGCCTGAGCATTCTGCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT CCGCAGTGGTTTATTAAAATTACCGCGTATGCGGATGAACTGCTGAA CGATCTGGATAAACTGGATCATTGGCCGGATACCGTGAAAACCATGC AGCGCAACTGGATTGGCCGCAGCGAAGGCGTGGAAATTACCTTTAAC GTGAACGATTATGATAACACCCTGACCGTGTATACCACCCGCCCGGA TGCGTTTATGGGCTGCACCTATCTGGCGGTGGCGGCGGGCCATCCGC TGGCGCAGAAAGCGGCGGAAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGGCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGATTTATGCGC GCTATACCTGCCCGCAGTATAAAGAAGGCATGCTGGATAGCGAAGCG GCGAACTATTGGCTGCCGGTGGATATTGCGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG |

| SEQUENCE LISTING | | |
| --- | --- | --- |

| SEQ ID NO | Description | Sequence |
| --- | --- | --- |
| | | CGAAAGCGCCGACCGATGGCGAACAGGATCGCGCGCTGATGCAGGAA<br>GCGCTGCTGGCGGTGGTGCGCATGCTGAACCCGTTTACCCCGCATAT<br>TTGCTTTACCCTGTGGCAGGAACTGAAAGGCGAAGGCGATATTGATA<br>ACGCGCCGTGGCCGGTGGCGGATGAAAAAGCGATGGTGGAAGATAGC<br>ACCCTGGTGGTGGTGCAGGTGAACGGCAAAGTGCGCGCGAAAATTAC<br>CGTGCCGGTGGATGCGACCGAAGAACAGGTGCGCGAACGCGCGGGCC<br>AGGAACATCTGGTGGCGAAATATCTGGATGGCGTGACCGTGCGCAAA<br>GTGATTTATGTGCCGGGCAAACTGCTGAACCTGGTGGTGGGCGGCCC<br>GGTG |
| 59 | V9 | ATGGAAGAACAGTATCGCCCGGAAGAAATTGAAAGCAAAGTGCAGCT<br>GCATTGGGATATGAAACGCACCTTTGAAGTGACCGAAGATGAAAGCA<br>AAGAAAAATATTATTGCCTGAGCATTAGCCCGTATCCGAGCGGCCGC<br>CTGCATATGGGCCATGTGCGCAACTATACCATTGGCGATGTGATTGC<br>GCGCTATCAGCGCATGCTGGGCAAAAACGTGCTGCAGCCGATTGGCT<br>GGGATGCGTTTGGCCTGCCGGCGGAAGGCGCGGCGGTGAAAAACAAC<br>ACCGCGCCGGCGCCGTGGACCTATGATAACATTGCGTATATGAAAAA<br>CCAGCTGAAAATGCTGGGCTTTGGCTATGATTGGAGCCGCGAACTGG<br>CGACCTGCACCCCGGAATATTATCGCTGGGAACAGAAATTTTTTACC<br>GAACTGTATAAAAAAGGCCTGGTGTATAAAAAAACCAGCGCGGTGAA<br>CTGGTGCCCGAACGATCAGACCGTGCTGGCGAACGAACAGGTGATTG<br>ATGGCTGCTGCTGGCGCTGCGATACCAAAGTGGAACGCAAAGAAATT<br>CCGCAGTGGTTTATTAAAATTACCGCGTATGCGGATGAACTGCTGAA<br>CGATCTGGATAAACTGGATCATTGGCCGGATACCGTGAAAACCATGC<br>AGCGCAACTGGATTGGCCGCAGCGAAGGCGTGGAAATTACCTTTAAC<br>GTGAACGATTATGATAACACCCTGACCGTGTATACCACCCGCCCGGA<br>TGCGTTTATGGGCTGCACCTATCTGGCGGTGGCGGCGGGCCATCCGC<br>TGGCGCAGAAAGCGGCGGAAAACAACCCGGAACTGGCGGCGTTTATT<br>GATGAATGCCGCAACACCAAAGTGGCGGAAGCGGAAATGGCGACCAT<br>GGAAAAAAAAGGCGTGGATACCGGCTTTAAAGCGGTGCATCCGCTGA<br>CCGGCGAAGAAATTCCGGTGTGGGCGGCGAACTTTGTGCTGATGGAA<br>TATGGCACCGGCGCGGTGATGGCGGTGCCGGGCCATGATCAGCGCGA<br>TTATGAATTTGCGAGCAAATATGGCCTGAACATTAAACCGGTGATTC<br>TGGCGGCGGATGGCAGCGAACCGGATCTGAGCCAGCAGGCGCTGACC<br>GAAAAAGGCGTGCTGTTTAACAGCGGCGAATTTAACGGCCTGGATCA<br>TGAAGCGGCGTTTAACGCGATTGCGGATAAACTGACCGCGATGGGCG<br>TGGGCGAACGCAAAGTGAACTATCGCCTGCGCGATTGGGGCGTGAGC<br>CGCCAGCGCTATTGGGCGCGCGCCGATTCCGATGGTGACCCTGGAAGA<br>TGGCACCGTGATGCCGACCCCGGATGATCAGCTGCCGGTGATTCTGC<br>CGGAAGATGTGGTGATGGATGGCATTACCAGCCCGATTAAAGCGGAT<br>CCGGAATGGGCGAAAACCACCGTGAACGGCATGCCGGCGCTGCGCGA<br>AACCGATACCTTTGATACCTTTATGGAAAGCAGCTGGATTTATGCGC<br>GCTATACCTGCCCGCAGTATAAAGAAGGCATGCTGGATAGCGAAGCG<br>GCGAACTATTGGCTGCCGGTGGATATTGCGATTGGCGGCATTGAACA<br>TGCGATTATGGGCCTGCTGTATTTTCGCTTTTTTCATAAACTGATGC<br>GCGATGCGGGCATGGTGAACAGCGATGAACCGGCGAAACAGCTGCTG<br>TGCCAGGGCATGGTGCTGGCGGATGCGTTTTATTATGTGGGCGAAAA<br>CGGCGAACGCAACTGGGTGAGCCCGGTGGATGCGATTGTGGAACGCG<br>ATGAAAAAGGCCGCATTGTGAAAGCGAAAGATGCGGCGGGCCATGAA<br>CTGGTGTATACCGGCATGAGCAAAATGAGCAAAAGCAAAAACAACGG<br>CATTGATCCGCAGGTGATGGTGGAACGCTATGGCGCGGATACCGTGC<br>GCCTGTTTATGATGTTTGCGAGCCCGGCGGATATGACCCTGGAATGG<br>CAGGAAAGCGGCGTGGAAGGCGCGAACCGCTTTCTGAAACGCGTGTG<br>GAAACTGGTGTATGAACATACCGCGAAAGGCGATGTGGCGGCGCTGA<br>ACGTGGATGCGCTGACCGAAAACCAGAAAGCGCTGCGCCGCGATGTG<br>CATAAAACCATTGCGAAAGTGACCGATGATATTGGCCGCCGCCAGAC<br>CTTTAACACCGCGATTGCGGCGATTATGGAACTGATGAACAAACTGG<br>CGAAAGCGCCGACCGATGGCGAACAGGATCGCGCGCTGATGCAGGAA<br>GCGCTGCTGGCGGTGGTGCGCATGCTGAACCCGTTTACCCCGCATAT<br>TTGCTTTACCCTGTGGCAGGAACTGAAAGGCGAAGGCGATATTGATA<br>ACGCGCCGTGGCCGGTGGCGGATGAAAAAGCGATGGTGGAAGATAGC<br>ACCCTGGTGGTGGTGCAGGTGAACGGCAAAGTGCGCGCGAAAATTAC<br>CGTGCCGGTGGATGCGACCGAAGAACAGGTGCGCGAACGCGCGGGCC<br>AGGAACATCTGGTGGCGAAATATCTGGATGGCGTGACCGTGCGCAAA<br>GTGATTTATGTGCCGGGCAAACTGCTGAACCTGGTGGTGGGCGGCCC<br>GGTG |
| 60 | V10 | ATGGAAGAACAGTATCGCCCGGAAGAAATTGAAAGCAAAGTGCAGCT<br>GCATTGGGATGTGAAACGCACCTTTGAAGTGACCGAAGATGAAAGCA<br>AAGAAAAATATTATTGCCTGAGCATTAGCCCGTATCCGAGCGGCCGC<br>CTGCATATGGGCCATGTGCGCAACTATACCATTGGCGATGTGATTGC<br>GCGCTATCAGCGCATGCTGGGCAAAAACGTGCTGCAGCCGATTGGCT<br>GGGATGCGTTTGGCCTGCCGGCGGAAGGCGCGGCGGTGAAAAACAAC |

-continued

| SEQUENCE LISTING | | |
| --- | --- | --- |
| SEQ ID NO | Description | Sequence |
| | | ACCGCGCCGGCGCCGTGGACCTATGATAACATTGCGTATATGAAAAA<br>CCAGCTGAAAATGCTGGGCTTTGGCTATGATTGGAGCCGCGAACTGG<br>CGACCTGCACCCCGGAATATTATCGCTGGGAACAGAAATTTTTTACC<br>GAACTGTATAAAAAAGGCCTGGTGTATAAAAAAACCAGCGCGGTGAA<br>CTGGTGCCCGAACGATCAGACCGTGCTGGCGAACGAACAGGTGATTG<br>ATGGCTGCTGCTGGCGCTGCGATACCAAAGTGGAACGCAAAGAAATT<br>CCGCAGTGGTTTATTAAAATTACCGCGTATGCGGATGAACTGCTGAA<br>CGATCTGGATAAACTGGATCATTGGCCGGATACCGTGAAAACCATGC<br>AGCGCAACTGGATTGGCCGCAGCGAAGGCGTGGAAATTACCTTTAAC<br>GTGAACGATTATGATAACACCCTGACCGTGTATACCACCCGCCCGGA<br>TGCGTTTATGGGCTGCACCTATCTGGCGGTGGCGGCGGGCCATCCGC<br>TGGCGCAGAAAGCGGCGGAAAACAACCCGGAACTGGCGGCGTTTATT<br>GATGAATGCCGCAACACCAAAGTGGCGGAAGCGGAAATGGCGACCAT<br>GGAAAAAAAAGGCGTGGATACCGGCTTTAAAGCGGTGCATCCGCTGA<br>CCGGCGAAGAAATTCCGGTGTGGGCGGCGAACTTTGTGCTGATGGAA<br>TATGGCACCGGCGCGGTGATGGCGGTGCCGGGCCATGATCAGCGCGA<br>TTATGAATTTGCGAGCAAATATGGCCTGAACATTAAACCGGTGATTC<br>TGGCGGCGGATGGCAGCGAACCGGATCTGAGCCAGCAGGCGCTGACC<br>GAAAAAGGCGTGCTGTTTAACAGCGGCGAATTTAACGGCCTGGATCA<br>TGAAGCGGCGTTTAACGCGATTGCGGATAAACTGACCGCGATGGGCG<br>TGGGCGAACGCAAAGTGAACTATCGCCTGCGCGATTGGGGCGTGAGC<br>CGCCAGCGCTATTGGGGCGCGCCGATTCCGATGGTGACCCTGGAAGA<br>TGGCACCGTGATGCCGACCCCGGATGATCAGCTGCCGGTGATTCTGC<br>CGGAAGATGTGGTGATGGATGGCATTACCAGCCCGATTAAAGCGGAT<br>CCGGAATGGGCGAAAACCACCGTGAACGGCATGCCGGCGCTGCGCGA<br>AACCGATACCTTTGATACCTTTATGGAAAGCAGCTGGATTTATGCGC<br>GCTATACCTGCCCGCAGTATAAAGAAGGCATGCTGGATAGCGAAGCG<br>GCGAACTATTGGCTGCCGGTGGATATTGCGATTGGCGGCATTGAACA<br>TGCGATTATGGGCCTGCTGTATTTTCGCTTTTTTCATAAACTGATGC<br>GCGATGCGGGCATGGTGAACAGCGATGAACCGGCGAAACAGCTGCTG<br>TGCCAGGGCATGGTGCTGGCGGATGCGTTTTATTATGTGGGCGAAAA<br>CGGCGAACGCAACTGGGTGAGCCCGGTGGATGCGATTGTGGAACGCG<br>ATGAAAAAGGCCGCATTGTGAAAGCGAAAGATGCGGCGGGCCATGAA<br>CTGGTGTATACCGGCATGAGCAAAATGAGCAAAAGCAAAAACAACGG<br>CATTGATCCGCAGGTGATGGTGGAACGCTATGGCGCGGATACCGTGC<br>GCCTGTTTATGATGTTTGCGAGCCCGGCGGATATGACCCTGGAATGG<br>CAGGAAAGCGGCGTGGAAGGCGCGAACCGCTTTCTGAAACGCGTGTG<br>GAAACTGGTGTATGAACATACCGCGAAAGGCGATGTGGCGGCGCTGA<br>ACGTGGATGCGCTGACCGAAAACCAGAAAGCGCTGCGCGCGCGATGTG<br>CATAAAACCATTGCGAAAGTGACCGATGATATTGGCCGCCGCCAGAC<br>CTTTAACACCGCGATTGCGGCGATTATGGAACTGATGAACAAACTGG<br>CGAAAGCGCCGACCGATGGCGAACAGGATCGCGCGCTGATGCAGGAA<br>GCGCTGCTGGCGGTGGTGCGCATGCTGAACCCGTTTACCCCGCATAT<br>TTGCTTTACCCTGTGGCAGGAACTGAAAGGCGAAGGCGATATTGATA<br>ACGCGCCGTGGCCGGTGGCGGATGAAAAAGCGATGGTGGAAGATAGC<br>ACCCTGGTGGTGGTGCAGGTGAACGGCAAAGTGCGCGCGAAAATTAC<br>CGTGCCGGTGGATGCGACCGAAGAACAGGTGCGCGAACGCGCGGGCC<br>AGGAACATCTGGTGGCGAAATATCTGGATGGCGTGACCGTGCGCAAA<br>GTGATTTATGTGCCGGGCAAACTGCTGAACCTGGTGGTGGGCGGCCC<br>GGTG |
| 61 | V26 | ATGGAAGAACAGTATCGCCCGGAAGAAATTGAAAGCAAAGTGCAGCT<br>GCATTGGGATAAAAAACGCACCTTTGAAGTGACCGAAGATGAAAGCA<br>AAGAAAAATATTATTGCCTGAGCATTGTGCCGTATCCGAGCGGCCGC<br>CTGCATATGGGCCATGTGCGCAACTATACCATTGGCGATGTGATTGC<br>GCGCTATCAGCGCATGCTGGGCAAAAACGTGCTGCAGCCGATTGGCT<br>GGGATGCGTTTGGCCTGCCGGCGGAAGGCGCGGCGGTGAAAAACAAC<br>ACCGCGCCGGCGCCGTGGACCTATGATAACATTGCGTATATGAAAAA<br>CCAGCTGAAAATGCTGGGCTTTGGCTATGATTGGAGCCGCGAACTGG<br>CGACCTGCACCCCGGAATATTATCGCTGGGAACAGAAATTTTTTACC<br>GAACTGTATAAAAAAGGCCTGGTGTATAAAAAAACCAGCGCGGTGAA<br>CTGGTGCCCGAACGATCAGACCGTGCTGGCGAACGAACAGGTGATTG<br>ATGGCTGCTGCTGGCGCTGCGATACCAAAGTGGAACGCAAAGAAATT<br>CCGCAGTGGTTTATTAAAATTACCGCGTATGCGGATGAACTGCTGAA<br>CGATCTGGATAAACTGGATCATTGGCCGGATACCGTGAAAACCATGC<br>AGCGCAACTGGATTGGCCGCAGCGAAGGCGTGGAAATTACCTTTAAC<br>GTGAACGATTATGATAACACCCTGACCGTGTATACCACCCGCCCGGA<br>TGCGTTTATGGGCTGCACCTATCTGGCGGTGGCGGCGGGCCATCCGC<br>TGGCGCAGAAAGCGGCGGAAAACAACCCGGAACTGGCGGCGTTTATT<br>GATGAATGCCGCAACACCAAAGTGGCGGAAGCGGAAATGGCGACCAT<br>GGAAAAAAAAGGCGTGGATACCGGCTTTAAAGCGGTGCATCCGCTGA<br>CCGGCGAAGAAATTCCGGTGTGGGCGGCGAACTTTGTGCTGATGGAA<br>TATGGCACCGGCGCGGTGATGGCGGTGCCGGGCCATGATCAGCGCGA |

-continued

| SEQUENCE LISTING | | |
| --- | --- | --- |

| SEQ<br>ID<br>NO | Description | Sequence |
| --- | --- | --- |
| | | TTATGAATTTGCGAGCAAATATGGCCTGAACATTAAACCGGTGATTC |
| | | TGGCGGCGGATGGCAGCGAACCGGATCTGAGCCAGCAGGCGCTGACC |
| | | GAAAAAGGCGTGCTGTTTAACAGCGGCGAATTTAACGGCCTGGATCA |
| | | TGAAGCGGCGTTTAACGCGATTGCGGATAAACTGACCGCGATGGGCG |
| | | TGGGCGAACGCAAAGTGAACTATCGCCTGCGCGATTGGGGCGTGAGC |
| | | CGCCAGCGCTATTGGGGCGCGCCGATTCCGATGGTGACCCTGGAAGA |
| | | TGGCACCGTGATGCCGACCCCGGATGATCAGCTGCCGGTGATTCTGC |
| | | CGGAAGATGTGGTGATGGATGGCATTACCAGCCCGATTAAAGCGGAT |
| | | CCGGAATGGGCGAAAACCACCGTGAACGGCATGCCGGCGCTGCGCGA |
| | | AACCGATACCTTTGATACCTTTATGGAAAGCAGCTGGATTTATGCGC |
| | | GCTATACCTGCCCCGCAGTATAAAGAAGGCATGCTGGATAGCGAAGCG |
| | | GCGAACTATTGGCTGCCGGTGGATATTGCGATTGGCGGCATTGAACA |
| | | TGCGATTATGGGCCTGCTGTATTTTCGCTTTTTTCATAAACTGATGC |
| | | GCGATGCGGGCATGGTGAACAGCGATGAACCGGCGAAACAGCTGCTG |
| | | TGCCAGGGCATGGTGCTGGCGGATGCGTTTTATTATGTGGGCGAAAA |
| | | CGGCGAACGCAACTGGGTGAGCCCGGTGGATGCGATTGTGGAACGCG |
| | | ATGAAAAAGGCCGCATTGTGAAAGCGAAAGATGCGGCGGGCCATGAA |
| | | CTGGTGTATACCGGCATGAGCAAAATGAGCAAAAGCAAAACAACGG |
| | | CATTGATCCGCAGGTGATGGTGGAACGCTATGGCGCGGATACCGTGC |
| | | GCCTGTTTATGATGTTTGCGAGCCCGGCGGATATGACCCTGGAATGG |
| | | CAGGAAAGCGGCGTGGAAGGCGCGAACCGCTTTCTGAAACGCGTGTG |
| | | GAAACTGGTGTATGAACATACCGCGAAAGGCGATGTGGCGGCGCTGA |
| | | ACGTGGATGCGCTGACCGAAAACCAGAAAGCGCTGCGCCGCGATGTG |
| | | CATAAAACCATTGCGAAAGTGACCGATGATATTGGCCGCGCCGCCAGAC |
| | | CTTTAACACCGCGATTGCGGCGATTATGGAACTGATGAACAAACTGG |
| | | CGAAAGCGCCGACCGATGGCGAACAGGATCGCGCGCTGATGCAGGAA |
| | | GCGCTGCTGGCGGTGGTGCGCATGCTGAACCCGTTTACCCCGCATAT |
| | | TTGCTTTACCCTGTGGCAGGAACTGAAAGGCGAAGGCGATATTGATA |
| | | ACGCGCCGTGGCCGGTGGCGGATGAAAAAGCGATGGTGGAAGATAGC |
| | | ACCCTGGTGGTGGTGCAGGTGAACGGCAAAGTGCGCGCGAAAATTAC |
| | | CGTGCCGGTGGATGCGACCGAAGAACAGGTGCGCGAACGCGCGGGCC |
| | | AGGAACATCTGGTGGCGAAATATCTGGATGGCGTGACCGTGCGCAAA |
| | | GTGATTTATGTGCCGGGCAAACTGCTGAACCTGGTGGTGGGCGGCCC |
| | | GGTG |
| 62 | V29 | ATGGAAGAACAGTATCGCCCGGAAGAAATTGAAAGCAAAGTGCAGCT |
| | | GCATTGGGATAAAAAACGCACCTTTGAAGTGACCGAAGATGAAAGCA |
| | | AAGAAAAATATTATTGCCTGAGCATTGCGCCGTATCCGAGCGGCCGC |
| | | CTGCATATGGGCCATGTGCGCAACTATACCATTGGCGATGTGATTGC |
| | | GCGCTATCAGCGCATGCTGGGCAAAAACGTGCTGCAGCCGATTGGCT |
| | | GGGATGCGTTTGGCCTGCCGGCGGAAGGCGCGGCGGTGAAAAACAAC |
| | | ACCGCGCCGGCCGCCGTGGACCTATGATAACATTGCGTATATGAAAAA |
| | | CCAGCTGAAAATGCTGGGCTTTGGCTATGATTGGAGCCGCGAACTGG |
| | | CGACCTGCACCCCGGAATATTATCGCTGGGAACAGAAATTTTTTACC |
| | | GAACTGTATAAAAAAGGCCTGGTGTATAAAAAAACCAGCGCGGTGAA |
| | | CTGGTGCCCGAACGATCAGACCGTGCTGGCGAACGAACAGGTGATTG |
| | | ATGGCTGCTGCTGGCGCTGCGATACCAAAGTGGAACGCAAAGAAATT |
| | | CCGCAGTGGTTTATTAAAATTACCGCGTATGCGGATGAACTGCTGAA |
| | | CGATCTGGATAAACTGGATCATTGGCCGGATACCGTGAAAACCATGC |
| | | AGCGCAACTGGATTGGCCGCAGCGAAGGCGTGGAAATTACCTTTAAC |
| | | GTGAACGATTATGATAACACCCTGACCGTGTATACCACCCGCCCGGA |
| | | TGCGTTTATGGGCTGCACCTATCTGGCGGTGGCGGCGGGCCATCCGC |
| | | TGGCGCAGAAAGCGGCGGAAAACAACCCGGAACTGGCCGGCGTTTATT |
| | | GATGAATGCCGCAACACCAAAGTGGCGGAAGCGGAAATGGCGACCAT |
| | | GGAAAAAAAAGGCGTGGATACCGGCTTTAAAGCGGTGCATCCGCTGA |
| | | CCGGCGAAGAAATTCCGGTGTGGGCGGCGAACTTTGTGCTGATGGAA |
| | | TATGGCACCGGCGCGGTGATGGCGGTGCCGGGCCATGATCAGCGCGA |
| | | TTATGAATTTGCGAGCAAATATGGCCTGAACATTAAACCGGTGATTC |
| | | TGGCGGCGGATGGCAGCGAACCGGATCTGAGCCAGCAGGCGCTGACC |
| | | GAAAAAGGCGTGCTGTTTAACAGCGGCGAATTTAACGGCCTGGATCA |
| | | TGAAGCGGCGTTTAACGCGATTGCGGATAAACTGACCGCGATGGGCG |
| | | TGGGCGAACGCAAAGTGAACTATCGCCTGCGCGATTGGGGCGTGAGC |
| | | CGCCAGCGCTATTGGGGCGCGCCGATTCCGATGGTGACCCTGGAAGA |
| | | TGGCACCGTGATGCCGACCCCGGATGATCAGCTGCCGGTGATTCTGC |
| | | CGGAAGATGTGGTGATGGATGGCATTACCAGCCCGATTAAAGCGGAT |
| | | CCGGAATGGGCGAAAACCACCGTGAACGGCATGCCGGCGCTGCGCGA |
| | | AACCGATACCTTTGATACCTTTATGGAAAGCAGCTGGATTTATGCGC |
| | | GCTATACCTGCCCCGCAGTATAAAGAAGGCATGCTGGATAGCGAAGCG |
| | | GCGAACTATTGGCTGCCGGTGGATATTGCGATTGGCGGCATTGAACA |
| | | TGCGATTATGGGCCTGCTGTATTTTCGCTTTTTTCATAAACTGATGC |
| | | GCGATGCGGGCATGGTGAACAGCGATGAACCGGCGAAACAGCTGCTG |
| | | TGCCAGGGCATGGTGCTGGCGGATGCGTTTTATTATGTGGGCGAAAA |
| | | CGGCGAACGCAACTGGGTGAGCCCGGTGGATGCGATTGTGGAACGCG |

-continued

| SEQUENCE LISTING | | |
| --- | --- | --- |
| SEQ ID NO | Description | Sequence |
| | | ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGTGCAGGTGAACGGCAAAGTGCGCGCGAAAATTAC CGTGCCGGTGGATGCGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 63 | V48 | ATGGAAGAACAGTATCGCCCGGAAGAAATTGAAAGCAAAGTGCAGCT GCATTGGGATAAAAAACGCACCTTTGAAGTGACCGAAGATGAAAGCA AAGAAAAATATTATTGCCTGAGCATTAGCCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT CCGCAGTGGTTTATTAAAATTACCGCGTATGCGGATGAACTGCTGAA CGATCTGGATAAACTGGATCATTGGCCGGATACCGTGAAAACCATGC AGCGCAACTGGATTGGCCGCAGCGAAGGCGTGGAAATTACCTTTAAC GTGAACGATTATGATAACACCCTGACCGTGTATACCACCCGCCCGGA TGCGTTTATGGGCTGCACCTATCTGGCGGTGGCGGCGGGCCATCCGC TGGCGCAGAAAGCGGCGGAAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGCCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGGCGTATGCGC GCTATACCTGCCCGCAGTATAAAGAAGGCATGCTGGATAGCGAAGCG GCGAACTATTGGCTGCCGGTGGATATTGCGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTAAACGCGTGTGGAA ACTGGTGTATGAACATACCGCGAAAGGCGATGTGGCGGCGCTGAACG TGGATGCGCTGACCGAAAACCAGAAAGCGCTGCGCCGCGATGTGCAT AAAACCATTGCGAAAGTGACCGATGATATTGGCCGCCGCCAGACCTT TAACACCGCGATTGCGGCGATTATGGAACTGATGAACAAACTGGCGA AAGCGCCGACCGATGGCGAACAGGATCGCGCGCTGATGCAGGAAGCG CTGCTGGCGGTGGTGCGCATGCTGAACCCGTTTACCCCGCATATTTG CTTTACCCTGTGGCAGGAACTGAAAGGCGAAGGCGATATTGATAACG CGCCGTGGCCGGTGGCGGATGAAAAAGCGATGGTGGAAGATAGCACC CTGGTGGTGGTGCAGGTGAACGGCAAAGTGCGCGCGAAAATTACCGT GCCGGTGGATGCGACCGAAGAACAGGTGCGCGAACGCGCGGGCCAGG |

| SEQUENCE LISTING | | |
| --- | --- | --- |
| SEQ ID NO | Description | Sequence |
| | | AACATCTGGTGGCGAAATATCTGGATGGCGTGACCGTGCGCAAAGTG ATTTATGTGCCGGGCAAACTGCTGAACCTGGTGGTGGGCGGCCCGGT G |
| 64 | V50 | ATGGAAGAACAGTATCGCCCGGAAGAAATTGAAAGCAAAGTGCAGCT GCATTGGGATAAAAAACGCACCTTTGAAGTGACCGAAGATGAAAGCA AAGAAAAATATTATTGCCTGAGCATTAGCCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT CCGCAGTGGTTTATTAAAAATTACCGCGTATGCGGATGAACTGCTGAA CGATCTGGATAAACTGGATCATTGGCCGGATACCGTGAAAACCATGC AGCGCAACTGGATTGGCCGCAGCGAAGGCGTGGAAATTACCTTTAAC GTGAACGATTATGATAACACCCTGACCGTGTATACCACCCGCCCCGGA TGCGTTTATGGGCTGCACCTATCTGGCGGTGGCGGCGGGCCATCCGC TGGCGCAGAAAGCGGCGGAAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGGCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGCATTATGCGC GCTATACCTGCCCGCAGTATAAAGAAGGCATGCTGGATAGCGAAGCG GCGAACTATTGGCTGCCGGTGGATATTGCGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGTGCAGGTGAACGGCAAAGTGCGCGCGAAAATTAC CGTGCCGGTGGATGCGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 65 | V54 | ATGGAAGAACAGTATCGCCCGGAAGAAATTGAAAGCAAAGTGCAGCT GCATTGGGATAAAAAACGCACCTTTGAAGTGACCGAAGATGAAAGCA AAGAAAAATATTATTGCCTGAGCATTAGCCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT |

| SEQUENCE LISTING | | |
| --- | --- | --- |
| SEQ ID NO | Description | Sequence |
| | | CCGCAGTGGTTTATTAAAATTACCGCGTATGCGGATGAACTGCTGAA |
| | | CGATCTGGATAAACTGGATCATTGGCCGGATACCGTGAAAACCATGC |
| | | AGCGCAACTGGATTGGCCGCAGCGAAGGCGTGGAAATTACCTTTAAC |
| | | GTGAACGATTATGATAACACCCTGACCGTGTATACCACCCGCCCGGA |
| | | TGCGTTTATGGGCTGCACCTATCTGGCGGTGGCGGCGGGCCATCCGC |
| | | TGGCGCAGAAAGCGGCGGAAAACAACCCGGAACTGGCGGCGTTTATT |
| | | GATGAATGCCGCAACACCAAAGTGGCGGAAGCGGAAATGGCGACCAT |
| | | GGAAAAAAAAGGCGTGGATACCGGCTTTAAAGCGGTGCATCCGCTGA |
| | | CCGGCGAAGAAATTCCGGTGTGGGCGGCGAACTTTGTGCTGATGGAA |
| | | TATGGCACCGGCGCGGTGATGGCGGTGCCGGGCCATGATCAGCGCGA |
| | | TTATGAATTTGCGAGCAAATATGGCCTGAACATTAAACCGGTGATTC |
| | | TGGCGGCGGATGGCAGCGAACCGGATCTGAGCCAGCAGGCGCTGACC |
| | | GAAAAAGGCGTGCTGTTTAACAGCGGCGAATTTAACGGCCTGGATCA |
| | | TGAAGCGGCGTTTAACGCGATTGCGGATAAACTGACCGCGATGGGCG |
| | | TGGGCGAACGCAAAGTGAACTATCGCCTGCGCGATTGGGGCGTGAGC |
| | | CGCCAGCGCTATTGGGGCGCGCCGATTCCGATGGTGACCCTGGAAGA |
| | | TGGCACCGTGATGCCGACCCCGGATGATCAGCTGCCGGTGATTCTGC |
| | | CGGAAGATGTGGTGATGGATGGCATTACCAGCCCGATTAAAGCGGAT |
| | | CCGGAATGGGCGAAAACCACCGTGAACGGCATGCCGGCGCTGCGCGA |
| | | AACCGATACCTTTGATACCTTTATGGAAAGCAGCTGGATTTATGCGC |
| | | GCTATACCTGCCCGCAGTATAAAGAAGGCATGCTGGATAGCGAAGCG |
| | | GCGAACTATTGGCTGCCGGTGGATATTATTATTGGCGGCATTGAACA |
| | | TGCGATTATGGGCCTGCTGTATTTTCGCTTTTTTCATAAACTGATGC |
| | | GCGATGCGGGCATGGTGAACAGCGATGAACCGGCGAAACAGCTGCTG |
| | | TGCCAGGGCATGGTGCTGGCGGATGCGTTTTATTATGTGGGCGAAAA |
| | | CGGCGAACGCAACTGGGTGAGCCCGGTGGATGCGGATTGTGGAACGCG |
| | | ATGAAAAAGGCCGCATTGTGAAAGCGAAAGATGCGGCGGGCCATGAA |
| | | CTGGTGTATACCGGCATGAGCAAAATGAGCAAAAGCAAAAACAACGG |
| | | CATTGATCCGCAGGTGATGGTGGAACGCTATGGCGCGGATACCGTGC |
| | | GCCTGTTTATGATGTTTGCGAGCCCGGCGGATATGACCCTGGAATGG |
| | | CAGGAAAGCGGCGTGGAAGGCGCGAACCGCTTTCTGAAACGCGTGTG |
| | | GAAACTGGTGTATGAACATACCGCGAAAGGCGATGTGGCGGCGCTGA |
| | | ACGTGGATGCGCTGACCGAAAACCAGAAAGCGCTGCGCCGCGATGTG |
| | | CATAAAACCATTGCGAAAGTGACCGATGATATTGGCCGCCGCCAGAC |
| | | CTTTAACACCGCGATTGCGGCGATTATGGAACTGATGAACAAACTGG |
| | | CGAAAGCGCCGACCGATGGCGAACAGGATCGCGCGCTGATGCAGGAA |
| | | GCGCTGCTGGCGGTGGTGCGCATGCTGAACCCGTTTACCCCGCATAT |
| | | TTGCTTTACCCTGTGGCAGGAACTGAAAGGCGAAGGCGATATTGATA |
| | | ACGCGCCGTGGCCGGTGGCGGATGAAAAAGCGATGGTGGAAGATAGC |
| | | ACCCTGGTGGTGGTGCAGGTGAACGGCAAAGTGCGCGCGAAAATTAC |
| | | CGTGCCGGTGGATGCGACCGAAGAACAGGTGCGCGAACGCGCGGGCC |
| | | AGGAACATCTGGTGGCGAAATATCTGGATGGCGTGACCGTGCGCAAA |
| | | GTGATTTATGTGCCGGGCAAACTGCTGAACCTGGTGGTGGGCGGCCC |
| | | GGTG |
| 66 | V55 | ATGGAAGAACAGTATCGCCCGGAAGAAATTGAAAGCAAAGTGCAGCT |
| | | GCATTGGGATAAAAAACGCACCTTTGAAGTGACCGAAGATGAAAGCA |
| | | AAGAAAAATATTATTGCCTGAGCATTAGCCCGTATCCGAGCGGCCGC |
| | | CTGCATATGGGCCATGTGCGCAACTATACCATTGGCGATGTGATTGC |
| | | GCGCTATCAGCGCATGCTGGGCAAAAACGTGCTGCAGCCGATTGGCT |
| | | GGGATGCGTTTGGCCTGCCGGCGGAAGGCGCGGCGGTGAAAAACAAC |
| | | ACCGCGCCGGCGCCGTGGACCTATGATAACATTGCGTATATGAAAAA |
| | | CCAGCTGAAAATGCTGGGCTTTGGCTATGATTGGAGCCGCGAACTGG |
| | | CGACCTGCACCCCGGAATATTATCGCTGGGAACAGAAATTTTTTACC |
| | | GAACTGTATAAAAAAGGCCTGGTGTATAAAAAAACCAGCGCGGTGAA |
| | | CTGGTGCCCGAACGATCAGACCGTGCTGGCGAACGAACAGGTGATTG |
| | | ATGGCTGCTGCTGGCGCTGCGATACCAAAGTGGAACGCAAAGAAATT |
| | | CCGCAGTGGTTTATTAAAATTACCGCGTATGCGGATGAACTGCTGAA |
| | | CGATCTGGATAAACTGGATCATTGGCCGGATACCGTGAAAACCATGC |
| | | AGCGCAACTGGATTGGCCGCAGCGAAGGCGTGGAAATTACCTTTAAC |
| | | GTGAACGATTATGATAACACCCTGACCGTGTATACCACCCGCCCGGA |
| | | TGCGTTTATGGGCTGCACCTATCTGGCGGTGGCGGCGGGCCATCCGC |
| | | TGGCGCAGAAAGCGGCGGAAAACAACCCGGAACTGGCGGCGTTTATT |
| | | GATGAATGCCGCAACACCAAAGTGGCGGAAGCGGAAATGGCGACCAT |
| | | GGAAAAAAAAGGCGTGGATACCGGCTTTAAAGCGGTGCATCCGCTGA |
| | | CCGGCGAAGAAATTCCGGTGTGGGCGGCGAACTTTGTGCTGATGGAA |
| | | TATGGCACCGGCGCGGTGATGGCGGTGCCGGGCCATGATCAGCGCGA |
| | | TTATGAATTTGCGAGCAAATATGGCCTGAACATTAAACCGGTGATTC |
| | | TGGCGGCGGATGGCAGCGAACCGGATCTGAGCCAGCAGGCGCTGACC |
| | | GAAAAAGGCGTGCTGTTTAACAGCGGCGAATTTAACGGCCTGGATCA |
| | | TGAAGCGGCGTTTAACGCGATTGCGGATAAACTGACCGCGATGGGCG |
| | | TGGGCGAACGCAAAGTGAACTATCGCCTGCGCGATTGGGGCGTGAGC |
| | | CGCCAGCGCTATTGGGGCGCGCCGATTCCGATGGTGACCCTGGAAGA |

| SEQUENCE LISTING | | |
| --- | --- | --- |
| SEQ ID NO | Description | Sequence |
| | | TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGATTTATGCGC GCTATACCTGCCCGCAGTATAAAGAAGGCATGCTGGATAGCGAAGCG GCGAACTATTGGCTGCCGGTGGATATTGTGATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGTGCAGGTGAACGGCAAAGTGCGCGCGAAAATTAC CGTGCCGGTGGATGCGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 67 | V56 | ATGGAAGAACAGTATCGCCCGGAAGAAATTGAAAGCAAAGTGCAGCT GCATTGGGATAAAAAACGCACCTTTGAAGTGACCGAAGATGAAAGCA AAGAAAAATATTATTGCCTGAGCATTAGCCCGTATCCGAGCGGCCGC CTGCATATGGGCCATGTGCGCAACTATACCATTGGCGATGTGATTGC GCGCTATCAGCGCATGCTGGGCAAAAACGTGCTGCAGCCGATTGGCT GGGATGCGTTTGGCCTGCCGGCGGAAGGCGCGGCGGTGAAAAACAAC ACCGCGCCGGCGCCGTGGACCTATGATAACATTGCGTATATGAAAAA CCAGCTGAAAATGCTGGGCTTTGGCTATGATTGGAGCCGCGAACTGG CGACCTGCACCCCGGAATATTATCGCTGGGAACAGAAATTTTTTACC GAACTGTATAAAAAAGGCCTGGTGTATAAAAAAACCAGCGCGGTGAA CTGGTGCCCGAACGATCAGACCGTGCTGGCGAACGAACAGGTGATTG ATGGCTGCTGCTGGCGCTGCGATACCAAAGTGGAACGCAAAGAAATT CCGCAGTGGTTTATTAAAATTACCGCGTATGCGGATGAACTGCTGAA CGATCTGGATAAACTGGATCATTGGCCGGATACCGTGAAAACCATGC AGCGCAACTGGATTGGCCGCAGCGAAGGCGTGGAAATTACCTTTAAC GTGAACGATTATGATAACACCCTGACCGTGTATACCACCCGCCCGGA TGCGTTTATGGGCTGCACCTATCTGGCGGTGGCGGCGGGCCATCCGC TGGCGCAGAAAGCGGCGGAAACAACCCGGAACTGGCGGCGTTTATT GATGAATGCCGCAACACCAAAGTGGCGGAAGCGGAAATGGCGACCAT GGAAAAAAAAGGCGTGGATACCGGCTTTAAAGCGGTGCATCCGCTGA CCGGCGAAGAAATTCCGGTGTGGGCGGCGAACTTTGTGCTGATGGAA TATGGCACCGGCGCGGTGATGGCGGTGCCGGGCCATGATCAGCGCGA TTATGAATTTGCGAGCAAATATGGCCTGAACATTAAACCGGTGATTC TGGCGGCGGATGGCAGCGAACCGGATCTGAGCCAGCAGGCGCTGACC GAAAAAGGCGTGCTGTTTAACAGCGGCGAATTTAACGGCCTGGATCA TGAAGCGGCGTTTAACGCGATTGCGGATAAACTGACCGCGATGGGCG TGGGCGAACGCAAAGTGAACTATCGCCTGCGCGATTGGGGCGTGAGC CGCCAGCGCTATTGGGGCGCGCCGATTCCGATGGTGACCCTGGAAGA TGGCACCGTGATGCCGACCCCGGATGATCAGCTGCCGGTGATTCTGC CGGAAGATGTGGTGATGGATGGCATTACCAGCCCGATTAAAGCGGAT CCGGAATGGGCGAAAACCACCGTGAACGGCATGCCGGCGCTGCGCGA AACCGATACCTTTGATACCTTTATGGAAAGCAGCTGGATTTATGCGC GCTATACCTGCCCGCAGTATAAAGAAGGCATGCTGGATAGCGAAGCG GCGAACTATTGGCTGCCGGTGGATATTGGCATTGGCGGCATTGAACA TGCGATTATGGGCCTGCTGTATTTTCGCTTTTTTCATAAACTGATGC GCGATGCGGGCATGGTGAACAGCGATGAACCGGCGAAACAGCTGCTG TGCCAGGGCATGGTGCTGGCGGATGCGTTTTATTATGTGGGCGAAAA CGGCGAACGCAACTGGGTGAGCCCGGTGGATGCGATTGTGGAACGCG ATGAAAAAGGCCGCATTGTGAAAGCGAAAGATGCGGCGGGCCATGAA CTGGTGTATACCGGCATGAGCAAAATGAGCAAAAGCAAAAACAACGG CATTGATCCGCAGGTGATGGTGGAACGCTATGGCGCGGATACCGTGC GCCTGTTTATGATGTTTGCGAGCCCGGCGGATATGACCCTGGAATGG CAGGAAAGCGGCGTGGAAGGCGCGAACCGCTTTCTGAAACGCGTGTG GAAACTGGTGTATGAACATACCGCGAAAGGCGATGTGGCGGCGCTGA |

-continued

| SEQUENCE LISTING | | |
| --- | --- | --- |

| SEQ ID NO | Description | Sequence |
| --- | --- | --- |
|  |  | ACGTGGATGCGCTGACCGAAAACCAGAAAGCGCTGCGCCGCGATGTG CATAAAACCATTGCGAAAGTGACCGATGATATTGGCCGCCGCCAGAC CTTTAACACCGCGATTGCGGCGATTATGGAACTGATGAACAAACTGG CGAAAGCGCCGACCGATGGCGAACAGGATCGCGCGCTGATGCAGGAA GCGCTGCTGGCGGTGGTGCGCATGCTGAACCCGTTTACCCCGCATAT TTGCTTTACCCTGTGGCAGGAACTGAAAGGCGAAGGCGATATTGATA ACGCGCCGTGGCCGGTGGCGGATGAAAAAGCGATGGTGGAAGATAGC ACCCTGGTGGTGGGTGCAGGTGAACGGCAAAGTGCGCGCGAAAATTAC CGTGCCGGTGGATGCGACCGAAGAACAGGTGCGCGAACGCGCGGGCC AGGAACATCTGGTGGCGAAATATCTGGATGGCGTGACCGTGCGCAAA GTGATTTATGTGCCGGGCAAACTGCTGAACCTGGTGGTGGGCGGCCC GGTG |
| 68 |  | GTGGGGTTCCCGAGCGGCCAAAGGGAGCAGACTtcAAATCTGCCGTC ACAGACTTCGAAGGTTCGAATCCTTCCCCCACCA |
| 69 |  | GTGGGGTTCCCGAGCGGCCAAAGGGAGCAGACTnnnAATCTGCCGTC ACAGACTTCGAAGGTTCGAATCCTTCCCCCACCA wherein nnn is CTA, TCA, or TTA |
| 70 |  | MASSNLIKQLQERGLVAQVTDEEALAERLAQGPIALVCGEDPTADSL HLGHLVPLLCLKRFQQAGHKPVALVGGATGLIGDPSFKAAERKLNTE ETVQEWVDKIRKQVAPFLDFDCGENSAIAANNYDWFGNMNVLTFLRD IGKHFSVNQMINKEAVKQRLNREDQGISFTEFSYNLLQGYSMACLNK QYGVVLQIGGSDQWGNITSGIDLTRRLHQNQVFGLTVPLITKADGTK FGKTEGGAVWLDPKKTSPYKFYQFWINTADADVYRFLKFFTFMSIEE INALEEEDKNSGKAPRAQYVLAEQVTRLVHGEEGLQAAKRITECLFS GSLSALSEADFEQLAQDGVPMVEMEKGADLMQALVDSELQPSRGQAR KTIASNAITINGEKQSDPEYFFKEEDRLFGRFTLLRRGKKNYCLICW KGPV |
| 71 |  | atggcaagcagtaacttgattaaacaattgcaagagcgggggctggt agcccaggtgacggacgaggaagcgttagcagagcgactggcgcaag gcccgatcgcactcGTGtgtggcttcgatcctaccgctgacagcttg catttggggcatcttgttccattgttatgcctgaaacgcttccagca ggcgggccacaagccggttgcgctggtaggcggcgcgacgggtctga ttggcgacccgagcttcaaagctgccgagcgtaagctgaacaccgaa gaaactgttcaggagtgggtggacaaaatccgtaagcaggttgcccc gttcctcgatttcgactgtggagaaaactctgctatcgcggccaata attatgactggttcggcaatatgaatgtgctgaccttcctgcgcgat attggcaaacacttctccgttaaccagatgatcaacaaagaagcggt taagcagcgtctcaaccgtgaagAtcaggggatttcgttcactgagt tttcctacaacctgctGcagggttatAgtatggcctgtTTGaacaaa cagtacggtgtggtgctgcaaattggtggttctgaccaatggggtaa catcacttctggtatcgacctgacccgtcgtctgcatcagaatcagg tgtttggcctgaccgttccgctgatcactaaagcagatggcaccaaa tttggtaaaactgaaggcggcgcagtctggtggacccgaagaaaac cagcccgtacaaattctaccagttctggatcaacactgcggatgccg acgtttaccgcttcctgaagttcttcacctttatgagcattgaagag atcaacgccctggaagaagaagataaaaacagcggtaaagcaccgcg cgcccagtatgtactggcggagcaggtgactcgtctggttcacggtg aagaaggtttacaggcggcaaaacgtattaccgaatgcctgttcagc ggttctttgagtgcgctgagtgaagcggacttcgaacagctggcgca ggacggcgtaccgatggttgagatggaaaagggcgcagacctgatgc aggcactggtcgattctgaactgcaaccttcccgtggtcaggcacgt aaaactatcgcctccaatgccatcaccattaacggtgaaaaacagtc cgatcctgaatacttctttaaagaagaagatcgtctgtttggtcgtt ttaccttactgcgtcgcggtaaaaagaattactgtctgatttgctgg aaagggcccgtttaa |
| 72 |  | GGAAACCTGATCATGTAGATCGAACGGACTCTAAATCCGTTCAGCCG GGTTAGATTCCCGGGGTTTCCG |
| 73 |  | GGAAACCTGATCATGTAGATCGAACGGACTnnnAATCCGTTCAGCCG GGTTAGATTCCCGGGGTTTCCG |
| 74 |  | gGAAACCugaucauguagaucgaacggacucuaaauccguucagccg gguuagauucccggGGUUUCcgcca |
| 75 |  | gGGCGGCugaucauguagaucgaacggacucuaaauccguucagccg gguuagauucccggGCUGCCcgcca |

-continued

| | | SEQUENCE LISTING |
|---|---|---|

| SEQ ID NO | Description | Sequence |
|---|---|---|
| 76 | | gGGUGACugaucauguagaucgaacggacucuaaauccguucagccg gguuagauucccggGUUGCCcgcca |
| 77 | | gGGGGGCugaucauguagaucgaacggacucuaaauccguucagccg gguuagauucccggGCUGCCcgcca |
| 78 | | gGGCGGCugaucauguagaucgaacggacucuaaauccguucagccg gguuagauucccggGUUGCCcgcca |
| 79 | | gGGCGCCugaucauguagaucgaacggacucuaaauccguucagccg gguuagauucccggGGCGCCcgcca |
| 80 | | gGGGAGGugaucauguagaucgaacggacucuaaauccguucagccg gguuagauucccggCCUCCCcgcca |
| 81 | | gGGGACCugaucauguagaucgaacggacucuaaauccguucagccg gguuagauucccggGGUCCCcgcca |
| 82 | | gGCCGGGugaucauguagaucgaacggacucuaaauccguucagccg gguuagauucccggCCUGGCcgcca |
| 83 | | gGGGACCugaucauguagaucgaacggacucuaaauccguucagccg gguuagauucccggGGUCCUcgcca |
| 84 | | gGGGCCCugaucauguagaucgaacggacucuaaauccguucagccg gguuagauucccggGGGUCCcgcca |
| 85 | | gGGGGCCugaucauguagaucgaacggacucuaaauccguucagccg gguuagauucccggGGGUCCcgcca |
| 86 | | gGGGUCCugaucauguagaucgaacggacucuaaauccguucagccg gguuagauucccggGGAUCCcgcca |
| 87 | | gGGGACCugaucauguagaucgaacggacucuaaauccguucagccg gguuagauucccggGGUUCCcgcca |
| 88 | | gGGGAGGugaucauguagaucgaacggacucuaaauccguucagccg gguuagauucccggUCUUCCcgcca |
| 89 | | gGGGGGGugaucauguagaucgaacggacucuaaauccguucagccg gguuagauucccggCCCCCUcgcca |
| 90 | | gGUGGGGugaucauguagaucgaacggacucuaaauccguucagccg gguuagauucccggCCCUACcgcca |
| 91 | | gGGGGUCugaucauguagaucgaacggacucuaaauccguucagccg gguuagauucccggGACUCCcgcca |
| 92 | | gGGUCCCugaucauguagaucgaacggacucuaaauccguucagccg gguuagauucccggGGGGUCcgcca |
| 93 | | gGGGACCugaucauguagaucgaacggacucuaaauccguucagccg gguuagauucccggGGUUCUcgcca |
| 94 | | gGGCGGCugaucauguagaucgaacggacucuaaauccguucagccg gguuagauucccggGCCGCCcgcca |
| 95 | | gAGCACCugaucauguagaucgaacggacucuaaauccguucagccg gguuagauucccggGGUGCUcgcca |
| 96 | | gGGGGGGugaucauguagaucgaacggacucuaaauccguucagccg gguuagauucccggCCCCCCcgcca |
| 97 | | gAGGGGGugaucauguagaucgaacggacucuaaauccguucagccg gguuagauucccggCCCCCUcgcca |
| 98 | | gGGAGCCugaucauguagaucgaacggacucuaaauccguucagccg gguuagauucccggGGUUCCcgcca |
| 99 | | gGGAGCCugaucauguagaucgaacggacucuaaauccguucagccg gguuagauucccggGGUUCCcgcca |

-continued

| SEQUENCE LISTING | | |
| --- | --- | --- |

| SEQ ID NO | Description | Sequence |
| --- | --- | --- |
| 100 | | gAGGACCugaucauguagaucgaacggacucuaaauccguucagccg ggguuagauucccggGGUUCUcgcca |
| 101 | | MDKKPLDVLISATGLWMSRTGTLHKIKHHEVSRSKIYIEMACGDHLV VNNSRSCRTARAFRHHKYRKTCKRCRVSDEDINNFLTRSTESKNSVK VRVVSAPKVKKAMPKSVSRAPKPLENSVSAKASTNTSRSVPSPAKST PNSSVPASAPAPSLTRSQLDRVEALLSPEDKISLNMAKPFRELEPEL VTRRKNDFQRLYTNDREDYLGKLERDITKFFVDRGFLEIKSPILIPA EYVERMGINNDTELSKQIFRVDKNLCLRPMLAPTLYNYLRKLDRILP GPIKIFEVGPCYRKESDGKEHLEEFTMVNFCQMGSGCTRENLEALIK EFLDYLEIDFEIVGDSCMVFGDTLDIMHGDLELSSAVVGPVSLDREW GIDKPWIGAGFGLERLLKVMHGFKNIKRASRSESYYNGISTNL |
| 102 | | ATGGATAAAAAACCATTAGATGTTTTAATATCTGCGACCGGGCTCTG GATGTCCAGGACTGGCACGCTCCACAAAATCAAGCACCATGAGGTCT CAAGAAGTAAAATATACATTGAAATGGCGTGTGGAGACCATCTTGTT GTGAATAATTCCAGGAGTTGTAGAACAGCCAGAGCATTCAGACATCA TAAGTACAGAAAAACCTGCAAACGATGTAGGGTTTCGGACGAGGATA TCAATAATTTTCTCACAAGATCAACCGAAAGCAAAAACAGTGTGAAA GTTAGGGTAGTTTCTGCTCCAAAGGTCAAAAAAGCTATGCCGAAATC AGTTTCAAGGGCTCCGAAGCCTCTGGAAAATTCTGTTTCTGCAAAGG CATCAACGAACACATCCAGATCTGTACCTTCGCCTGCAAAATCAACT CCAAATTCGTCTGTTCCCGCATCGGCTCCTGCTCCTTCACTTACAAG AAGCCAGCTTGATAGGGTTGAGGCTCTCTTAAGTCCAGAGGATAAAA TTTCTCTAAATATGGCAAAGCCTTTCAGGGAACTTGAGCCTGAACTT GTGACAAGAAGAAAAAACGATTTTCAGCGGCTCTATACCAATGATAG AGAAGACTAGCTCGGTAAACTCGAACGTGATATTACGAAATTTTTCG TAGACCGGGGTTTTCTGGAGATAAAGTCTCCTATCCTTATTCCGGCG GAATACGTGGAGAGAATGGGTATTAATAATGATACTGAACTTTCAAA ACAGATCTTCCGGGTGGATAAAAATCTCTGCTTGAGGCCAATGCTTG CCCCGACTCTTTACAACTATCTGCGAAAACTCGATAGGATTTTACCA GGCCCCAATAAAAATTTTCGAAGTCGGACCTTGTTACCGGAAAGAGTC TGACGGCAAAGAGCACCTGGAAGAATTTAGTATGGTGAACTTCTGTC AGATGGGTTCGGGATGTACTCGGGAAAATCTTGAAGCTCTCATCAAA GAGTTTCTGGACTATCTGGAAATCGACTTCGAAATCGTAGGAGATTC CTGTATGGTCTtTGGGGATACTCTTGATATAATGCACGGGGACCTGG AGCTTTCTTCGGCAGTCGTCGGGCCAGTTTCTCTTGATAGAGAATGG GGTATTGACAAACCATGGATAGGTGCAGGTTTTGGTCTTGAACGCTT GCTCAAGGTTATGCACGGCTTTAAAAACATTAAGAGGGCATCAAGGT CCGAATCTTACTATAATGGGATTTCAACCAATCTGTAA |
| 103 | TrpRS.h14 | ATGACTAAGCCCATCGTTTTTgctGGCGCACAGCCCTCAGGTGAATT GACCATTGGTAACTACATGGGTGCGCTGCGTCAGTGGGTAAACATGC AGGATGACTACCATTGCATTTACTGTATCGTTGACCAACACGCGATC ACCGTGCGCCAGGATGCACAGAAGCTGCGTAAAGCGACGCTGGATAC GCTGGCCTTGTATCTGGCTTGTGGTATCGATCCTGAGAAAAGCACCA TTTTTGTTCAGTCCCACGTGCCGGAACATGCACAGTTAGGCTGGGCA CTGAACTGCTATACCTACTTCGGCGAACTGAGTCGCATGACGCAGTT TAAAGATAAATCTGCGCGTTATGCCGAGAACATCAACGCTGGTCTGT TTGACTATCCGGTGCTGATGGCAGCGGACATCCTGCTGTATCAAACT AATCTGggtccttgtGGTGAAGACCAGAAACAGCACCTCGAACTGAG CCGCGATATTGCCCAGCGTTTCAACGCGCTGTATGGCGAGATCTTTA AGGTGCCGGAGCCGTTTATTCCGAAATCTGGCGCGCGCGTAATGTCG CTGCTGGAGCCGACCAAGAAGATGTCCAAGTCTGACGATAATCGCAA TAACGTTATCGGCCTGCTGGAAGATCCGAAATCGGTAGTGAAGAAAA TCAAACGTGCGGTCACTGACTCCGACGAGCCGCCGGTAGTTCGCTAC GATGTGCAGAACAAAGCGGGCGTTTCCAACCTGTTGGATATCCTTTC AGCGGTAACGGGCCAGAGCATCCCAGAACTGGAAAAACAGTTCGAAG GCAAGATGTATGGTCATCTGAAAGGTGAAGTGGCTGATGCCGTTTCC GGTATGCTGACTGAATTGCAGGAACGCTATCACCGTTTCCGCAACGA TGAAGCCTTCCTGCAACAGGTGATGAAAGATGGCGCGGAAAAAGCCA GCGCGCACGCTTCCCGTACGCTAAAAGCGGTGTACGAAGCGATTGGT TTTGTGGCGAAGCCGTAA |
| 104 | | GTGGGGTTCCCGAGCGGCCAAAGGGAGCAGACTtcAAATCTGCCGTC ACAGACTTCGAAGGTTCGAATCCTTCCCCCACCACCA |
| 105 | | GTGGGGTTCCCGAGCGGCCAAAGGGAGCAGACTnnnAATCTGCCGTC ACAGACTTCGAAGGTTCGAATCCTTCCCCCACCACCA wherein nnn is CTA, TCA, or TTA |
| 106 | | GGAAACCTGATCATGTAGATCGAACGGACTCTAAATCCGTTCAGCCG GGTTAGATTCCCGGGGTTTCCGCCA |

-continued

| SEQUENCE LISTING | | |
| --- | --- | --- |
| SEQ ID NO | Description | Sequence |
| 107 | | GGAAACCTGATCATGTAGATCGAACGGACTnnnAATCCGTTCAGCCG GGTTAGATTCCCGGGGTTTCCGCCA |
| 108 | | AGGGGCGTAGTTCAATTGGTAGAGCACCGGTCTccaAAACCGGGTGT TGGGAGTTCGAGTCTCTCCGCCCCTG |
| 109 | | AGGGGCGTAGTTCAATTGGTAGAGCACCGGTCTctaAAACCGGGTGT TGGGAGTTCGAGTCTCTCCGCCCCTG |
| 110 | | AGGGGCGTAGTTCAATTGGTAGAGCACCGGTCTtcaAAACCGGGTGT TGGGAGTTCGAGTCTCTCCGCCCCTG |
| 111 | | AGGGGCGTAGTTCAATTGGTAGAGCACCGGTCTttaAAACCGGGTGT TGGGAGTTCGAGTCTCTCCGCCCCTG |
| 112 | | TGGGGTATCGCCAAGCGGTAAGGCACCGGATTCnnnTTCCGGCATTC CGAGGTTCGAATCCTCGTACCCCAG wherein nnn is CTA, TCA, or TTA |
| 113 | | AGGGGCATAGCTCAAGCGGTAAAGCACCGGACTnnnAAACCGGCAGT CCGAAGTTCGAATCCCCCCACCCCAG wherein nnn is CTA, TCA, or TTA |
| 114 | H. sapiens IgG1 Constant Region | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG K |
| 115 | H. sapiens Kappa constant region | TVAAPSVFIFPPPSDEQLKSGTASVVCLLNNFYPREAKVQWKVDNALQ SGNSQESVTEQDSKDSTYSLSSTLTLSKADYEKHKVYACEVTHQGLS SPVTKSFNRGEC |
| 116 | | VVTVPSSSLGTQTYICNVNHKPSN |
| 117 | | TFGQGTKVEIKRTVAAPSVFIF |

EXAMPLES

The following Examples are merely illustrative and are not intended to limit the scope or content of the invention in any way.

Example 1—Multisite Incorporation Scheme for Incorporation of Multiple Unnatural Amino Acids (UAAs) in a Protein This Example describes the approach utilized for incorporation of multiple UAAs into a single protein.

Figure 7:
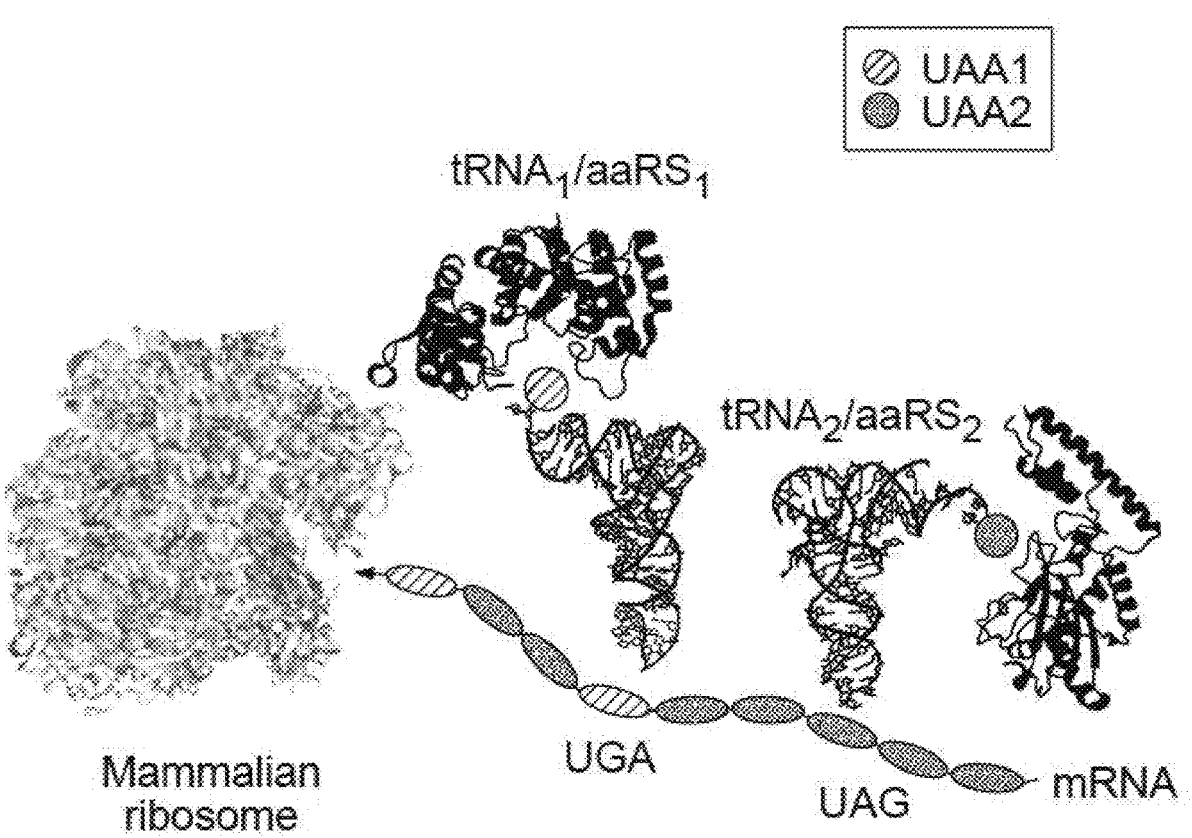
FIG. 7 is a schematic overview of site-specific incorporation of two distinct unnatural amino acids (UAAs).

FIG. 7 depicts the general scheme for site-specific incorporation of two distinct UAAs into proteins expressed in mammalian cells. A UGA codon is used with an appropriate tRNA/aminoacyl-tRNA synthetase (aaRS) pair 1 to incorporate a first UAA (UAA1), while a UAG codon is used with a second tRNA/aaRS pair 2 to incorporate a second UAA (UAA2). Regardless of codon location, two distinct codons in combination with appropriate tRNA/aaRS pairs will generate a ribosomally-expressed protein including two distinct UAA incorporated at their respective sites.

Selection of the components that allow for successful, efficient incorporation of multiple UAAs in a protein is challenging given that there are over two million possible combinations of distinct aaRS, tRNA, UAA, codon, and pair combinations that could be used for such multisite incorporation. As a result, it is challenging to find specific combinations of these elements that are suitable for use for site-specific incorporation of two distinct bioconjugation handles.

Example 2—TGA-Stop Codon Mediated Suppression Comparison in Mammalian Cells

This Example describes studies for analyzing effectiveness of the TGA-stop codon for incorporation of multiple UAAs into a single protein.

The following protocol was used for all small scale EGFP incorporation analyses. HEK293T cells were seeded at a density of 600,000 cells per well for a 12-well plate the day before transfection. A total amount of 1.2 µg DNA+4 µl PEI+20 µl DMEM was used for transfection of each well. For the modular three-plasmid transfection, 0.4 µg of each plasmid was used. For two-plasmid transfections, 0.6 µg of each plasmid was used. Fluorescence images were acquired by fluorescent microscopy and subsequent EGFP expression analysis were performed 48 hours post transfection. To obtain EGFP expression data, cells were harvested and lysed as described before (see PCT/US2020/045506). EGFP fluorescence in the lysate was collected in a 96-well plate using a SpectraMAX M5 (Molecular Devices) (ex=480 nm and em=530 nm). The mean of three independent experiments was reported, and error bars represent standard deviation.

For larger scale protein expression studies incorporating two UAAs, HEK293T cells were seeded in 100 mm cell culture dishes (5 million cells per dish) two days before transfection. A reaction mixture of 12 μg DNA+50 μl PEI+200 μl DMEM was used to transfect cells that were between 80%-90% confluency. The UAAs were supplemented at 1 mM final concentration at the time of transfection. Cells were harvested 48 hours post-transfection, lysed with CelLytic M, and the C-terminally polyhistidine tagged protein was purified using cobalt-containing TALON metal affinity resin columns (Clontech) following the manufacturer's protocol. Purified proteins were subjected to, for example, SDS-PAGE gels and electrospray-ionization mass spectrometry (ESI-MS) (Agilent TOF HPLC-MS) for further characterization.

Figure 8:
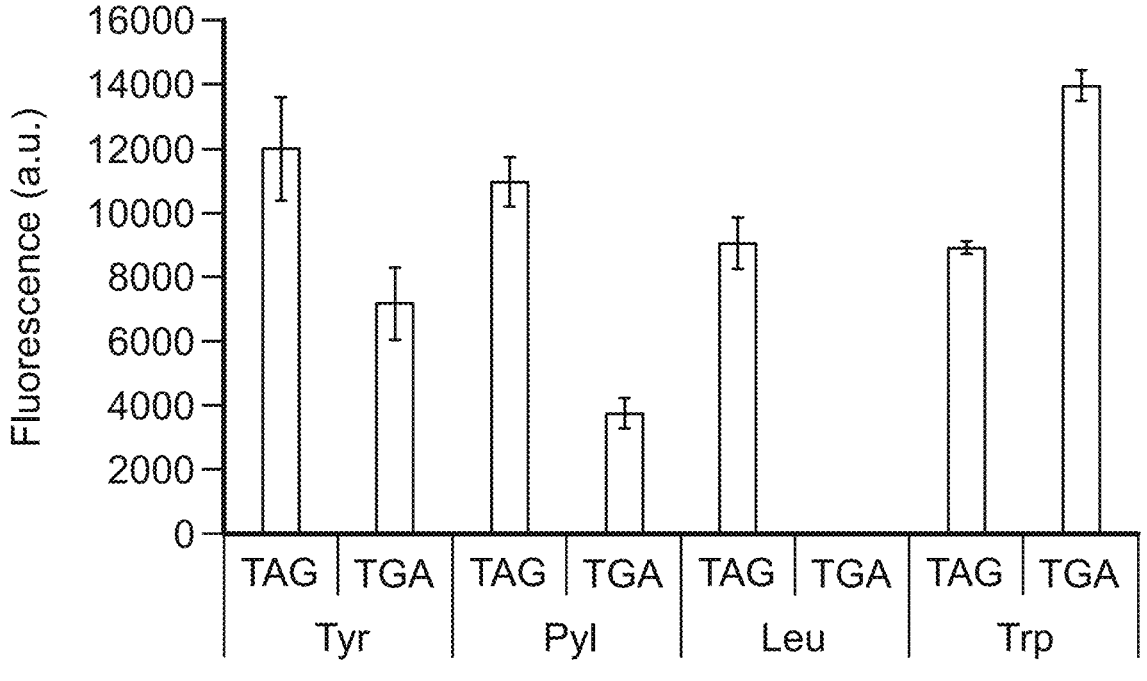
FIG. 8 depicts a comparison of TGA-stop codon suppression in mammalian cells of exemplary tRNA/aminoacyl tRNA synthetase (aaRS) pairs using a fluorescent reporter.

FIG. 8 describes a comparison of different codon incorporation efficiencies between tRNA/aaRS pairs using pAc-Bac plasmids with the aminoacyl tRNA synthetase (aaRS) under a CMV promoter and tRNA under h1/U6 promoters. tRNA/aaRS used in this study were *E. coli* tyrosine, pyrrolysine, *E. coli* leucyl, and *E. coli* tryptophan with 1 mM OmeY, BocK, C5Az (FIG. 2, Formula 1, X=S, n=3), and HTP, respectively. Full-length EGFP reporter expression, measured by characteristic fluorescence in cell-free extract, was determined in each case to represent nonsense suppression efficiency. Each aaRS (Tyr, Pyl, Leu, or Trp) was cotransfected with either TAG or TGA suppressors of its cognate tRNA and the appropriate EGFP-mutant (TAG or TGA) to evaluate how well each pair suppressed the two different nonsense codons.

The following tRNA/aaRS pairs were used in the studies corresponding to FIG. 8: tyrosine—SEQ ID NOs: 70, 69 (CUA), and 68, pyrrolysine—SEQ ID NOs: 101, 73 (CUA), and 72, leucyl—SEQ ID NOs: 4, 16, and 17, and tryptophan—SEQ ID NOs: 45, 50, and 51.

In these studies, tryptophan displayed the highest TGA expression levels.

Example 3—Analysis of Cross Reactivity of Synthetases

This example provides an investigation of cross reactivity of selected combinations of tRNA/aaRS pairs.

An EGFP TAG or TGA reporter was used following the same protocol as described in PCT/US2020/045506. 1 mM of the UAAs OmeY, BocK, C5Az, or HTP were used, in combination with each tRNA, and with the respective LeuRS, TyrRS, PylRS, and TrpRS synthetase (FIG. 9). The following tRNA/aaRS pairs were used in the studies corresponding to FIG. 9: tyrosine—SEQ ID NOs: 70, 69 (CUA), and 68, pyrrolysine—SEQ ID NOs: 101, 73 (CUA), and 72, leucyl—SEQ ID NOs: 4, 16, and 17, and tryptophan—SEQ ID NOs: 45, 50, and 51.

Figure 9A:
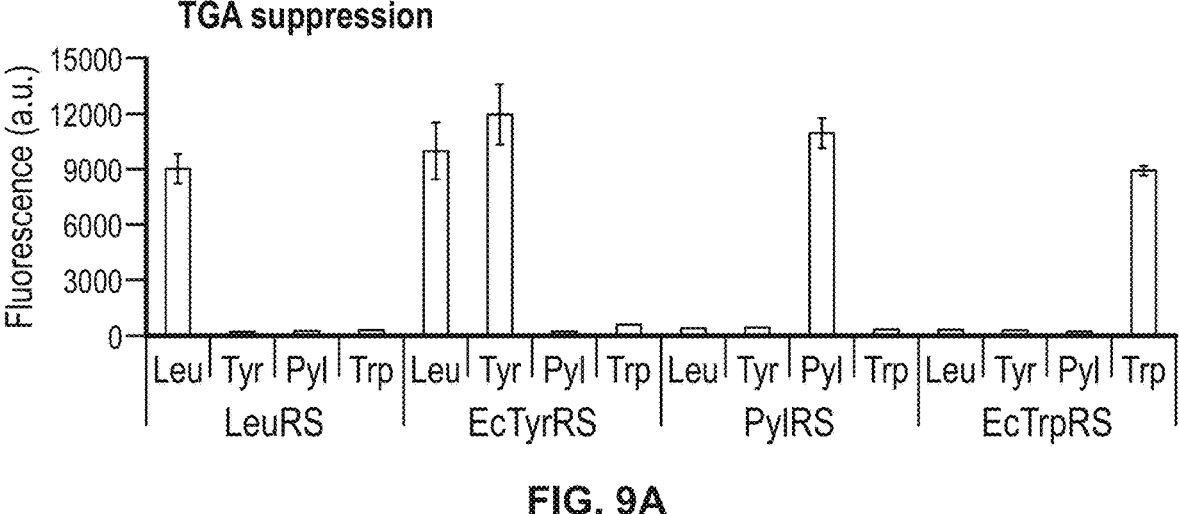
FIGS. 9A-9B demonstrate cross-reactivity of tested tRNA-synthetase pairs.
Figure 9B:
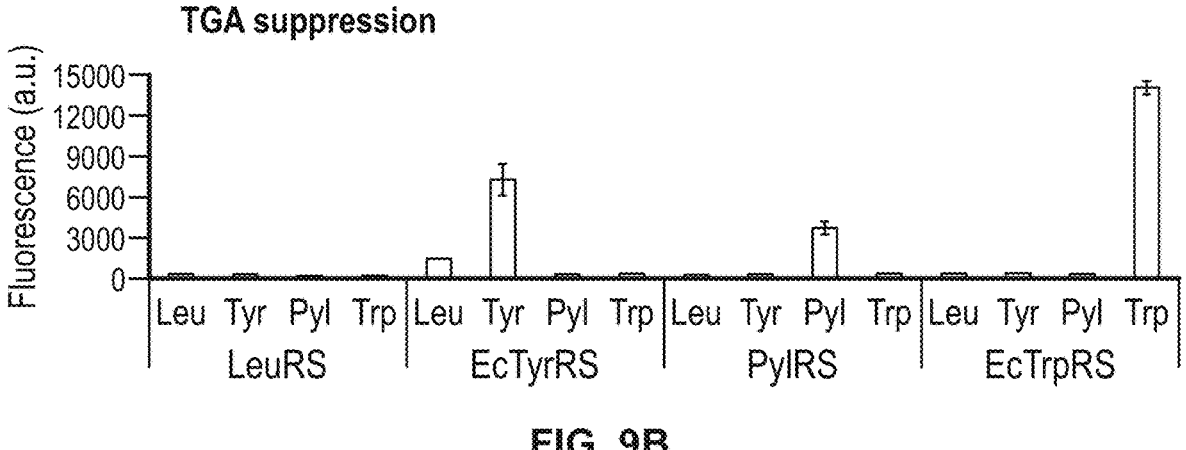

FIG. 9A highlights the cross reactivity using TAG suppressor tRNAs, while FIG. 9B highlights the cross reactivity using TGA suppressor tRNAs. For example, the LeuRS only displayed selectivity towards its cognate tRNA (FIG. 9A), making LeuRS a strong candidate for use in multisite UAA incorporation; by contrast, the EcTyrRS is able to charge OmeY onto its cognate tyrosine tRNA, but was additionally cross reactive to the Leu-tRNA$_{CUA}$ (FIG. 9A). This crossreactive trend was also observed with TGA suppression between the tyrosyl aaRS and leucyl tRNA, albeit at a lower rate (FIG. 9B). Cross reactivity between tyrosyl and leucyl tRNA/aaRS pairs is due to the EcTyrRS, which is capable of charging the leucyl suppressor tRNAs, and therefore makes this combination incompatible for double suppression in this setting.

Example 4—Site-Specific Incorporation of Two UAAs as Demonstrated Via EGFP** Reporter Assay This example demonstrates that it is possible to incorporate two UAAs into a protein in a mammalian cell using an EGFP reporter system.

Plasmids were constructed specifically for dual UAA incorporation. Typically, plasmid components for each pair include a CMV promoted aaRS and a multicopy cassette of tRNAs, ranging from 4-16 copies, under a U6/H1 promoter. It is contemplated that introducing the reporter under a constitutive promoter on one of the plasmids would reduce the number of plasmids needed in transfection.

Figure 10A:
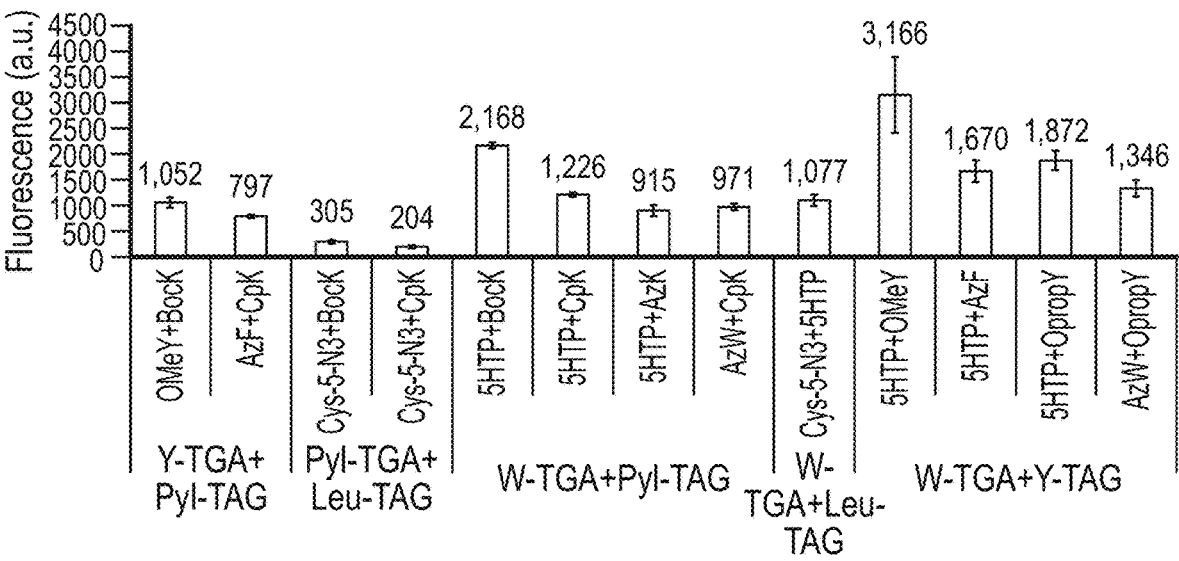
FIGS. 10A-10B demonstrate site-specific incorporation of two UAAs.

The following tRNA/aaRS pairs were used in the studies corresponding to FIG. 10: tyrosine—SEQ ID NOs: 70, 69 (CUA), and 68, pyrrolysine—SEQ ID NOs: 101, 73 (CUA), and 72, leucyl—SEQ ID NOs: 4, 16, and 17, and tryptophan—SEQ ID NOs: 45, 50, and 51.

In some examples, for EcTyr$_{TGA}$+Pyl$_{TAG}$, plasmid pAcBac3-EcTyrrGA-EGFP (EGFP stands for EGFP-39TAG-151TGA) and pAcBac1-UbiCMbPylRS-8×tRNA$_{CUA}$ Pyl were constructed. For EcTyr$_{TAG}$+Pyl$_{TGA}$, plasmids pAcBac3-EcTyr$_{TAG}$EGFP and pAcBac1-CMV-MbPylRS-8×tRNA$_{UCA}$ Pyl were constructed. pAcBac3-EcTyr$_{TAG}$-EGFP was constructed as previously described (see, for example, Zheng et al. (2017) CHEM SCI. 8(10):7211-7217), except only 16 tRNA copies were incorporated (instead of 20 copies in the original pAcBac3). The analogous pAcBac3-EcTyr$_{TGA}$-EGFP plasmid was similarly created, except 8 tRNA copies were incorporated. To generate the pAcBac1-CMV-MbPylRS-8×tRNA$_{UCA}$ Pyl plasmid, a pIDT-Kan-8×tRNA$_{UCA}$ Pyl plasmid was first prepared containing 8 copies of tandem tRNAuCA Pyl, each driven by the U6 promoter. The 8×tRNA cassette was excised out of this plasmid by NheI/AvrII digestion and inserted into the SpeI site of the previously reported pAcBac1-MbPylRS plasmid. An analogous cloning strategy was used to create the corresponding TAG-suppressing plasmid pAcBac1-UbiC-MbPylRS8×tRNA$_{CUA}$ Pyl. For the construction of the pAcBac3-EcLeuTAG-EGFP plasmid, a DNA sequence encoding EcLeuRS was PCR amplified to replace the AnapRS in the previously reported plasmid pAcBac2R-8×EcLtR-AnapRS3 by NheI and EcoRI restriction enzyme sites. The EcLeuRS gene was also replaced by the other aaRS variants in the below-described work. EGFP** was then PCR amplified and inserted into the SfiI sites to make the final plasmid. Similarly designed plasmids were generated for the *E. coli* TrpRS/tRNA pair, with minimal differences in DNA regions.

Figure 10B:
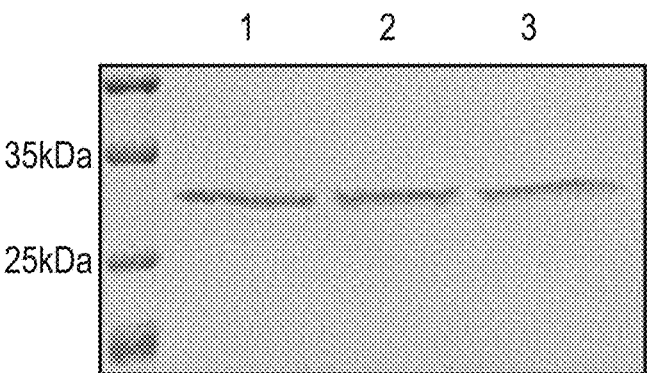

The expression levels of the multisite UAA incorporation in an EGFP reporter were determined in FIG. 10 using a variety of combinations of pAcBac-tRNA/aaRS and pAcBac-tRNA/aaRS/EGFP. 1 mM of each UAA was used. For example, the first plasmid combination of the tyrosine TGA suppressor and pyrrolysine TAG suppressor plasmid resulted in relatively low yields of EGFP** containing either the UAA combination OMeY+BocK or the UAA combination AzF+CpK. It is important to compare the fluorescence levels of poor but bioconjugation relevant amino acid combinations, such as AzF+CpK (797), and Cy5-N3+CpK (204), to higher yielding combinations, such as 5HTP+CpK (1226), Cy5-N3+5HTP (1077), and 5HTP+AzF (1670), which are 2-10× improved in yield compared to all other existing bioconjugation options. For the tested UAA combinations, a single band, demonstrating a homogenous product, was observed when the protein was analyzed by SDS-PAGE (FIG. 10B).

Figure 11A:
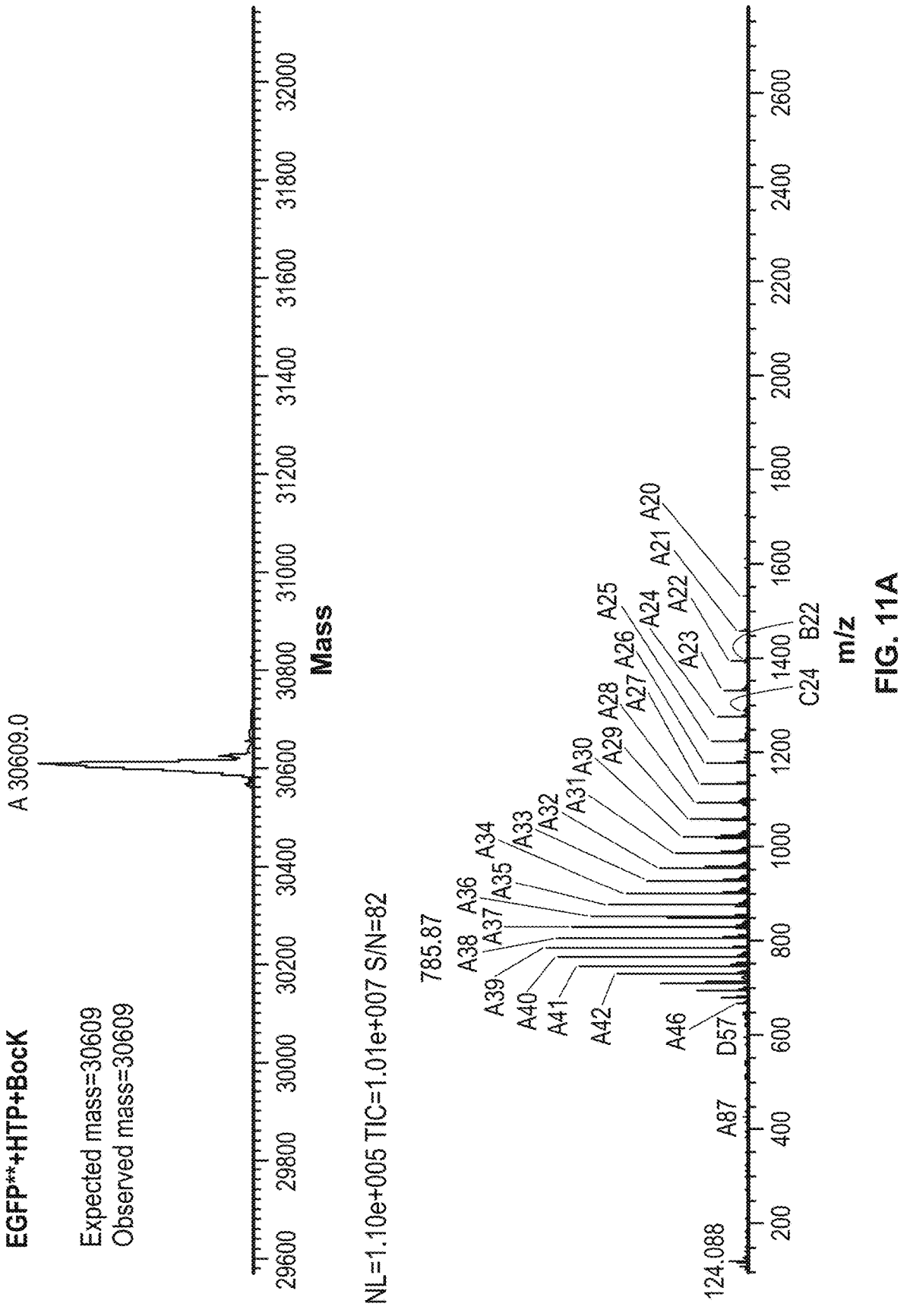
FIGS. 11A-11J demonstrate electrospray-ionization mass spectrometry (ESI-MS) results of EGFP protein containing two UAAs.
Figures 11B, 11C:
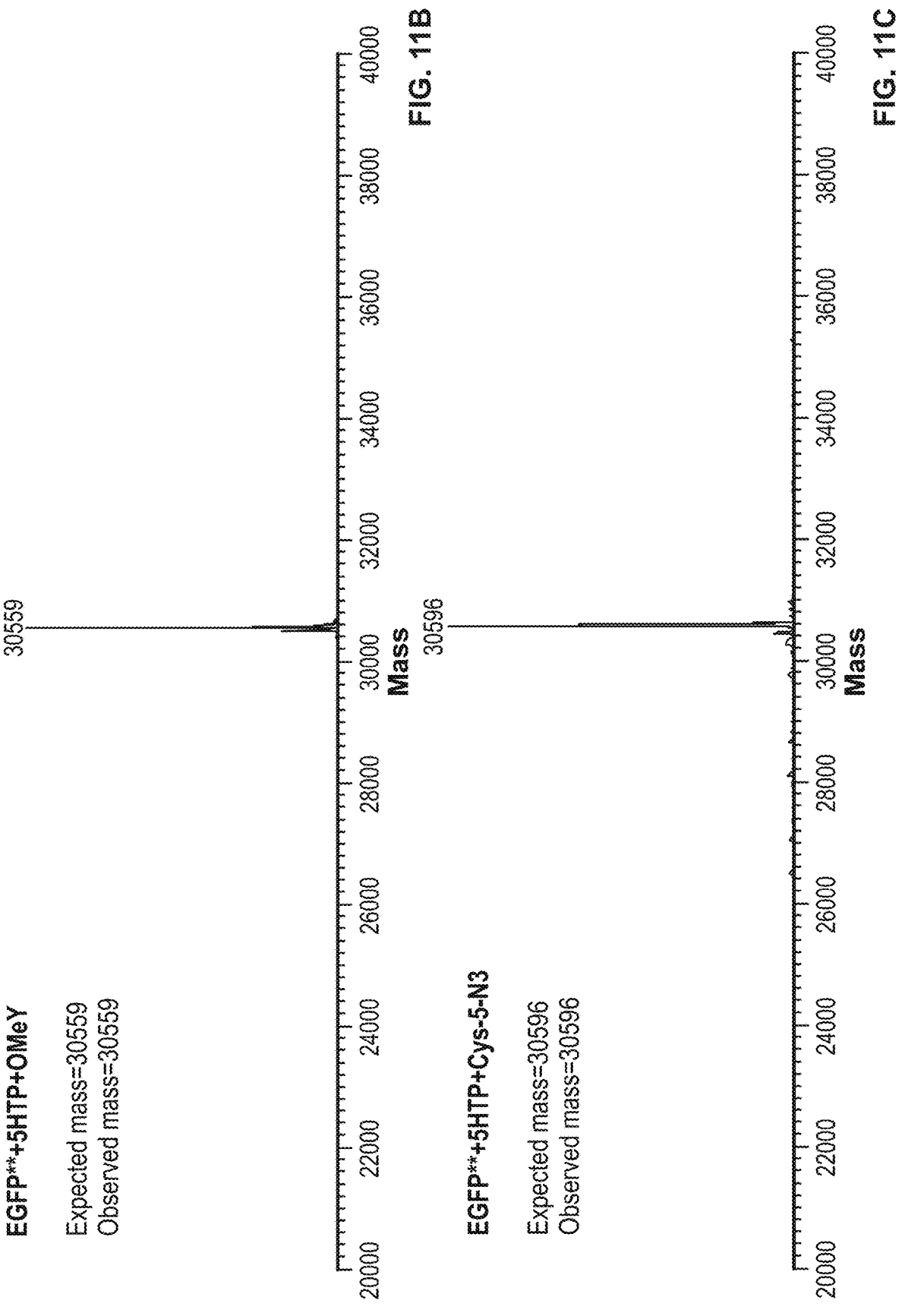
Figure 11D:
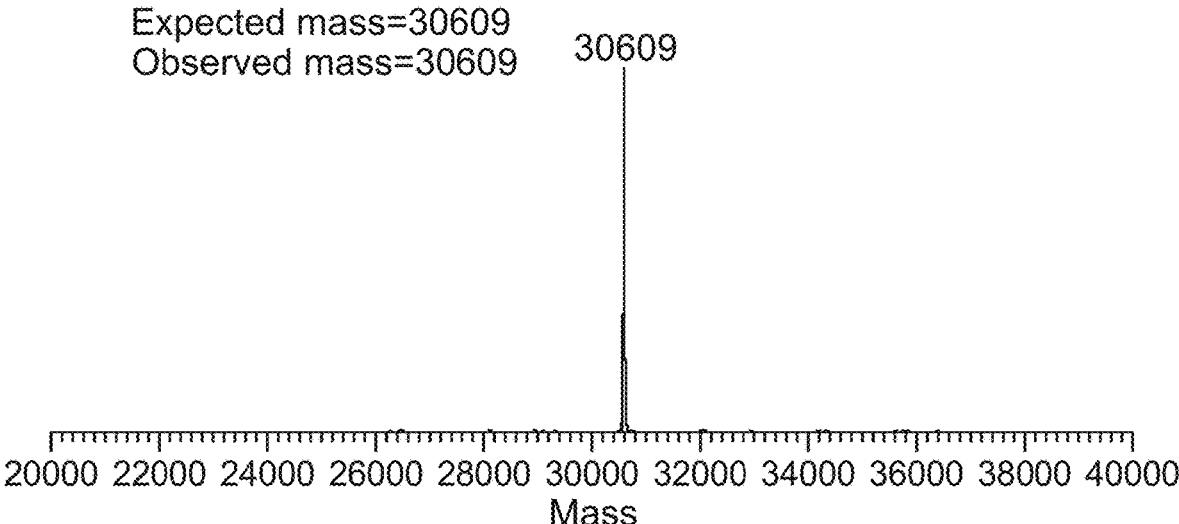
Figure 11E:
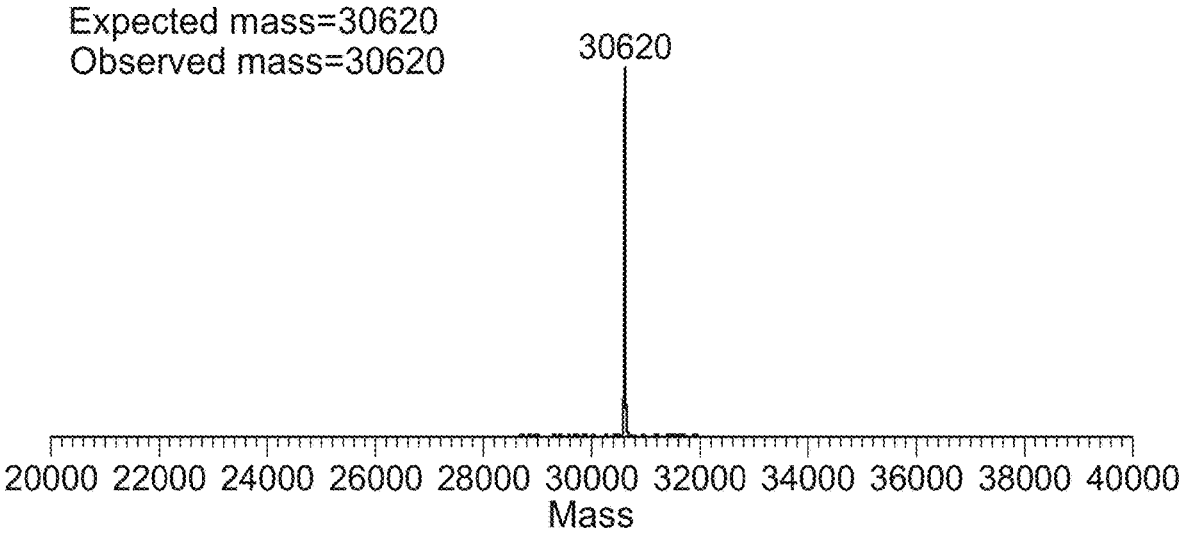
Figure 11F:
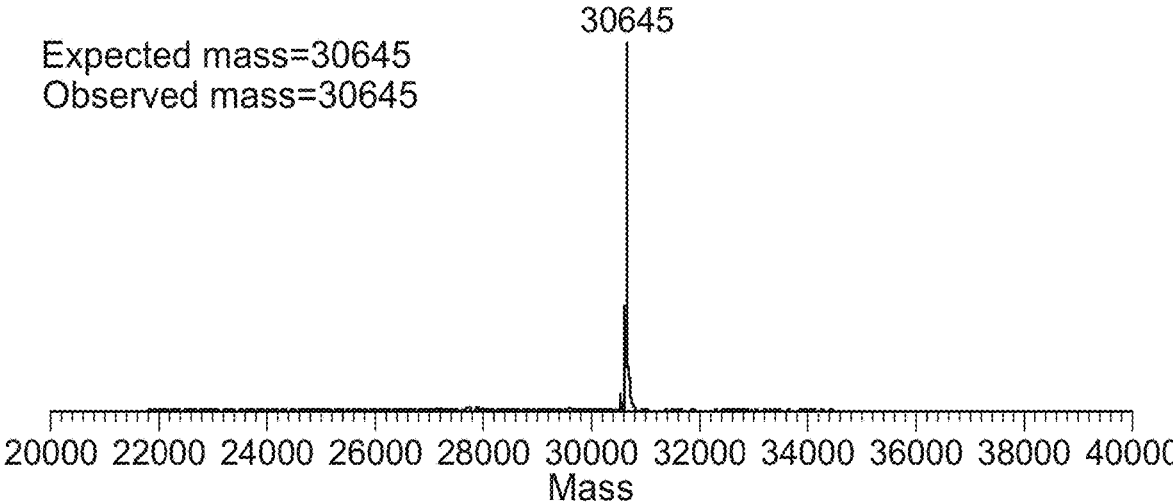
Figure 11G:
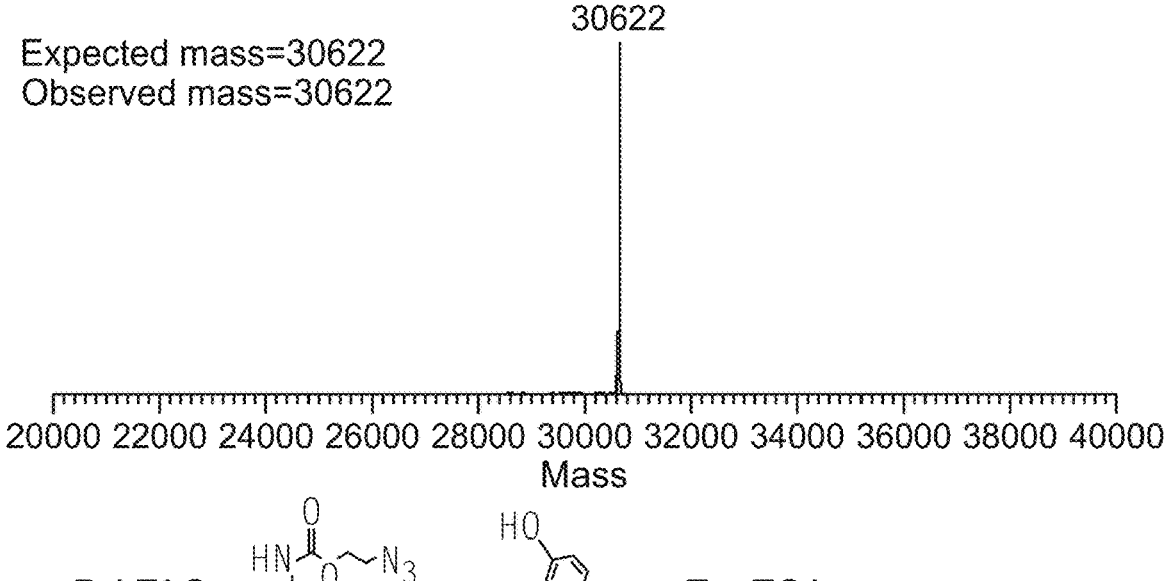

Standard whole protein ESI-MS analysis was performed for ten EGFP** variants as described above. In FIGS. 11A-G, unlabeled proteins containing two distinct UAA were analyzed for molecular weight and purity: FIG. 11A shows results of EGFP containing the UAAs HTP and BocK, FIG. 11B shows results of EGFP containing the UAAs 5HTP and OMeY, FIG. 11C shows results of EGFP containing the UAAs 5HTP and Cys-5-N3, FIG. 11D shows results of EGFP containing the UAAs 5HTP and BocK, FIG. 11E shows results of EGFP containing the UAAs 5HTP and Cyclopropene-K, FIG. 11F shows results of EGFP containing the UAAs AzW and Cyclopropene-K, and FIG. 11G shows results of EGFP containing the UAAs 5HTP and AzK. All protein samples were homogenous, demonstrating the site-specific incorporation of each UAAs. The expected mass was observed in each instance.

Figure 11H:
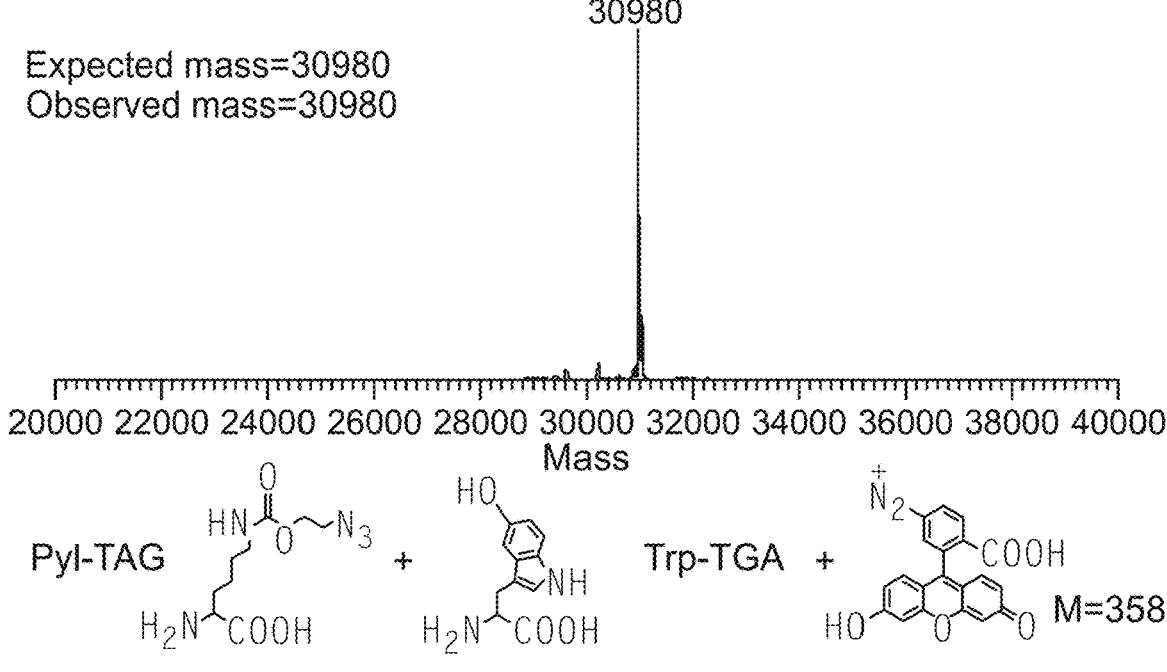
Figure 11I:
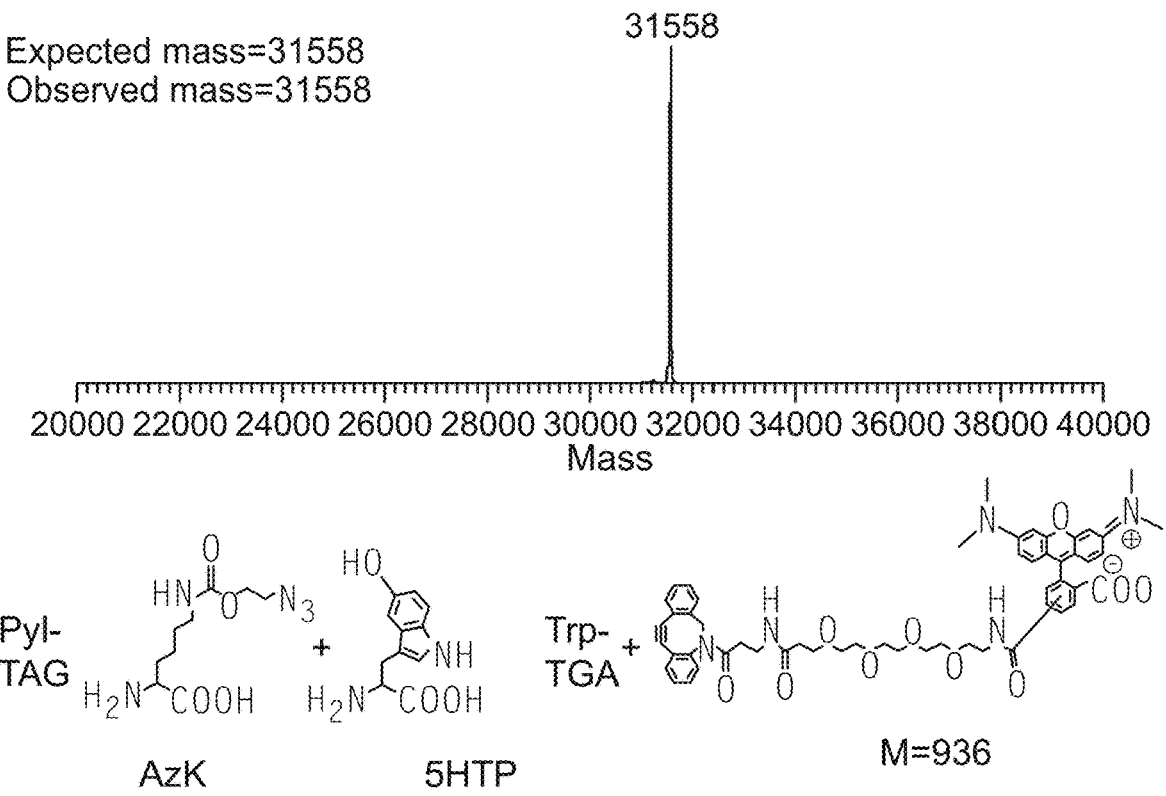
Figure 11J:
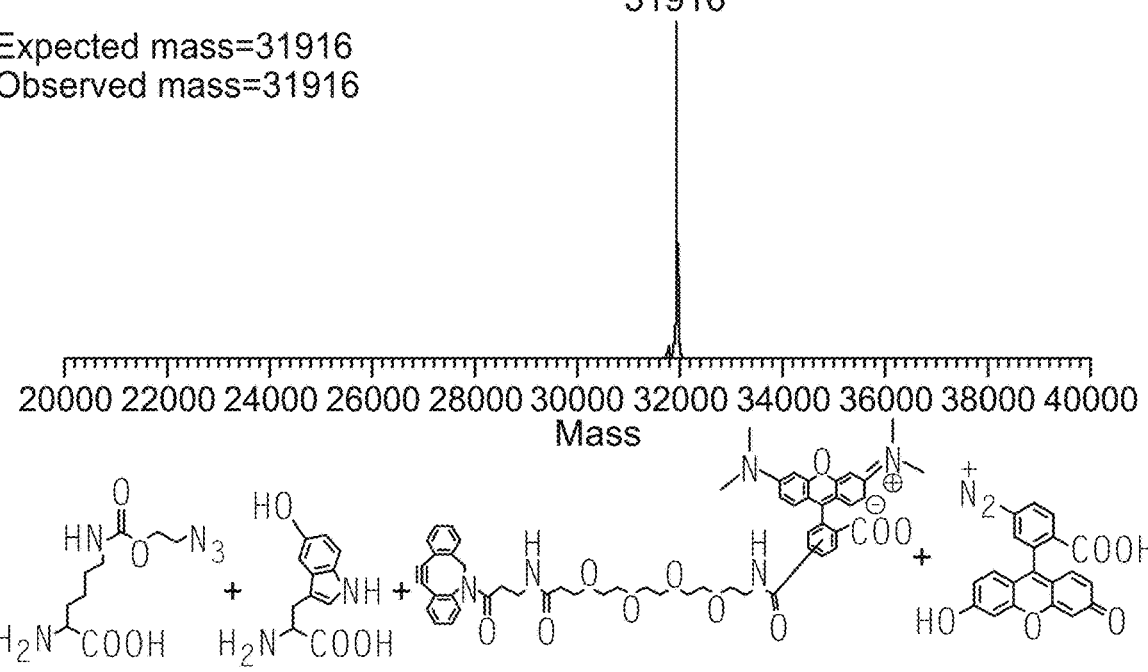

An EGFP reporter contains the EGFP protein with two stop codons (TAG and TGA). Fluorophores were subsequently conjugated to the variants in one pot reactions. For click-labeling, the EGFP protein containing an azide, 1 µg of purified EGFP was incubated with 20 µM DBCO-Cy5 (Sigma). For EGFP containing alkyne UAA, 1 µg protein was incubated with 50 µM Alexa Fluor 488 picolyl azide (Fisher Scientific) for 2 hours at room temperature. Identical reactions were set up with wild-type EGFP as control experiments. For labeling EGFP containing CpK, 5 µM of protein was incubated with 200 µM tetrazine-fluorescein at room temperature in PBS for 30 min. For protein containing 5HTP, 1 µg of purified EGFP (approximately 6-10 µM) was labeled with 5× excess diazonium. FIG. 11H depicts the liquid chromatography mass spectrometry (LCMS) result of the single labeling of EGFP containing 5HTP and AzK with a diazonium fluorophore where only the target 5HTP is labeled, using the above described conditions and depicting a single expected mass shift from the unlabeled FIG. 11G. FIG. 11I demonstrates the LCMS result of the single labeling of EGFP containing 5HTP and AzK with DBCO-TAMRA, where only the target Azide is labeled, using the above described conditions and depicting a single expected mass shift from the unlabeled FIG. 11G. FIG. 11J demonstrates the LCMS result of the double labeling of EGFP containing 5HTP and AzK with a diazonium fluorophore and DBCO-TAMRA, using the above described conditions and depicting a single expected mass shift from the unlabeled FIG. 11G, where 5HTP is selectively labeled with diazonium and AzK is selectively labeled with DBCO-TAMRA.

After labeling, the resulting proteins were also subjected to SDS-PAGE analysis and imaged by either the fluorescein or TAMRA settings on a BioRad Chemidoc imager. Only bands containing labeled protein are visible under these settings; the results of this analysis are shown in FIG. 12.

Example 5—Incorporation of Multiple Distinct UAA into an Antibody and Subsequent Characterization This Example describes incorporation of two UAAs into an antibody and subsequent characterization of the antibody protein.

Figures 14A, 14B, 15:
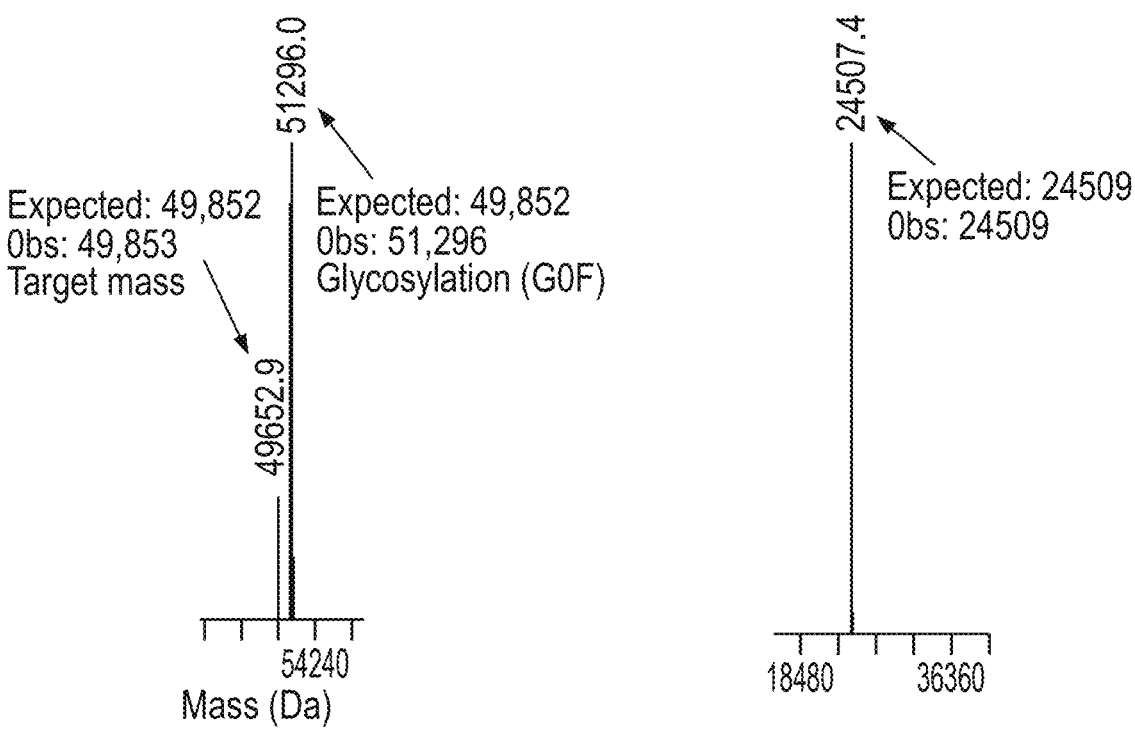
FIGS. 14A-14B demonstrate ESI-MS results of EGFP protein containing two UAAs.
FIG. 15 depicts the conserved regions of the IgG protein structure utilized for site-specific incorporation of multiple UAAs.

The ability to incorporate two distinct UAAs into a protein was extended to an antibody. The antibody utilized in this study was a full length, human IgG1 subclass monoclonal antibody (mAb) containing homologous regions to antibodies such as trastuzumab (Herceptin). A tryptophan plasmid was constructed containing a CMV promoted TrpRS.h14 (SEQ ID NO: 45) with a 4×U6 promoted Trp-tRNA$_{UCA}$ (SEQ ID NO: 51). A leucyl suppressor plasmid was construction containing a CMV promoted LeuRS.v1 (SEQ ID NO: 2) with a 4×U6 promoted LeutRNA$_{CUA}$ (SEQ ID NO: 16). Light chain (LC) and heavy chain (HC) antibody fragments were expressed constitutively under a CMV promoter. It is contemplated herein that an improved system would introduce the LC and HC antibody fragments onto the suppressor plasmids to increase the transient transfection yields, which are already significantly higher than any other reported multisite suppression protein. These plasmids were transfected in Expi293 according to the manufacturer's protocols, along with one plasmid containing the HC mutants and one plasmid containing the LC mutant with a stop codon as depicted in FIG. 15.

Figures 12A, 12B, 13A, 13B:
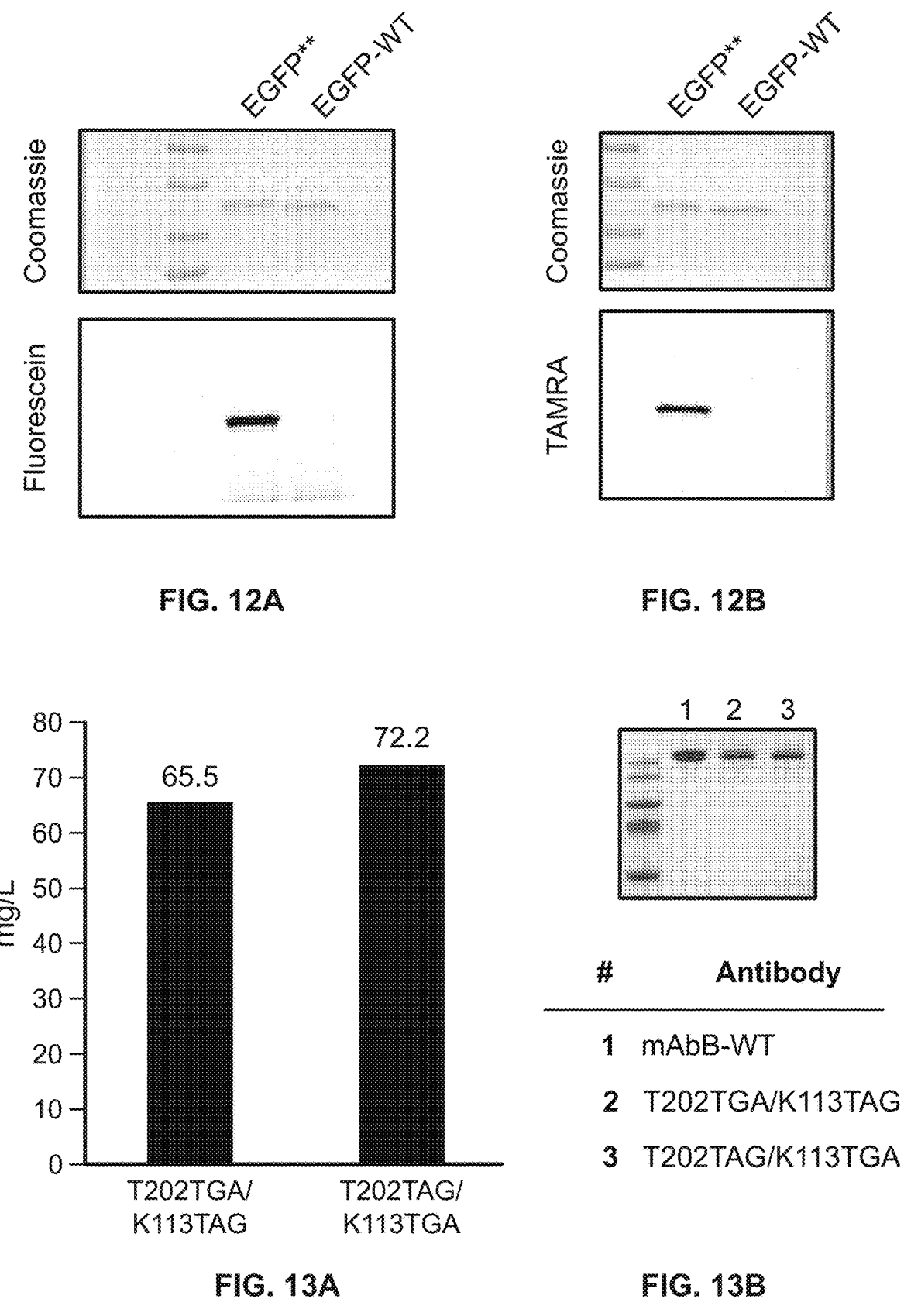
FIGS. 12A-12B are SDS-PAGE gels demonstrating production of fluorescently labeled EGFP with fluorescein (FIG. 12A) and TAMRA (FIG. 12B).
FIGS. 13A-13B demonstrate protein yield of IgG containing two UAAs.

Proteins were purified via standard Protein G columns to yield 66 mg/L and 72 mg/L total protein for HC-T202-TGA/LC-K113-TAG (incorporating the UAAs HTP and LCA) and HC-T202-TAG/LC-K113-TGA (incorporating the UAAs LCA and HTP) antibodies using 1 mM UAA as described in the manufacturer protocol and as described above. Protein yield is shown in FIG. 13A. Protein concentration was measured using the Bradford assay or Ultraviolet-visible (UV/Vis) absorbance using a Nanodrop with IgG settings. SDS-PAGE analysis (FIG. 13B) depicts clean bands for WildType (WT) (1), HTP/LCA (2) and LCA/HTP (3) with no major truncation observed. These antibodies contain two site-specific distinct UAAs with orthogonal/compatible conjugation chemistries. FIG. 14 depicts target PNGase/reduced LCMS data. The target mass of the LC containing K113-LCA is solely observed (FIG. 14A). Two peaks are observed for the HC mass (FIG. 14A). The deglycosylated target mass of 49,853 was observed, but partial de-glycosylation resulted in a glycosylation product (51,296). Without wishing to be bound by theory, this outcome may occur if the site of UAA introduction was sterically close to the glycosylation site. Regardless, importantly, a pure whole-protein mass is observed in the absence of PNGase/reduction.

Figure 16:
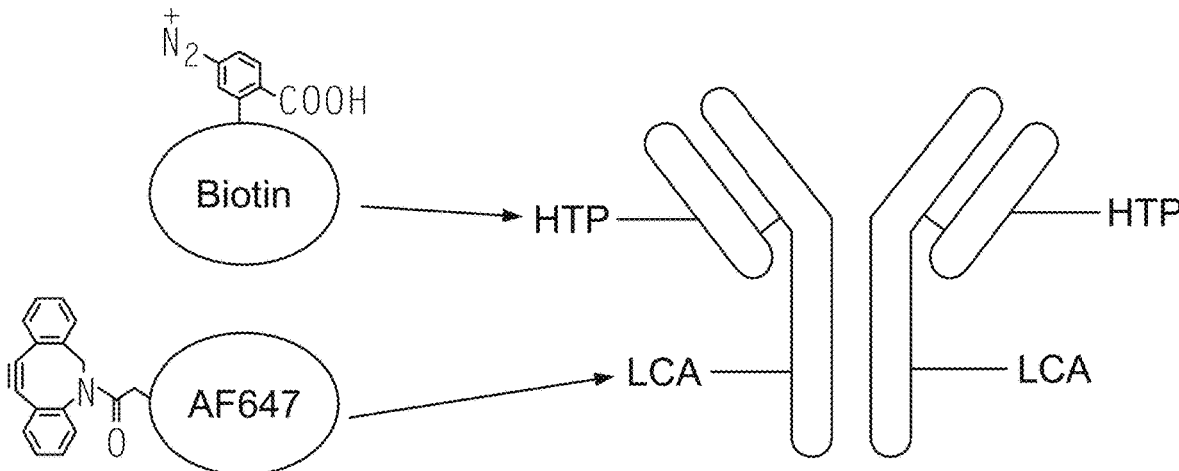
FIG. 16 depicts a schematic diagram of an antibody including the UAAs HTP and LCA, labeled with Click-Chemistry and Diazo coupling, e.g., for mass spectrometry studies.
Figure 17A:
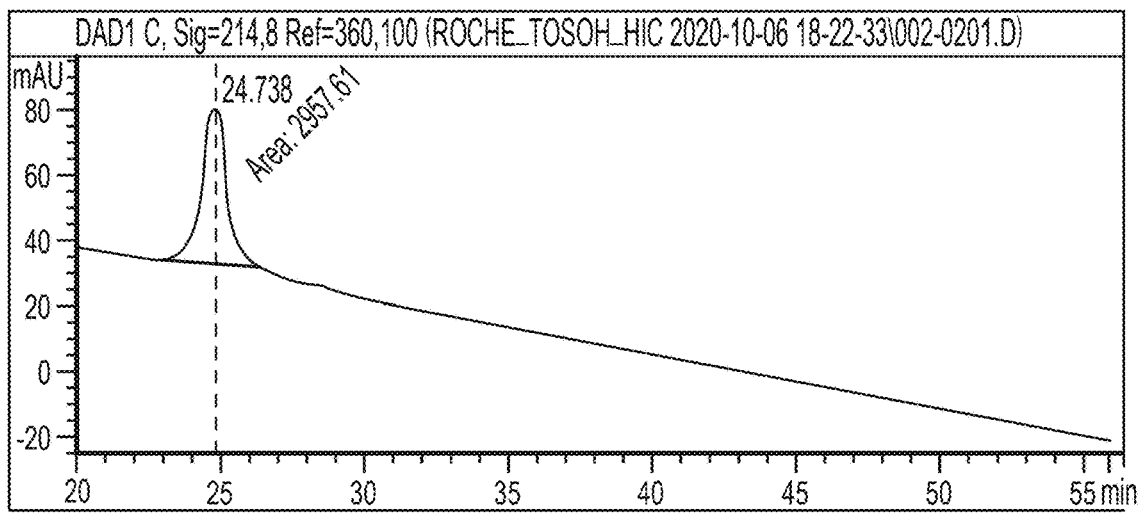
FIGS. 17A-17E display high performance liquid chromatography hydrophobic interaction chromatography (HPLC-HIC) traces of an antibody including the UAAs HTP and LCA, labeled with Click-Chemistry and Diazo coupling.
Figure 17B:
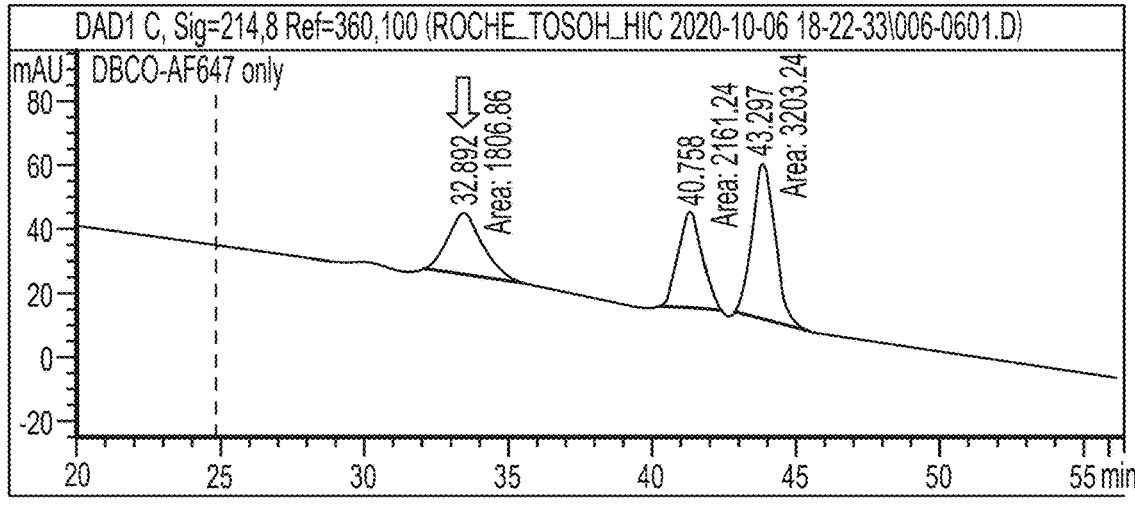
Figure 17C:
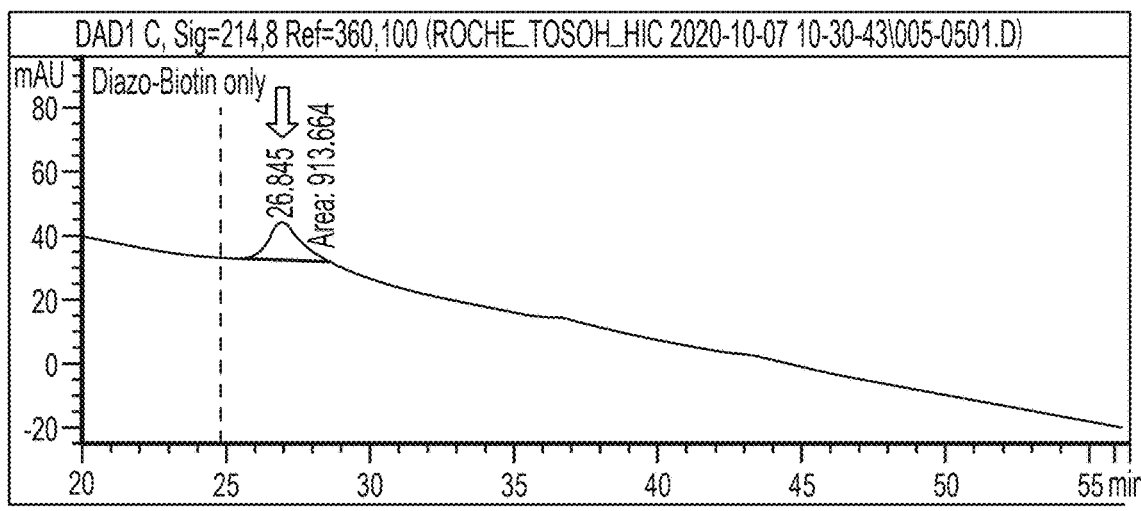
Figure 17D:
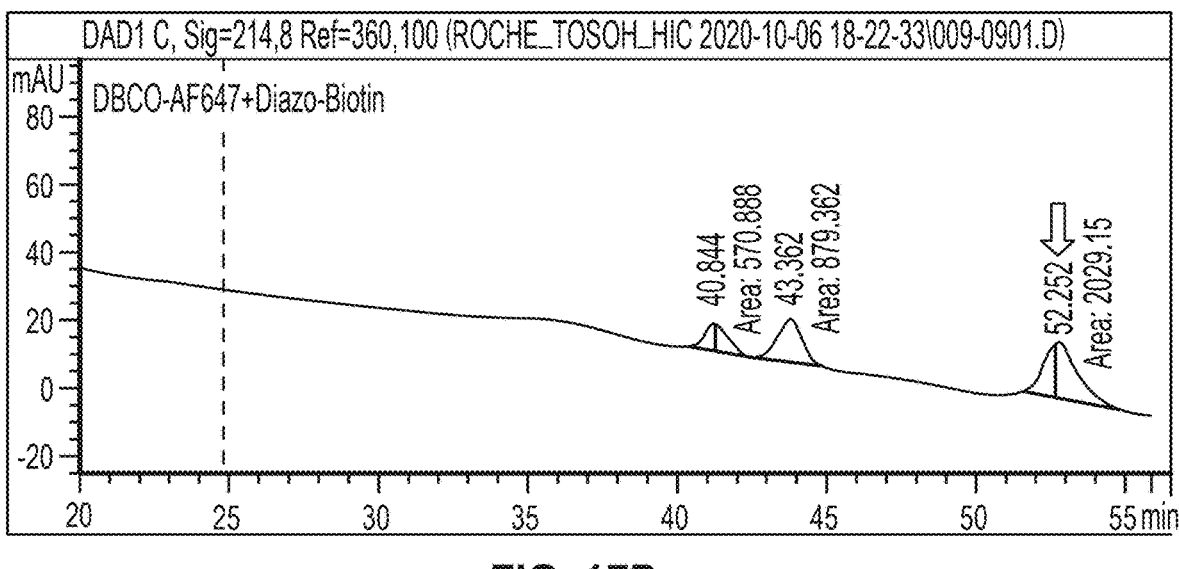
Figure 17E:
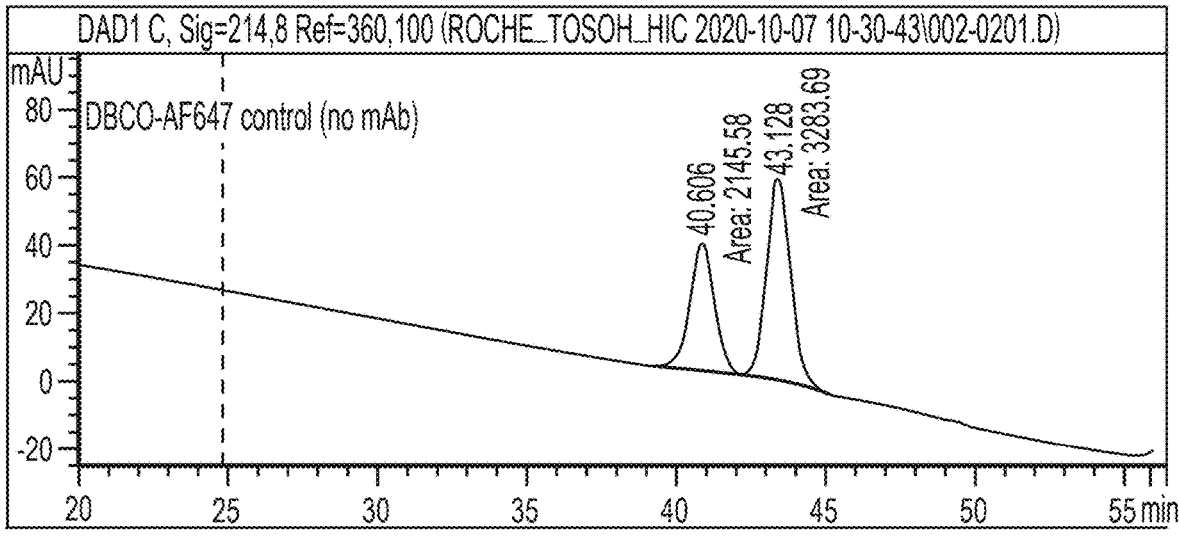

HC-T202-TGA/LC-K113-TAG (HTP/LCA) antibody was labeled with diazo-PEG4-Biotin and DBCO-AF647, depicted schematically in FIG. 16, using methodologies as described above. FIG. 16 is a simplified depiction, as each labeling reagent would label the antibody twice (resulting in 4 total conjugates) due to the dimeric nature of mAbs. HPLC-HIC traces in FIG. 17 showed the appropriate shifts upon the addition of the hydrophobic molecules AF647 and biotin. FIG. 17A shows an unlabeled LC and HC peak. FIG. 17B shows the LC peak shift with the addition of DBCO-AF647. Two additional peaks are seen, but these correspond to the DBCO-AF647 additive, as clarified by a DBCO-AF647 only control, where no mAb is included (FIG. 17E) and therefore are not indicative of decreased sample purity. FIG. 17C shows the HC peak shift with the addition of diazo-biotin. FIG. 17D shows a full shift to a more hydrophobic peak when labeled together. Overall, about 100% labeling was observed by HPLC-HIC, indicating that the overall protein purity was very high.

Overall, these studies demonstrate the ability to incorporate multiple distinct UAAs into an antibody and the capability to label these antibodies (as performed with the EGFP** reporter experiments above) with therapeutic payloads or fluorophores.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A protein expressed in a mammalian cell, wherein the protein comprises two distinct unnatural amino acids incorporated into the protein at two site-specific locations, wherein the first unnatural amino acid (UAA) is a tryptophan analog selected from 5-HTP and 5-AzW and the second UAA is a leucine analog selected from LCA and Cys-5-N3.

2. The protein of claim 1, wherein a detectable label or molecule is covalently coupled to the protein via the first UAA.

3. The protein of claim 1, wherein a detectable label or molecule is covalently coupled to the protein via the second UAA.

4. The protein of claim 3, wherein the detectable label or molecule coupled to the protein via the first UAA is different from the detectable label or molecule coupled to the protein via the second UAA.

5. The protein of claim 1, wherein the protein is an antibody or an antigen-binding fragment thereof, a bispecific antibody, nanobody, affibody, viral protein, chemokine, cytokine, antigen, blood coagulation factor, hormone, growth factor, enzyme or a cell signaling protein.

6. The protein of claim 5, wherein the protein is an antibody or an antigen-binding fragment thereof.

7. The antibody of claim 6, wherein the antibody is a human IgG antibody, and wherein the first UAA is incorporated into a light chain of the antibody and the second UAA is incorporated into a heavy chain of the antibody.

8. The antibody of claim 7, wherein the first UAA is either 5-HTP or 5-AzW and the second UAA is either LCA or Cys-5-N3.

9. The antibody of claim 8, wherein the first UAA and the second UAA are chemically conjugated to a detectable label, a small molecule, or a drug.

* * * * *

SEQUENCE LISTING

```
<160> NUMBER OF SEQ ID NOS: 117

<210> SEQ ID NO 1
<211> LENGTH: 863
<212> TYPE: PRT
<213> ORGANISM: Escherichia coli

<400> SEQUENCE: 1

Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
            20                  25                  30

Glu Lys Tyr Tyr Cys Leu Ser Met Leu Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285
```

-continued

```
Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
                340                 345                 350

Gly Leu Asn Ile Lys Pro Val Ile Leu Ala Ala Asp Gly Ser Glu Pro
                355                 360                 365

Asp Leu Ser Gln Gln Ala Leu Thr Glu Lys Gly Val Leu Phe Asn Ser
                370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Tyr Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Tyr Ile
                515                 520                 525

Gly Gly Ile Glu His Ala Ile Met His Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
                595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
                675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
```

```
705              710              715              720

Thr Phe Asn Thr Ala Ile Ala Ala Ile Met Glu Leu Met Asn Lys Leu
            725              730              735

Ala Lys Ala Pro Thr Asp Gly Glu Gln Asp Arg Ala Leu Met Gln Glu
            740              745              750

Ala Leu Leu Ala Val Val Arg Met Leu Asn Pro Phe Thr Pro His Ile
            755              760              765

Cys Phe Thr Leu Trp Gln Glu Leu Lys Gly Glu Gly Asp Ile Asp Asn
            770              775              780

Ala Pro Trp Pro Val Ala Asp Glu Lys Ala Met Val Glu Asp Ser Thr
785              790              795              800

Leu Val Val Val Gln Val Asn Gly Lys Val Arg Ala Lys Ile Thr Val
            805              810              815

Pro Val Asp Ala Thr Glu Glu Gln Val Arg Glu Arg Ala Gly Gln Glu
            820              825              830

His Leu Val Ala Lys Tyr Leu Asp Gly Val Thr Val Arg Lys Val Ile
            835              840              845

Tyr Val Pro Gly Lys Leu Leu Asn Leu Val Val Gly Gly Pro Val
    850              855              860

<210> SEQ ID NO 2
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Glu Gln Tyr Arg Pro Glu Glu Ile Glu Ser Lys Val Gln Leu
1               5               10              15

His Trp Asp Lys Lys Arg Thr Phe Glu Val Thr Glu Asp Glu Ser Lys
            20              25              30

Glu Lys Tyr Tyr Cys Leu Ser Ile Ser Pro Tyr Pro Ser Gly Arg Leu
            35              40              45

His Met Gly His Val Arg Asn Tyr Thr Ile Gly Asp Val Ile Ala Arg
    50              55              60

Tyr Gln Arg Met Leu Gly Lys Asn Val Leu Gln Pro Ile Gly Trp Asp
65              70              75              80

Ala Phe Gly Leu Pro Ala Glu Gly Ala Ala Val Lys Asn Asn Thr Ala
            85              90              95

Pro Ala Pro Trp Thr Tyr Asp Asn Ile Ala Tyr Met Lys Asn Gln Leu
            100             105             110

Lys Met Leu Gly Phe Gly Tyr Asp Trp Ser Arg Glu Leu Ala Thr Cys
            115             120             125

Thr Pro Glu Tyr Tyr Arg Trp Glu Gln Lys Phe Phe Thr Glu Leu Tyr
            130             135             140

Lys Lys Gly Leu Val Tyr Lys Lys Thr Ser Ala Val Asn Trp Cys Pro
145             150             155             160

Asn Asp Gln Thr Val Leu Ala Asn Glu Gln Val Ile Asp Gly Cys Cys
            165             170             175

Trp Arg Cys Asp Thr Lys Val Glu Arg Lys Glu Ile Pro Gln Trp Phe
            180             185             190

Ile Lys Ile Thr Ala Tyr Ala Asp Glu Leu Leu Asn Asp Leu Asp Lys
            195             200             205
```

-continued

```
Leu Asp His Trp Pro Asp Thr Val Lys Thr Met Gln Arg Asn Trp Ile
    210             215             220

Gly Arg Ser Glu Gly Val Glu Ile Thr Phe Asn Val Asn Asp Tyr Asp
225             230             235             240

Asn Thr Leu Thr Val Tyr Thr Thr Arg Pro Asp Ala Phe Met Gly Cys
            245             250             255

Thr Tyr Leu Ala Val Ala Ala Gly His Pro Leu Ala Gln Lys Ala Ala
            260             265             270

Glu Asn Asn Pro Glu Leu Ala Ala Phe Ile Asp Glu Cys Arg Asn Thr
            275             280             285

Lys Val Ala Glu Ala Glu Met Ala Thr Met Glu Lys Lys Gly Val Asp
    290             295             300

Thr Gly Phe Lys Ala Val His Pro Leu Thr Gly Glu Glu Ile Pro Val
305             310             315             320

Trp Ala Ala Asn Phe Val Leu Met Glu Tyr Gly Thr Gly Ala Val Met
            325             330             335

Ala Val Pro Gly His Asp Gln Arg Asp Tyr Glu Phe Ala Ser Lys Tyr
            340             345             350

Gly Leu Asn Ile Lys Pro Val Ile Leu Ala Ala Asp Gly Ser Glu Pro
            355             360             365

Asp Leu Ser Gln Gln Ala Leu Thr Glu Lys Gly Val Leu Phe Asn Ser
    370             375             380

Gly Glu Phe Asn Gly Leu Asp His Glu Ala Ala Phe Asn Ala Ile Ala
385             390             395             400

Asp Lys Leu Thr Ala Met Gly Val Gly Glu Arg Lys Val Asn Tyr Arg
            405             410             415

Leu Arg Asp Trp Gly Val Ser Arg Gln Arg Tyr Trp Gly Ala Pro Ile
            420             425             430

Pro Met Val Thr Leu Glu Asp Gly Thr Val Met Pro Thr Pro Asp Asp
    435             440             445

Gln Leu Pro Val Ile Leu Pro Glu Asp Val Val Met Asp Gly Ile Thr
    450             455             460

Ser Pro Ile Lys Ala Asp Pro Glu Trp Ala Lys Thr Thr Val Asn Gly
465             470             475             480

Met Pro Ala Leu Arg Glu Thr Asp Thr Phe Asp Thr Phe Met Glu Ser
            485             490             495

Ser Trp Ile Tyr Ala Arg Tyr Thr Cys Pro Gln Tyr Lys Glu Gly Met
            500             505             510

Leu Asp Ser Glu Ala Ala Asn Tyr Trp Leu Pro Val Asp Ile Ala Ile
            515             520             525

Gly Gly Ile Glu His Ala Ile Met Gly Leu Leu Tyr Phe Arg Phe Phe
    530             535             540

His Lys Leu Met Arg Asp Ala Gly Met Val Asn Ser Asp Glu Pro Ala
545             550             555             560

Lys Gln Leu Leu Cys Gln Gly Met Val Leu Ala Asp Ala Phe Tyr Tyr
            565             570             575

Val Gly Glu Asn Gly Glu Arg Asn Trp Val Ser Pro Val Asp Ala Ile
            580             585             590

Val Glu Arg Asp Glu Lys Gly Arg Ile Val Lys Ala Lys Asp Ala Ala
            595             600             605

Gly His Glu Leu Val Tyr Thr Gly Met Ser Lys Met Ser Lys Ser Lys
    610             615             620

Asn Asn Gly Ile Asp Pro Gln Val Met Val Glu Arg Tyr Gly Ala Asp
```

-continued

```
625              630              635              640

Thr Val Arg Leu Phe Met Met Phe Ala Ser Pro Ala Asp Met Thr Leu
            645              650              655

Glu Trp Gln Glu Ser Gly Val Glu Gly Ala Asn Arg Phe Leu Lys Arg
            660              665              670

Val Trp Lys Leu Val Tyr Glu His Thr Ala Lys Gly Asp Val Ala Ala
            675              680              685

Leu Asn Val Asp Ala Leu Thr Glu Asn Gln Lys Ala Leu Arg Arg Asp
    690              695              700

Val His Lys Thr Ile Ala Lys Val Thr Asp Asp Ile Gly Arg Arg Gln
705              710              715              720

Thr Phe Asn Thr Ala Ile Ala Ala Ile Met Glu Leu Met Asn Lys Leu
            725              730              735

Ala Lys Ala Pro Thr Asp Gly Glu Gln Asp Arg Ala Leu Met Gln Glu
            740              745              750

Ala Leu Leu Ala Val Val Arg Met Leu Asn Pro Phe Thr Pro His Ile
            755              760              765

Cys Phe Thr Leu Trp Gln Glu Leu Lys Gly Glu Gly Asp Ile Asp Asn
    770              775              780

Ala Pro Trp Pro Val Ala Asp Glu Lys Ala Met Val Glu Asp Ser Thr
785              790              795              800

Leu Val Val Val Gln Val Asn Gly Lys Val Arg Ala Lys Ile Thr Val
            805              810              815

Pro Val Asp Ala Thr Glu Glu Gln Val Arg Glu Arg Ala Gly Gln Glu
            820              825              830

His Leu Val Ala Lys Tyr Leu Asp Gly Val Thr Val Arg Lys Val Ile
            835              840              845

Tyr Val Pro Gly Lys Leu Leu Asn Leu Val Val Gly Gly Pro Val
    850              855              860
```

<210> SEQ ID NO 3
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Glu Glu Gln Tyr Arg Pro Glu Glu Ile Glu Ser Lys Val Gln Leu
1               5               10              15

His Trp Asp Lys Lys Arg Thr Phe Glu Val Thr Glu Asp Glu Ser Lys
            20              25              30

Glu Lys Tyr Tyr Cys Leu Ser Val Ser Pro Tyr Pro Ser Gly Arg Leu
            35              40              45

His Met Gly His Val Arg Asn Tyr Thr Ile Gly Asp Val Ile Ala Arg
    50              55              60

Tyr Gln Arg Met Leu Gly Lys Asn Val Leu Gln Pro Ile Gly Trp Asp
65              70              75              80

Ala Phe Gly Leu Pro Ala Glu Gly Ala Ala Val Lys Asn Asn Thr Ala
            85              90              95

Pro Ala Pro Trp Thr Tyr Asp Asn Ile Ala Tyr Met Lys Asn Gln Leu
            100             105             110

Lys Met Leu Gly Phe Gly Tyr Asp Trp Ser Arg Glu Leu Ala Thr Cys
            115             120             125
```

-continued

```
Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
            195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Arg Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
    275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ser Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Leu Ile
            515                 520                 525

Gly Gly Ile Glu His Ala Ile Met Gly Leu Leu Tyr Phe Arg Phe Phe
    530                 535                 540

His Lys Leu Met Arg Asp Ala Gly Met Val Asn Ser Asp Glu Pro Ala
```

-continued

```
545              550              555              560

Lys Gln Leu Leu Cys Gln Gly Met Val Leu Ala Asp Ala Phe Tyr Tyr
                 565              570              575

Val Gly Glu Asn Gly Glu Arg Asn Trp Val Ser Pro Val Asp Ala Ile
                 580              585              590

Val Glu Arg Asp Glu Lys Gly Arg Ile Val Lys Ala Lys Asp Ala Ala
                 595              600              605

Gly His Glu Leu Val Tyr Thr Gly Met Ser Lys Met Ser Lys Ser Lys
        610              615              620

Asn Asn Gly Ile Asp Pro Gln Val Met Val Glu Arg Tyr Gly Ala Asp
625              630              635              640

Thr Val Arg Leu Phe Met Met Phe Ala Ser Pro Ala Asp Met Thr Leu
                 645              650              655

Glu Trp Gln Glu Ser Gly Val Glu Gly Ala Asn Arg Phe Leu Lys Arg
                 660              665              670

Val Trp Lys Leu Val Tyr Glu His Thr Ala Lys Gly Asp Val Ala Ala
                 675              680              685

Leu Asn Val Asp Ala Leu Thr Glu Asn Gln Lys Ala Leu Arg Arg Asp
        690              695              700

Val His Lys Thr Ile Ala Lys Val Thr Asp Asp Ile Gly Arg Arg Gln
705              710              715              720

Thr Phe Asn Thr Ala Ile Ala Ala Ile Met Glu Leu Met Asn Lys Leu
                 725              730              735

Ala Lys Ala Pro Thr Asp Gly Glu Gln Asp Arg Ala Leu Met Gln Glu
                 740              745              750

Ala Leu Leu Ala Val Val Arg Met Leu Asn Pro Phe Thr Pro His Ile
                 755              760              765

Cys Phe Thr Leu Trp Gln Glu Leu Lys Gly Glu Gly Asp Ile Asp Asn
        770              775              780

Ala Pro Trp Pro Val Ala Asp Glu Lys Ala Met Val Glu Asp Ser Thr
785              790              795              800

Leu Val Val Val Gln Val Asn Gly Lys Val Arg Ala Lys Ile Thr Val
                 805              810              815

Pro Val Asp Ala Thr Glu Glu Gln Val Arg Glu Arg Ala Gly Gln Glu
                 820              825              830

His Leu Val Ala Lys Tyr Leu Asp Gly Val Thr Val Arg Lys Val Ile
        835              840              845

Tyr Val Pro Gly Lys Leu Leu Asn Leu Val Val Gly Gly Pro Val
        850              855              860
```

<210> SEQ ID NO 4
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Glu Glu Gln Tyr Arg Pro Glu Glu Ile Glu Ser Lys Val Gln Leu
1               5               10              15

His Trp Asp Glu Lys Arg Thr Phe Glu Val Thr Glu Asp Glu Ser Lys
                20              25              30

Glu Lys Tyr Tyr Cys Leu Ser Ile Leu Pro Tyr Pro Ser Gly Arg Leu
        35              40              45
```

```
His Met Gly His Val Arg Asn Tyr Thr Ile Gly Asp Val Ile Ala Arg
    50              55              60

Tyr Gln Arg Met Leu Gly Lys Asn Val Leu Gln Pro Ile Gly Trp Asp
65              70              75              80

Ala Phe Gly Leu Pro Ala Glu Gly Ala Ala Val Lys Asn Asn Thr Ala
            85              90              95

Pro Ala Pro Trp Thr Tyr Asp Asn Ile Ala Tyr Met Lys Asn Gln Leu
            100             105             110

Lys Met Leu Gly Phe Gly Tyr Asp Trp Ser Arg Glu Leu Ala Thr Cys
            115             120             125

Thr Pro Glu Tyr Tyr Arg Trp Glu Gln Lys Phe Phe Thr Glu Leu Tyr
    130             135             140

Lys Lys Gly Leu Val Tyr Lys Lys Thr Ser Ala Val Asn Trp Cys Pro
145             150             155             160

Asn Asp Gln Thr Val Leu Ala Asn Glu Gln Val Ile Asp Gly Cys Cys
            165             170             175

Trp Arg Cys Asp Thr Lys Val Glu Arg Lys Glu Ile Pro Gln Trp Phe
            180             185             190

Ile Lys Ile Thr Ala Tyr Ala Asp Glu Leu Leu Asn Asp Leu Asp Lys
            195             200             205

Leu Asp His Trp Pro Asp Thr Val Lys Thr Met Gln Arg Asn Trp Ile
    210             215             220

Gly Arg Ser Glu Gly Val Glu Ile Thr Phe Asn Val Asn Asp Tyr Asp
225             230             235             240

Asn Thr Leu Thr Val Tyr Thr Thr Arg Pro Asp Ala Phe Met Gly Cys
            245             250             255

Thr Tyr Leu Ala Val Ala Ala Gly His Pro Leu Ala Gln Lys Ala Ala
            260             265             270

Glu Asn Asn Pro Glu Leu Ala Ala Phe Ile Asp Glu Cys Arg Asn Thr
    275             280             285

Lys Val Ala Glu Ala Glu Met Ala Thr Met Glu Lys Lys Gly Val Asp
    290             295             300

Thr Gly Phe Lys Ala Val His Pro Leu Thr Gly Glu Glu Ile Pro Val
305             310             315             320

Trp Ala Ala Asn Phe Val Leu Met Glu Tyr Gly Thr Gly Ala Val Met
            325             330             335

Ala Val Pro Gly His Asp Gln Arg Asp Tyr Glu Phe Ala Ser Lys Tyr
            340             345             350

Gly Leu Asn Ile Lys Pro Val Ile Leu Ala Ala Asp Gly Ser Glu Pro
            355             360             365

Asp Leu Ser Gln Gln Ala Leu Thr Glu Lys Gly Val Leu Phe Asn Ser
    370             375             380

Gly Glu Phe Asn Gly Leu Asp His Glu Ala Ala Phe Asn Ala Ile Ala
385             390             395             400

Asp Lys Leu Thr Ala Met Gly Val Gly Glu Arg Lys Val Asn Tyr Arg
            405             410             415

Leu Arg Asp Trp Gly Val Ser Arg Gln Arg Tyr Trp Gly Ala Pro Ile
            420             425             430

Pro Met Val Thr Leu Glu Asp Gly Thr Val Met Pro Thr Pro Asp Asp
            435             440             445

Gln Leu Pro Val Ile Leu Pro Glu Asp Val Val Met Asp Gly Ile Thr
    450             455             460

Ser Pro Ile Lys Ala Asp Pro Glu Trp Ala Lys Thr Thr Val Asn Gly
```

```
465                 470                 475                 480

Met Pro Ala Leu Arg Glu Thr Asp Thr Phe Asp Thr Phe Met Glu Ser
            485                 490                 495

Ser Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ala Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
            690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly Gly Pro Val
        850                 855                 860
```

<210> SEQ ID NO 5
<211> LENGTH: 863
<212> TYPE: PRT
<213> ORGANISM: Artificial Sequence -continued
<220> FEATURE:
<223> OTHER INFORMATION: Description of Artificial Sequence: Synthetic
      polypeptide

<400> SEQUENCE: 5

```
Met Glu Glu Gln Tyr Arg Pro Glu Glu Ile Glu Ser Lys Val Gln Leu
1               5                   10                  15

His Trp Asp Met Lys Arg Thr Phe Glu Val Thr Glu Asp Glu Ser Lys
            20                  25                  30

Glu Lys Tyr Tyr Cys Leu Ser Ile Ser Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
            165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
            245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
            325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
```

```
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ile Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Ala Ile
                515                 520                 525

Gly Gly Ile Glu His Ala Ile Met Gly Leu Leu Tyr Phe Arg Phe Phe
    530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
                595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
                675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
                770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815
```

-continued

```
Pro Val Asp Ala Thr Glu Glu Gln Val Arg Glu Arg Ala Gly Gln Glu
        820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly Gly Pro Val
        850                 855                 860
```

<210> SEQ ID NO 6
<211> LENGTH: 863
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 6

```
Met Glu Glu Gln Tyr Arg Pro Glu Glu Ile Glu Ser Lys Val Gln Leu
1               5                   10                  15

His Trp Asp Val Lys Arg Thr Phe Glu Val Thr Glu Asp Glu Ser Lys
        20                  25                  30

Glu Lys Tyr Tyr Cys Leu Ser Ile Ser Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
        100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
        180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
        210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
                245                 250                 255

Thr Tyr Leu Ala Val Ala Ala Gly His Pro Leu Ala Gln Lys Ala Ala
        260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
```

-continued

```
305             310             315             320

Trp Ala Ala Asn Phe Val Leu Met Glu Tyr Gly Thr Gly Ala Val Met
            325             330             335

Ala Val Pro Gly His Asp Gln Arg Asp Tyr Glu Phe Ala Ser Lys Tyr
            340             345             350

Gly Leu Asn Ile Lys Pro Val Ile Leu Ala Ala Asp Gly Ser Glu Pro
            355             360             365

Asp Leu Ser Gln Gln Ala Leu Thr Glu Lys Gly Val Leu Phe Asn Ser
            370             375             380

Gly Glu Phe Asn Gly Leu Asp His Glu Ala Ala Phe Asn Ala Ile Ala
385             390             395             400

Asp Lys Leu Thr Ala Met Gly Val Gly Glu Arg Lys Val Asn Tyr Arg
                405             410             415

Leu Arg Asp Trp Gly Val Ser Arg Gln Arg Tyr Trp Gly Ala Pro Ile
            420             425             430

Pro Met Val Thr Leu Glu Asp Gly Thr Val Met Pro Thr Pro Asp Asp
            435             440             445

Gln Leu Pro Val Ile Leu Pro Glu Asp Val Val Met Asp Gly Ile Thr
    450             455             460

Ser Pro Ile Lys Ala Asp Pro Glu Trp Ala Lys Thr Thr Val Asn Gly
465             470             475             480

Met Pro Ala Leu Arg Glu Thr Asp Thr Phe Asp Thr Phe Met Glu Ser
                485             490             495

Ser Trp Ile Tyr Ala Arg Tyr Thr Cys Pro Gln Tyr Lys Glu Gly Met
            500             505             510

Leu Asp Ser Glu Ala Ala Asn Tyr Trp Leu Pro Val Asp Ile Ala Ile
            515             520             525

Gly Gly Ile Glu His Ala Ile Met Gly Leu Leu Tyr Phe Arg Phe Phe
    530             535             540

His Lys Leu Met Arg Asp Ala Gly Met Val Asn Ser Asp Glu Pro Ala
545             550             555             560

Lys Gln Leu Leu Cys Gln Gly Met Val Leu Ala Asp Ala Phe Tyr Tyr
                565             570             575

Val Gly Glu Asn Gly Glu Arg Asn Trp Val Ser Pro Val Asp Ala Ile
            580             585             590

Val Glu Arg Asp Glu Lys Gly Arg Ile Val Lys Ala Lys Asp Ala Ala
            595             600             605

Gly His Glu Leu Val Tyr Thr Gly Met Ser Lys Met Ser Lys Ser Lys
    610             615             620

Asn Asn Gly Ile Asp Pro Gln Val Met Val Glu Arg Tyr Gly Ala Asp
625             630             635             640

Thr Val Arg Leu Phe Met Met Phe Ala Ser Pro Ala Asp Met Thr Leu
                645             650             655

Glu Trp Gln Glu Ser Gly Val Glu Gly Ala Asn Arg Phe Leu Lys Arg
            660             665             670

Val Trp Lys Leu Val Tyr Glu His Thr Ala Lys Gly Asp Val Ala Ala
            675             680             685

Leu Asn Val Asp Ala Leu Thr Glu Asn Gln Lys Ala Leu Arg Arg Asp
    690             695             700

Val His Lys Thr Ile Ala Lys Val Thr Asp Asp Ile Gly Arg Arg Gln
705             710             715             720

Thr Phe Asn Thr Ala Ile Ala Ala Ile Met Glu Leu Met Asn Lys Leu
                725             730             735
```

```
Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
            770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                405                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly Gly Pro Val
    850                 855                 860
```

<210> SEQ ID NO 7
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Glu Glu Gln Tyr Arg Pro Glu Glu Ile Glu Ser Lys Val Gln Leu
1               5                   10                  15

His Trp Asp Lys Lys Arg Thr Phe Glu Val Thr Glu Asp Glu Ser Lys
            20                  25                  30

Glu Lys Tyr Tyr Cys Leu Ser Ile Val Pro Tyr Pro Ser Gly Arg Leu
            35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
            85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
            115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
            165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
            195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
```

```
225              230              235              240

Asn Thr Leu Thr Val Tyr Thr Thr Arg Pro Asp Ala Phe Met Gly Cys
             245              250              255

Thr Tyr Leu Ala Val Ala Ala Gly His Pro Leu Ala Gln Lys Ala Ala
             260              265              270

Glu Asn Asn Pro Glu Leu Ala Ala Phe Ile Asp Glu Cys Arg Asn Thr
             275              280              285

Lys Val Ala Glu Ala Glu Met Ala Thr Met Glu Lys Lys Gly Val Asp
             290              295              300

Thr Gly Phe Lys Ala Val His Pro Leu Thr Gly Glu Glu Ile Pro Val
305              310              315              320

Trp Ala Ala Asn Phe Val Leu Met Glu Tyr Gly Thr Gly Ala Val Met
             325              330              335

Ala Val Pro Gly His Asp Gln Arg Asp Tyr Glu Phe Ala Ser Lys Tyr
             340              345              350

Gly Leu Asn Ile Lys Pro Val Ile Leu Ala Ala Asp Gly Ser Glu Pro
             355              360              365

Asp Leu Ser Gln Gln Ala Leu Thr Glu Lys Gly Val Leu Phe Asn Ser
             370              375              380

Gly Glu Phe Asn Gly Leu Asp His Glu Ala Ala Phe Asn Ala Ile Ala
385              390              395              400

Asp Lys Leu Thr Ala Met Gly Val Gly Glu Arg Lys Val Asn Tyr Arg
             405              410              415

Leu Arg Asp Trp Gly Val Ser Arg Gln Arg Tyr Trp Gly Ala Pro Ile
             420              425              430

Pro Met Val Thr Leu Glu Asp Gly Thr Val Met Pro Thr Pro Asp Asp
             435              440              445

Gln Leu Pro Val Ile Leu Pro Glu Asp Val Val Met Asp Gly Ile Thr
             450              455              460

Ser Pro Ile Lys Ala Asp Pro Glu Trp Ala Lys Thr Thr Val Asn Gly
465              470              475              480

Met Pro Ala Leu Arg Glu Thr Asp Thr Phe Asp Thr Phe Met Glu Ser
             485              490              495

Ser Trp Ile Tyr Ala Arg Tyr Thr Cys Pro Gln Tyr Lys Glu Gly Met
             500              505              510

Leu Asp Ser Glu Ala Ala Asn Tyr Trp Leu Pro Val Asp Ile Ala Ile
             515              520              525

Gly Gly Ile Glu His Ala Ile Met Gly Leu Leu Tyr Phe Arg Phe Phe
             530              535              540

His Lys Leu Met Arg Asp Ala Gly Met Val Asn Ser Asp Glu Pro Ala
545              550              555              560

Lys Gln Leu Leu Cys Gln Gly Met Val Leu Ala Asp Ala Phe Tyr Tyr
             565              570              575

Val Gly Glu Asn Gly Glu Arg Asn Trp Val Ser Pro Val Asp Ala Ile
             580              585              590

Val Glu Arg Asp Glu Lys Gly Arg Ile Val Lys Ala Lys Asp Ala Ala
             595              600              605

Gly His Glu Leu Val Tyr Thr Gly Met Ser Lys Met Ser Lys Ser Lys
             610              615              620

Asn Asn Gly Ile Asp Pro Gln Val Met Val Glu Arg Tyr Gly Ala Asp
625              630              635              640

Thr Val Arg Leu Phe Met Met Phe Ala Ser Pro Ala Asp Met Thr Leu
             645              650              655
```

-continued

```
Glu Trp Gln Glu Ser Gly Val Glu Gly Ala Asn Arg Phe Leu Lys Arg
        660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
                820                 825                 830

His Leu Val Ala Lys Tyr Leu Asp Gly Val Thr Val Arg Lys Val Ile
                835                 840                 845

Tyr Val Pro Gly Lys Leu Leu Asn Leu Val Val Gly Gly Pro Val
        850                 855                 860
```

```
<210> SEQ ID NO 8
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

```
Met Glu Glu Gln Tyr Arg Pro Glu Glu Ile Glu Ser Lys Val Gln Leu
1               5                   10                  15

His Trp Asp Lys Lys Arg Thr Phe Glu Val Thr Glu Asp Glu Ser Lys
                20                  25                  30

Glu Lys Tyr Tyr Cys Leu Ser Ile Ala Pro Tyr Pro Ser Gly Arg Leu
        35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
                100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
```

-continued

```
145              150              155              160
Asn Asp Gln Thr Val Leu Ala Asn Glu Gln Val Ile Asp Gly Cys Cys
                165              170              175
Trp Arg Cys Asp Thr Lys Val Glu Arg Lys Glu Ile Pro Gln Trp Phe
                180              185              190
Ile Lys Ile Thr Ala Tyr Ala Asp Glu Leu Leu Asn Asp Leu Asp Lys
                195              200              205
Leu Asp His Trp Pro Asp Thr Val Lys Thr Met Gln Arg Asn Trp Ile
    210              215              220
Gly Arg Ser Glu Gly Val Glu Ile Thr Phe Asn Val Asn Asp Tyr Asp
225              230              235              240
Asn Thr Leu Thr Val Tyr Thr Thr Arg Pro Asp Ala Phe Met Gly Cys
                245              250              255
Thr Tyr Leu Ala Val Ala Ala Gly His Pro Leu Ala Gln Lys Ala Ala
                260              265              270
Glu Asn Asn Pro Glu Leu Ala Ala Phe Ile Asp Glu Cys Arg Asn Thr
                275              280              285
Lys Val Ala Glu Ala Glu Met Ala Thr Met Glu Lys Lys Gly Val Asp
    290              295              300
Thr Gly Phe Lys Ala Val His Pro Leu Thr Gly Glu Glu Ile Pro Val
305              310              315              320
Trp Ala Ala Asn Phe Val Leu Met Glu Tyr Gly Thr Gly Ala Val Met
                325              330              335
Ala Val Pro Gly His Asp Gln Arg Asp Tyr Glu Phe Ala Ser Lys Tyr
                340              345              350
Gly Leu Asn Ile Lys Pro Val Ile Leu Ala Ala Asp Gly Ser Glu Pro
                355              360              365
Asp Leu Ser Gln Gln Ala Leu Thr Glu Lys Gly Val Leu Phe Asn Ser
    370              375              380
Gly Glu Phe Asn Gly Leu Asp His Glu Ala Ala Phe Asn Ala Ile Ala
385              390              395              400
Asp Lys Leu Thr Ala Met Gly Val Gly Glu Arg Lys Val Asn Tyr Arg
                405              410              415
Leu Arg Asp Trp Gly Val Ser Arg Gln Arg Tyr Trp Gly Ala Pro Ile
                420              425              430
Pro Met Val Thr Leu Glu Asp Gly Thr Val Met Pro Thr Pro Asp Asp
                435              440              445
Gln Leu Pro Val Ile Leu Pro Glu Asp Val Val Met Asp Gly Ile Thr
    450              455              460
Ser Pro Ile Lys Ala Asp Pro Glu Trp Ala Lys Thr Thr Val Asn Gly
465              470              475              480
Met Pro Ala Leu Arg Glu Thr Asp Thr Phe Asp Thr Phe Met Glu Ser
                485              490              495
Ser Trp Ile Tyr Ala Arg Tyr Thr Cys Pro Gln Tyr Lys Glu Gly Met
                500              505              510
Leu Asp Ser Glu Ala Ala Asn Tyr Trp Leu Pro Val Asp Ile Ala Ile
                515              520              525
Gly Gly Ile Glu His Ala Ile Met Gly Leu Leu Tyr Phe Arg Phe Phe
    530              535              540
His Lys Leu Met Arg Asp Ala Gly Met Val Asn Ser Asp Glu Pro Ala
545              550              555              560
Lys Gln Leu Leu Cys Gln Gly Met Val Leu Ala Asp Ala Phe Tyr Tyr
                565              570              575
```

-continued

```
Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
        625                 630                 635                 640

Thr Val Arg Leu Phe Met Met Phe Ala Ser Pro Ala Asp Met Thr Leu
            645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
            690                 695                 700

Val His Lys Thr Ile Ala Lys Val Thr Asp Asp Ile Gly Arg Arg Gln
        705                 710                 715                 720

Thr Phe Asn Thr Ala Ile Ala Ala Ile Met Glu Leu Met Asn Lys Leu
            725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
        785                 790                 795                 800

Leu Val Val Val Gln Val Asn Gly Lys Val Arg Ala Lys Ile Thr Val
            805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
            835                 840                 845

Tyr Val Pro Gly Lys Leu Leu Asn Leu Val Val Gly Gly Pro Val
        850                 855                 860
```

```
<210> SEQ ID NO 9
<211> LENGTH: 862
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

```
Met Glu Glu Gln Tyr Arg Pro Glu Glu Ile Glu Ser Lys Val Gln Leu
1                 5                 10                 15

His Trp Asp Lys Lys Arg Thr Phe Glu Val Thr Glu Asp Glu Ser Lys
            20                 25                 30

Glu Lys Tyr Tyr Cys Leu Ser Ile Ser Pro Tyr Pro Ser Gly Arg Leu
            35                 40                 45

His Met Gly His Val Arg Asn Tyr Thr Ile Gly Asp Val Ile Ala Arg
        50                 55                 60

Tyr Gln Arg Met Leu Gly Lys Asn Val Leu Gln Pro Ile Gly Trp Asp
```

```
65                    70                    75                    80

Ala Phe Gly Leu Pro Ala Glu Gly Ala Ala Val Lys Asn Asn Thr Ala
                85                    90                    95

Pro Ala Pro Trp Thr Tyr Asp Asn Ile Ala Tyr Met Lys Asn Gln Leu
            100                   105                   110

Lys Met Leu Gly Phe Gly Tyr Asp Trp Ser Arg Glu Leu Ala Thr Cys
            115                   120                   125

Thr Pro Glu Tyr Tyr Arg Trp Glu Gln Lys Phe Phe Thr Glu Leu Tyr
        130                   135                   140

Lys Lys Gly Leu Val Tyr Lys Lys Thr Ser Ala Val Asn Trp Cys Pro
145                   150                   155                   160

Asn Asp Gln Thr Val Leu Ala Asn Glu Gln Val Ile Asp Gly Cys Cys
                165                   170                   175

Trp Arg Cys Asp Thr Lys Val Glu Arg Lys Glu Ile Pro Gln Trp Phe
            180                   185                   190

Ile Lys Ile Thr Ala Tyr Ala Asp Glu Leu Leu Asn Asp Leu Asp Lys
            195                   200                   205

Leu Asp His Trp Pro Asp Thr Val Lys Thr Met Gln Arg Asn Trp Ile
        210                   215                   220

Gly Arg Ser Glu Gly Val Glu Ile Thr Phe Asn Val Asn Asp Tyr Asp
225                   230                   235                   240

Asn Thr Leu Thr Val Tyr Thr Thr Arg Pro Asp Ala Phe Met Gly Cys
                245                   250                   255

Thr Tyr Leu Ala Val Ala Ala Gly His Pro Leu Ala Gln Lys Ala Ala
            260                   265                   270

Glu Asn Asn Pro Glu Leu Ala Ala Phe Ile Asp Glu Cys Arg Asn Thr
            275                   280                   285

Lys Val Ala Glu Ala Glu Met Ala Thr Met Glu Lys Lys Gly Val Asp
        290                   295                   300

Thr Gly Phe Lys Ala Val His Pro Leu Thr Gly Glu Glu Ile Pro Val
305                   310                   315                   320

Trp Ala Ala Asn Phe Val Leu Met Glu Tyr Gly Thr Gly Ala Val Met
                325                   330                   335

Ala Val Pro Gly His Asp Gln Arg Asp Tyr Glu Phe Ala Ser Lys Tyr
            340                   345                   350

Gly Leu Asn Ile Lys Pro Val Ile Leu Ala Ala Asp Gly Ser Glu Pro
            355                   360                   365

Asp Leu Ser Gln Gln Ala Leu Thr Glu Lys Gly Val Leu Phe Asn Ser
        370                   375                   380

Gly Glu Phe Asn Gly Leu Asp His Glu Ala Ala Phe Asn Ala Ile Ala
385                   390                   395                   400

Asp Lys Leu Thr Ala Met Gly Val Gly Glu Arg Lys Val Asn Tyr Arg
                405                   410                   415

Leu Arg Asp Trp Gly Val Ser Arg Gln Arg Tyr Trp Gly Ala Pro Ile
            420                   425                   430

Pro Met Val Thr Leu Glu Asp Gly Thr Val Met Pro Thr Pro Asp Asp
            435                   440                   445

Gln Leu Pro Val Ile Leu Pro Glu Asp Val Val Met Asp Gly Ile Thr
        450                   455                   460

Ser Pro Ile Lys Ala Asp Pro Glu Trp Ala Lys Thr Thr Val Asn Gly
465                   470                   475                   480

Met Pro Ala Leu Arg Glu Thr Asp Thr Phe Asp Thr Phe Met Glu Ser
                485                   490                   495
```

-continued

```
Ser Trp Ala Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ala Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                    565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                    645                 650                 655

Glu Trp Gln Glu Ser Gly Val Glu Gly Ala Asn Arg Phe Lys Arg Val
                    660                 665                 670

Trp Lys Leu Val Tyr Glu His Thr Ala Lys Gly Asp Val Ala Ala Leu
            675                 680                 685

Asn Val Asp Ala Leu Thr Glu Asn Gln Lys Ala Leu Arg Arg Asp Val
            690                 695                 700

His Lys Thr Ile Ala Lys Val Thr Asp Asp Ile Gly Arg Arg Gln Thr
705                 710                 715                 720

Phe Asn Thr Ala Ile Ala Ala Ile Met Glu Leu Met Asn Lys Leu Ala
                    725                 730                 735

Lys Ala Pro Thr Asp Gly Glu Gln Asp Arg Ala Leu Met Gln Glu Ala
            740                 745                 750

Leu Leu Ala Val Val Arg Met Leu Asn Pro Phe Thr Pro His Ile Cys
            755                 760                 765

Phe Thr Leu Trp Gln Glu Leu Lys Gly Glu Gly Asp Ile Asp Asn Ala
770                 775                 780

Pro Trp Pro Val Ala Asp Glu Lys Ala Met Val Glu Asp Ser Thr Leu
785                 790                 795                 800

Val Val Val Gln Val Asn Gly Lys Val Arg Ala Lys Ile Thr Val Pro
                    805                 810                 815

Val Asp Ala Thr Glu Glu Gln Val Arg Glu Arg Ala Gly Gln Glu His
            820                 825                 830

Leu Val Ala Lys Tyr Leu Asp Gly Val Thr Val Arg Lys Val Ile Tyr
            835                 840                 845

Val Pro Gly Lys Leu Leu Asn Leu Val Val Gly Gly Pro Val
    850                 855                 860
```

```
<210> SEQ ID NO 10
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 10

Met Glu Glu Gln Tyr Arg Pro Glu Glu Ile Glu Ser Lys Val Gln Leu
1               5                   10                  15

His Trp Asp Lys Lys Arg Thr Phe Glu Val Thr Glu Asp Glu Ser Lys
            20                  25                  30

Glu Lys Tyr Tyr Cys Leu Ser Ile Ser Pro Tyr Pro Ser Gly Arg Leu
        35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
            165                 170                 175

Trp Arg Cys Asp Thr Lys Val Glu Arg Lys Glu Ile Pro Gln Trp Phe
        180                 185                 190

Ile Lys Ile Thr Ala Tyr Ala Asp Glu Leu Leu Asn Asp Leu Asp Lys
    195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
            245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
            275                 280                 285

Lys Val Ala Glu Ala Glu Met Ala Thr Met Glu Lys Lys Gly Val Asp
    290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
            325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
        355                 360                 365

Asp Leu Ser Gln Gln Ala Leu Thr Glu Lys Gly Val Leu Phe Asn Ser
    370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415
```

```
Leu Arg Asp Trp Gly Val Ser Arg Gln Arg Tyr Trp Gly Ala Pro Ile
        420                 425                 430

Pro Met Val Thr Leu Glu Asp Gly Thr Val Met Pro Thr Pro Asp Asp
        435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp His Tyr Ala Arg Tyr Thr Cys Pro Gln Tyr Lys Glu Gly Met
        500                 505                 510

Leu Asp Ser Glu Ala Ala Asn Tyr Trp Leu Pro Val Asp Ile Ala Ile
        515                 520                 525

Gly Gly Ile Glu His Ala Ile Met Gly Leu Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830
```

-continued

```
His Leu Val Ala Lys Tyr Leu Asp Gly Val Thr Val Arg Lys Val Ile
        835                 840                 845

Tyr Val Pro Gly Lys Leu Leu Asn Leu Val Val Gly Gly Pro Val
    850                 855                 860

<210> SEQ ID NO 11
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Glu Gln Tyr Arg Pro Glu Glu Ile Glu Ser Lys Val Gln Leu
1                 5                  10                 15

His Trp Asp Lys Lys Arg Thr Phe Glu Val Thr Glu Asp Glu Ser Lys
            20                  25                  30

Glu Lys Tyr Tyr Cys Leu Ser Ile Ser Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
            115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
            195                 200                 205

Leu Asp His Trp Pro Asp Thr Val Lys Thr Met Gln Arg Asn Trp Ile
        210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
                245                 250                 255

Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
            275                 280                 285

Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335
```

```
Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
            370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
            420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
    450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ile Tyr Ala Arg Tyr Thr Cys Pro Gln Tyr Lys Glu Gly Met
            500                 505                 510

Leu Asp Ser Glu Ala Ala Asn Tyr Trp Leu Pro Val Asp Ile Ile Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
    610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
    690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750
```

```
Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
    770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
            820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly Gly Pro Val
    850                 855                 860
```

<210> SEQ ID NO 12
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Glu Glu Gln Tyr Arg Pro Glu Glu Ile Glu Ser Lys Val Gln Leu
1                   5                   10                  15

His Trp Asp Lys Lys Arg Thr Phe Glu Val Thr Glu Asp Glu Ser Lys
            20                  25                  30

Glu Lys Tyr Tyr Cys Leu Ser Ile Ser Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
        210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Ala Phe Met Gly Cys
                245                 250                 255
```

```
Thr Tyr Leu Ala Val Ala Ala Gly His Pro Leu Ala Gln Lys Ala Ala
            260                 265                 270

Glu Asn Asn Pro Glu Leu Ala Ala Phe Ile Asp Glu Cys Arg Asn Thr
            275                 280                 285

Lys Val Ala Glu Ala Glu Met Ala Thr Met Glu Lys Lys Gly Val Asp
            290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
            340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
            370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
            450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Ile Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Val Ile
            515                 520                 525

Gly Gly Ile Glu His Ala Ile Met Gly Leu Leu Tyr Phe Arg Phe Phe
            530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
            580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
            610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670
```

-continued

```
Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
                820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly Gly Pro Val
        850                 855                 860

<210> SEQ ID NO 13
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Glu Gln Tyr Arg Pro Glu Glu Ile Glu Ser Lys Val Gln Leu
1               5                   10                  15

His Trp Asp Lys Lys Arg Thr Phe Glu Val Thr Glu Asp Glu Ser Lys
                20                  25                  30

Glu Lys Tyr Tyr Cys Leu Ser Ile Ser Pro Tyr Pro Ser Gly Arg Leu
        35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
                100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175
```

```
Trp Arg Cys Asp Thr Lys Val Glu Arg Lys Glu Ile Pro Gln Trp Phe
            180                 185             190

Ile Lys Ile Thr Ala Tyr Ala Asp Glu Leu Leu Asn Asp Leu Asp Lys
            195                 200             205

Leu Asp His Trp Pro Asp Thr Val Lys Thr Met Gln Arg Asn Trp Ile
    210                 215             220

Gly Arg Ser Glu Gly Val Glu Ile Thr Phe Asn Val Asn Asp Tyr Asp
225                 230             235                 240

Asn Thr Leu Thr Val Tyr Thr Thr Arg Pro Asp Ala Phe Met Gly Cys
            245             250                 255

Thr Tyr Leu Ala Val Ala Ala Gly His Pro Leu Ala Gln Lys Ala Ala
            260                 265             270

Glu Asn Asn Pro Glu Leu Ala Ala Phe Ile Asp Glu Cys Arg Asn Thr
            275                 280             285

Lys Val Ala Glu Ala Glu Met Ala Thr Met Glu Lys Lys Gly Val Asp
    290                 295             300

Thr Gly Phe Lys Ala Val His Pro Leu Thr Gly Glu Glu Ile Pro Val
305                 310             315                 320

Trp Ala Ala Asn Phe Val Leu Met Glu Tyr Gly Thr Gly Ala Val Met
            325                 330             335

Ala Val Pro Gly His Asp Gln Arg Asp Tyr Glu Phe Ala Ser Lys Tyr
            340                 345             350

Gly Leu Asn Ile Lys Pro Val Ile Leu Ala Ala Asp Gly Ser Glu Pro
            355                 360             365

Asp Leu Ser Gln Gln Ala Leu Thr Glu Lys Gly Val Leu Phe Asn Ser
    370                 375             380

Gly Glu Phe Asn Gly Leu Asp His Glu Ala Ala Phe Asn Ala Ile Ala
385                 390             395                 400

Asp Lys Leu Thr Ala Met Gly Val Gly Glu Arg Lys Val Asn Tyr Arg
            405                 410             415

Leu Arg Asp Trp Gly Val Ser Arg Gln Arg Tyr Trp Gly Ala Pro Ile
            420                 425             430

Pro Met Val Thr Leu Glu Asp Gly Thr Val Met Pro Thr Pro Asp Asp
            435                 440             445

Gln Leu Pro Val Ile Leu Pro Glu Asp Val Val Met Asp Gly Ile Thr
    450                 455             460

Ser Pro Ile Lys Ala Asp Pro Glu Trp Ala Lys Thr Thr Val Asn Gly
465                 470             475                 480

Met Pro Ala Leu Arg Glu Thr Asp Thr Phe Asp Thr Phe Met Glu Ser
            485                 490             495

Ser Trp Ile Tyr Ala Arg Tyr Thr Cys Pro Gln Tyr Lys Glu Gly Met
            500                 505             510

Leu Asp Ser Glu Ala Ala Asn Tyr Trp Leu Pro Val Asp Ile Gly Ile
            515                 520             525

Gly Gly Ile Glu His Ala Ile Met Gly Leu Leu Tyr Phe Arg Phe Phe
    530                 535             540

His Lys Leu Met Arg Asp Ala Gly Met Val Asn Ser Asp Glu Pro Ala
545                 550             555                 560

Lys Gln Leu Leu Cys Gln Gly Met Val Leu Ala Asp Ala Phe Tyr Tyr
            565                 570             575

Val Gly Glu Asn Gly Glu Arg Asn Trp Val Ser Pro Val Asp Ala Ile
            580                 585             590
```

-continued

```
Val Glu Arg Asp Glu Lys Gly Arg Ile Val Lys Ala Lys Asp Ala Ala
        595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
        675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
        755                 760                 765

Cys Phe Thr Leu Trp Gln Glu Leu Lys Gly Glu Gly Asp Ile Asp Asn
        770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
                820                 825                 830

His Leu Val Ala Lys Tyr Leu Asp Gly Val Thr Val Arg Lys Val Ile
        835                 840                 845

Tyr Val Pro Gly Lys Leu Leu Asn Leu Val Val Gly Gly Pro Val
    850                 855                 860
```

<210> SEQ ID NO 14
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Q or E
<220> FEATURE:
<221> NAME/KEY: MOD_RES
<222> LOCATION: (20)..(20)
<223> OTHER INFORMATION: E, K, V or M
<220> FEATURE:
<221> NAME/KEY: MOD_RES
<222> LOCATION: (40)..(40)
<223> OTHER INFORMATION: M, I, or V
<220> FEATURE:
<221> NAME/KEY: MOD_RES
<222> LOCATION: (41)..(41)
<223> OTHER INFORMATION: L, S, V, or A
<220> FEATURE:
<221> NAME/KEY: MOD_RES
<222> LOCATION: (252)..(252)
<223> OTHER INFORMATION: T, A, or R

```
<220> FEATURE:
<221> NAME/KEY: MOD_RES
<222> LOCATION: (499)..(499)
<223> OTHER INFORMATION: Y, A, I, H, or S
<220> FEATURE:
<221> NAME/KEY: MOD_RES
<222> LOCATION: (527)..(527)
<223> OTHER INFORMATION: Y, A, I, L, or V
<220> FEATURE:
<221> NAME/KEY: MOD_RES
<222> LOCATION: (537)..(537)
<223> OTHER INFORMATION: H or G

<400> SEQUENCE: 14

Met Xaa Glu Gln Tyr Arg Pro Glu Glu Ile Glu Ser Lys Val Gln Leu
1               5                   10                  15

His Trp Asp Xaa Lys Arg Thr Phe Glu Val Thr Glu Asp Glu Ser Lys
                20                  25                  30

Glu Lys Tyr Tyr Cys Leu Ser Xaa Xaa Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
                100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
        130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
                180                 185                 190

Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
        210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Xaa Phe Met Gly Cys
                245                 250                 255

Thr Tyr Leu Ala Val Ala Ala Gly His Pro Leu Ala Gln Lys Ala Ala
        260                 265                 270

Glu Asn Asn Pro Glu Leu Ala Ala Phe Ile Asp Glu Cys Arg Asn Thr
        275                 280                 285

Lys Val Ala Glu Ala Glu Met Ala Thr Met Glu Lys Lys Gly Val Asp
        290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
```

```
                340                 345                 350

Gly Leu Asn Ile Lys Pro Val Ile Leu Ala Ala Asp Gly Ser Glu Pro
            355                 360                 365

Asp Leu Ser Gln Gln Ala Leu Thr Glu Lys Gly Val Leu Phe Asn Ser
        370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
            435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Xaa Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Xaa Ile
            515                 520                 525

Gly Gly Ile Glu His Ala Ile Met Xaa Leu Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
        610                 615                 620

Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
            660                 665                 670

Val Trp Lys Leu Val Tyr Glu His Thr Ala Lys Gly Asp Val Ala Ala
            675                 680                 685

Leu Asn Val Asp Ala Leu Thr Glu Asn Gln Lys Ala Leu Arg Arg Asp
        690                 695                 700

Val His Lys Thr Ile Ala Lys Val Thr Asp Asp Ile Gly Arg Arg Gln
705                 710                 715                 720

Thr Phe Asn Thr Ala Ile Ala Ala Ile Met Glu Leu Met Asn Lys Leu
                725                 730                 735

Ala Lys Ala Pro Thr Asp Gly Glu Gln Asp Arg Ala Leu Met Gln Glu
            740                 745                 750

Ala Leu Leu Ala Val Val Arg Met Leu Asn Pro Phe Thr Pro His Ile
            755                 760                 765
```

-continued

```
Cys Phe Thr Leu Trp Gln Glu Leu Lys Gly Glu Gly Asp Ile Asp Asn
    770             775             780

Ala Pro Trp Pro Val Ala Asp Glu Lys Ala Met Val Glu Asp Ser Thr
785             790             795             800

Leu Val Val Val Gln Val Asn Gly Lys Val Arg Ala Lys Ile Thr Val
                805             810             815

Pro Val Asp Ala Thr Glu Glu Gln Val Arg Glu Arg Ala Gly Gln Glu
            820             825             830

His Leu Val Ala Lys Tyr Leu Asp Gly Val Thr Val Arg Lys Val Ile
        835             840             845

Tyr Val Pro Gly Lys Leu Leu Asn Leu Val Val Gly Gly Pro Val
    850             855             860
```

```
<210> SEQ ID NO 15
<211> LENGTH: 863
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: K, V or M
<220> FEATURE:
<221> NAME/KEY: MOD_RES
<222> LOCATION: (41)..(41)
<223> OTHER INFORMATION: S, V, or A
<220> FEATURE:
<221> NAME/KEY: MOD_RES
<222> LOCATION: (499)..(499)
<223> OTHER INFORMATION: A, I, or H
<220> FEATURE:
<221> NAME/KEY: MOD_RES
<222> LOCATION: (527)..(527)
<223> OTHER INFORMATION: A, I, or V
```

```
<400> SEQUENCE: 15
```

```
Met Glu Glu Gln Tyr Arg Pro Glu Glu Ile Glu Ser Lys Val Gln Leu
1               5               10              15

His Trp Asp Xaa Lys Arg Thr Phe Glu Val Thr Glu Asp Glu Ser Lys
            20              25              30

Glu Lys Tyr Tyr Cys Leu Ser Ile Xaa Pro Tyr Pro Ser Gly Arg Leu
        35              40              45

His Met Gly His Val Arg Asn Tyr Thr Ile Gly Asp Val Ile Ala Arg
    50              55              60

Tyr Gln Arg Met Leu Gly Lys Asn Val Leu Gln Pro Ile Gly Trp Asp
65              70              75              80

Ala Phe Gly Leu Pro Ala Glu Gly Ala Ala Val Lys Asn Asn Thr Ala
            85              90              95

Pro Ala Pro Trp Thr Tyr Asp Asn Ile Ala Tyr Met Lys Asn Gln Leu
            100             105             110

Lys Met Leu Gly Phe Gly Tyr Asp Trp Ser Arg Glu Leu Ala Thr Cys
        115             120             125

Thr Pro Glu Tyr Tyr Arg Trp Glu Gln Lys Phe Phe Thr Glu Leu Tyr
    130             135             140

Lys Lys Gly Leu Val Tyr Lys Lys Thr Ser Ala Val Asn Trp Cys Pro
145             150             155             160

Asn Asp Gln Thr Val Leu Ala Asn Glu Gln Val Ile Asp Gly Cys Cys
            165             170             175
```

-continued

```
Trp Arg Cys Asp Thr Lys Val Glu Arg Lys Glu Ile Pro Gln Trp Phe
            180             185             190

Ile Lys Ile Thr Ala Tyr Ala Asp Glu Leu Leu Asn Asp Leu Asp Lys
            195             200             205

Leu Asp His Trp Pro Asp Thr Val Lys Thr Met Gln Arg Asn Trp Ile
    210             215             220

Gly Arg Ser Glu Gly Val Glu Ile Thr Phe Asn Val Asn Asp Tyr Asp
225             230             235             240

Asn Thr Leu Thr Val Tyr Thr Thr Arg Pro Asp Ala Phe Met Gly Cys
            245             250             255

Thr Tyr Leu Ala Val Ala Ala Gly His Pro Leu Ala Gln Lys Ala Ala
            260             265             270

Glu Asn Asn Pro Glu Leu Ala Ala Phe Ile Asp Glu Cys Arg Asn Thr
    275             280             285

Lys Val Ala Glu Ala Glu Met Ala Thr Met Glu Lys Lys Gly Val Asp
    290             295             300

Thr Gly Phe Lys Ala Val His Pro Leu Thr Gly Glu Glu Ile Pro Val
305             310             315             320

Trp Ala Ala Asn Phe Val Leu Met Glu Tyr Gly Thr Gly Ala Val Met
            325             330             335

Ala Val Pro Gly His Asp Gln Arg Asp Tyr Glu Phe Ala Ser Lys Tyr
            340             345             350

Gly Leu Asn Ile Lys Pro Val Ile Leu Ala Ala Asp Gly Ser Glu Pro
            355             360             365

Asp Leu Ser Gln Gln Ala Leu Thr Glu Lys Gly Val Leu Phe Asn Ser
    370             375             380

Gly Glu Phe Asn Gly Leu Asp His Glu Ala Ala Phe Asn Ala Ile Ala
385             390             395             400

Asp Lys Leu Thr Ala Met Gly Val Gly Glu Arg Lys Val Asn Tyr Arg
            405             410             415

Leu Arg Asp Trp Gly Val Ser Arg Gln Arg Tyr Trp Gly Ala Pro Ile
            420             425             430

Pro Met Val Thr Leu Glu Asp Gly Thr Val Met Pro Thr Pro Asp Asp
            435             440             445

Gln Leu Pro Val Ile Leu Pro Glu Asp Val Val Met Asp Gly Ile Thr
    450             455             460

Ser Pro Ile Lys Ala Asp Pro Glu Trp Ala Lys Thr Thr Val Asn Gly
465             470             475             480

Met Pro Ala Leu Arg Glu Thr Asp Thr Phe Asp Thr Phe Met Glu Ser
            485             490             495

Ser Trp Xaa Tyr Ala Arg Tyr Thr Cys Pro Gln Tyr Lys Glu Gly Met
            500             505             510

Leu Asp Ser Glu Ala Ala Asn Tyr Trp Leu Pro Val Asp Ile Xaa Ile
            515             520             525

Gly Gly Ile Glu His Ala Ile Met Gly Leu Leu Tyr Phe Arg Phe Phe
    530             535             540

His Lys Leu Met Arg Asp Ala Gly Met Val Asn Ser Asp Glu Pro Ala
545             550             555             560

Lys Gln Leu Leu Cys Gln Gly Met Val Leu Ala Asp Ala Phe Tyr Tyr
            565             570             575

Val Gly Glu Asn Gly Glu Arg Asn Trp Val Ser Pro Val Asp Ala Ile
            580             585             590

Val Glu Arg Asp Glu Lys Gly Arg Ile Val Lys Ala Lys Asp Ala Ala
```

```
          595                    600                    605

Gly His Glu Leu Val Tyr Thr Gly Met Ser Lys Met Ser Lys Ser Lys
    610                    615                    620

Asn Asn Gly Ile Asp Pro Gln Val Met Val Glu Arg Tyr Gly Ala Asp
625                    630                    635                    640

Thr Val Arg Leu Phe Met Met Phe Ala Ser Pro Ala Asp Met Thr Leu
                   645                    650                    655

Glu Trp Gln Glu Ser Gly Val Glu Gly Ala Asn Arg Phe Leu Lys Arg
              660                    665                    670

Val Trp Lys Leu Val Tyr Glu His Thr Ala Lys Gly Asp Val Ala Ala
              675                    680                    685

Leu Asn Val Asp Ala Leu Thr Glu Asn Gln Lys Ala Leu Arg Arg Asp
    690                    695                    700

Val His Lys Thr Ile Ala Lys Val Thr Asp Asp Ile Gly Arg Arg Gln
705                    710                    715                    720

Thr Phe Asn Thr Ala Ile Ala Ala Ile Met Glu Leu Met Asn Lys Leu
                   725                    730                    735

Ala Lys Ala Pro Thr Asp Gly Glu Gln Asp Arg Ala Leu Met Gln Glu
              740                    745                    750

Ala Leu Leu Ala Val Val Arg Met Leu Asn Pro Phe Thr Pro His Ile
              755                    760                    765

Cys Phe Thr Leu Trp Gln Glu Leu Lys Gly Glu Gly Asp Ile Asp Asn
    770                    775                    780

Ala Pro Trp Pro Val Ala Asp Glu Lys Ala Met Val Glu Asp Ser Thr
785                    790                    795                    800

Leu Val Val Val Gln Val Asn Gly Lys Val Arg Ala Lys Ile Thr Val
                   805                    810                    815

Pro Val Asp Ala Thr Glu Glu Gln Val Arg Glu Arg Ala Gly Gln Glu
              820                    825                    830

His Leu Val Ala Lys Tyr Leu Asp Gly Val Thr Val Arg Lys Val Ile
              835                    840                    845

Tyr Val Pro Gly Lys Leu Leu Asn Leu Val Val Gly Gly Pro Val
    850                    855                    860
```

<210> SEQ ID NO 16
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcccggatgg tggaatcggt agacacaagg gattctaaat ccctcggcgt tcgcgctgtg      60
cgggttcaag tcccgctccg ggta                                             84

<210> SEQ ID NO 17
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcccggatgg tggaatcggt agacacaagg gatttcaaat ccctcggcgt tcgcgctgtg      60
cgggttcaag tcccgctccg ggta                                             84

-continued

```
<210> SEQ ID NO 18
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gcccggatgg tggaatcggt agacacaagg gattttaaat ccctcggcgt tcgcgctgtg      60
cgggttcaag tcccgctccg ggta                                             84

<210> SEQ ID NO 19
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcccggatgg tggaatcggt agacacaagg gactctaaat ccctcggcgt tcgcgctgtg      60
cgggttcaag tcccgctccg ggca                                             84

<210> SEQ ID NO 20
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcccggatgg tggaatcggt agacacaagg gacttcaaat ccctcggcgt tcgcgctgtg      60
cgggttcaag tcccgctccg ggca                                             84

<210> SEQ ID NO 21
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcccggatgg tggaatcggt agacacaagg gactttaaat ccctcggcgt tcgcgctgtg      60
cgggttcaag tcccgctccg ggca                                             84

<210> SEQ ID NO 22
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcccggatgg tggaatcggt agacacaagg gattctaaat ccctcggcgt tcgcgctgtg      60
cgggttcaag tcccgctccg ggtacca                                          87

<210> SEQ ID NO 23
<211> LENGTH: 87
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcccggatgg tggaatcggt agacacaagg gatttcaaat ccctcggcgt tcgcgctgtg        60
cgggttcaag tcccgctccg ggtacca                                           87

<210> SEQ ID NO 24
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcccggatgg tggaatcggt agacacaagg gattttaaat ccctcggcgt tcgcgctgtg        60
cgggttcaag tcccgctccg ggtacca                                           87

<210> SEQ ID NO 25
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcccggatgg tggaatcggt agacacaagg gactctaaat ccctcggcgt tcgcgctgtg        60
cgggttcaag tcccgctccg ggcacca                                           87

<210> SEQ ID NO 26
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcccggatgg tggaatcggt agacacaagg gacttcaaat ccctcggcgt tcgcgctgtg        60
cgggttcaag tcccgctccg ggcacca                                           87

<210> SEQ ID NO 27
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcccggatgg tggaatcggt agacacaagg gactttaaat ccctcggcgt tcgcgctgtg        60
cgggttcaag tcccgctccg ggcacca                                           87

<210> SEQ ID NO 28
<211> LENGTH: 87
<212> TYPE: DNA
<213> ORGANISM: Artificial Sequence
<220> FEATURE:
<223> OTHER INFORMATION: Description of Artificial Sequence: Synthetic
```

```
          oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 28
gcccggatgg tggaatcggt agacacaagg gactnnnaat ccctcggcgt tcgcgctgtg      60
cgggttcaag tcccgctccg ggcacca                                         87

<210> SEQ ID NO 29
<211> LENGTH: 87
<212> TYPE: DNA
<213> ORGANISM: Artificial Sequence
<220> FEATURE:
<223> OTHER INFORMATION: Description of Artificial Sequence: Synthetic
          oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 29
gggcgtgtgg tggaatcggt agacacaagg gattnnnaat ccctcggcgt tcgcgctgtg      60
cgggttcaag tcccgccgcg cccacca                                         87

<210> SEQ ID NO 30
<211> LENGTH: 87
<212> TYPE: DNA
<213> ORGANISM: Artificial Sequence
<220> FEATURE:
<223> OTHER INFORMATION: Description of Artificial Sequence: Synthetic
          oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 30
gggcgcgtgg tggaatcggt agacacaagg gattnnnaat ccctcggcgt tcgcgctgtg      60
cgggttcaag tcccgccgcg cccacca                                         87

<210> SEQ ID NO 31
<211> LENGTH: 87
<212> TYPE: DNA
<213> ORGANISM: Artificial Sequence
<220> FEATURE:
<223> OTHER INFORMATION: Description of Artificial Sequence: Synthetic
          oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 31
gggcatgtgg tggaatcggt agacacaagg gattnnnaat ccctcggcgt tcgcgctgtg      60
cgggttcaag tcccgccatg cccacca                                         87

<210> SEQ ID NO 32
<211> LENGTH: 87
<212> TYPE: DNA
<213> ORGANISM: Artificial Sequence
<220> FEATURE:
<223> OTHER INFORMATION: Description of Artificial Sequence: Synthetic
          oligonucleotide
<220> FEATURE:
<221> NAME/KEY: misc_feature
```

-continued

```
<222> LOCATION: (35)..(37)
<223> OTHER INFORMATION: This region may encompass CTA, TCA, or TTA

<400> SEQUENCE: 32
gggcacgtgg tggaatcggt agacacaagg gattnnnaat ccctcggcgt tcgcgctgtg         60
cgggttcaag tcccgccgtg cccacca                                           87

<210> SEQ ID NO 33
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 33
gggggtgtgg tggaatcggt agacacaagg gattnnnaat ccctcggcgt tcgcgctgtg         60
cgggttcaag tcccgccgcc cccacca                                           87

<210> SEQ ID NO 34
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 34
gggggcgtgg tggaatcggt agacacaagg gattnnnaat ccctcggcgt tcgcgctgtg         60
cgggttcaag tcccgccgtc cccacca                                           87

<210> SEQ ID NO 35
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 35
ggggatgtgg tggaatcggt agacacaagg gattnnnaat ccctcggcgt tcgcgctgtg         60
cgggttcaag tcccgccgtc cccacca                                           87

<210> SEQ ID NO 36
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA
```

```
<400> SEQUENCE: 36
ggggacgtgg tggaatcggt agacacaagg gattnnnaat ccctcggcgt tcgcgctgtg      60
cgggttcaag tcccgccgtc cccacca                                         87

<210> SEQ ID NO 37
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 37
gcccgtatgg tggaatcggt agacacaagg gattnnnaat ccctcggcgt tcgcgctgtg      60
cgggttcaag tcccgctgcg ggcacca                                         87

<210> SEQ ID NO 38
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 38
gggatagtgg tggaatcggt agacacaagg gattnnnaat ccctcggcgt tcgcgctgtg      60
cgggttcaag tcccgcctat cccacca                                         87

<210> SEQ ID NO 39
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 39
gggcatgtgg tggaatcggt agacacaagg gattnnnaat ccctcggcgt tcgcgctgtg      60
cgggttcaag tcccgccgtg cccacca                                         87

<210> SEQ ID NO 40
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 40
gggcagatgg tggaatcggt agacacaagg gattnnnaat ccctcggcgt tcgcgctgtg      60
```
cgggttcaag tcccgctctg cccacca                                       87

<210> SEQ ID NO 41
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 41
gggcgtatgg tggaatcggt agacacaagg gattnnnaat ccctcggcgt tcgcgctgtg      60
cgggttcaag tcccgctgcg cccacca                                       87

<210> SEQ ID NO 42
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 42
gggcaagtgg tggaatcggt agacacaagg gattnnnaat ccctcggcgt tcgcgctgtg      60
cgggttcaag tcccgccttg cccacca                                       87

<210> SEQ ID NO 43
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (35)..(37)
<223> OTHER INFORMATION: This region may encompass CTA, TCA, or TTA

<400> SEQUENCE: 43
gcacacatgg tggaatcggt agacacaagg gattnnnaat ccctcggcgt tcgcgctgtg      60
cgggttcaag tcccgctgtg tgcacca                                       87

<210> SEQ ID NO 44
<211> LENGTH: 334
<212> TYPE: PRT
<213> ORGANISM: Escherichia coli

<400> SEQUENCE: 44

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

-continued

```
Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
                100                 105                 110

Lys Ser Ala Arg Tyr Ala Glu Asn Ile Asn Ala Gly Leu Phe Asp Tyr
            115                 120                 125

Pro Val Leu Met Ala Ala Asp Ile Leu Leu Tyr Gln Thr Asn Leu Val
    130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
                180                 185                 190

Thr Lys Lys Met Ser Lys Ser Asp Asp Asn Arg Asn Asn Val Ile Gly
            195                 200                 205

Leu Leu Glu Asp Pro Lys Ser Val Val Lys Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
                260                 265                 270

Leu Lys Gly Glu Val Ala Asp Ala Val Ser Gly Met Leu Thr Glu Leu
            275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```

<210> SEQ ID NO 45
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Met Thr Lys Pro Ile Val Phe Ala Gly Ala Gln Pro Ser Gly Glu Leu
1                   5                   10                  15

Thr Ile Gly Asn Tyr Met Gly Ala Leu Arg Gln Trp Val Asn Met Gln
                20                  25                  30

Asp Asp Tyr His Cys Ile Tyr Cys Ile Val Asp Gln His Ala Ile Thr
            35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
```

-continued

```
                     85                  90                  95

Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
            115                 120                 125

Pro Val Leu Met Ala Ala Asp Ile Leu Leu Tyr Gln Thr Asn Leu Gly
            130                 135                 140

Pro Cys Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
                180                 185                 190

Thr Lys Lys Met Ser Lys Ser Asp Asp Asn Arg Asn Asn Val Ile Gly
                195                 200                 205

Leu Leu Glu Asp Pro Lys Ser Val Val Lys Lys Ile Lys Arg Ala Val
            210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
                260                 265                 270

Leu Lys Gly Glu Val Ala Asp Ala Val Ser Gly Met Leu Thr Glu Leu
            275                 280                 285

Gln Glu Arg Tyr His Arg Phe Arg Asn Asp Glu Ala Phe Leu Gln Gln
            290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```

<210> SEQ ID NO 46
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Met Thr Lys Pro Ile Val Phe Ala Gly Ala Gln Pro Ser Gly Glu Leu
1               5                   10                  15

Thr Ile Gly Asn Tyr Met Gly Ala Leu Arg Gln Trp Val Asn Met Gln
                20                  25                  30

Asp Asp Tyr His Cys Ile Tyr Cys Ile Val Asp Gln His Ala Ile Thr
            35                  40                  45

Val Arg Gln Asp Ala Gln Lys Leu Arg Lys Ala Thr Leu Asp Thr Leu
        50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110
```

```
Lys Ser Ala Arg Tyr Ala Glu Asn Ile Asn Ala Gly Leu Phe Asp Tyr
        115                 120             125

Pro Val Leu Met Ala Ala Asp Ile Leu Leu Tyr Gln Thr Asn Leu Ala
        130                 135             140

Pro Ala Gly Glu Asp Gln Lys Gln His Leu Glu Leu Ser Arg Asp Ile
145                 150             155                 160

Ala Gln Arg Phe Asn Ala Leu Tyr Gly Glu Ile Phe Lys Val Pro Glu
                165             170             175

Pro Phe Ile Pro Lys Ser Gly Ala Arg Val Met Ser Leu Leu Glu Pro
                180             185             190

Thr Lys Lys Met Ser Lys Ser Asp Asp Asn Arg Asn Asn Val Ile Gly
        195                 200             205

Leu Leu Glu Asp Pro Lys Ser Val Val Lys Lys Ile Lys Arg Ala Val
        210                 215             220

Thr Asp Ser Asp Glu Pro Pro Val Val Arg Tyr Asp Val Gln Asn Lys
225                 230             235                 240

Ala Gly Val Ser Asn Leu Leu Asp Ile Leu Ser Ala Val Thr Gly Gln
                245             250             255

Ser Ile Pro Glu Leu Glu Lys Gln Phe Glu Gly Lys Met Tyr Gly His
                260             265             270

Leu Lys Gly Glu Val Ala Asp Ala Val Ser Gly Met Leu Thr Glu Leu
        275                 280             285

Gln Glu Arg Tyr His Arg Phe Arg Asn Asp Glu Ala Phe Leu Gln Gln
        290                 295             300

Val Met Lys Asp Gly Ala Glu Lys Ala Ser Ala His Ala Ser Arg Thr
305                 310             315                 320

Leu Lys Ala Val Tyr Glu Ala Ile Gly Phe Val Ala Lys Pro
                325             330
```

```
<210> SEQ ID NO 47
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

```
Met Thr Lys Pro Ile Val Phe Ala Gly Ala Gln Pro Ser Gly Glu Leu
1               5                   10              15

Thr Ile Gly Asn Tyr Met Gly Ala Leu Arg Gln Trp Val Asn Met Gln
                20                  25              30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
        50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
                100             105                 110

Lys Ser Ala Arg Tyr Ala Glu Asn Ile Asn Ala Gly Leu Phe Asp Tyr
        115                 120             125

Pro Val Leu Met Ala Ala Asp Ile Leu Leu Tyr Gln Thr Asn Leu Ser
        130                 135             140
```

```
Pro Ala Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
                180                 185                 190

Thr Lys Lys Met Ser Lys Ser Asp Asp Asn Arg Asn Asn Val Ile Gly
                195                 200                 205

Leu Leu Glu Asp Pro Lys Ser Val Val Lys Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
                260                 265                 270

Leu Lys Gly Glu Val Ala Asp Ala Val Ser Gly Met Leu Thr Glu Leu
    275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```

```
<210> SEQ ID NO 48
<211> LENGTH: 334
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Thr Lys Pro Ile Val Phe Ala Gly Ala Gln Pro Ser Gly Glu Leu
1               5                   10                  15

Thr Ile Gly Asn Tyr Met Gly Ala Leu Arg Gln Trp Val Asn Met Gln
                20                  25                  30

Asp Asp Tyr His Cys Ile Tyr Cys Ile Val Asp Gln His Ala Ile Thr
                35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
                100                 105                 110

Lys Ser Ala Arg Tyr Ala Glu Asn Ile Asn Ala Gly Leu Phe Asp Tyr
                115                 120                 125

Pro Val Leu Met Ala Ala Asp Ile Leu Leu Tyr Gln Thr Asn Leu Gly
    130                 135                 140

Pro Ala Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
```

-continued

```
            165              170              175
Pro Phe Ile Pro Lys Ser Gly Ala Arg Val Met Ser Leu Leu Glu Pro
            180              185              190

Thr Lys Lys Met Ser Lys Ser Asp Asp Asn Arg Asn Asn Val Ile Gly
            195              200              205

Leu Leu Glu Asp Pro Lys Ser Val Val Lys Lys Ile Lys Arg Ala Val
            210              215              220

Thr Asp Ser Asp Glu Pro Pro Val Val Arg Tyr Asp Val Gln Asn Lys
        225              230              235              240

Ala Gly Val Ser Asn Leu Leu Asp Ile Leu Ser Ala Val Thr Gly Gln
            245              250              255

Ser Ile Pro Glu Leu Glu Lys Gln Phe Glu Gly Lys Met Tyr Gly His
            260              265              270

Leu Lys Gly Glu Val Ala Asp Ala Val Ser Gly Met Leu Thr Glu Leu
            275              280              285

Gln Glu Arg Tyr His Arg Phe Arg Asn Asp Glu Ala Phe Leu Gln Gln
            290              295              300

Val Met Lys Asp Gly Ala Glu Lys Ala Ser Ala His Ala Ser Arg Thr
        305              310              315              320

Leu Lys Ala Val Tyr Glu Ala Ile Gly Phe Val Ala Lys Pro
            325              330
```

```
<210> SEQ ID NO 49
<211> LENGTH: 76
<212> TYPE: DNA
<213> ORGANISM: Escherichia coli

<400> SEQUENCE: 49
aggggcgtag ttcaattggt agagcaccgg tctccaaaac cgggtgttgg gagttcgagt      60
ctctccgccc ctgcca                                                       76

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
aggggcgtag ttcaattggt agagcaccgg tctctaaaac cgggtgttgg gagttcgagt      60
ctctccgccc ctgcca                                                       76

<210> SEQ ID NO 51
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
aggggcgtag ttcaattggt agagcaccgg tcttcaaaac cgggtgttgg gagttcgagt      60
ctctccgccc ctgcca                                                       76

<210> SEQ ID NO 52
<211> LENGTH: 76
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 52
aggggcgtag ttcaattggt agagcaccgg tctttaaaac cgggtgttgg gagttcgagt      60
ctctccgccc ctgcca                                                      76

<210> SEQ ID NO 53
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 53
tggggtatcg ccaagcggta aggcaccgga ttcnnnttcc ggcattccga ggttcgaatc      60
ctcgtacccc agcca                                                       75

<210> SEQ ID NO 54
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 54
aggggcatag ctcaagcggt aaagcaccgg actnnnaaac cggcagtccg aagttcgaat      60 cccccccaccc cagcca                                                     76

<210> SEQ ID NO 55
<211> LENGTH: 2589
<212> TYPE: DNA
<213> ORGANISM: Escherichia coli

<400> SEQUENCE: 55
atgcaggaac agtatcgccc ggaagaaatt gaaagcaaag tgcagctgca ttgggatgaa      60
aaacgcacct ttgaagtgac cgaagatgaa agcaaagaaa atattattg cctgagcatg     120 ctgccgtatc cgagcggccg cctgcatatg ggccatgtgc gcaactatac cattggcgat     180
gtgattgcgc gctatcagcg catgctgggc aaaaacgtgc tgcagccgat tggctgggat     240
gcgtttggcc tgccggcgga aggcgcggcg gtgaaaaaca caccgcgcc ggcgccgtgg      300 acctatgata acattgcgta tatgaaaaac cagctgaaaa tgctgggctt tggctatgat     360
tggagccgcg aactggcgac ctgcaccccg gaatattatc gctgggaaca gaaatttttt     420
accgaactgt ataaaaaagg cctggtgtat aaaaaaacca gcgcggtgaa ctggtgcccg     480
aacgatcaga ccgtgctggc gaacgaacag gtgattgatg gctgctgctg gcgctgcgat     540
accaaagtgg aacgcaaaga aattccgcag tggtttatta aaattaccgc gtatgcggat     600
gaactgctga cgatctggga taaactggat cattggccgg ataccgtgaa aaccatgcag     660
cgcaactgga ttggccgcag cgaaggcgtg gaaattacct ttaacgtgaa cgattatgat     720
```

-continued

```
aacaccctga ccgtgtatac caccccgcccg gataccttta tgggctgcac ctatctggcg       780
gtggcggcgg gccatccgct ggcgcagaaa gcggcgggaaa acaacccgga actggcggcg      840
tttattgatg aatgccgcaa caccaaagtg gcggaagcgg aaatggcgac catggaaaaa       900
aaaggcgtgg ataccggctt taaagcggtg catccgctga ccggcgaaga aattccggtg       960
tgggcggcga actttgtgct gatggaatat ggcaccggcg cggtgatggc ggtgccgggc      1020
catgatcagc gcgattatga atttgcgagc aaatatggcc tgaacattaa accggtgatt      1080
ctggcggcgg atggcagcga accggatctg agccagcagg cgctgaccga aaaaggcgtg      1140
ctgtttaaca gcggcgaatt taacggcctg gatcatgaag cggcgtttaa cgcgattgcg      1200
gataaactga ccgcgatggg cgtgggcgaa cgcaaagtga actatcgcct gcgcgattgg      1260
ggcgtgagcc gccagcgcta ttgggggcgcg ccgattccga tggtgacccct ggaagatggc      1320 accgtgatgc cgacccccgga tgatcagctg ccggtgattc tgccggaaga tgtggtgatg      1380
gatggcatta ccagcccgat taaagcggat ccggaatggg cgaaaaccac cgtgaacggc      1440
atgccggcgc tgcgcgaaac cgatacccttt gataccttta tggaaagcag ctggtattat      1500
gcgcgctata cctgccccgca gtataaagaa ggcatgctgg atagcgaagc ggcgaactat      1560
tggctgccgg tggatatttta tattggcggc attgaacatg cgattatgca tctgctgtat      1620
tttcgctttt ttcataaact gatgcgcgat gcgggcatgg tgaacagcga tgaaccggcg      1680
aaacagctgc tgtgccaggg catggtgctg gcggatgcgt tttattatgt gggcgaaaac      1740
ggcgaacgca actgggtgag cccggtggat gcgattgtgg aacgcgatga aaaaggccgc      1800
attgtgaaag cgaaagatgc ggcgggccat gaactggtgt ataccggcat gagcaaaatg      1860
agcaaaagca aaaacaacgg cattgatccg caggtgatgg tggaacgcta tggcgcggat      1920
accgtgcgcc tgttttatgat gtttgcgagc ccggcggata tgaccctgga atggcaggaa      1980
agcggcgtgg aaggcgcgaa ccgctttctg aaacgcgtgt ggaaactggt gtatgaacat      2040
accgcgaaag gcgatgtggc ggcgctgaac gtggatgcgt tgaccgaaaa ccagaaagcg      2100
ctgcgccgcg atgtgcataa aaccattgcg aaagtgaccg atgatattgg ccgccgccag      2160
acctttaaca ccgcgattgc ggcgattatg gaactgatga caaaactggc gaaagcgccg      2220
accgatggcg aacaggatcg cgcgctgatg caggaagcgc tgctggcggt ggtgcgcatg      2280
ctgaacccgt ttaccccgca tatttgcttt accctgtggc aggaactgaa aggcgaaggc      2340
gatattgata cgcgccgtg gccggtggcg gatgaaaaag cgatggtgga agatagcacc      2400
ctggtggtgg tgcaggtgaa cggcaaagtg cgcgcgaaaa ttaccgtgcc ggtggatgcg      2460
accgaagaac aggtgcgcga acgcgcgggc caggaacatc tggtggcgaa atatctggat      2520
ggcgtgaccg tgcgcaaagt gatttatgtg ccgggcaaac tgctgaacct ggtggtgggc      2580
ggcccggtg                                                              2589
```

```
<210> SEQ ID NO 56
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggaagaac agtatcgccc ggaagaaatt gaaagcaaag tgcagctgca ttgggataaa        60
aaacgcacct ttgaagtgac cgaagatgaa agcaaagaaa aatattattg cctgagcatt       120
```

-continued

```
agcccgtatc cgagcggccg cctgcatatg ggccatgtgc gcaactatac cattggcgat    180
gtgattgcgc gctatcagcg catgctgggc aaaaacgtgc tgcagccgat tggctgggat    240
gcgtttggcc tgccggcgga aggcgcggcg gtgaaaaaca acaccgcgcc ggcgccgtgg    300
acctatgata acattgcgta tatgaaaaac cagctgaaaa tgctgggctt tggctatgat    360
tggagccgcg aactggcgac ctgcacccccg gaatattatc gctgggaaca gaaatttttt    420
accgaactgt ataaaaaagg cctggtgtat aaaaaaacca gcgcggtgaa ctggtgcccg    480
aacgatcaga ccgtgctggc gaacgaacag gtgattgatg gctgctgctg gcgctgcgat    540
accaaagtgg aacgcaaaga aattccgcag tggtttatta aaattaccgc gtatgcggat    600
gaactgctga acgatctgga taaactggat cattggccgg ataccgtgaa aaccatgcag    660
cgcaactgga ttggccgcag cgaaggcgtg gaaattacct ttaacgtgaa cgattatgat    720
aacaccctga ccgtgtatac cacccgcccg gatgcgttta tgggctgcac ctatctggcg    780
gtggcggcgg ccatccgct ggcgcagaaa gcggcggaaa acaacccgga actggcggcg    840
tttattgatg aatgccgcaa caccaaagtg gcggaagcgg aaatggcgac catggaaaaa    900
aaaggcgtgg ataccggctt taaagcggtg catccgctga ccggcgaaga aattccggtg    960
tgggcggcga actttgtgct gatggaatat ggcaccggcg cggtgatggc ggtgccgggc   1020
catgatcagc gcgattatga atttgcgagc aaatatggcc tgaacattaa accggtgatt   1080
ctggcggcgg atggcagcga accggatctg agccagcagg cgctgaccga aaaaggcgtg   1140
ctgtttaaca gcggcgaatt taacggcctg gatcatgaag cggcgtttaa cgcgattgcg   1200
gataaactga ccgcgatggg cgtgggcgaa cgcaaagtga actatcgcct gcgcgattgg   1260
ggcgtgagcc gccagcgcta ttggggcgcg ccgattccga tggtgaccct ggaagatggc   1320
accgtgatgc cgacccccgga tgatcagctg ccggtgattc tgccggaaga tgtggtgatg   1380
gatggcatta ccagcccgat taaagcggat ccggaatggg cgaaaaccac cgtgaacggc   1440
atgccggcgc tgcgcgaaac cgataccttt gataccttta tggaaagcag ctggatttat   1500
gcgcgctata cctgcccgca gtataaagaa ggcatgctgg atagcgaagc ggcgaactat   1560
tggctgccgg tggatattgc gattggcggc attgaacatg cgattatggg cctgctgtat   1620
tttcgctttt ttcataaact gatgcgcgat gcgggcatgg tgaacagcga tgaaccggcg   1680
aaacagctgc tgtgccaggg catggtgctg gcggatgcgt tttattatgt gggcgaaaac   1740
ggcgaacgca actgggtgag cccggtggat gcgattgtgg aacgcgatga aaaaggccgc   1800
attgtgaaag cgaaagatgc ggcgggccat gaactggtgt ataccggcat gagcaaaatg   1860
agcaaaagca aaaacaacgg cattgatccg caggtgatgg tggaacgcta tggcgcggat   1920
accgtgcgcc tgtttatgat gtttgcgagc ccggcggata tgaccctgga atggcaggaa   1980
agcggcgtgg aaggcgcgaa ccgctttctg aaacgcgtgt ggaaactggt gtatgaacat   2040
accgcgaaag cgatgtggc ggcgctgaac gtggatgcgc tgaccgaaaa ccagaaagcg   2100
ctgcgccgcg atgtgcataa aaccattgcg aaagtgaccg atgatattgg ccgccgccag   2160
acctttaaca ccgcgattgc ggcgattatg gaactgatga caaactggc gaaagcgccg   2220 accgatggcg aacaggatcg cgcgctgatg caggaagcg tgctggcggt ggtgcgcatg   2280
ctgaacccgt ttacccccgca tatttgcttt accctgtggc aggaactgaa aggcgaaggc   2340
gatattgata cgcgccgtg gccggtggcg gatgaaaaag cgatggtgga agatagcacc   2400
ctggtggtgg tgcaggtgaa cggcaaagtg cgcgcgaaaa ttaccgtgcc ggtggatgcg   2460
```

-continued

```
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                            2589

<210> SEQ ID NO 57
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atggaagaac agtatcgccc ggaagaaatt gaaagcaaag tgcagctgca ttgggataaa      60
aaacgcacct ttgaagtgac cgaagatgaa agcaaagaaa aatattattg cctgagcgtg     120
agcccgtatc cgagcggccg cctgcatatg ggccatgtgc gcaactatac cattggcgat     180
gtgattgcgc gctatcagcg catgctgggc aaaaacgtgc tgcagccgat tggctgggat     240
gcgtttggcc tgccggcgga aggcgcggcg gtgaaaaaca caccgcgcc  ggcgccgtgg     300 acctatgata acattgcgta tatgaaaaac cagctgaaaa tgctgggctt tggctatgat     360
tggagccgcg aactggcgac ctgcacc ccg gaatattatc gctgggaaca gaaatttttt    420
accgaactgt ataaaaaagg cctggtgtat aaaaaaacca gcgcggtgaa ctggtgcccg     480
aacgatcaga ccgtgctggc gaacgaacag gtgattgatg gctgctgctg gcgctgcgat     540
accaaagtgg aacgcaaaga aattccgcag tggtttatta aaattaccgc gtatgcggat     600
gaactgctga cgatctgga  taaactggat cattggccgg ataccgtgaa aaccatgcag     660
cgcaactgga ttggccgcag cgaaggcgtg gaaattacct ttaacgtgaa cgattatgat     720
aacaccctga ccgtgtatac cacccgcccg gatcgcttta tgggctgcac ctatctggcg     780
gtggcggcgg gccatccgct ggcgcagaaa gcggcggaaa acaacccgga actggcggcg     840
tttattgatg aatgccgcaa caccaaagtg gcggaagcgg aaatggcgac catggaaaaa     900
aaaggcgtgg ataccggctt taaagcggtg catccgctga ccggcgaaga aattccggtg     960
tgggcggcga ctttgtgct  gatggaatat ggcaccggcg cggtgatggc ggtgccgggc    1020
catgatcagc gcgattatga atttgcgagc aaatatggcc tgaacattaa accggtgatt    1080 ctggcggcg  atggcagcga accggatctg agccagcagg cgctgaccga aaaaggcgtg    1140
ctgtttaaca gcggcgaatt taacggcctg gatcatgaag cggcgtttaa cgcgattgcg    1200
gataaactga ccgcgatggg cgtgggcgaa cgcaaagtga actatcgcct gcgcgattgg    1260
ggcgtgagcc gccagcgcta ttggggcgcg ccgattccga tggtgaccct ggaagatggc    1320
accgtgatgc cgaccccgga tgatcagctg ccggtgattc tgccggaaga tgtggtgatg    1380
gatggcatta ccagcccgat taaagcggat ccggaatggg cgaaaaccac cgtgaacggc    1440
atgccggcgc tgcgcgaaac cgataccttt gataccttta tggaaagcag ctggagctat    1500
gcgcgctata cctgcccgca gtataaagaa ggcatgctgg atagcgaagc ggcgaactat    1560
tggctgccgg tggatattct gattggcggc attgaacatg cgattatggg cctgctgtat    1620
tttcgctttt ttcataaact gatgcgcgat gcggcatgg  tgaacagcga tgaaccggcg    1680
aaacagctgc tgtgccaggg catggtgctg gcggatgcgt tttattatgt gggcgaaaac    1740
ggcgaacgca actgggtgag cccggtggat gcgattgtgg aacgcgatga aaaaggccgc    1800
attgtgaaag cgaaagatgc ggcgggccat gaactggtgt ataccggcat gagcaaaatg    1860
```

-continued

```
agcaaaagca aaaacaacgg cattgatccg caggtgatgg tggaacgcta tggcgcggat      1920
accgtgcgcc tgtttatgat gtttgcgagc ccggcggata tgaccctgga atggcaggaa      1980
agcggcgtgg aaggcgcgaa ccgctttctg aaacgcgtgt ggaaactggt gtatgaacat      2040
accgcgaaag gcgatgtggc ggcgctgaac gtggatgcgc tgaccgaaaa ccagaaagcg      2100
ctgcgccgcg atgtgcataa aaccattgcg aaagtgaccg atgatattgg ccgccgccag      2160
acctttaaca ccgcgattgc ggcgattatg gaactgatga caaaactggc gaaagcgccg      2220
accgatggcg aacaggatcg cgcgctgatg caggaagcgc tgctggcggt ggtgcgcatg      2280
ctgaacccgt ttaccccgca tatttgcttt accctgtggc aggaactgaa aggcgaaggc      2340
gatattgata acgcgccgtg gccggtggcg gatgaaaaag cgatggtgga agatagcacc      2400
ctggtggtgg tgcaggtgaa cggcaaagtg cgcgcgaaaa ttaccgtgcc ggtggatgcg      2460
accgaagaac aggtgcgcga acgcgcgggc caggaacatc tggtggcgaa atatctggat      2520
ggcgtgaccg tgcgcaaagt gatttatgtg ccgggcaaac tgctgaacct ggtggtgggc      2580
ggcccggtg                                                              2589

<210> SEQ ID NO 58
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atggaagaac agtatcgccc ggaagaaatt gaaagcaaag tgcagctgca ttgggatgaa        60
aaacgcacct ttgaagtgac cgaagatgaa agcaaagaaa aatattattg cctgagcatt       120
ctgccgtatc cgagcggccg cctgcatatg ggccatgtgc gcaactatac cattggcgat       180
gtgattgcgc gctatcagcg catgctgggc aaaaacgtgc tgcagccgat tggctgggat       240
gcgtttggcc tgccggcgga aggcgcggcg gtgaaaaaca caccgcgcc ggcgccgtgg         300 acctatgata acattgcgta tatgaaaaac cagctgaaaa tgctgggctt tggctatgat       360
tggagccgcg aactggcgac ctgcaccccg gaatattatc gctgggaaca gaaatttttt       420
accgaactgt ataaaaaagg cctggtgtat aaaaaaacca gcgcggtgaa ctggtgcccg       480
aacgatcaga ccgtgctggc gaacgaacag gtgattgatg ctgctgctg gcgctgcgat        540 accaaagtgg aacgcaaaga aattccgcag tggtttatta aaattaccgc gtatgcggat       600
gaactgctga cgatctgga taaactggat cattggccgg ataccgtgaa aaccatgcag        660
cgcaactgga ttggccgcag cgaaggcgtg gaaattacct ttaacgtgaa cgattatgat       720
aacaccctga ccgtgtatac caccgcccg gatgcgttta tgggctgcac ctatctggcg        780
gtggcggcgg gccatccgct ggcgcagaaa gcggcggaaa caacccgga actggcggcg        840 tttattgatg aatgccgcaa caccaaagtg gcggaagcgg aaatggcgac catggaaaaa       900
aaaggcgtgg ataccggctt taaagcggtg catccgctga ccggcgaaga aattccggtg       960
tgggcggcga actttgtgct gatggaatat ggcaccggcg cggtgatggc ggtgccgggc      1020
catgatcagc gcgattatga atttgcgagc aaatatggcc tgaacattaa accggtgatt      1080
ctggcggcgg atggcagcga accggatctg agccagcagg cgctgaccga aaaaggcgtg      1140
ctgtttaaca gcgcgcgaatt taacggcctg gatcatgaag cggcgtttaa cgcgattgcg      1200
gataaactga ccgcgatggg cgtgggcgaa cgcaaagtga ctatcgcct gcgcgattgg      1260
```

-continued

```
ggcgtgagcc gccagcgcta ttggggcgcg ccgattccga tggtgaccct ggaagatggc    1320
accgtgatgc cgaccccgga tgatcagctg ccggtgattc tgccggaaga tgtggtgatg    1380
gatggcatta ccagcccgat taaagcggat ccggaatggg cgaaaaccac cgtgaacggc    1440
atgccggcgc tgcgcgaaac cgatacccttt gataccttta tggaaagcag ctggatttat    1500
gcgcgctata cctgcccgca gtataaagaa ggcatgctgg atagcgaagc ggcgaactat    1560
tggctgccgg tggatattgc gattggcggc attgaacatg cgattatggg cctgctgtat    1620
tttcgctttt ttcataaact gatgcgcgat gcgggcatgg tgaacagcga tgaaccggcg    1680
aaacagctgc tgtgccaggg catggtgctg cgcgatgcgt tttattatgt gggcgaaaac    1740
ggcgaacgca actgggtgag cccggtggat gcgattgtgg aacgcgatga aaaaggccgc    1800
attgtgaaag cgaaagatgc ggcgggccat gaactggtgt ataccggcat gagcaaaatg    1860
agcaaaagca aaaacaacgg cattgatccg caggtgatgg tggaacgcta tggcgcggat    1920
accgtgcgcc tgtttatgat gtttgcgagc ccggcggata tgaccctgga tggcaggaa    1980 agcggcgtgg aaggcgcgaa ccgctttctg aaacgcgtgt ggaaactggt gtatgaacat    2040
accgcgaaag gcgatgtggc ggcgctgaac gtggatgcgc tgaccgaaaa ccagaaagcg    2100
ctgcgccgcg atgtgcataa aaccattgcg aaagtgaccg atgatattgg ccgccgccag    2160
acctttaaca ccgcgattgc ggcgattatg gaactgatga caaactggc gaaagcgccg    2220 accgatggc aacaggatcg cgcgctgatg caggaagcgc tgctggcggt ggtgcgcatg    2280
ctgaacccgt ttaccccgca tatttgcttt accctgtggc aggaactgaa aggcgaaggc    2340
gatattgata cgcgccgtg gccggtggcg gatgaaaaag cgatggtgga agatagcacc    2400
ctggtggtgg tgcaggtgaa cggcaaagtg cgcgcgaaaa ttaccgtgcc ggtggatgcg    2460
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                           2589
```

<210> SEQ ID NO 59
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atggaagaac agtatcgccc ggaagaaatt gaaagcaaag tgcagctgca ttgggatatg     60
aaacgcacct ttgaagtgac cgaagatgaa agcaaagaaa atattattg cctgagcatt    120 agcccgtatc cgagcggccg cctgcatatg ggccatgtgc gcaactatac cattggcgat    180
gtgattgcgc gctatcagcg catgctgggc aaaaacgtgc tgcagccgat tggctgggat    240
gcgtttggcc tgccggcgga aggcgcggcg gtgaaaaaca caccgcgcc ggcgccgtgg    300 acctatgata acattgcgta tatgaaaaac cagctgaaaa tgctgggctt tggctatgat    360
tggagccgcg aactggcgac ctgcaccccg gaatattatc gctgggaaca gaaatttttt    420
accgaactgt ataaaaaagg cctggtgtat aaaaaaacca gcgcggtgaa ctggtgcccg    480
aacgatcaga ccgtgctggc gaacgaacag gtgattgatg gctgctgctg cgcgctgcgat    540 accaaagtgg aacgcaaaga aattccgcag tggtttatta aaattaccgc gtatgcggat    600
gaactgctga cgatctggat taaactggat cattggccgg ataccgtgaa aaccatgcag    660
```

-continued

```
cgcaactgga ttggccgcag cgaaggcgtg gaaattacct ttaacgtgaa cgattatgat      720
aacaccctga ccgtgtatac cacccgcccg gatgcgttta tgggctgcac ctatctggcg      780
gtggcggcgg gccatccgct ggcgcagaaa gcggcggaaa acaacccgga actggcggcg      840
tttattgatg aatgccgcaa caccaaagtg gcggaagcgg aaatggcgac catggaaaaa      900
aaaggcgtgg ataccggctt taaagcggtg catccgctga ccggcgaaga aattccggtg      960
tgggcggcga actttgtgct gatggaatat ggcaccggcg cggtgatggc ggtgccgggc     1020
catgatcagc gcgattatga atttgcgagc aaatatggcc tgaacattaa accggtgatt     1080
ctggcggcgg atggcagcga accggatctg agccagcagg cgctgaccga aaaaggcgtg     1140
ctgtttaaca gcggcgaatt taacggcctg gatcatgaag cggcgtttaa cgcgattgcg     1200
gataaactga ccgcgatggg cgtgggcgaa cgcaaagtga actatcgcct gcgcgattgg     1260
ggcgtgagcc gccagcgcta ttggggcgcg ccgattccga tggtgaccct ggaagatggc     1320
accgtgatgc cgaccccgga tgatcagctg ccggtgattc tgccggaaga tgtggtgatg     1380
gatggcatta ccagcccgat taaagcggat ccggaatggg cgaaaaccac cgtgaacggc     1440
atgccggcgc tgcgcgaaac cgataccttt gataccttta tggaaagcag ctggatttat     1500
gcgcgctata cctgcccgca gtataaagaa ggcatgctgg atagcgaagc ggcgaactat     1560
tggctgccgg tggatattgc gattggcggc attgaacatg cgattatggg cctgctgtat     1620
tttcgctttt ttcataaact gatgcgcgat gcgggcatgg tgaacagcga tgaaccggcg     1680
aaacagctgc tgtgccaggg catggtgctg gcggatgcgt tttattatgt gggcgaaaac     1740
ggcgaacgca actgggtgag cccggtggat gcgattgtgg aacgcgatga aaaaggccgc     1800
attgtgaaag cgaaagatgc ggcgggccat gaactggtgt ataccggcat gagcaaaatg     1860
agcaaaagca aaaacaacgg cattgatccg caggtgatgg tggaacgcta tggcgcggat     1920
accgtgcgcc tgtttatgat gtttgcgagc ccggcggata tgaccctgga atggcaggaa     1980
agcggcgtgg aaggcgcgaa ccgctttctg aaacgcgtgt ggaaactggt gtatgaacat     2040
accgcgaaag gcgatgtggc ggcgctgaac gtggatgcgc tgaccgaaaa ccagaaagcg     2100 ctgccgccgcg atgtgcataa aaccattgcg aaagtgaccg atgatattgg ccgccgccag     2160
acctttaaca ccgcgattgc ggcgattatg gaactgatga caaactggc gaaagcgccg       2220 accgatggcg aacaggatcg cgcgctgatg caggaagcgc tgctggcggt ggtgcgcatg     2280
ctgaacccgt ttaccccgca tatttgcttt accctgtggc aggaactgaa aggcgaaggc     2340
gatattgata cgcgccgtg gccggtggcg gatgaaaaag cgatggtgga agatagcacc     2400
ctggtggtgg tgcaggtgaa cggcaaagtg cgcgcgaaaa ttaccgtgcc ggtggatgcg     2460
accgaagaac aggtgcgcga acgcgcgggc caggaacatc tggtggcgaa atatctggat     2520
ggcgtgaccg tgcgcaaagt gatttatgtg ccgggcaaac tgctgaacct ggtggtgggc     2580
ggcccggtg                                                             2589
```

```
<210> SEQ ID NO 60
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
atggaagaac agtatcgccc ggaagaaatt gaaagcaaag tgcagctgca ttgggatgtg       60
```

```
aaacgcacct ttgaagtgac cgaagatgaa agcaaagaaa aatattattg cctgagcatt      120
agcccgtatc cgagcggccg cctgcatatg ggccatgtgc gcaactatac cattggcgat      180
gtgattgcgc gctatcagcg catgctgggc aaaaacgtgc tgcagccgat tggctgggat      240
gcgtttggcc tgccggcgga aggcgcggcg gtgaaaaaca acaccgcgcc ggcgccgtgg      300
acctatgata acattgcgta tatgaaaaac cagctgaaaa tgctgggctt tggctatgat      360
tggagccgcg aactggcgac ctgcaccccg gaatattatc gctgggaaca gaaatttttt      420
accgaactgt ataaaaaagg cctggtgtat aaaaaaacca gcgcggtgaa ctggtgcccg      480
aacgatcaga ccgtgctggc gaacgaacag gtgattgatg gctgctgctg cgcctgcgat      540
accaaagtgg aacgcaaaga aattccgcag tggtttatta aaattaccgc gtatgcggat      600
gaactgctga cgatctggta taaactggat cattggccgg ataccgtgaa aaccatgcag      660
cgcaactgga ttggccgcag cgaaggcgtg gaaattacct ttaacgtgaa cgattatgat      720
aacaccctga ccgtgtatac cacccgcccg gatgcgttta tgggctgcac ctatctggcg      780
gtggcggcgg gccatccgct ggcgcagaaa gcggcggaaa acaacccgga actggcggcg      840
tttattgatg aatgccgcaa caccaaagtg gcggaagcgg aaatggcgac catggaaaaa      900
aaaggcgtgg ataccggctt taaagcggtg catccgctga ccggcgaaga aattccggtg      960
tgggcggcga actttgtgct gatggaatat ggcaccggcg cggtgatggc ggtgccgggc     1020
catgatcagc gcgattatga atttgcgagc aaatatggcc tgaacattaa accggtgatt     1080
ctggcggcgg atggcagcga accggatctg agccagcagg cgctgaccga aaaaggcgtg     1140
ctgtttaaca gcgcgcgaatt taacggcctg gatcatgaag cggcgtttaa cgcgattgcg     1200
gataaactga ccgcgatggg cgtgggcgaa cgcaaagtga actatcgcct gcgcgattgg     1260
ggcgtgagcc gccagcgcta ttggggcgcg ccgattccga tggtgaccct ggaagatggc     1320
accgtgatgc cgaccccgga tgatcagctg ccggtgattc tgccggaaga tgtggtgatg     1380
gatggcatta ccagcccgat taaagcggat ccggaatggg cgaaaaccac cgtgaacggc     1440
atgccggcgc tgcgcgaaac cgataccttt gatacctta tggaaagcag ctggatttat     1500
gcgcgctata cctgcccgca gtataaagaa ggcatgctgg atagcgaagc ggcgaactat     1560
tggctgccgg tggatattgc gattggcggc attgaacatg cgattatggg cctgctgtat     1620
tttcgctttt ttcataaact gatgcgcgat gcgggcatgg tgaacagcga tgaaccggcg     1680
aaacagctgc tgtgccaggg catggtgctg gcggatgcgt tttattatgt gggcgaaaac     1740
ggcgaacgca actgggtgag cccggtggat gcgattgtgg aacgcgatga aaaaggccgc     1800
attgtgaaag cgaaagatgc ggcgggccat gaactggtgt ataccggcat gagcaaaatg     1860
agcaaaagca aaaacaacgg cattgatccg caggtgatgg tggaacgcta tggcgcggat     1920
accgtgcgcc tgtttatgat gtttgcgagc ccggcggata tgaccctgga atggcaggaa     1980
agcggcgtgg aaggcgcgaa ccgctttctg aaacgcgtgt ggaaactggt gtatgaacat     2040
accgcgaaag cgatgtggc ggcgctgaac gtggatgcgc tgaccgaaaa ccagaaagcg     2100
ctgcgccgcg atgtgcataa aaccattgcg aaagtgaccg atgatattgg ccgccgccag     2160
acctttaaca ccgcgattgc ggcgattatg gaactgatga caaactggc gaaagcgccg     2220 accgatggcg aacaggatcg cgcgctgatg caggaagcgc tgctggcggt ggtgcgcatg     2280
ctgaacccgt ttaccccgca tatttgcttt accctgtggc aggaactgaa aggcgaaggc     2340
gatattgata cgcgccgtg gccggtggcg gatgaaaaag cgatggtgga agatagcacc     2400
ctggtggtgg tgcaggtgaa cggcaaagtg cgcgcgaaaa ttaccgtgcc ggtggatgcg     2460
```

```
accgaagaac aggtgcgcga acgcgcgggc caggaacatc tggtggcgaa atatctggat      2520
ggcgtgaccg tgcgcaaagt gatttatgtg ccgggcaaac tgctgaacct ggtggtgggc      2580
ggcccggtg                                                              2589
```

<210> SEQ ID NO 61
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atggaagaac agtatcgccc ggaagaaatt gaaagcaaag tgcagctgca ttgggataaa        60
aaacgcacct ttgaagtgac cgaagatgaa agcaaagaaa aatattattg cctgagcatt       120
gtgccgtatc cgagcggccg cctgcatatg ggccatgtgc gcaactatac cattggcgat       180
gtgattgcgc gctatcagcg catgctgggc aaaaacgtgc tgcagccgat tggctgggat       240
gcgtttggcc tgccggcgga aggcgcggcg gtgaaaaaca caccgcgcc ggcgccgtgg         300 acctatgata acattgcgta tatgaaaaac cagctgaaaa tgctgggctt tggctatgat       360
tggagccgcg aactggcgac ctgcaccccg gaatattatc gctgggaaca gaaatttttt       420
accgaactgt ataaaaaagg cctggtgtat aaaaaaacca gcgcggtgaa ctggtgcccg       480
aacgatcaga ccgtgctggc gaacgaacag gtgattgatg gctgctgctg gcgctgcgat       540
accaaagtgg aacgcaaaga aattccgcag tggtttatta aaattaccgc gtatgcggat       600
gaactgctga acgatctgga taaactggat cattggccgg ataccgtgaa aaccatgcag       660
cgcaactgga ttggccgcag cgaaggcgtg gaaattacct ttaacgtgaa cgattatgat       720
aacaccctga ccgtgtatac cacccgcccg gatgcgttta tgggctgcac ctatctggcg       780
gtggcggcgg gccatccgct ggcgcagaaa gcggcggaaa acaacccgga actggcggcg       840
tttattgatg aatgccgcaa caccaaagtg gcggaagcgg aaatggcgac catggaaaaa       900
aaaggcgtgg ataccggctt taaagcggtg catccgctga ccggcgaaga aattccggtg       960
tgggcggcga actttgtgct gatggaatat ggcaccggcg cggtgatggc ggtgccgggc      1020
catgatcagc gcgattatga atttgcgagc aaatatggcc tgaacattaa accggtgatt      1080
ctggcggcgg atggcagcga accggatctg agccagcagg cgctgaccga aaaaggcgtg      1140
ctgtttaaca gcgcggcgaa ttaacggcctg gatcatgaag cggcgtttaa cgcgattgcg      1200
gataaactga ccgcgatggg cgtgggcgaa cgcaaagtga ctatcgcct gcgcgattgg      1260 ggcgtgagcc gccagcgcta ttggggcgcg ccgattccga tggtgaccct ggaagatggc      1320
accgtgatgc cgacccccgga tgatcagctg ccggtgattc tgccggaaga tgtggtgatg      1380
gatggcatta ccagcccgat taaagcggat ccggaatggg cgaaaaccac cgtgaacggc      1440
atgccggcgc tgcgcgaaac cgataccttt gataccttta tggaaagcag ctggattat      1500 gcgcgctata cctgcccgca gtataaagaa ggcatgctgg atagcgaagc ggcgaactat      1560
tggctgccgg tggatattgc gattggcggc attgaacatg cgattatggg cctgctgtat      1620
tttcgctttt ttcataaact gatgcgcgat gcgggcatgg tgaacagcga tgaaccggcg      1680
aaacagctgc tgtgccaggg catggtgctg gcggatgcgt tttattatgt gggcgaaaac      1740
ggcgaacgca actgggtgag cccggtggat gcgattgtga acgcgatga aaaaggccgc      1800 attgtgaaag cgaaagatgc ggcgggccat gaactggtgt ataccggcat gagcaaaatg      1860
```

```
agcaaaagca aaaacaacgg cattgatccg caggtgatgg tggaacgcta tggcgcggat    1920
accgtgcgcc tgtttatgat gtttgcgagc ccggcggata tgaccctgga atggcaggaa    1980
agcggcgtgg aaggcgcgaa ccgctttctg aaacgcgtgt ggaaactggt gtatgaacat    2040
accgcgaaag gcgatgtggc ggcgctgaac gtggatgcgc tgaccgaaaa ccagaaagcg    2100
ctgcgccgcg atgtgcataa aaccattgcg aaagtgaccg atgatattgg ccgccgccag    2160
acctttaaca ccgcgattgc ggcgattatg gaactgatga caaaactggc gaaagcgccg    2220
accgatggcg aacaggatcg cgcgctgatg caggaagcgc tgctggcggt ggtgcgcatg    2280
ctgaacccgt ttaccccgca tatttgcttt accctgtggc aggaactgaa aggcgaaggc    2340
gatattgata cgcgccgtg gccggtggcg gatgaaaaag cgatggtgga agatagcacc    2400
ctggtggtgg tgcaggtgaa cggcaaagtg cgcgcgaaaa ttaccgtgcc ggtggatgcg    2460
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                            2589

<210> SEQ ID NO 62
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atggaagaac agtatcgccc ggaagaaatt gaaagcaaag tgcagctgca ttgggataaa      60
aaacgcacct ttgaagtgac cgaagatgaa agcaaagaaa aatattattg cctgagcatt     120
gcgccgtatc cgagcggccg cctgcatatg ggccatgtgc gcaactatac cattggcgat     180
gtgattgcgc gctatcagcg catgctgggc aaaaacgtgc tgcagccgat ggctgggat      240 gcgtttggcc tgccggcgga aggcgcggcg gtgaaaaaca caccgcgcc ggcgccgtgg      300 acctatgata acattgcgta tatgaaaaac cagctgaaaa tgctgggctt tggctatgat     360
tggagccgcg aactggcgac ctgcacccg gaatattatc gctgggaaca gaaatttttt     420
accgaactgt ataaaaaagg cctggtgtat aaaaaaacca gcgcggtgaa ctggtgcccg     480
aacgatcaga ccgtgctggc gaacgaacag gtgattgatg gctgctgctg cgctgcgat     540 accaaagtgg aacgcaaaga aattccgcag tggtttatta aaattaccgc gtatgcggat     600
gaactgctga cgatctgga taaactggat cattggccgg ataccgtgaa aaccatgcag     660
cgcaactgga ttggccgcag cgaaggcgtg aaattaccct ttaacgtgaa cgattatgat     720
aacaccctga ccgtgtatac caccgcccg gatgcgttta tgggctgcac ctatctggcg     780
gtggcggcgg ccatccgct ggcgcagaaa gcggcggaaa caacccgga actggcggcg      840 tttattgatg aatgccgcaa caccaaagtg gcggaagcgg aaatggcgac catggaaaaa     900
aaaggcgtgg ataccggctt taaagcggtg catccgctga ccggcgaaga aattccggtg     960
tgggcggcga ctttgtgct gatggaatat ggcaccggcg cggtgatggc ggtgccgggc    1020
catgatcagc gcgattatga atttgcgagc aaatatggcc tgaacattaa accggtgatt    1080 ctggcggcg atggcagcga accggatctg agccagcagg cgctgaccga aaaaggcgtg    1140
ctgtttaaca gcggcgaatt taacggcctg gatcatgaag cggcgtttaa cgcgattgcg    1200
gataaactga ccgcgatggg cgtgggcgaa cgcaaagtga actatcgcct gcgcgattgg    1260
```

```
ggcgtgagcc gccagcgcta ttggggcgcg ccgattccga tggtgaccct ggaagatggc    1320
accgtgatgc cgaccccgga tgatcagctg ccggtgattc tgccggaaga tgtggtgatg    1380
gatggcatta ccagcccgat taaagcggat ccggaatggg cgaaaaccac cgtgaacggc    1440
atgccggcgc tgcgcgaaac cgataccttt gataccttta tggaaagcag ctggatttat    1500
gcgcgctata cctgcccgca gtataaagaa ggcatgctgg atagcgaagc ggcgaactat    1560
tggctgccgg tggatattgc gattggcggc attgaacatg cgattatggg cctgctgtat    1620
tttcgctttt ttcataaact gatgcgcgat gcgggcatgg tgaacagcga tgaaccggcg    1680
aaacagctgc tgtgccaggg catggtgctg cggatgcgt tttattatgt gggcgaaaac     1740
ggcgaacgca actgggtgag cccggtggat gcgattgtgg aacgcgatga aaaaggccgc    1800
attgtgaaag cgaaagatgc ggcgggccat gaactggtgt ataccggcat gagcaaaatg    1860
agcaaaagca aaaacaacgg cattgatccg caggtgatgg tggaacgcta tggcgcggat    1920 accgtgcgc tgtttatgat gtttgcgagc ccggcggata tgaccctgga atggcaggaa     1980
agcggcgtgg aaggcgcgaa ccgctttctg aaacgcgtgt ggaaactggt gtatgaacat    2040
accgcgaaag cgatgtggc ggcgctgaac gtggatgcgc tgaccgaaaa ccagaaagcg     2100
ctgcgccgcg atgtgcataa aaccattgcg aaagtgaccg atgatattgg ccgccgccag    2160
acctttaaca ccgcgattgc ggcgattatg gaactgatga caaactggc gaaagcgccg      2220 accgatggcg aacaggatcg cgcgctgatg caggaagcgc tgctggcggt ggtgcgcatg    2280
ctgaacccgt ttaccccgca tatttgcttt accctgtggc aggaactgaa aggcgaaggc    2340
gatattgata acgcgccgtg gccggtggcg gatgaaaaag cgatggtgga agatagcacc    2400
ctggtggtgg tgcaggtgaa cggcaaagtg cgcgcgaaaa ttaccgtgcc ggtggatgcg    2460
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                             2589
```

```
<210> SEQ ID NO 63
<211> LENGTH: 2586
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
```

```
atggaagaac agtatcgccc ggaagaaatt gaaagcaaag tgcagctgca ttgggataaa      60
aaacgcacct ttgaagtgac cgaagatgaa agcaaagaaa atattattg cctgagcatt      120 agcccgtatc cgagcggccg cctgcatatg ggccatgtgc gcaactatac cattggcgat     180
gtgattgcgc gctatcagcg catgctgggc aaaaacgtgc tgcagccgat tggctgggat    240
gcgtttggcc tgccggcgga aggcgcggcg gtgaaaaaca caccgcgcc ggcgccgtgg     300 acctatgata acattgcgta tatgaaaaac cagctgaaaa tgctgggctt tggctatgat    360
tggagccgcg aactggcgac ctgcacccg gaatattatc gctgggaaca gaaattttt     420 accgaactgt ataaaaaagg cctggtgtat aaaaaaacca gcgcggtgaa ctggtgcccg    480
aacgatcaga ccgtgctggc gaacgaacag gtgattgatg ctgctgctg gcgctgcgat    540 accaaagtgg aacgcaaaga aattccgcag tggtttatta aaattaccgc gtatgcggat    600
gaactgctga cgatctgga taaactggat cattggccgg ataccgtgaa aaccatgcag    660
```

-continued

```
cgcaactgga ttggccgcag cgaaggcgtg gaaattacct ttaacgtgaa cgattatgat      720
aacaccctga ccgtgtatac cacccgcccg gatgcgttta tgggctgcac ctatctggcg      780
gtggcggcgg gccatccgct ggcgcagaaa gcggcggaaa acaacccgga actggcggcg      840
tttattgatg aatgccgcaa caccaaagtg gcggaagcgg aaatggcgac catggaaaaa      900
aaaggcgtgg ataccggctt taaagcggtg catccgctga ccggcgaaga aattccggtg      960
tgggcggcga actttgtgct gatggaatat ggcaccggcg cggtgatggc ggtgccgggc     1020
catgatcagc gcgattatga atttgcgagc aaatatggcc tgaacattaa accggtgatt     1080
ctggcggcgc atggcagcga accggatctg agccagcagg cgctgaccga aaaaggcgtg     1140
ctgtttaaca gcggcgaatt taacggcctg gatcatgaag cggcgtttaa cgcgattgcg     1200
gataaactga ccgcgatggg cgtgggcgaa cgcaaagtga actatcgcct gcgcgattgg     1260
ggcgtgagcc gccagcgcta ttggggcgcg ccgattccga tggtgaccct ggaagatggc     1320
accgtgatgc cgaccccgga tgatcagctg ccggtgattc tgccggaaga tgtggtgatg     1380
gatggcatta ccagcccgat taaagcggat ccggaatggg cgaaaaccac cgtgaacggc     1440
atgccggcgc tgcgcgaaac cgataccttt gatacctta tggaaagcag ctgggcgtat     1500
gcgcgctata cctgcccgca gtataaagaa ggcatgctgg atagcgaagc ggcgaactat     1560
tggctgccgg tggatattgc gattggcggc attgaacatg cgattatggg cctgctgtat     1620
tttcgctttt ttcataaact gatgcgcgat gcgggcatgg tgaacagcga tgaaccggcg     1680
aaacagctgc tgtgccaggg catggtgctg cgcgatgcgt tttattatgt gggcgaaaac     1740
ggcgaacgca actgggtgag cccggtggat gcgattgtgg aacgcgatga aaaaggccgc     1800
attgtgaaag cgaaagatgc ggcgggccat gaactggtgt ataccggcat gagcaaaatg     1860
agcaaaagca aaaacaacgg cattgatccg caggtgatgg tggaacgcta tggcgcggat     1920
accgtgcgcc tgtttatgat gtttgcgagc ccggcggata tgaccctgga atggcaggaa     1980
agcggcgtgg aaggcgcgaa ccgctttaaa cgcgtgtgga aactggtgta tgaacatacc     2040
gcgaaaggcg atgtggcggc gctgaacgtg gatgcgctga ccgaaaacca gaaagcgctg     2100
cgccgcgatg tgcataaaac cattgcgaaa gtgaccgatg atattggccg ccgccagacc     2160
tttaacaccg cgattgcggc gattatggaa ctgatgaaca aactggcgaa agcgccgacc     2220
gatggcgaac aggatcgcgc gctgatgcag gaagcgctgc tggcggtggt cgcatgctg     2280 aacccgtttta ccccgcatat ttgctttacc ctgtggcagg aactgaaagg cgaaggcgat     2340
attgataacg cgccgtggcc ggtggcggat gaaaaagcga tggtggaaga tagcaccctg     2400
gtggtggtgc aggtgaacgg caaagtgcgc gcgaaaatta ccgtgccggt ggatgcgacc     2460
gaagaacagg tgcgcgaacg cgcgggccag gaacatctgg tggcgaaata tctggatggc     2520
gtgaccgtgc gcaaagtgat ttatgtgccg ggcaaactgc tgaacctggt ggtgggcggc     2580
ccggtg                                                              2586
```

<210> SEQ ID NO 64
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
atggaagaac agtatcgccc ggaagaaatt gaaagcaaag tgcagctgca ttgggataaa       60
```

-continued

```
aaacgcacct ttgaagtgac cgaagatgaa agcaaagaaa aatattattg cctgagcatt     120
agcccgtatc cgagcggccg cctgcatatg ggccatgtgc gcaactatac cattggcgat     180
gtgattgcgc gctatcagcg catgctgggc aaaaacgtgc tgcagccgat tggctgggat     240
gcgtttggcc tgccggcgga aggcgcggcg gtgaaaaaca acaccgcgcc ggcgccgtgg     300
acctatgata acattgcgta tatgaaaaac cagctgaaaa tgctgggctt tggctatgat     360
tggagccgcg aactggcgac ctgcaccccg gaatattatc gctgggaaca gaaatttttt     420
accgaactgt ataaaaaagg cctggtgtat aaaaaaacca gcgcggtgaa ctggtgcccg     480
aacgatcaga ccgtgctggc gaacgaacag gtgattgatg gctgctgctg gcgctgcgat     540
accaaagtgg aacgcaaaga aattccgcag tggtttatta aaattaccgc gtatgcggat     600
gaactgctga cgatctggat aaaactggat cattggccgg ataccgtgaa aaccatgcag     660
cgcaactgga ttggccgcag cgaaggcgtg gaaattacct ttaacgtgaa cgattatgat     720
aacaccctga ccgtgtatac caccgccccg gatgcgttta tgggctgcac ctatctggcg     780
gtggcggcgg gccatccgct ggcgcagaaa gcggcggaaa acaacccgga actggcggcg     840
tttattgatg aatgccgcaa caccaaagtg gcggaagcgg aaatggcgac catggaaaaa     900
aaaggcgtgg ataccggctt taaagcggtg catccgctga ccggcgaaga aattccggtg     960
tgggcggcga actttgtgct gatggaatat ggcaccggcg cggtgatggc ggtgccgggc    1020
catgatcagc gcgattatga atttgcgagc aaatatggcc tgaacattaa accggtgatt    1080
ctggcggcgg atggcagcga accggatctg agccagcagg cgctgaccga aaaaggcgtg    1140
ctgtttaaca gcggcgaatt taacggcctg gatcatgaag cggcgtttaa cgcgattgcg    1200
gataaactga ccgcgatggg cgtgggcgaa cgcaaagtga actatcgcct gcgcgattgg    1260
ggcgtgagcc gccagcgcta ttggggcgcg ccgattccga tggtgaccct ggaagatggc    1320
accgtgatgc cgaccccgga tgatcagctg ccggtgattc tgccggaaga tgtggtgatg    1380
gatggcatta ccagcccgat taaagcggat ccggaatggg cgaaaaccac cgtgaacggc    1440
atgccggcgc tgcgcgaaac cgataccttt gataccttta tggaaagcag ctggcattat    1500
gcgcgctata cctgcccgca gtataaagaa ggcatgctgg atagcgaagc ggcgaactat    1560
tggctgccgg tggatattgc gattggcggc attgaacatg cgattatggg cctgctgtat    1620
tttcgctttt ttcataaact gatgcgcgat gcgggcatgg tgaacagcga tgaaccggcg    1680
aaacagctgc tgtgccaggg catggtgctg gcggatgcgt tttattatgt gggcgaaaac    1740
ggcgaacgca actgggtgag cccggtggat gcgattgtgg aacgcgatga aaaaggccgc    1800
attgtgaaag cgaaagatgc ggcgggccat gaactggtgt ataccggcat gagcaaaatg    1860
agcaaaagca aaaacaacgg cattgatccg caggtgatgg tggaacgcta tggcgcggat    1920
accgtgcgcc tgtttatgat gtttgcgagc ccggcggata tgaccctgga atggcaggaa    1980
agcggcgtgg aaggcgcgaa ccgctttctg aaacgcgtgt ggaaactggt gtatgaacat    2040
accgcgaaag cgatgtggc ggcgctgaac gtggatgcgc tgaccgaaaa ccagaaagcg    2100
ctgcgccgcg atgtgcataa aaccattgcg aaagtgaccg atgatattgg ccgccgccag    2160
acctttaaca ccgcgattgc ggcgattatg gaactgatga caaactggc gaaagcgccg    2220 accgatggcg aacaggatcg cgcgctgatg caggaagcgc tgctggcggt ggtgcgcatg    2280
ctgaacccgt ttaccccgca tatttgcttt accctgtggc aggaactgaa aggcgaaggc    2340
gatattgata acgcgccgtg gccggtggcg gatgaaaaag cgatggtgga agatagcacc    2400
```

-continued

```
ctggtggtgg tgcaggtgaa cggcaaagtg cgcgcgaaaa ttaccgtgcc ggtggatgcg    2460
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                            2589

<210> SEQ ID NO 65
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggaagaac agtatcgccc ggaagaaatt gaaagcaaag tgcagctgca ttgggataaa      60
aaacgcacct ttgaagtgac cgaagatgaa agcaaagaaa aatattattg cctgagcatt     120
agcccgtatc cgagcggccg cctgcatatg ggccatgtgc gcaactatac cattggcgat     180
gtgattgcgc gctatcagcg catgctgggc aaaaacgtgc tgcagccgat tggctgggat     240
gcgtttggcc tgccggcgga aggcgcggcg gtgaaaaaca caccgcgcc ggcgccgtgg     300 acctatgata acattgcgta tatgaaaaac cagctgaaaa tgctgggctt tggctatgat     360
tggagccgcg aactggcgac ctgcacccg aatattatc gctgggaaca gaaatttttt     420
accgaactgt ataaaaaagg cctggtgtat aaaaaaacca gcgcggtgaa ctggtgcccg     480
aacgatcaga ccgtgctggc gaacgaacag gtgattgatg gctgctgctg gcgctgcgat     540
accaaagtgg aacgcaaaga aattccgcag tggtttatta aaattaccgc gtatgcggat     600
gaactgctga cgatctggat aaaactggat cattggccgg ataccgtgaa aaccatgcag     660
cgcaactgga ttggccgcag cgaaggcgtg gaaattacct ttaacgtgaa cgattatgat     720 aacacccctga ccgtgtatac cacccgcccg gatgcgttta tgggctgcac ctatctggcg     780
gtggcggcgg gccatccgct ggcgcagaaa gcggcggaaa acaacccgga actggcggcg     840
tttattgatg aatgccgcaa caccaaagtg gcggaagcgg aaatggcgac catggaaaaa     900
aaaggcgtgg ataccggctt taaagcggtg catccgctga ccggcgaaga aattccggtg     960
tgggcggcga actttgtgct gatggaatat ggcaccggcg cggtgatggc ggtgccgggc    1020
catgatcagc gcgattatga atttgcgagc aaatatggcc tgaacattaa accggtgatt    1080
ctggcggcgg atggcagcga accggatctg agccagcagg cgctgaccga aaaaggcgtg    1140
ctgtttaaca gcgcggaatt taacggcctg atcatgaag cggcgtttaa cgcgattgcg    1200
gataaactga ccgcgatggg cgtgggcgaa cgcaaagtga actatcgcct gcgcgattgg    1260
ggcgtgagcc gccagcgcta ttggggcgcg ccgattccga tggtgaccct ggaagatggc    1320
accgtgatgc cgacccccgga tgatcagctg ccggtgattc tgccggaaga gtggtgatg    1380 gatggcatta ccagcccgat taaagcggat ccggaatggg cgaaaaccac cgtgaacggc    1440
atgccggcgc tgcgcgaaac cgatacctt gatacctta tggaaagcag ctggatttat    1500
gcgcgctata cctgcccgca gtataaagaa ggcatgctgg atagcgaagc ggcgaactat    1560
tggctgccgg tggatattat tattggcggc attgaacatg cgattatggg cctgctgtat    1620
tttcgctttt ttcataaact gatgcgcgat gcgggcatgg tgaacagcga tgaaccggcg    1680
aaacagctgc tgtgccaggg catggtgctg cgcgatgcgt tttattatgt gggcgaaaac    1740
ggcgaacgca actgggtgag cccggtggat gcgattgtgg aacgcgatga aaaaggccgc    1800
```

-continued

```
attgtgaaag cgaaagatgc ggcgggccat gaactggtgt ataccggcat gagcaaaatg    1860
agcaaaagca aaaacaacgg cattgatccg caggtgatgg tggaacgcta tggcgcggat    1920
accgtgcgcc tgtttatgat gtttgcgagc ccggcggata tgaccctgga atggcaggaa    1980
agcggcgtgg aaggcgcgaa ccgctttctg aaacgcgtgt ggaaactggt gtatgaacat    2040
accgcgaaag gcgatgtggc ggcgctgaac gtggatgcgc tgaccgaaaa ccagaaagcg    2100
ctgcgccgcg atgtgcataa aaccattgcg aaagtgaccg atgatattgg ccgccgccag    2160
acctttaaca ccgcgattgc ggcgattatg gaactgatga caaaactggc gaaagcgccg    2220
accgatggcg aacaggatcg cgcgctgatg caggaagcgc tgctggcggt ggtgcgcatg    2280
ctgaacccgt ttaccccgca tatttgcttt accctgtggc aggaactgaa aggcgaaggc    2340
gatattgata cgcgccgtg gccggtggcg gatgaaaaag cgatggtgga agatagcacc    2400
ctggtggtgg tgcaggtgaa cggcaaagtg cgcgcgaaaa ttaccgtgcc ggtggatgcg    2460
accgaagaac aggtgcgcga acgcgcgggc caggaacatc tggtggcgaa atatctggat    2520
ggcgtgaccg tgcgcaaagt gatttatgtg ccgggcaaac tgctgaacct ggtggtgggc    2580
ggcccggtg                                                            2589
```

<210> SEQ ID NO 66
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
atggaagaac agtatcgccc ggaagaaatt gaaagcaaag tgcagctgca ttgggataaa      60
aaacgcacct ttgaagtgac cgaagatgaa agcaaagaaa aatattattg cctgagcatt     120
agcccgtatc cgagcggccg cctgcatatg ggccatgtgc gcaactatac cattggcgat     180
gtgattgcgc gctatcagcg catgctgggc aaaaacgtgc tgcagccgat tggctgggat     240
gcgtttggcc tgccggcgga aggcgcggcg gtgaaaaaca caccgcgcc ggcgccgtgg      300 acctatgata acattgcgta tatgaaaaac cagctgaaaa tgctgggctt tggctatgat     360
tggagccgcg aactggcgac ctgcacccg gaatattatc gctgggaaca gaaatttttt     420
accgaactgt ataaaaaagg cctggtgtat aaaaaaacca gcgcggtgaa ctggtgcccg     480
aacgatcaga ccgtgctggc gaacgaacag gtgattgatg gctgctgctg gcgctgcgat     540
accaaagtga aacgcaaaga aattccgcag tggtttatta aaattaccgc gtatgcggat     600
gaactgctga cgatctgga taaactggat cattggccgg ataccgtgaa aaccatgcag     660
cgcaactgga ttggccgcag cgaaggcgtg gaaattaccct ttaacgtgaa cgattatgat     720 aacacctga ccgtgtatac caccgcccg gatgcgttta tgggctgcac ctatctggcg     780
gtggcggcgg ccatccgct ggcgcagaaa gcgcgcgaaa caacccgga actggcggcg      840 tttattgatg aatgccgcaa caccaaagtg gcggaagcgg aaatggcgac catggaaaaa     900
aaaggcgtgg ataccggctt taaagcggtg catccgctga ccggcgaaga aattccggtg     960
tgggcggcga ctttgtgct gatggaatat ggcaccggcg cggtgatggc ggtgccgggc    1020
catgatcagc gcgattatga atttgcgagc aaatatggcc tgaacattaa accggtgatt    1080 ctggcggcg atggcagcga accggatctg agccagcagg cgctgaccga aaaaggcgtg    1140
ctgtttaaca gcggcgaatt taacggcctg gatcatgaag cggcgtttaa cgcgattgcg    1200
```

-continued

```
gataaactga ccgcgatggg cgtgggcgaa cgcaaagtga actatcgcct gcgcgattgg      1260
ggcgtgagcc gccagcgcta ttggggcgcg ccgattccga tggtgaccct ggaagatggc      1320
accgtgatgc cgaccccgga tgatcagctg ccggtgattc tgccggaaga tgtggtgatg      1380
gatggcatta ccagcccgat taaagcggat ccggaatggg cgaaaaccac cgtgaacggc      1440
atgccggcgc tgcgcgaaac cgataccttt gataccttta tggaaagcag ctggatttat      1500
gcgcgctata cctgcccgca gtataaagaa ggcatgctgg atagcgaagc ggcgaactat      1560
tggctgccgg tggatattgt gattggcggc attgaacatg cgattatggg cctgctgtat      1620
tttcgctttt ttcataaact gatgcgcgat gcgggcatgg tgaacagcga tgaaccggcg      1680
aaacagctgc tgtgccaggg catggtgctg gcggatgcgt tttattatgt gggcgaaaac      1740
ggcgaacgca actgggtgag cccggtggat gcgattgtgg aacgcgatga aaaaggccgc      1800
attgtgaaag cgaaagatgc ggcgggccat gaactggtgt ataccggcat gagcaaaatg      1860
agcaaaagca aaaacaacgg cattgatccg caggtgatgg tggaacgcta tggcgcggat      1920
accgtgcgcc tgtttatgat gtttgcgagc ccggcggata tgaccctgga atggcaggaa      1980
agcggcgtgg aaggcgcgaa ccgctttctg aaacgcgtgt ggaaactggt gtatgaacat      2040
accgcgaaag cgatgtggc ggcgctgaac gtggatgcgc tgaccgaaaa ccagaaagcg      2100
ctgcgccgcg atgtgcataa aaccattgcg aaagtgaccg atgatattgg ccgccgccag      2160
acctttaaca ccgcgattgc ggcgattatg gaactgatga caaactggc gaaagcgccg      2220 accgatggcg aacaggatcg cgcgctgatg caggaagcgc tgctggcggt ggtgcgcatg      2280
ctgaacccgt ttaccccgca tatttgcttt accctgtggc aggaactgaa aggcgaaggc      2340
gatattgata cgcgccgtg gccggtggcg gatgaaaaag cgatggtgga agatagcacc      2400
ctggtggtgg tgcaggtgaa cggcaaagtg cgcgcgaaaa ttaccgtgcc ggtggatgcg      2460
accgaagaac aggtgcgcga acgcgcgggc caggaacatc tggtggcgaa atatctggat      2520
ggcgtgaccg tgcgcaaagt gatttatgtg ccgggcaaac tgctgaacct ggtggtgggc      2580
ggcccggtg                                                              2589
```

```
<210> SEQ ID NO 67
<211> LENGTH: 2589
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
```

```
atggaagaac agtatcgccc ggaagaaatt gaaagcaaag tgcagctgca ttgggataaa       60
aaacgcacct ttgaagtgac cgaagatgaa agcaaagaaa atattattg cctgagcatt      120 agcccgtatc cgagcggccg cctgcatatg ggccatgtgc gcaactatac cattggcgat      180
gtgattgcgc gctatcagcg catgctgggc aaaaacgtgc tgcagccgat ggctgggat       240 gcgtttggcc tgccggcgga aggcgcggcg gtgaaaaaca caccgcgcc ggcgccgtgg       300 acctatgata cattgcgta tatgaaaaac cagctgaaaa tgctgggctt tggctatgat       360
tggagccgcg aactggcgac ctgcacccg gaatattatc gctgggaaca gaaattttt       420 accgaactgt ataaaaaagg cctggtgtat aaaaaaacca gcgcggtgaa ctggtgcccg       480
aacgatcaga ccgtgctggc gaacgaacag gtgattgatg ctgctgctg cgctgcgat       540 accaaagtgg aacgcaaaga aattccgcag tggtttatta aaattaccgc gtatgcggat       600
```

-continued

```
gaactgctga acgatctgga taaactggat cattggccgg ataccgtgaa aaccatgcag    660
cgcaactgga ttggccgcag cgaaggcgtg gaaattacct ttaacgtgaa cgattatgat    720
aacaccctga ccgtgtatac cacccgcccg gatgcgttta tgggctgcac ctatctggcg    780
gtggcggcgg gccatccgct ggcgcagaaa gcggcggaaa acaacccgga actggcggcg    840
tttattgatg aatgccgcaa caccaaagtg gcggaagcgg aaatggcgac catggaaaaa    900
aaaggcgtgg ataccggctt taaagcggtg catccgctga ccggcgaaga aattccggtg    960
tgggcggcga actttgtgct gatggaatat ggcaccggcg cggtgatggc ggtgccgggc   1020
catgatcagc gcgattatga atttgcgagc aaatatggcc tgaacattaa accggtgatt   1080
ctggcggcgg atggcagcga accggatctg agccagcagg cgctgaccga aaaaggcgtg   1140
ctgtttaaca gcggcgaatt taacggcctg gatcatgaag cggcgtttaa cgcgattgcg   1200
gataaactga ccgcgatggg cgtgggcgaa cgcaaagtga actatcgcct gcgcgattgg   1260
ggcgtgagcc gccagcgcta ttggggcgcg ccgattccga tggtgaccct ggaagatggc   1320
accgtgatgc cgacccccgga tgatcagctg ccggtgattc tgccggaaga tgtggtgatg   1380
gatggcatta ccagcccgat taaagcggat ccggaatggg cgaaaaccac cgtgaacggc   1440
atgccggcgc tgcgcgaaac cgataccttt gataccttta tggaaagcag ctggatttat   1500
gcgcgctata cctgcccgca gtataaagaa ggcatgctgg atagcgaagc ggcgaactat   1560
tggctgccgg tggatattgg cattggcggc attgaacatg cgattatggg cctgctgtat   1620
tttcgctttt ttcataaact gatgcgcgat gcgggcatgg tgaacagcga tgaaccggcg   1680
aaacagctgc tgtgccaggg catggtgctg gcggatgcgt tttattatgt gggcgaaaac   1740
ggcgaacgca actgggtgag cccggtggat gcgattgtgg aacgcgatga aaaaggccgc   1800
attgtgaaag cgaaagatgc ggcgggccat gaactggtgt ataccggcat gagcaaaatg   1860
agcaaaagca aaaacaacgg cattgatccg caggtgatgg tggaacgcta tggcgcggat   1920
accgtgcgcc tgtttatgat gtttgcgagc ccggcggata tgaccctgga atggcaggaa   1980
agcggcgtgg aaggcgcgaa ccgctttctg aaacgcgtgt ggaaactggt gtatgaacat   2040
accgcgaaag cgatgtggc ggcgctgaac gtggatgcgc tgaccgaaaa ccagaaagcg   2100
ctgcgccgcg atgtgcataa aaccattgcg aaagtgaccg atgatattgg ccgccgccag   2160
acctttaaca ccgcgattgc ggcgattatg gaactgatga caaactggc gaaagcgccg   2220 accgatggcg aacaggatcg cgcgctgatg caggaagcgc tgctggcggt ggtgcgcatg   2280
ctgaacccgt ttaccccgca tatttgcttt accctgtggc aggaactgaa aggcgaaggc   2340
gatattgata acgcgccgtg gccggtggcg gatgaaaaag cgatggtgga agatagcacc   2400
ctggtggtgg tgcaggtgaa cggcaaagtg cgcgcgaaaa ttaccgtgcc ggtggatgcg   2460
accgaagaac aggtgcgcga acgcgcgggc caggaacatc tggtggcgaa atatctggat   2520
ggcgtgaccg tgcgcaaagt gatttatgtg ccgggcaaac tgctgaacct ggtggtgggc   2580
ggcccggtg                                                           2589
```

<210> SEQ ID NO 68
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

```
gtggggttcc cgagcggcca aagggagcag acttcaaatc tgccgtcaca gacttcgaag      60
gttcgaatcc ttcccccacc a                                                81
```

<210> SEQ ID NO 69
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 69

```
gtggggttcc cgagcggcca aagggagcag actnnnaatc tgccgtcaca gacttcgaag      60
gttcgaatcc ttcccccacc a                                                81
```

<210> SEQ ID NO 70
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240
```

```
Gly Gly Ala Val Trp Leu Asp Pro Lys Lys Thr Ser Pro Tyr Lys Phe
            245             250             255

Tyr Gln Phe Trp Ile Asn Thr Ala Asp Ala Asp Val Tyr Arg Phe Leu
            260             265             270

Lys Phe Phe Thr Phe Met Ser Ile Glu Glu Ile Asn Ala Leu Glu Glu
        275             280             285

Glu Asp Lys Asn Ser Gly Lys Ala Pro Arg Ala Gln Tyr Val Leu Ala
    290             295             300

Glu Gln Val Thr Arg Leu Val His Gly Glu Glu Gly Leu Gln Ala Ala
305             310             315             320

Lys Arg Ile Thr Glu Cys Leu Phe Ser Gly Ser Leu Ser Ala Leu Ser
            325             330             335

Glu Ala Asp Phe Glu Gln Leu Ala Gln Asp Gly Val Pro Met Val Glu
            340             345             350

Met Glu Lys Gly Ala Asp Leu Met Gln Ala Leu Val Asp Ser Glu Leu
            355             360             365

Gln Pro Ser Arg Gly Gln Ala Arg Lys Thr Ile Ala Ser Asn Ala Ile
    370             375             380

Thr Ile Asn Gly Glu Lys Gln Ser Asp Pro Glu Tyr Phe Phe Lys Glu
385             390             395             400

Glu Asp Arg Leu Phe Gly Arg Phe Thr Leu Leu Arg Arg Gly Lys Lys
            405             410             415

Asn Tyr Cys Leu Ile Cys Trp Lys Gly Pro Val
            420             425
```

<210> SEQ ID NO 71
<211> LENGTH: 1284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atggcaagca gtaacttgat taaacaattg caagagcggg ggctggtagc ccaggtgacg      60
gacgaggaag cgttagcaga gcgactggcg caaggcccga tcgcactcgt gtgtggcttc     120
gatcctaccg ctgacagctt gcatttgggg catcttgttc cattgttatg cctgaaacgc     180
ttccagcagg cgggccacaa gccggttgcg ctggtaggcg gcgcgacggg tctgattggc     240
gacccgagct tcaaagctgc cgagcgtaag ctgaacaccg aagaaactgt tcaggagtgg     300
gtggacaaaa tccgtaagca ggttgccccg ttcctcgatt tcgactgtgg agaaaactct     360
gctatcgcgg ccaataatta tgactggttc ggcaatatga atgtgctgac cttcctgcgc     420
gatattggca aacacttctc cgttaaccag atgatcaaca agaagcggt taagcagcgt      480 ctcaaccgtg aagatcaggg gatttcgttc actgagtttt cctacaacct gctgcagggt     540
tatagtatgg cctgtttgaa caaacagtac ggtgtggtgc tgcaaattgg tggttctgac     600
caatggggta acatcacttc tggtatcgac ctgacccgtc gtctgcatca gaatcaggtg     660
tttggcctga ccgttccgct gatcactaaa gcagatggca ccaaatttgg taaaactgaa     720
ggcggcgcag tctggttgga cccgaagaaa accagcccgt acaaattcta ccagttctgg     780
atcaacactg cggatgccga cgtttaccgc ttcctgaagt tcttcacctt tatgagcatt     840
gaagagatca cgccctgga agaagaagat aaaaacagcg gtaaagcacc gcgcgcccag     900
tatgtactgg cggagcaggt gactcgtctg gttcacggtg aagaaggttt acaggcggca     960
```

-continued

```
aaacgtatta ccgaatgcct gttcagcggt tctttgagtg cgctgagtga agcggacttc    1020
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc ctgaatactt ctttaaagaa    1200
gaagatcgtc tgtttggtcg ttttacctta ctgcgtcgcg gtaaaaagaa ttactgtctg    1260
atttgctgga aagggcccgt ttaa                                          1284
```

```
<210> SEQ ID NO 72
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ggaaacctga tcatgtagat cgaacggact ctaaatccgt tcagccgggt tagattcccg    60
gggtttccg                                                            69
```

```
<210> SEQ ID NO 73
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (31)..(33)
<223> OTHER INFORMATION: This region may encompass CTA, TCA, or TTA

<400> SEQUENCE: 73
ggaaacctga tcatgtagat cgaacggact nnnaatccgt tcagccgggt tagattcccg    60
gggtttccg                                                            69
```

```
<210> SEQ ID NO 74
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
ggaaaccuga ucauguagau cgaacggacu cuaaauccgu ucagccgggu uagauucccg    60
ggguuuccgc ca                                                        72
```

```
<210> SEQ ID NO 75
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
gggcggcuga ucauguagau cgaacggacu cuaaauccgu ucagccgggu uagauucccg    60
ggcugcccgc ca                                                        72
```

```
<210> SEQ ID NO 76
<211> LENGTH: 72
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gggugacuga ucauguagau cgaacggacu cuaaauccgu ucagccgggu uagauucccg      60
gguugcccgc ca                                                          72

<210> SEQ ID NO 77
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77 gggggcuga ucauguagau cgaacggacu cuaaauccgu ucagccgggu uagauucccg       60 ggcucccgc ca                                                           72

<210> SEQ ID NO 78
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
gggcggcuga ucauguagau cgaacggacu cuaaauccgu ucagccgggu uagauucccg      60
gguugcccgc ca                                                          72

<210> SEQ ID NO 79
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gggcgccuga ucauguagau cgaacggacu cuaaauccgu ucagccgggu uagauucccg      60
gggcgcccgc ca                                                          72

<210> SEQ ID NO 80
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
ggggagguga ucauguagau cgaacggacu cuaaauccgu ucagccgggu uagauucccg      60 gccucccgc ca                                                           72

<210> SEQ ID NO 81
<211> LENGTH: 72
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 81 gggggaccuga ucauguagau cgaacggacu cuaaauccgu ucagccgggu uagauucccg          60 gggucccccgc ca                                                              72

<210> SEQ ID NO 82
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
ggccggguga ucauguagau cgaacggacu cuaaauccgu ucagccgggu uagauucccg          60
gccuggccgc ca                                                              72

<210> SEQ ID NO 83
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83 gggggaccuga ucauguagau cgaacggacu cuaaauccgu ucagccgggu uagauucccg         60 gggguccucgc ca                                                             72

<210> SEQ ID NO 84
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84 gggggcccuga ucauguagau cgaacggacu cuaaauccgu ucagccgggu uagauucccg         60 gggguucccgc ca                                                             72

<210> SEQ ID NO 85
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gggggccuga ucauguagau cgaacggacu cuaaauccgu ucagccgggu uagauucccg          60
gggcucccgc ca                                                              72

<210> SEQ ID NO 86
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86

-continued

```
ggggguccuga ucauguagau cgaacggacu cuaaauccgu ucagccgggu uagauucccg      60
gggaucccgc ca                                                          72

<210> SEQ ID NO 87
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ggggaccuga ucauguagau cgaacggacu cuaaauccgu ucagccgggu uagauucccg       60
ggguucccgc ca                                                          72

<210> SEQ ID NO 88
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggggagguga ucauguagau cgaacggacu cuaaauccgu ucagccgggu uagauucccg       60
gucuucccgc ca                                                          72

<210> SEQ ID NO 89
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89 gggggg guga ucauguagau cgaacggacu cuaaauccgu ucagccgggu uagauucccg      60
gcccccucgc ca                                                          72

<210> SEQ ID NO 90
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ggugggguga ucauguagau cgaacggacu cuaaauccgu ucagccgggu uagauucccg       60
gcccuaccgc ca                                                          72

<210> SEQ ID NO 91
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gggggucuga ucauguagau cgaacggacu cuaaauccgu ucagccgggu uagauucccg       60
ggacucccgc ca                                                          72
```

<210> SEQ ID NO 92
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gggucccuga ucauguagau cgaacggacu cuaaauccgu ucagccgggu uagauucccg        60
ggggguccgc ca                                                            72

<210> SEQ ID NO 93
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
ggggaccuga ucauguagau cgaacggacu cuaaauccgu ucagccgggu uagauucccg        60
ggguucucgc ca                                                            72

<210> SEQ ID NO 94
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gggcggcuga ucauguagau cgaacggacu cuaaauccgu ucagccgggu uagauucccg        60
ggccgcccgc ca                                                            72

<210> SEQ ID NO 95
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
gagcaccuga ucauguagau cgaacggacu cuaaauccgu ucagccgggu uagauucccg        60
gggugcucgc ca                                                            72

<210> SEQ ID NO 96
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ggggggguga ucauguagau cgaacggacu cuaaauccgu ucagccgggu uagauucccg        60
gcccccccgc ca                                                            72

<210> SEQ ID NO 97
<211> LENGTH: 72
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 97
gaggggguga ucauguagau cgaacggacu cuaaauccgu ucagccgggu uagauucccg      60
gcccccucgc ca                                                          72

<210> SEQ ID NO 98
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
gggagccuga ucauguagau cgaacggacu cuaaauccgu ucagccgggu uagauucccg      60
ggguucccgc ca                                                          72

<210> SEQ ID NO 99
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
gggagccuga ucauguagau cgaacggacu cuaaauccgu ucagccgggu uagauucccg      60
ggguucccgc ca                                                          72

<210> SEQ ID NO 100
<211> LENGTH: 72
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
gaggaccuga ucauguagau cgaacggacu cuaaauccgu ucagccgggu uagauucccg      60
ggguucucgc ca                                                          72

<210> SEQ ID NO 101
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60
```

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
            165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
            245                 250                 255

Asp Lys Asn Leu Cys Leu Arg Pro Met Leu Ala Pro Thr Leu Tyr Asn
        260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
            325                 330                 335

Ile Asp Phe Glu Ile Val Gly Asp Ser Cys Met Val Phe Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
            405                 410                 415

Thr Asn Leu

<210> SEQ ID NO 102
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

-continued

```
atggataaaa aaccattaga tgtttttaata tctgcgaccg ggctctggat gtccaggact      60
ggcacgctcc acaaaatcaa gcaccatgag gtctcaagaa gtaaaatata cattgaaatg     120
gcgtgtggag accatcttgt tgtgaataat tccaggagtt gtagaacagc cagagcattc     180
agacatcata agtacagaaa aacctgcaaa cgatgtaggg tttcggacga ggatatcaat     240
aattttctca caagatcaac cgaaagcaaa aacagtgtga aagttagggt agtttctgct     300
ccaaaggtca aaaaagctat gccgaaatca gtttcaaggg ctccgaagcc tctggaaaat     360
tctgtttctg caaaggcatc aacgaacaca tccagatctg taccttcgcc tgcaaaatca     420
actccaaatt cgtctgttcc cgcatcggct cctgctcctt cacttacaag aagccagctt     480
gatagggttg aggctctctt aagtccagag gataaaattt ctctaaatat ggcaaagcct     540 ttcaggggaac ttgagcctga acttgtgaca agaagaaaaa acgattttca gcggctctat     600
accaatgata gagaagacta cctcggtaaa ctcgaacgtg atattacgaa attttttcgta     660 gaccgggggtt ttctggagat aaagtctcct atccttattc cggcggaata cgtggagaga     720
atgggtatta ataatgatac tgaactttca aaacagatct tccgggtgga taaaaatctc     780
tgcttgaggc caatgcttgc cccgactctt tacaactatc tgcgaaaact cgataggatt     840
ttaccaggcc aataaaaat tttcgaagtc ggaccttgtt accggaaaga gtctgacggc     900
aaagagcacc tggaagaatt tactatggtg aacttctgtc agatgggttc gggatgtact     960
cgggaaaatc ttgaagctct catcaaagag tttctggact atctggaaat cgacttcgaa    1020
atcgtaggag attcctgtat ggtctttggg gatactcttg atataatgca cggggacctg    1080
gagctttctt cggcagtcgt cgggccagtt tctcttgata gagaatgggg tattgacaaa    1140
ccatggatag gtgcaggttt tggtcttgaa cgcttgctca aggttatgca cggctttaaa    1200
aacattaaga gggcatcaag gtccgaatct tactataatg ggatttcaac caatctgtaa    1260
```

```
<210> SEQ ID NO 103
<211> LENGTH: 1005
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
```

```
atgactaagc ccatcgtttt tgctggcgca cagccctcag gtgaattgac cattggtaac      60
tacatgggtg cgctgcgtca gtgggtaaac atgcaggatg actaccattg catttactgt     120
atcgttgacc aacacgcgat caccgtgcgc caggatgcac agaagctgcg taaagcgacg     180
ctggatacgc tggccttgta tctggcttgt ggtatcgatc ctgagaaaag caccattttt     240
gttcagtccc acgtgccgga acatgcacag ttaggctggg cactgaactg ctataccttac     300 ttcggcgaac tgagtcgcat gacgcagttt aaagataaat ctgcgcgtta tgccgagaac     360
atcaacgctg gtctgtttga ctatccggtc ctgatggcag cggacatcct gctgtatcaa     420
actaatctgg gtccttgtgg tgaagaccag aaacagcacc tcgaactgag ccgcgatatt     480
gcccagcgtt tcaacgcgct gtatggcgag atctttaagg tgccggagcc gtttattccg     540
aaatctggcg cgcgcgtaat gtcgctgctg agccgaccca agaagatgtc caagtctgac     600
gataatcgca ataacgttat cggcctgctg gaagatccga aatcggtagt gaagaaaatc     660
aaacgtgcgg tcactgactc cgacgagccg ccggtagttc gctacgatgt gcagaacaaa     720
gcgggcgttt ccaacctgtt ggatatcctt tcagcggtaa cgggccagag catcccagaa     780
```

-continued

```
ctggaaaaac agttcgaagg caagatgtat ggtcatctga aaggtgaagt ggctgatgcc        840
gtttccggta tgctgactga attgcaggaa cgctatcacc gtttccgcaa cgatgaagcc        900
ttcctgcaac aggtgatgaa agatggcgcg gaaaaagcca gcgcgcacgc ttcccgtacg        960
ctaaaagcgg tgtacgaagc gattggtttt gtggcgaagc cgtaa                        1005

<210> SEQ ID NO 104
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtggggttcc cgagcggcca aagggagcag acttcaaatc tgccgtcaca gacttcgaag         60
gttcgaatcc ttcccccacc acca                                                84

<210> SEQ ID NO 105
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 105
gtggggttcc cgagcggcca aagggagcag actnnnaatc tgccgtcaca gacttcgaag         60
gttcgaatcc ttcccccacc acca                                                84

<210> SEQ ID NO 106
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
ggaaacctga tcatgtagat cgaacggact ctaaatccgt tcagccgggt tagattcccg         60
gggtttccgc ca                                                             72

<210> SEQ ID NO 107
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (31)..(33)
<223> OTHER INFORMATION: This region may encompass CTA, TCA, or TTA

<400> SEQUENCE: 107
ggaaacctga tcatgtagat cgaacggact nnnaatccgt tcagccgggt tagattcccg         60
gggtttccgc ca                                                             72

<210> SEQ ID NO 108
<211> LENGTH: 73
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aggggcgtag ttcaattggt agagcaccgg tctccaaaac cgggtgttgg gagttcgagt     60
ctctccgccc ctg                                                        73

<210> SEQ ID NO 109
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aggggcgtag ttcaattggt agagcaccgg tctctaaaac cgggtgttgg gagttcgagt     60
ctctccgccc ctg                                                        73

<210> SEQ ID NO 110
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aggggcgtag ttcaattggt agagcaccgg tcttcaaaac cgggtgttgg gagttcgagt     60
ctctccgccc ctg                                                        73

<210> SEQ ID NO 111
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
aggggcgtag ttcaattggt agagcaccgg tctttaaaac cgggtgttgg gagttcgagt     60
ctctccgccc ctg                                                        73

<210> SEQ ID NO 112
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 112
tggggtatcg ccaagcggta aggcaccgga ttcnnnttcc ggcattccga ggttcgaatc     60
ctcgtacccc ag                                                         72

<210> SEQ ID NO 113
<211> LENGTH: 73

-continued

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (34)..(36)
<223> OTHER INFORMATION: This region may encompass CTA, TCA, or TTA

<400> SEQUENCE: 113
aggggcatag ctcaagcggt aaagcaccgg actnnnaaac cggcagtccg aagttcgaat        60 cccccaccc cag                                                           73

<210> SEQ ID NO 114
<211> LENGTH: 330
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn

-continued

```
        290              295              300

Val Phe Ser Cys Ser Val Met His Glu Ala Leu His Asn His Tyr Thr
305                     310              315                  320

Gln Lys Ser Leu Ser Leu Ser Pro Gly Lys
                325              330

<210> SEQ ID NO 115
<211> LENGTH: 106
<212> TYPE: PRT
<213> ORGANISM: Homo sapiens

<400> SEQUENCE: 115

Thr Val Ala Ala Pro Ser Val Phe Ile Phe Pro Pro Ser Asp Glu Gln
1                   5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 116
<211> LENGTH: 24
<212> TYPE: PRT
<213> ORGANISM: Homo sapiens

<400> SEQUENCE: 116

Val Val Thr Val Pro Ser Ser Ser Leu Gly Thr Gln Thr Tyr Ile Cys
1                   5                  10                  15

Asn Val Asn His Lys Pro Ser Asn
                20

<210> SEQ ID NO 117
<211> LENGTH: 22
<212> TYPE: PRT
<213> ORGANISM: Homo sapiens

<400> SEQUENCE: 117

Thr Phe Gly Gln Gly Thr Lys Val Glu Ile Lys Arg Thr Val Ala Ala
1                   5                  10                  15

Pro Ser Val Phe Ile Phe
                20
```